US012319717B2

(12) United States Patent
Mosher

(10) Patent No.: US 12,319,717 B2
(45) Date of Patent: Jun. 3, 2025

(54) BRASSICA PLANTS WITH INCREASED LOCULES

(71) Applicant: Arizona Board of Regents on Behalf of the University of Arizona, Tucson, AZ (US)

(72) Inventor: Rebecca Mosher, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 18/278,283

(22) PCT Filed: Feb. 21, 2022

(86) PCT No.: PCT/US2022/017153
§ 371 (c)(1),
(2) Date: Aug. 22, 2023

(87) PCT Pub. No.: WO2022/178352
PCT Pub. Date: Aug. 25, 2022

(65) Prior Publication Data

US 2024/0034756 A1 Feb. 1, 2024

Related U.S. Application Data

(60) Provisional application No. 63/152,025, filed on Feb. 22, 2021.

(51) Int. Cl.
*C07K 14/41* (2006.01)
*A01H 6/20* (2018.01)
*C07K 14/415* (2006.01)
*C12N 9/22* (2006.01)
*C12N 15/82* (2006.01)

(52) U.S. Cl.
CPC ............. *C07K 14/415* (2013.01); *A01H 6/20* (2018.05); *C12N 9/22* (2013.01); *C12N 15/8205* (2013.01); *C12N 15/8287* (2013.01); *C12N 2310/20* (2017.05)

(58) Field of Classification Search
CPC ................................ C07K 14/415; A01H 6/20
See application file for complete search history.

(56) References Cited

U.S. PATENT DOCUMENTS

2011/0016586 A1 1/2011 Sanz Molinero et al.

FOREIGN PATENT DOCUMENTS

WO WO 2008/062049 A1 5/2008

OTHER PUBLICATIONS

Xiao et al., 2018, Mutations in the CDS and promoter of BjuA 0 7. CLV1 cause a multilocular trait in Brassica juncea. Scientific Reports, 8(1), 5339. (Year: 2018).*
Xiao et al., 2018, Mutations in the CDS and promoter of BjuA 0 7. CLV1 cause a multilocular trait in Brassica juncea, Supplementary Inforamtion. Scientific Reports, 8(1), 5339. (Year: 2018).*
Hypothetical protein BRARA_G03381 [Brassica rapa], GenBank: RID56165.1, NCBI protein database, https://www.ncbi.nlm.nih.gov/protein/RID56165.1?report=genbank&log$=protalign&blast_rank=5&RID=SWGYK0CU013, Accessed Dec. 29, 2023. (Year: 2023).*
Bashyal et al., 2023, CLAVATA signaling in plant-environment interactions. Plant Physiology, kiad591. (Year: 2023).*
Yasmeen et al., 2023, Designing artificial synthetic promoters for accurate, smart, and versatile gene expression in plants. Plant Communications, 4(4). (Year: 2023).*
Chow et al., "A novel CLAVATA1 mutation causes multilocularity in *Brassica rapa," Plant Direct.* 7:e476, 2023.
GenBank Accession No. FX693195, TSA: *Brassica rapa* subsp. pekinensis RNA, contig: CF3_10396, transcribed RNA sequence, Dec. 17, 2014 [online]. [Retrieved on Jun. 20, 2022]. Retrieved from the internet: <URL: https://www.ncbi.nlm.nih.gov/nuccore/FX693195>.
International Search Report mailed on Jul. 7, 2023 in International Application No. PCT/US2022/017153 (5 pages).
Written Opinion mailed on Jul. 7, 2023 in International Application No. PCT/US2022/017153 (7 pages).

* cited by examiner

*Primary Examiner* — David H Kruse
*Assistant Examiner* — Santosh Sharma
(74) *Attorney, Agent, or Firm* — Klarquist Sparkman, LLP

(57) ABSTRACT

The disclosure provides mutant Brassica plants that have increased locules and seed production relative to native wild-type plants. Such plants include a point mutation in the clavata 1 gene (CLV1), such as a G→A substitution at position 1745 of the *Brassica rapa* coding sequence, which leads to an S582N substitution in the protein sequence. Equivalent substitutions can be made in any Brassicaceae coding/protein sequence. Also provided are methods of using such plants in breeding programs, as well as parts of such plants (such as seeds), and methods of making commodity products from such plants (e.g., oil). Also provided are mutant CLV1 sequences. Brassica plants harboring the disclosed CLV1 mutation can include other desirable traits, such as herbicide tolerance.

16 Claims, 12 Drawing Sheets

Specification includes a Sequence Listing.

FIG. 1

*Brassica rapa CLV1* coding sequence (A07p048430.1 BraROA)

ATGAGACTTCTGAAAACTCACCTTCTGTTTCTCCATCTTCATTACGTTATCTCGATTTCGCTTCTATGTTTCTCACCATGCCTCGCTTCCACTGACATG
GACCATCTCCTCAACCTCAAATCCTCCATGATTGGTCCCAACGGCAACGGCCTCCACGACTGGGTTCACTCCCCTTCCCCCACAGCTCACTGTTCTTTC
TCCGGCGTTTCCTGCGACGGCGACGCTCGTGTCATCTCCCTCAACGTCTCTTTCACTCCTCTCTTCGGAACCATCTCCCCGGAGATTGGGATGCTGAAC
CGTCTTGTGAATCTCACGTTAGCTGCTAATAACTTCTCCGGTATGTTGCCGTTAGAGATGAAGAGTCTCACTTCTCTAAAGGTTCTCAACATCTCCAAC
AACGTAAACCTCAACGGAACGTTCCCCGGAGAGATTCTCACTCCCATGGTCGACCTCGAAGTCCTCGACGCGTACAACAACAACTTCACAGGCCCATTA
CCGCCAGAGATCCCCGGGCTCAAGAAACTGAGACACCTCTCTCTCGGAGGAAACTTCTTAACCGGAGAGATCCCAGAGAGTTACGGAGATATCCAAAGC
TTGGAGTATCTCGGCCTCAACGGAGCCGGACTCTCCGGTGAATCTCCGGCGTTCTTGTCACGCCTCAAGAATCTTAAAGAAATGTACGTCGGCTACTTC
AACAGCTACACCGGCGGCGTACCGCCGGAGTTCGGTGAATTGACAAACTTAGAAGTCCTCGACATGGCGAGCTGTACTCTCACCGGAGAGATTCCGACA
ACACTAAGTAATCTAAAACATTTGCACACTTTGTTTCTCCACATCAACAACTTAACCGGAAACATCCCACCCGAACTCTCCGGTTTAATCAGCTTAAAA
TCTCTAGACCTCTCAATAAACCAGCTAACCGGAGAGATTCCTCAGAGCTTCATCTCCCTAGGGAACATCACTCTCATCAACCTCTTCCGAAACAATCTC
CACGGGCCGATACCGGACTTCATCGGAGACATGCCGAACCTCCAAGTCCTCCAGGTGTGGGAGAACAACTTCACGCTAGAGCTACCGGCGAATCTCGGC
CGGAACGGGAATCTGAAAAAGCTCGACGTCTCTGATAACCATCTCACCGGACTCATCCCCATGGATTTGTGCAGAGGCGGGAAGCTGGAGACGCTGGTG
CTCTCCAACAACTTCTTCTTCGGCTCGATCCCTGAGAAGCTAGGTCAATGCAAATCGCTAAACAAGATCAGAATCGTCAAGAATCTCCTCAACGGCACG
GTTCCGGAGGGCTTATTCAATCTACCGCTCGTAACGATCATCGAGCTCACCGATAACTTCTTCTCCGGGGAGCTTCCGGGGGAGATGTCAGGCGACGTT
CTCGATCATATCTACTTATCTAACAATTGGTTTACCGGTTTAATCCCCCCGGCTATCGGTAATTTTAAAAATCTACAGGATTTATTCTTAGACCGGAAC
CGGTTTAGCGGGAATATTCCGAGAGAAGTTTTCGAGTTGAAGCATCTAACGAAGATCAACACGAGTGCTAACAACCTAACCGGCGATATCCCTGACTCA
ATCTCACGTTGCACTTCCTTAATCTCCGTCGATCTCAGCCGTAACCGAATCGGCGGAGATATCCCTAAAGACATCCACGATGTGATCAATCTCGGAACT
CTAAATCTCTCCGGGAATCAACTCACCGGCTCGATCCCGATCGGAATCGGGAAGATGACGAGCTTAACCACTCTGGATCTCTCCTTCAACGACCTCTCC
GGGAGAGTCCCACTCGGCGGCCAGTTCCTAGTCTTCAACGACACTTCCTTCGCCGGAAACCCTTACCTCTGCCTCCCTCACCACGTCTCGTGCCTTACG
CGTCCGGAACAAACCTCCGATCGTATCCACACGGCTCTCTTCTCTCCGTCGAGGATCGTTATCACGATCGTCGCGGCGATAACGGCGTTGATCCTCATC
AGCGTCGCGATTCGTCAGATGAACAAGAAGAAACACGAGAGGTCTCTCTCGTGGAAGCTAACCGCCTTCCAAAGACTCGATTTCAAAGCGGAAGACGTC
CTCGAGTGTCTCCAGGAAGAGAACATAATCGGCAAAGGCGGAGCTGGGATCGTCTACCGCGGATCCATGCCGAACAACGTAGACGTCGCGATCAAACGG
TTAGTAGGACGCGGAACAGGGAGGAGCGATCACGGATTCACGGCGGAGATACAAACTCTAGGGAGAATCCGCCACCGTCATATAGTGAGACTCCTCGGA
TACGTGGCGAACAAGGACACGAACCTGCTTCTCTACGAGTACATGCCTAACGGGAGCCTCGGGGAGCTTTTGCACGGATCTAAAGGAGGTCATCTTCAG
TGGGAGACGAGGCACAGAGTAGCCGTGGAAGCGGCGAAAGGACTGTGTTATCTTCATCATGACTGTTCGCCGTTGATCTTGCATAGAGACGTTAAGTCC
AATAACATACTACTGGACTCTGATTTTGAGGCCCATGTTGCTGATTTTGGGCTTGCTAAGTTCTTAGTGGACGGTGCTGCTTCTGAGTGTATGTCTTCG
ATAGCTGGCTCCTATGGATACATCGCTCCAGAGTATGCTTACACTCTCAAAGTGGACGAGAAGAGTGATGTGTATAGTTTCGGAGTGGTGTTATTGGAA
CTGATAGCTGGGAAGAAACCGGTTGGTGAGTTTGGGGAAGGAGTGGATATAGTGAGGTGGGTGAGGAACACGGAGGGTGAGATACCTCAGCCGTCGGAT
GCAGCTACTGTTGTGGCGATCGTTGACCAGAGGTTGACTGGTTACCCGTTGACTAGTGTGATTCACGTGTTCAAGATAGCGATGATGTGTGTGGAGGAT
GAGGCAGCGACAAGGCCGACGATGAGGGAAGTTGTGCACATGCTCACTAACCCTCCCAAGTCCGTCACTAACTTGATCGCCTTCTGA

FIG. 2

*Brassica rapa CLV1* protein sequence (A07p048430.1 BraROA)

MRLLKTHLLFLHLHYVISISLLCFSPCLASTDMDHLLNLKSSMIGPNGNGLHDWVHSPSPTAHCSFS
GVSCDGDARVISLNVSFTPLFGTISPEIGMLNRLVNLTLAANNFSGMLPLEMKSLTSLKVLNISNNV
NLNGTFPGEILTPMVDLEVLDAYNNNFTGPLPPEIPGLKKLRHLSLGGNFLTGEIPESYGDIQSLEY
LGLNGAGLSGESPAFLSRLKNLKEMYVGYFNSYTGGVPPEFGELTNLEVLDMASCTLTGEIPTTLSN
LKHLHTLFLHINNLTGNIPPELSGLISLKSLDLSINQLTGEIPQSFISLGNITLINLFRNNLHGPIP
DFIGDMPNLQVLQVWENNFTLELPANLGRNGNLKKLDVSDNHLTGLIPMDLCRGGKLETLVLSNNFF
FGSIPEKLGQCKSLNKIRIVKNLLNGTVPEGLFNLPLVTIIELTDNFFSGELPGEMSGDVLDHIYLS
NNWFTGLIPPAIGNFKNLQDLFLDRNRFSGNIPREVFELKHLTKINTSANNLTGDIPDSISRCTSLI
SVDLSRNRIGGDIPKDIHDVINLGTLNLSGNQLTGSIPIGIGKMTSLTTLDLSFNDLSGRVPLGGQF
LVFNDTSFAGNPYLCLPHHVSCLTRPEQTSDRIHTALFSPSRIVITIVAAITALILISVAIRQMNKK
KHERSLSWKLTAFQRLDFKAEDVLECLQEENIIGKGGAGIVYRGSMPNNVDVAIKRLVGRGTGRSDH
GFTAEIQTLGRIRHRHIVRLLGYVANKDTNLLLYEYMPNGSLGELLHGSKGGHLQWETRHRVAVEAA
KGLCYLHHDCSPLILHRDVKSNNILLDSDFEAHVADFGLAKFLVDGAASECMSSIAGSYGYIAPEYA
YTLKVDEKSDVYSFGVVLLELIAGKKPVGEFGEGVDIVRWVRNTEGEIPQPSDAATVVAIVDQRLTG
YPLTSVIHVFKIAMMCVEDEAATRPTMREVVHMLTNPPKSVTNLIAF

FIG. 3

| | |
|---|---|
| wild type CLV1 | GGCTCGATCCCGATCGGAATCGGGAAGATGACGAGCTTAACCACTCTGGATCTCTCCTTCAACGACCTC |
| | G S I P I G I G K M T S L T T L D L S F N D L |
| sup-c (clv1) | GGCTCGATCCCGATCGGAATCGGGAAGATGACGAACTTAACCACTCTGGATCTCTCCTTCAACGACCTC |
| | G S I P I G I G K M T N L T T L D L S F N D L |

FIG. 4B

% identity between CLV1 protein sequences among important Brassicaceae oil-seed crops

| | B. napus a | B. napus b | B. oleracea | C. sativa a | C. sativa b | C. sativa c | T. arvense |
|---|---|---|---|---|---|---|---|
| B. rapa CLV1 | 97.8 | 97.2 | 98.0 | 89.1 | 89.5 | 88.8 | 90.5 |
| B. napus a | | 95.3 | 98.9 | 88.4 | 88.7 | 87.8 | 90.0 |
| B. napus b | | | 95.5 | 86.8 | 87.1 | 86.2 | 88.3 |
| B. oleracea | | | | 88.3 | 88.6 | 87.7 | 90.1 |
| C. sativa a | | | | | 97.7 | 97.2 | 89.9 |
| C. sativa b | | | | | | 97.7 | 90.8 |
| C. sativa c | | | | | | | 90.6 |

BRASSICA PLANTS WITH INCREASED LOCULES

CROSS-REFERENCE TO RELATED APPLICATION

This is the U.S. National Stage of International Application No. PCT/US2022/017153, filed Feb. 21, 2022, which was published in English under PCT Article 21(2), which in turn claims the benefit of U.S. Provisional Application No. 63/152,025, filed Feb. 22, 2021, all herein incorporated by reference in their entireties.

ACKNOWLEDGMENT OF GOVERNMENT SUPPORT

This invention was made with government support under Grant No. 2021-67013-33797 awarded by USDA/NIFA. The government has certain rights in the invention.

INCORPORATION OF ELECTRONIC SEQUENCE LISTING

The electronic sequence listing, submitted herewith as a txt file named seq listing.txt (596,527 bytes), created on Aug. 10, 2023, is herein incorporated by reference in its entirety.

FIELD

Provided herein are mutant clavata 1 (CLV1) protein and nucleic acid molecules, which include or encode an S582N substitution (or equivalent thereof), as well as plants and plant cells including such nucleic acid molecules and proteins. This mutation can produce a plant with an increased number of locules and/or increase seed production as compared to a native plant or tree of the same species, such as an increase of at least 10%, at least 20%, at least 30%, at least 40%, or at least 50%.

SUMMARY

Provided herein are mutant clavata 1 (CLV1) protein and nucleic acid molecules, which include or encode an S582N substitution (for example due to an adenine (A) nucleotide at position 1745), or its equivalent (e.g., a Ser to Asn substitution in the sequence SLT located in the C-terminal half of the protein, for example between aa 500 and 900 of a native CLV1 sequence, such as between about aa 540 and 600 or about aa 540 to 860, see for example FIGS. 5A, 5B). Also provided are vectors (such as a plasmid or viral vector) including such nucleic acid molecules. Also provided are plants and plant cells containing such mutant protein and nucleic acid molecules, such those having an S582N mutation in their CLV1 protein (or equivalent mutation). In some examples, the plant is a Brassicaceae plant.

In some examples, this disclosed S582N substitution in CLV1 results in plants with an increased number of locules as compared to a native plant or tree of the same species, such as an increase of at least 10%, at least 20%, at least 30%, at least 40%, or at least 50%, for example as compared to plants with a native CLV1 sequence (e.g., SEQ ID NO: 1, 2, 5, 6, 7, 8, 9, 10, 11, 12, 13, 14, 15, 16, 17, 18, 25, 27, 29, 31, 33, 35, 37, 39, 41, 43, 45, 47, 49, 51, 53, 55, 57, 59, 61, 63, 67, 69, 71, 73, 75, 77, 79, 81, 83, 85, 87, 89, 91, 93, 95, 97, or 99). In some examples, this disclosed S582N substitution in CLV1 results in plants with increased seed production as compared to a native plant or tree of the same species, such as an increase of at least 10%, at least 20%, at least 30%, at least 40%, or at least 50%, for example as compared to plants with a native CLV1 sequence (e.g., SEQ ID NO: 1, 2, 5, 6, 7, 8, 9, 10, 11, 12, 13, 14, 15, 16, 17, 18, 25, 27, 29, 31, 33, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, or 99). In some examples, combinations of such effects are achieved.

In some examples, a mutant CLV1 nucleic acid molecule comprises at least 80%, at least 85%, at least 90%, at least 95%, at least 96%, at least 97%, at least 98%, at least 99%, or 100% identity to SEQ ID NO: 3, and encodes a S582N substitution (or its equivalent, e.g., a Ser to Asn substitution in the sequence SLT located in the C-terminal half of the protein, for example between aa 500 and 900 of a native CLV1 sequence, such as between about aa 540 and 600 or about aa 540 to 860, see for example FIGS. 5A, 5B).

In some examples, a mutant CLV1 protein comprises at least 80%, at least 85%, at least 90%, at least 95%, at least 96%, at least 97%, at least 98%, at least 99%, or 100% identity to SEQ ID NO: 4, and includes a S582N substitution (or its equivalent, e.g., a Ser to Asn substitution in the sequence SLT located in the C-terminal half of the protein, for example between aa 500 and 900 of a native CLV1 sequence, such as between about aa 540 and 600 or about aa 540 to 860, see for example FIGS. 5A, 5B).

The foregoing and other objects and features of the disclosure will become more apparent from the following detailed description, which proceeds with reference to the accompanying figures.

BRIEF DESCRIPTION OF THE DRAWINGS

FIG. 1 shows an exemplary native *Brassica rapa* CLV1 coding sequence (SEQ ID NO: 1). nt 1745 in bold/underline. This nt can be changed to an A to encode an S582N mutation.

FIG. 2 shows an exemplary native *Brassica rapa* CLV1 protein sequence (SEQ ID NO: 2). S582 in bold/underline. This amino acid can be mutated to an N to cause multilocularity and increase organ number and seed production.

FIG. 3 shows the G to A substitution at nt 175 (codon 582) resulting in a S582N substitution in the CLV1 protein (top sequence nt 1711 to 1779 of SEQ ID NO: 1, aa 571 to 593 of SEQ ID NO: 2, bottom sup-c (clv1) sequence nt 1711 to 1779 of SEQ ID NO: 3, aa 571 to 593 of SEQ ID NO: 4).

FIG. 4B shows the % sequence identity of the native CLV1 protein sequence for several Brassicaceae plants.

SEQUENCE LISTING

Figure 4A:
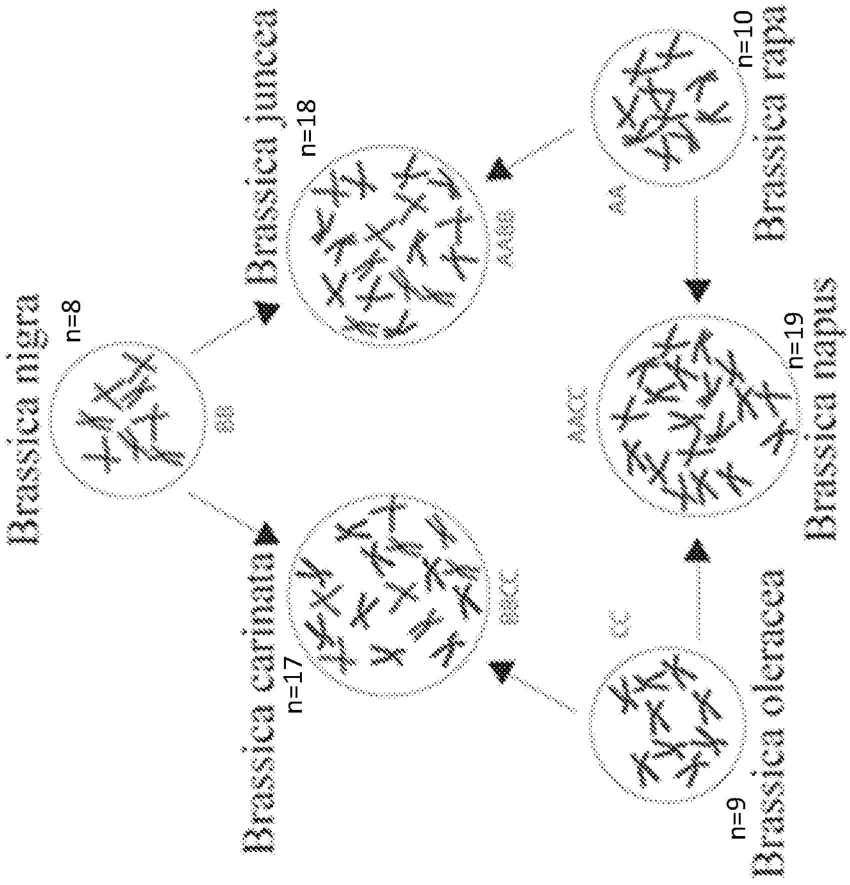
FIG. 4A shows the relationship of the diploid and tetraploid members of the *Brassica* genus [figure from Wikimedia Commons]. Other important Brassicaceae oil-seed crops include *Thlaspi arvense* (pennycress) and *Camelina sativa* (false flax, an allohexaploid).

The nucleic and amino acid sequences listed in the accompanying sequence listing are shown using standard letter abbreviations for nucleotide bases, and single letter code for amino acids, for example as defined in 37 C.F.R. 1.822. Only one strand of each nucleic acid sequence is shown, but the complementary strand is understood as included by any reference to the displayed strand. The sequence listing generated on Feb. 21, 2022, 582 kB, and filed herewith is incorporated by reference. In the accompanying sequence listing:

SEQ ID NOS: 1 and 2 are an exemplary native *Brassica rapa* CLV1 coding and protein sequences, respectively (A07p048430.1_BraROA).

SEQ ID NOS: 3 and 4 are an exemplary mutant CLV1 coding and protein sequences, respectively, which result in large locules. Nucleotide 1745 is mutated to A (G→A), resulting in an S582N substitution in the protein (underlined)

```
ATGAGACTTCTGAAAACTCACCTTCTGTTTCTCCATCTTCA
TTACGTTATCTCGATTTCGCTTCTATGTTTCTCACCATGC
CTCGCTTCCACTGACATGGACCATCTCCTCAACCTCAAAT
```

-continued

```
CCTCCATGATTGGTCCCAACGGCAACGGCCTCCACGACTG
GGTTCACTCCCCTTCCCCCACAGCTCACTGTTCTTTCTCC
GGCGTTTCCTGCGACGGCGACGCTCGTGTCATCTCCCTCA
ACGTCTCTTTCACTCCTCTCTTCGGAACCATCTCCCCGGA
GATTGGGATGCTGAACCGTCTTGTGAATCTCACGTTAGCT
GCTAATAACTTCTCCGGTATGTTGCCGTTAGAGATGAAGA
GTCTCACTTCTCTAAAGGTTCTCAACATCTCCAACAACGT
AAACCTCAACGGAACGTTCCCCGGAGAGATTCTCACTCCC
ATGGTCGACCTCGAAGTCCTCGACGCGTACAACAACAACT
TCACAGGCCCATTACCGCCAGAGATCCCCGGGCTCAAGAA
ACTGAGACACCTCTCTCTCGGAGGAAACTTCTTAACCGGA
GAGATCCCAGAGAGTTACGGAGATATCCAAAGCTTGGAGT
ATCTCGGCCTCAACGGAGCCGGACTCTCCGGTGAATCTCC
GGCGTTCTTGTCACGCCTCAAGAATCTTAAAGAAATGTAC
GTCGGCTACTTCAACAGCTACACCGGCGGCGTACCGCCGG
AGTTCGGTGAATTGACAAACTTAGAAGTCCTCGACATGGC
GAGCTGTACTCTCACCGGAGAGATTCCGACAACACTAAGT
AATCTAAAACATTTGCACACTTTGTTTCTCCACATCAACA
ACTTAACCGGAAACATCCCACCCGAACTCTCCGGTTTAAT
CAGCTTAAAATCTCTAGACCTCTCAATAAACCAGCTAACC
GGAGAGATTCCTCAGAGCTTCATCTCCCTAGGGAACATCA
CTCTCATCAACCTCTTCCGAAACAATCTCCACGGGCCGAT
ACCGGACTTCATCGGAGACATGCCGAACCTCCAAGTCCTC
CAGGTGTGGGAGAACAACTTCACGCTAGAGCTACCGGCGA
ATCTCGGCCGGAACGGGAATCTGAAAAAGCTCGACGTCTC
TGATAACCATCTCACCGGACTCATCCCCATGGATTTGTGC
AGAGGCGGGAAGCTGGAGACGCTGGTGCTCTCCAACAACT
TCTTCTTCGGCTCGATCCCTGAGAAGCTAGGTCAATGCAA
ATCGCTAAACAAGATCAGAATCGTCAAGAATCTCCTCAAC
GGCACGGTTCCGGAGGGCTTATTCAATCTACCGCTCGTAA
CGATCATCGAGCTCACCGATAACTTCTTCTCCGGGGAGCT
TCCGGGGGAGATGTCAGGCGACGTTCTCGATCATATCTAC
TTATCTAACAATTGGTTTACCGGTTTAATCCCCCCGGCTA
TCGGTAATTTTAAAAATCTACAGGATTTATTCTTAGACCG
GAACCGGTTTAGCGGGAATATTCCGAGAGAAGTTTTCGAG
TTGAAGCATCTAACGAAGATCAACACGAGTGCTAACAACC
TAACCGGCGATATCCCTGACTCAATCTCACGTTGCACTTC
CTTAATCTCCGTCGATCTCAGCCGTAACCGAATCGGCGGA
GATATCCCTAAAGACATCCACGATGTGATCAATCTCGGAA
CTCTAAATCTCTCCGGGAATCAACTCACCGGCTCGATCCC
```

-continued

GATCGGAATCGGGAAGATGACGAACTTAACCACTCTGGAT

CTCTCCTTCAACGACCTCTCCGGGAGAGTCCCACTCGGCG

GCCAGTTCCTAGTCTTCAACGACACTTCCTTCGCCGGAAA

CCCTTACCTCTGCCTCCCTCACCACGTCTCGTGCCTTACG

CGTCCGGAACAAACCTCCGATCGTATCCACACGGCTCTCT

TCTCTCCGTCGAGGATCGTTATCACGATCGTCGCGGCGAT

AACGGCGTTGATCCTCATCAGCGTCGCGATTCGTCAGATG

AACAAGAAGAAACACGAGAGGTCTCTCTCGTGGAAGCTAA

CCGCCTTCCAAAGACTCGATTTCAAAGCGGAAGACGTCCT

CGAGTGTCTCCAGGAAGAGAACATAATCGGCAAAGGCGGA

GCTGGGATCGTCTACCGCGGATCCATGCCGAACAACGTAG

ACGTCGCGATCAAACGGTTAGTAGGACGCGGAACAGGGAG

GAGCGATCACGGATTCACGGCGGAGATACAAACTCTAGGG

AGAATCCGCCACCGTCATATAGTGAGACTCCTCGGATACG

TGGCGAACAAGGACACGAACCTGCTTCTCTACGAGTACAT

GCCTAACGGGAGCCTCGGGGAGCTTTTGCACGGATCTAAA

GGAGGTCATCTTCAGTGGGAGACGAGGCACAGAGTAGCCG

TGGAAGCGGCGAAAGGACTGTGTTATCTTCATCATGACTG

TTCGCCGTTGATCTTGCATAGAGACGTTAAGTCCAATAAC

ATACTACTGGACTCTGATTTTGAGGCCCATGTTGCTGATT

TTGGGCTTGCTAAGTTCTTAGTGGACGGTGCTGCTTCTGA

GTGTATGTCTTCGATAGCTGGCTCCTATGGATACATCGCT

CCAGAGTATGCTTACACTCTCAAAGTGGACGAGAAGAGTG

ATGTGTATAGTTTCGGAGTGGTGTTATTGGAACTGATAGC

TGGGAAGAAACCGGTTGGTGAGTTTGGGGAAGGAGTGGAT

ATAGTGAGGTGGGTGAGGAACACGGAGGGTGAGATACCTC

AGCCGTCGGATGCAGCTACTGTTGTGGCGATCGTTGACCA

GAGGTTGACTGGTTACCCGTTGACTAGTGTGATTCACGTG

TTCAAGATAGCGATGATGTGTGTGGAGGATGAGGCAGCGA

CAAGGCCGACGATGAGGGAAGTTGTGCACATGCTCACTAA

CCCTCCCAAGTCCGTCACTAACTTGATCGCCTTCTGAMRL

LKTHLLFLHLHYVISISLLCFSPCLASTDMDHLLNLKSSM

IGPNGNGLHDWVHSPSPTAHCSFSGVSCDGDARVISLNVS

FTPLFGTISPEIGMLNRLVNLTLAANNFSGMLPLEMKSLT

SLKVLNISNNVNLNGTFPGEILTPMVDLEVLDAYNNNFTG

PLPPEIPGLKKLRHLSLGGNFLTGEIPESYGDIQSLEYLG

LNGAGLSGESPAFLSRLKNLKEMYVGYFNSYTGGVPPEFG

ELTNLEVLDMASCTLTGEIPTTLSNLKHLHTLFLHINNLT

GNIPPELSGLISLKSLDLSINQLTGEIPQSFISLGNITLI

NLFRNNLHGPIPDFIGDMPNLQVLQVWENNFTLELPANLG

RNGNLKKLDVSDNHLTGLIPMDLCRGGKLETLVLSNNFFF

-continued

GSIPEKLGQCKSLNKIRIVKNLLNGTVPEGLFNLPLVTII

ELTDNFFSGELPGEMSGDVLDHIYLSNNWFTGLIPPAIGN

FKNLQDLFLDRNRFSGNIPREVFELKHLTKINTSANNLTG

DIPDSISRCTSLISVDLSRNRIGGDIPKDIHDVINLGTLN

LSGNQLTGSIPIGIGKMTNLTTLDLSFNDLSGRVPLGGQF

LVFNDTSFAGNPYLCLPHHVSCLTRPEQTSDRIHTALFSP

SRIVITIVAAITALILISVAIRQMNKKKHERSLSWKLTAF

QRLDFKAEDVLECLQEENIIGKGGAGIVYRGSMPNNVDVA

IKRLVGRGTGRSDHGFTAEIQTLGRIRHRHIVRLLGYVAN

KDTNLLLYEYMPNGSLGELLHGSKGGHLQWETRHRVAVEA

AKGLCYLHHDCSPLILHRDVKSNNILLDSDFEAHVADFGL

AKFLVDGAASECMSSIAGSYGYIAPEYAYTLKVDEKSDVY

SFGVVLLELIAGKKPVGEFGEGVDIVRWVRNTEGEIPQPS

DAATVVAIVDQRLTGYPLTSVIHVFKIAMMCVEDEAATRP

TMREVVHMLTNPPKSVTNLIAF

SEQ ID NOS: 5 and 6 are exemplary CLV1a coding and protein sequences from *B. napus*. S562 can be mutated to N (i.e., is equivalent to S582N provided herein).

SEQ ID NOS: 7 and 8 are exemplary CLV1b coding and protein sequences from *B. napus*. S584 can be mutated to N (i.e., is equivalent to S582N provided herein).

SEQ ID NOS: 9 and 10 are exemplary CLV1 coding and protein sequences from *B. oleracea*. S584 can be mutated to N (i.e., is equivalent to S582N provided herein).

SEQ ID NOS: 11 and 12 are exemplary CLV1a coding and protein sequences from *C. sativa*. S589 can be mutated to N (i.e., is equivalent to S582N provided herein).

SEQ ID NOS: 13 and 14 are exemplary CLV1b coding and protein sequences from *C. sativa*. S590 can be mutated to N (i.e., is equivalent to S582N provided herein).

SEQ ID NOS: 15 and 16 are exemplary CLV1c coding and protein sequences from *C. sativa*. S857 can be mutated to N (i.e., is equivalent to S582N provided herein).

SEQ ID NOS: 17 and 18 are exemplary CLV1 coding and protein sequences from *T. arvense*. S586 can be mutated to N (i.e., is equivalent to S582N provided herein).

SEQ ID NO: 19 is a fragment of the CLV1a protein (aa 529-593) from *B. napus*.

SEQ ID NO: 20 is a fragment of the CLV1b protein (aa 551-615) from *B. napus*.

SEQ ID NO: 21 is a fragment of the CLV1 protein (aa 551-615) from *B. oleracea*.

SEQ ID NO: 22 is a fragment of the CLV1a (aa 556-620), CLV1b (aa 557-621), and CLV1c (aa 824-888) proteins from *C. sativa*.

SEQ ID NO: 23 is a fragment of the CLV1 protein (aa 553-617) from *T. arvense*.

SEQ ID NO: 24 is a fragment of the CLV1 protein (aa 549-613) from *B. rapa*.

SEQ ID NO: 25 is an exemplary CLV1 protein from *M. domestica* (MDP0000392374). S541 is equivalent to S582 of SEQ ID NO: 2, and can be mutated to N (i.e., is equivalent to S582N provided herein).

SEQ ID NO: 26 is fragment of an CLV1 protein (aa 515-570) from *M. domestica*.

SEQ ID NO: 27 is an exemplary CLV1 protein from *M. domestica* (MDP0000523939). S571 is equivalent to S582 of SEQ ID NO: 2, and can be mutated to N (i.e., is equivalent to S582N provided herein).

SEQ ID NO: 28 is fragment of an CLV1 protein (aa 545-600) from *M. domestica.*

SEQ ID NO: 29 is an exemplary CLV1 protein from *M. domestica* (MDP0000618819). S570 is equivalent to S582 of SEQ ID NO: 2, and can be mutated to N (i.e., is equivalent to S582N provided herein).

SEQ ID NO: 30 is fragment of an CLV1 protein (aa 544-599) from *M. domestica.*

SEQ ID NO: 31 is an exemplary CLV1 protein from *M. domestica* (MDP0000804361). S575 is equivalent to S582 of SEQ ID NO: 2, and can be mutated to N (i.e., is equivalent to S582N provided herein).

SEQ ID NO: 32 is fragment of an CLV1 protein (aa 549-604) from *M. domestica.*

SEQ ID NO: 33 is an exemplary CLV1 protein from *M. domestica* (MDP0000804929). S575 is equivalent to S582 of SEQ ID NO: 2, and can be mutated to N (i.e., is equivalent to S582N provided herein).

SEQ ID NO: 34 is fragment of an CLV1 protein (aa 549-604) from *M. domestica.*

SEQ ID NO: 35 is an exemplary CLV1 protein from *M. domestica* (MDP0000897253). S575 is equivalent to S582 of SEQ ID NO: 2, and can be mutated to N (i.e., is equivalent to S582N provided herein).

SEQ ID NO: 36 is fragment of an CLV1 protein (aa 549-604) from *M. domestica.*

SEQ ID NO: 37 is an exemplary CLV1 protein from *Prunus persica* (Prupe.1G363300). S578 is equivalent to S582 of SEQ ID NO: 2, and can be mutated to N (i.e., is equivalent to S582N provided herein).

SEQ ID NO: 38 is fragment of an CLV1 protein (aa 552-607) from *Prunus persica.*

SEQ ID NO: 39 is an exemplary CLV1 protein from *Prunus persica* (Prupe.6G163000). S580 is equivalent to S582 of SEQ ID NO: 2, and can be mutated to N (i.e., is equivalent to S582N provided herein).

SEQ ID NO: 40 is fragment of an CLV1 protein (aa 554-607) from *Prunus persica.*

SEQ ID NO: 41 is an exemplary CLV1 protein from *Prunus persica* (Prupe.6G212200). S570 is equivalent to S582 of SEQ ID NO: 2, and can be mutated to N (i.e., is equivalent to S582N provided herein).

SEQ ID NO: 42 is fragment of an CLV1 protein (aa 544-599) from *Prunus persica.*

SEQ ID NO: 43 is an exemplary CLV1 protein from *Citrus sinensis* (orange1.1g001816m.g). S568 is equivalent to S582 of SEQ ID NO: 2, and can be mutated to N (i.e., is equivalent to S582N provided herein).

SEQ ID NO: 44 is fragment of an CLV1 protein (aa 542-597) from *Citrus sinensis.*

SEQ ID NO: 45 is an exemplary CLV1 protein from *Citrus sinensis* (orange1.1g001922m.g). S575 is equivalent to S582 of SEQ ID NO: 2, and can be mutated to N (i.e., is equivalent to S582N provided herein).

SEQ ID NO: 46 is fragment of an CLV1 protein (aa 549-604) from *Citrus sinensis.*

SEQ ID NO: 47 is an exemplary CLV1 protein from *Citrus sinensis* (orange1.1g002010m.g). S577 is equivalent to S582 of SEQ ID NO: 2, and can be mutated to N (i.e., is equivalent to S582N provided herein).

SEQ ID NO: 48 is fragment of an CLV1 protein (aa 551-606) from *Citrus sinensis.*

SEQ ID NO: 49 is an exemplary CLV1 protein from *Ananas comosus* (Aco030123). S592 is equivalent to S582 of SEQ ID NO: 2, and can be mutated to N (i.e., is equivalent to S582N provided herein).

SEQ ID NO: 50 is fragment of an CLV1 protein (aa 566-621) from *Ananas comosus.*

SEQ ID NO: 51 is an exemplary CLV1 protein from *Solanum lycopersicum* (Solyc01g103530.2). S570 is equivalent to S582 of SEQ ID NO: 2, and can be mutated to N (i.e., is equivalent to S582N provided herein).

SEQ ID NO: 52 is fragment of an CLV1 protein (aa 544-599) from *Solanum lycopersicum.*

SEQ ID NO: 53 is an exemplary CLV1 protein from *Solanum lycopersicum* (Solyc02g091840.2). S572 is equivalent to S582 of SEQ ID NO: 2, and can be mutated to N (i.e., is equivalent to S582N provided herein).

SEQ ID NO: 54 is fragment of an CLV1 protein (aa 546-601) from *Solanum lycopersicum.*

SEQ ID NO: 55 is an exemplary CLV1 protein from *Glycine max* (Glyma.01G197800). S573 is equivalent to S582 of SEQ ID NO: 2, and can be mutated to N (i.e., is equivalent to S582N provided herein).

SEQ ID NO: 56 is fragment of an CLV1 protein (aa 547-602) from *Glycine max.*

SEQ ID NO: 57 is an exemplary CLV1 protein from *Glycine max* (Glyma.05G110400). S568 is equivalent to S582 of SEQ ID NO: 2, and can be mutated to N (i.e., is equivalent to S582N provided herein).

SEQ ID NO: 58 is fragment of an CLV1 protein (aa 542-597) from *Glycine max.*

SEQ ID NO: 59 is an exemplary CLV1 protein from *Glycine max* (Glyma.11G043800). S573 is equivalent to S582 of SEQ ID NO: 2, and can be mutated to N (i.e., is equivalent to S582N provided herein).

SEQ ID NO: 60 is fragment of an CLV1 protein (aa 547-602) from *Glycine max.*

SEQ ID NO: 61 is an exemplary CLV1 protein from *Glycine max* (Glyma.11G114100). S579 is equivalent to S582 of SEQ ID NO: 2, and can be mutated to N (i.e., is equivalent to S582N provided herein).

SEQ ID NO: 62 is fragment of an CLV1 protein (aa 553-608) from *Glycine max.*

SEQ ID NO: 63 is an exemplary CLV1 protein from *Glycine max* (Glyma.12G040000). S579 is equivalent to S582 of SEQ ID NO: 2, and can be mutated to N (i.e., is equivalent to S582N provided herein).

SEQ ID NO: 64 is fragment of an CLV1 protein (aa 553-608) from *Glycine max.*

SEQ ID NO: 65 is an exemplary CLV1 protein from *Glycine max* (Glyma.17G156300). S568 is equivalent to S582 of SEQ ID NO: 2, and can be mutated to N (i.e., is equivalent to S582N provided herein).

SEQ ID NO: 66 is fragment of an CLV1 protein (aa 542-597) from *Glycine max.*

SEQ ID NO: 67 is an exemplary CLV1 protein from *Phaseolus vulgaris* (Phvul.003G231400). S575 is equivalent to S582 of SEQ ID NO: 2, and can be mutated to N (i.e., is equivalent to S582N provided herein).

SEQ ID NO: 68 is fragment of an CLV1 protein (aa 549-604) from *Phaseolus vulgaris.*

SEQ ID NO: 69 is an exemplary CLV1 protein from *Phaseolus vulgaris* (Phvul.003G231400). S596 is equivalent to S582 of SEQ ID NO: 2, and can be mutated to N (i.e., is equivalent to S582N provided herein).

SEQ ID NO: 70 is fragment of an CLV1 protein (aa 570-625) from *Phaseolus vulgaris.*

SEQ ID NO: 71 is an exemplary CLV1 protein from *Cucumis sativus* (Cucsa.103590). S574 is equivalent to S582 of SEQ ID NO: 12, and can be mutated to N (i.e., is equivalent to S582N provided herein)

SEQ ID NO: 72 is fragment of an CLV1 protein (aa 548-603) from *Cucumis sativus.*

SEQ ID NO: 73 is an exemplary CLV1 protein from *Cucumis sativus* (Cucsa.343120). S581 is equivalent to S582 of SEQ ID NO: 2, and can be mutated to N (i.e., is equivalent to S582N provided herein).

SEQ ID NO: 74 is fragment of an CLV1 protein (aa 548-603) from *Cucumis sativus.*

SEQ ID NO: 75 is an exemplary CLV1 protein from *Theobroma cacao* (Thecc1EG000890). S573 is equivalent to S582 of SEQ ID NO: 2, and can be mutated to N (i.e., is equivalent to S582N provided herein).

SEQ ID NO: 76 is fragment of an CLV1 protein (aa 547-602) from *Theobroma cacao.*

SEQ ID NO: 77 is an exemplary CLV1 protein from *Theobroma cacao* (Thecc1EG034252). S577 is equivalent to S582 of SEQ ID NO: 2, and can be mutated to N (i.e., is equivalent to S582N provided herein)

SEQ ID NO: 78 is fragment of an CLV1 protein (aa 551-606) from *Theobroma cacao.*

SEQ ID NO: 79 is an exemplary CLV1 protein from *Zea mays* (GRMZM2G072569). S574 is equivalent to S582 of SEQ ID NO: 2, and can be mutated to N (i.e., is equivalent to S582N provided herein).

SEQ ID NO: 80 is fragment of an CLV1 protein (aa 548-603) from *Zea mays.*

SEQ ID NO: 81 is an exemplary CLV1 protein from *Zea mays* (GRMZM2G141517). S581 is equivalent to S582 of SEQ ID NO: 2, and can be mutated to N (i.e., is equivalent to S582N provided herein).

SEQ ID NO: 82 is fragment of an CLV1 protein (aa 555-610) from *Zea mays.*

SEQ ID NO: 83 is an exemplary CLV1 protein from *Zea mays* (GRMZM2G300133). S588 is equivalent to S582 of SEQ ID NO: 2, and can be mutated to N (i.e., is equivalent to S582N provided herein).

SEQ ID NO: 84 is fragment of an CLV1 protein (aa 562-617) from *Zea mays.*

SEQ ID NO: 85 is an exemplary CLV1 protein from *Oryza sativa* (LOC_Os03g12730). S571 is equivalent to S582 of SEQ ID NO: 2, and can be mutated to N (i.e., is equivalent to S582N provided herein).

SEQ ID NO: 86 is fragment of an CLV1 protein (aa 545-600) from *Oryza sativa.*

SEQ ID NO: 87 is an exemplary CLV1 protein from *Oryza sativa* (LOC_Os03g56270). S578 is equivalent to S582 of SEQ ID NO: 2, and can be mutated to N (i.e., is equivalent to S582N provided herein).

SEQ ID NO: 88 is fragment of an CLV1 protein (aa 567-607) from *Oryza sativa.*

SEQ ID NO: 89 is an exemplary CLV1 protein from *Oryza sativa* (LOC_Os06g50340). S581 is equivalent to S582 of SEQ ID NO: 2, and can be mutated to N (i.e., is equivalent to S582N provided herein).

SEQ ID NO: 90 is fragment of an CLV1 protein (aa 556-610) from *Oryza sativa.*

SEQ ID NO: 91 is an exemplary CLV1 protein from *Oryza sativa* (LOC_Os07g04190). S577 is equivalent to S582 of SEQ ID NO: 2, and can be mutated to N (i.e., is equivalent to S582N provided herein).

SEQ ID NO: 92 is fragment of an CLV1 protein (aa 551-606) from *Oryza sativa.*

SEQ ID NO: 93 is an exemplary CLV1 protein from *Sorghum bicolor* (Sobic.001G074000). S580 is equivalent to S582 of SEQ ID NO: 2, and can be mutated to N (i.e., is equivalent to S582N provided herein).

SEQ ID NO: 94 is fragment of an CLV1 protein (aa 554-609) from *Sorghum bicolor.*

SEQ ID NO: 95 is an exemplary CLV1 protein from *Sorghum bicolor* (Sobic.001G446400). S565 is equivalent to S582 of SEQ ID NO: 2, and can be mutated to N (i.e., is equivalent to S582N provided herein).

SEQ ID NO: 96 is fragment of an CLV1 protein (aa 539-594) from *Sorghum bicolor.*

SEQ ID NO: 97 is an exemplary CLV1 protein from *Sorghum bicolor* (Sobic.002G027600). S579 is equivalent to S582 of SEQ ID NO: 2, and can be mutated to N (i.e., is equivalent to S582N provided herein).

SEQ ID NO: 98 is fragment of an CLV1 protein (aa 553-608) from *Sorghum bicolor.*

SEQ ID NO: 99 is an exemplary CLV1 protein from *Sorghum bicolor* (Sobic.010G267700). S589 is equivalent to S582 of SEQ ID NO: 2, and can be mutated to N (i.e., is equivalent to S582N provided herein).

SEQ ID NO: 100 is fragment of an CLV1 protein (aa 563-618) from *Sorghum bicolor.*

SEQ ID NO: 101 is fragment of an CLV1 protein (aa 556-611) from *B. rapa.*

SEQ ID NOS: 102 and 103 are plasmid sequences used to express CLV1 S582N in *A. thaliana*. The T-DNA is from nt 11,693-9,207 (i.e., nt 11,693-11,743+1-9,207). The CLV1 cassette is nt 11-7,672.

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All GenBank® Accession numbers cited herein are incorporated by reference in their entirety for the sequence available on Feb. 22, 2021.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Allele: refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

Backcross: The mating of a hybrid to one of its parents. For example hybrid progeny, for example a first generation hybrid (FA can be crossed back one or more times to one of its parents. Backcrossing can be used to introduce one or more single locus conversions (such as one or more desirable traits) from one genetic background into another.

Biomass: Organic matter derived from an organism, such as a plant or part thereof. In some examples, biomass refers to all the above ground plant material at a particular point of time, thus including the leaves, stems and may include flowers (at varying stages of development given the flowering period ranges over a period of time). Biomass can include all vegetative and reproductive material produced by the plant at time of harvest.

Brassicaceae: A family of flowering plants commonly known as mustards, crucifers, or cabbage. The family contains the cruciferous vegetables, including species such as *Brassica oleracea* (e.g., broccoli, cabbage, cauliflower, kale, brussels sprouts, collards), *Brassica rapa* (turnip, Chinese cabbage, rutabaga, bok choy, etc.), *Brassica napus* (rapeseed, etc.), *Raphanus sativus* (common radish), *Armoracia rusticana* (horseradish), Matthiola and *Arabidopsis thaliana* (thale cress). Includes members of the *Brassica, Draba, Erysimum, Lepidium, Cardamine*, and *Alyssum* genera. Other specific examples include canola, penny-cress, and camelina.

Cas9: An RNA-guided DNA endonuclease enzyme that can cut DNA. Cas9 has two active cutting sites (HNH and RuvC), one for each strand of a double helix. Catalytically inactive (deactivated) Cas9 (dCas9) is also encompassed by this disclosure. In some examples, a dCas9 includes one or more of the following point mutations: D10A, H840A, and N863A.

Cas9 nucleic acid and protein sequences are publicly available. For example, GenBank® Accession Nos. nucleotides 796693 . . . 800799 of CP012045.1 and nucleotides 1100046 . . . 1104152 of CP014139.1 disclose Cas9 nucleic acids, and GenBank® Accession Nos. AMA70685.1 and AKP81606.1 disclose Cas9 proteins. In some examples, the Cas9 is a deactivated form of Cas9 (dCas9), such as one that is nuclease deficient (e.g., those shown in GenBank® Accession Nos. AKA60242.1 and KR011748.1). In certain examples, Cas9 has at least 80% sequence identity, for example at least 85%, at least 90%, at least 95%, at least 96%, at least 97%, at least 98%, or at least 99% sequence identity to such sequences, and retains the ability to cut DNA.

Cell. Cell as used herein includes a plant cell, whether isolated, in tissue culture or incorporated in a plant or plant part.

Clavata 1 (CLV1): A receptor kinase with an extracellular leucine-rich domain. Controls shoot and floral meristem size, and contributes to establish and maintain floral meristem identity. Negatively regulated by KAPP (kinase-associated protein phosphatase). CLV3 peptide binds directly CLV1 ectodomain.

Figure 5A:
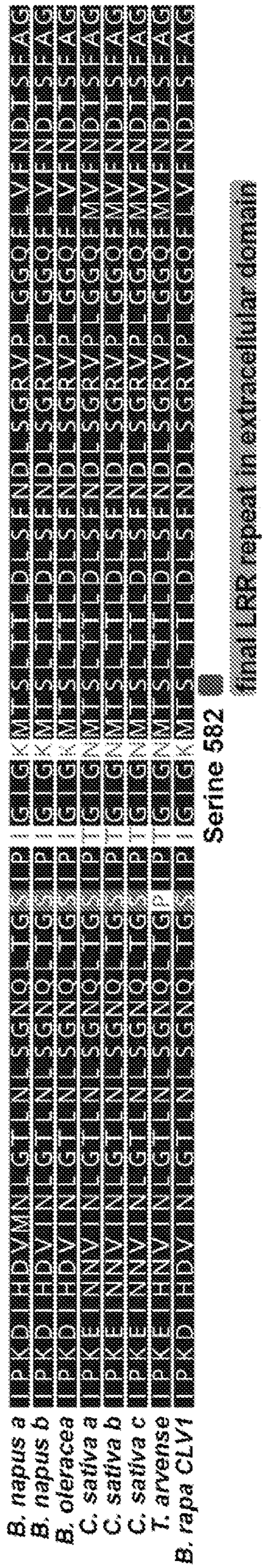
FIGS. 5A and 5B show alignments for several CLV1 proteins (including homologs of SEQ ID NO: 1). Using this information, one skilled in the art can make equivalent S582N substitution in any CLV1 protein (or make an appropriate mutation to the coding sequence). (A) Alignment of Brassicaceae CLV1 proteins from *B. napus* (SEQ ID NOS: 19 and 20), *B. oleracea* (SEQ ID NO: 21), *C. sativa* (SEQ ID NO: 22), *T. arvense* (SEQ ID NO: 23), and *B. rapa* (SEQ ID NO: 24); (B) Alignment of several CLV1 sequences from flowering plants, including important crops, showing Serine 582 is highly conserved. Apple (SEQ ID NOS: 26, 28, 30, 32, 34, 36), peach (SEQ ID NOS: 38, 40, 42), orange (SEQ ID NOS: 44, 46, 48), banana (SEQ ID NO: 50), tomato (SEQ ID NOS: 52, 54), soybean (SEQ ID NOS: 56, 58, 60, 62, 64, 66), bean (SEQ ID NOS: 68, 70), cucumber (SEQ ID NOS: 72, 74), chocolate (SEQ ID NOS: 76, 78), corn (SEQ ID NOS: 80, 82, 84), rice (SEQ ID NOS: 86, 88, 90, 92), sorghum (SEQ ID NOS: 94, 96, 98, 100), and *B. rapa* (SEQ ID NO: 101).
Figure 5B:
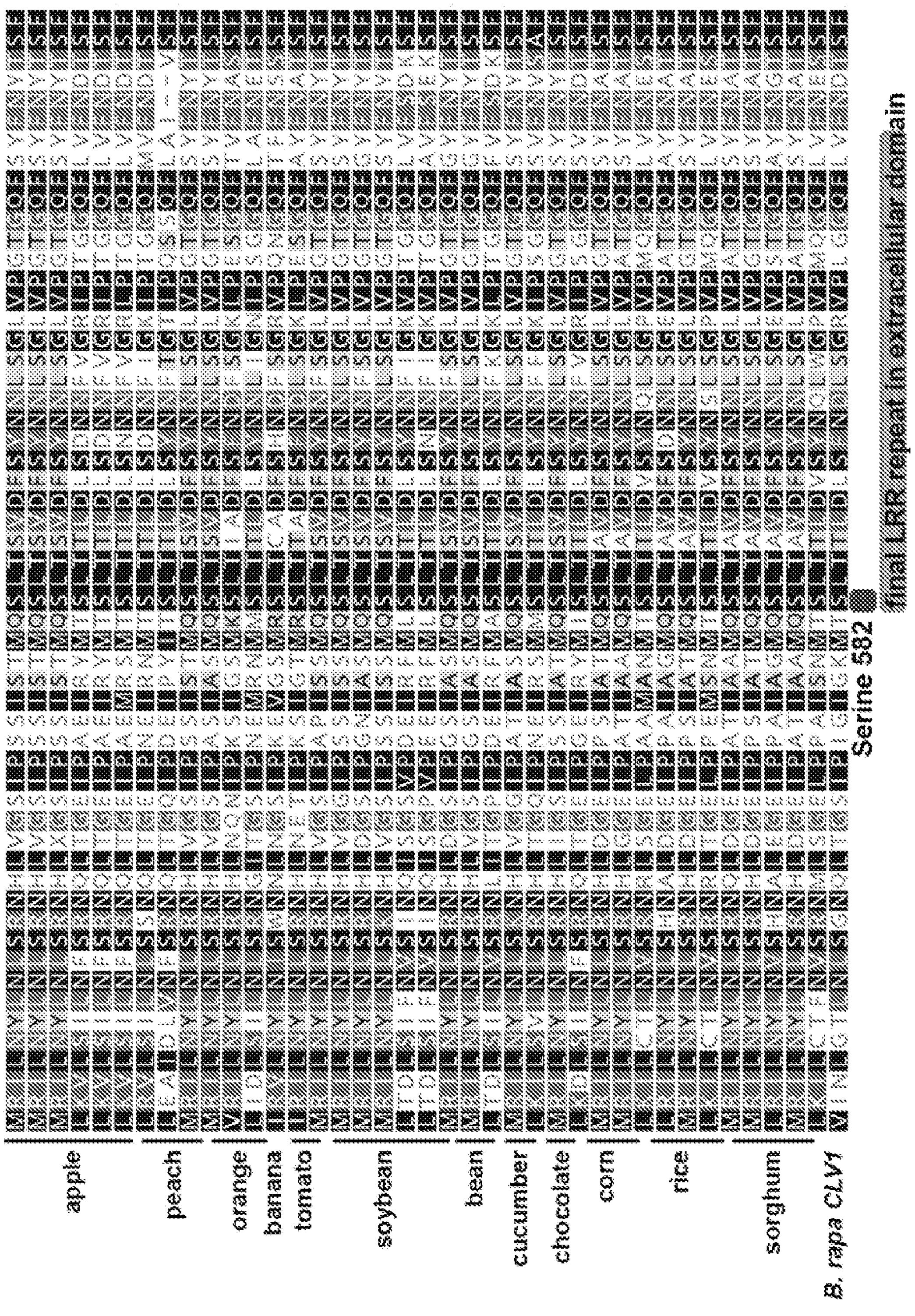
Figure 6B:
FIGS. 6A-6D show the phenotype of a mutant CLV1 protein containing an S582N substitution. This mutation causes multilocularity and increased organ number and seed production. (A) Top, dried siliques from WT and a CLV1 S582N mutant (sup-c). Locule edges are marked with dots. Bottom, quantification of locule number in 10 siliques. nrpd1 has no impact on locule number, while sup-c plants have elevated number of locules. (B) Digital image showing sup-c mutants (CLV1 S582N mutants) have increased numbers of petals and stamens. (C) Digital image showing sup-c mutants (CLV1 S582N mutants) have a moderately reduced plant height. (D) Bar graph showing increased seed production in the sup-c mutants (CLV1 S582N mutants) is independent from loss of RdDM. This result was generated from an F2 mapping population, not grown specifically for seed quantification. The difference between genotypes is significant.
Figure 6A:
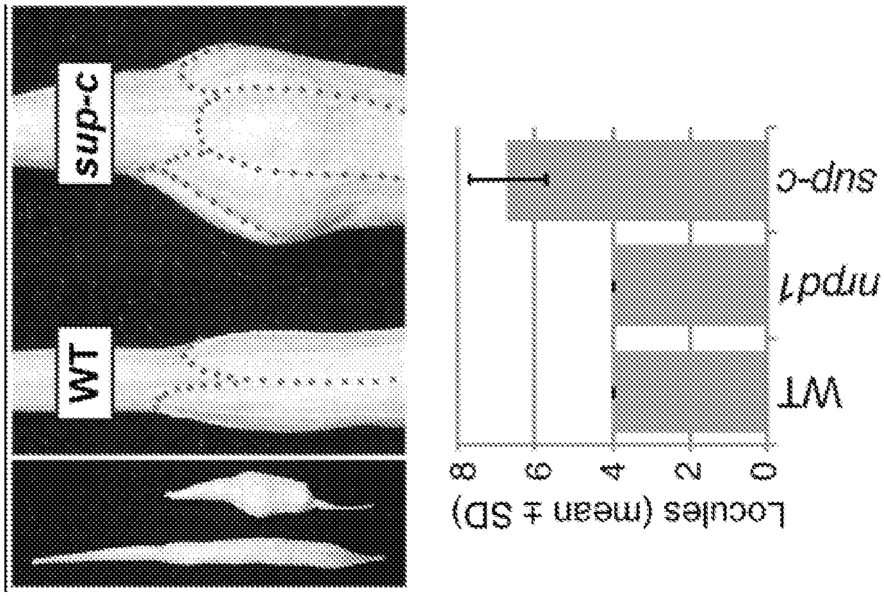
Figure 6D:
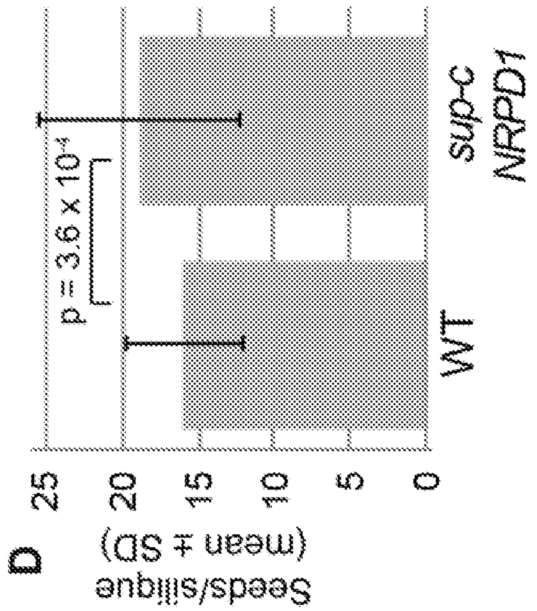
Figure 6C:
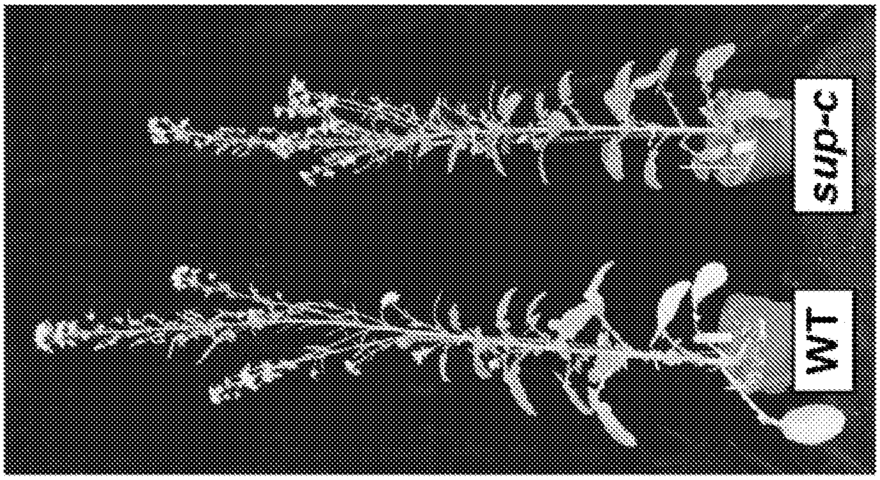

It is shown herein that introduction of a S582N substitution (or its equivalent, e.g., a Ser to Asn substitution in the sequence SLT located between aa 500 and 900 of a native CLV1 sequence, such as between about aa 540 and 600 or about aa 540 to 860, see for example FIGS. 5A, 5B) in CLV1 can increase the number of locules and/or seed production in a plant.

Native CLV1 sequences are publicly available. For example, GenBank® Accession Nos: CACSHJ010000087.1 and CAA0336861.1 disclose native *Arabidopsis thaliana* CLV1 nucleic acid and protein sequences, respectively. One skilled in the art will appreciate that these and other native CLV1 sequences can be mutated to include a coding sequence that results in a S582N substitution (or equivalent, which can be determined using sequence alignments, e.g., see FIGS. 5A, 5B). For example, S582 of SEQ ID NO: 2 is equivalent to S577 of GenBank CAA0336861.1, S562 of SEQ ID NO: 6, S584 of SEQ ID NOs: 8 and 10, S589 of SEQ ID NO: 12 and 99, S590 of SEQ ID NO; 14, S857 of SEQ ID NO: 16, S586 of SEQ ID NO: 18, S541 of SEQ ID NO: 25, S571 of SEQ ID NO: 27 and 85, S570 of SEQ ID NO: 29, 41, and 51, S575 of SEQ ID NO: 31, 33, 35, 45, and 67, S578 of SEQ ID NO: 37 and 87, S580 of SEQ ID NO: 39 and 93, S568 of SEQ ID NO: 43, 57, and 65, S577 of SEQ ID NO: 47, 77 and 91, S592 of SEQ ID NO: 49, S572 of SEQ ID NO: 53, S573 of SEQ ID NO: 55, 59 and 75, S579 of SEQ ID NO: 61, 63 and 97, S596 of SEQ ID NO: 69, S574 of SEQ ID NO: 71 and 79, S581 of SEQ ID NO: 73, 81 and 89, S588 of SEQ ID NO: 83 and S565 of SEQ ID NO: 95.

An exemplary CLV1 protein sequence from *B. rapa* is shown in SEQ ID NO: 2, and a mutant CLV1 S582N sequence in SEQ ID NO: 4. The disclosure thus provides CLV1 proteins having at least 80%, at least 85%, at least 90%, at least 95%, at least 96%, at least 97%, at least 98%, at least 99%, or 100% sequence identity to SEQ ID NO: 3 or 4, which include a S582N mutation (or its equivalent, e.g., a Ser to Asn substitution in the sequence SLT located between aa 500 and 900 of a native CLV1 sequence, such as between about aa 540 and 600 or about aa 540 to 860, see for example FIGS. 5A, 5B). An exemplary CLV1 coding sequence from *B. rapa* is shown in SEQ ID NO: 1, and SEQ ID NO: 3 provides a coding sequence with a mutation at nt 1745 that results in an S582N substitution. The disclosure thus provides CLV1 encoding nucleic acid molecules, including genomic DNA and cDNA having at least 80%, at least 85%, at least 90%, at least 95%, at least 96%, at least 97%, at least 98%, at least 99%, or 100% sequence identity to SEQ ID NO: 1 or 3 which include a mutation at codon 582 (or its equivalent) that encodes an N amino acid.

Complementarity: The ability of a nucleic acid to form hydrogen bond(s) with another nucleic acid sequence by either traditional Watson-Crick base pairing or other nontraditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

CRISPRs (Clustered Regularly InterSpaced Short Palindromic Repeats): A family of DNA sequences found in the genome of prokaryotic systems, including many bacteria and archaea. These sequences are derived from DNA fragments of bacteriophages that had previously infected the prokaryote. They are used to detect and destroy DNA from similar bacteriophages during subsequent infections. CRISPRs are often associated with cas genes that code for proteins related to CRISPRs (such as Cas9 and Cas13d proteins; exemplary Cas13d proteins can be found in WO 2019/040664). Non-limiting examples of Cas nucleases include Cas1, Cas1B, Cas2, Cas3, Cas4, Cas5, Cas6, Cas7, Cas8, Cas9 (also known as Csn1 and Csx12), Cas10, Cas13d, Cpf1, C2c3, C2c2 and C2c1Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, Csx10, Csx16, CsaX, Csx3, Csx1, Csx15, Csf1, Csf2, Csf3, and Csf4.

CRISPR/Cas nuclease editing systems can be used for nucleic acid targeting, for example to detect a target DNA or RNA, modify a target DNA or RNA at any desired location, or cut the target DNA or RNA at any desired location. Thus, such methods can be used to modify a native CLV sequence, for example by introducing a S582N mutation (or its equivalent, e.g., a Ser to Asn substitution in the sequence SLT located between aa 500 and 900 of a native CLV1 sequence, such as between about aa 540 and 600 or about aa 540 to 860, see for example FIGS. 5A, 5B).

By delivering a Cas9 protein and appropriate guide RNAs into a cell, the organism's genome can be cut at any desired location (such as a plant CLV1 gene). In some examples a CRISPR/Cas9 system is used to introduce a DNA CLV1 S582N mutation (or its equivalent, e.g., a Ser to Asn substitution in the sequence SLT located between aa 500 and 900 of a native CLV1 sequence, such as between about aa 540 and 600 or about aa 540 to 860, see for example FIGS. 5A, 5B) into a plant or plant cell. In another example, a CRISPR/Cas13d system is used to introduce an RNA CLV1 S582N mutation (or its equivalent, e.g., a Ser to Asn substitution in the sequence SLT located between aa 500 and 900 of a native CLV1 sequence, such as between about aa 540 and 600 or about aa 540 to 860, see for example FIGS. 5A, 5B) into a plant or plant cell.

Cross. Synonymous with hybridize or crossbreed. Includes the mating of genetically different individual plants, such as the mating of two parent plants.

Cross-pollination: Fertilization by the union of two gametes from different plants.

Endogenous: With reference to a nucleic acid and/or protein refers to the nucleic acid and/or protein in question as found in a plant in its natural form (i.e., without any human intervention).

Exogenous: As used herein with reference to nucleic acid molecule, protein, vector, or cell, refers to any such molecule/cell that does not originate from that particular cell or plant as found in nature. Thus, a non-naturally-occurring nucleic acid or vector is exogenous to a cell once introduced into the cell. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. A mutant plant/plant part/cell provided herein in some examples includes an exogenous nucleic acid encoding for a CLV1 S582N mutation (or equivalent thereof).

$F_1$ hybrid: The first generation progeny of the cross of two stable parents that are nonisogenic or isogenic plants.

Gene editing: A type of gene modification in which a nucleic acid molecule, such as DNA, is inserted, deleted or replaced in a native genome of a cell (such as a plant cell) using engineered nucleases, which create site-specific double-strand breaks (DSBs) at desired locations in the genome, and resulting in a non-native genomic sequence. Thus, the resulting genome is one that does not occur in nature. In some examples, a gene editing results in the introduction of an exogenous transgene (e.g., one that does not occur naturally in the cell into which it is introduced) into the genome. Such edited plants, plant parts, and cells can be referred to as gene-edited plants, gene-edited plant parts, and gene-edited plant cells, respectively. The induced double-strand breaks are repaired through nonhomologous end-joining (NHEJ) or homologous recombination (HR), resulting in targeted mutations or repairs. CRISPR/Cas methods can be used to edit the sequence of one or more target genes, such as CLV1. In addition, other nucleases can be used to edit the sequence of one or more target genes, such as CLV1, such as TALEN nucleases, meganucleases, and zinc finger nucleases. In one example, homology directed repair methods are used to edit the sequence of one or more target genes, such as CLV1. For example, gene editing in a plant can be used to confer a desirable trait to the plant, such as increased locule number and/or seed production.

Genotype. The genetic constitution of a cell, an organism, or an individual (i.e., the specific allele makeup of the individual) usually with reference to a specific character under consideration.

Guide sequence: A polynucleotide sequence having sufficient complementarity with a target polynucleotide sequence to hybridize with the target sequence and direct sequence-specific binding of a Cas protein (such as Cas9) to the target sequence (such as CLV1). In some examples, the guide sequence is RNA. In some examples, the guide sequence is DNA. The guide nucleic acid can include modified bases or chemical modifications (e.g., see Latorre et al., *Angewandte Chemie* 55:3548-50, 2016). In some embodiments, the degree of complementarity between a guide sequence and its corresponding target sequence (e.g., a native CLV1 sequence), when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about, or at least, about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, a guide sequence is 15-25 nucleotides (such as 18-22 or 18 nucleotides).

The ability of a guide sequence to direct sequence-specific binding of a CRISPR complex to a target sequence may be assessed by a suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

Increase or Decrease: A statistically significant positive or negative change, respectively, in quantity from a control value. An increase is a positive change, such as an increase at least 10%, at least 20%, at least 25%, at least 30%, at least 40%, at least 50%, at least 60%, at least 70%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95% or no more than 99%. In some examples, the control value is a value or range of values expected for the same plant with a native CLV1 sequence, e.g., a wild-type plant (e.g., without an S582N substitution, e.g., SEQ ID NO: 1, 2, 6, 7, 8, 9, 10, 11, 12, 13, 14, 15, 16, 17, 18, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, or 99).

Isolated: An "isolated" biological component (such as a protein, nucleic acid, guide sequence, or cell) has been substantially separated, produced apart from, or purified away from other biological components in the cell or tissue of a plant in which the component occurs, such as other cells, chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Isolated nucleic acid molecules (such as guide nucleic acids or a vector comprising such), or cells containing such, in some examples are at least 50% pure, such as at least 75%, at least 80%, at least 90%, at least 95%, at least 98%, or at least 100% pure.

Non-naturally occurring or engineered: Terms used herein as interchangeably and indicate the involvement of the hand of man. The terms, when referring to nucleic acid molecules or polypeptides indicate that the nucleic acid molecule or the polypeptide is at least substantially free from at least one other component with which they are naturally associated in nature and as found in nature. In addition, the terms can indicate that the nucleic acid molecules or polypeptides have a sequence not found in nature.

Operably linked: A first nucleic acid sequence is operably linked with a second nucleic acid sequence when the first nucleic acid sequence is placed in a functional relationship with the second nucleic acid sequence. For instance, a promoter is operably linked to a nucleic acid sequence (such as a guide nucleic acid sequence) if the promoter affects the transcription or expression of the nucleic acid sequence. Generally, operably linked DNA sequences are contiguous and, where necessary to join two protein-coding regions, in the same reading frame.

Plant: Includes reference to an immature or mature whole plant, including a plant from which seed, roots, or leaves have been removed. Seed or embryo that will produce the plant is also considered to be the plant. The present disclosure also includes seeds produced by the plants provided herein, wherein the seeds can include a nucleic acid encoding a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B). In one embodiment, the seeds can develop into plants having increased locule number and/or seed production, as compared to a wild-type variety of the plant seed. As used herein, a "plant cell" includes, but is not limited to, a protoplast, gamete producing cell, and a cell that regenerates into a whole plant.

Any commercially or scientifically valuable plant can be used in accordance with this disclosure. Exemplary plants include plants belonging to the super family Viridiplantae, such as monocotyledonous and dicotyledonous plants including a fodder or forage legume, ornamental plant, food crop, tree, or shrub, such as *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lo tonus bainesli, Lotus* spp., *Macro tyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canadensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, switchgrass, Miscanthus, Setaria, fescue, eucalyptus, a tree, an ornamental plant, a perennial grass and a forage crop. In a specific example, the plant is a Brassicaceae plant, such as a *B. rapa, B. napus*, or *B. oleracea* plant. Other exemplary Brassicaceae are provided herein. In one example the plant is a flowering plant. In one example the plant is one listed in FIG. 5A or 5B.

Plant parts: Includes protoplasts, leaves, stems, roots, root tips, anthers, pistils, seed, embryo, pollen, stamen, ovule, microspore, protoplast, sporophyte, gametophyte, cotyledon, hypocotyl, flower, shoot, tissue, petiole, cells, meristematic cells and the like. Includes plant cells of a tissue culture from which plants can be regenerated. In one example a plant part is a plant cell.

Progeny: Offspring; descendants.

Promoter: An array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some examples, a promoter used for recombinant expression of a nucleic acid molecule is not naturally occurring in the cell into which it is introduced, is not native to the nucleic acid molecule to which it is attached, or both. In one example, a promoter used is not endogenous (i.e., is exogenous) to the plant in which it is introduced.

Recombinant or host cell: A cell that has been genetically altered, or is capable of being genetically altered by introduction of an exogenous polynucleotide, such as a recombinant plasmid or vector, such as one that expresses one or more exogenous nucleic acid molecules that encode a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B). Typically, a host cell is a cell in which a vector can be propagated and its nucleic acid expressed. In specific examples, such cells are plant cells, such as from a monocot or dicot. The term also includes any progeny of the subject host cell. It is understood that all progeny may not be identical to the parental cell since there may be mutations that occur during replication. However, such progeny are included when the term "host cell" is used.

Regeneration: The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Self-pollination: The transfer of pollen from the anther to the stigma of the same plant.

Sequence identity/similarity: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Variants of protein sequences known and disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. These sequence identity ranges are provided for guidance only; it is entirely possible that strongly significant homologs could be obtained that fall outside of the ranges provided.

Thus, in some examples, a native CLV1 protein has at least about 80%, at least 90%, at least 95%, at least 96%, at least 97%, at least 98% or at least 99% sequence identity to SEQ ID NO: 2, 6, 8, 10, 12, 14, 16, 18, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, or 99, and includes a Ser at position 582 or equivalent thereof (e.g., a Ser to Asn substitution in the sequence SLT located between aa 500 and 900 of a native CLV1 sequence, such as between about aa 540 and 600 or about aa 540 to 860, see for example FIGS. 5A, 5B). In some examples, a mutant CLV1 protein with an S582N substitution has at least about 80%, at least 90%, at least 95%, at least 96%, at least 97%, at least 98% or at least 99% sequence identity to SEQ ID NO: 4, 6, 8, 10, 12, 14, 16, 18, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, or 99 and includes an S582N substitution or equivalent thereof (e.g., a Ser to Asn substitution in the sequence SLT located between aa 500 and 900 of a native CLV1 sequence, such as between about aa 540 and 600 or about aa 540 to 860, see for example FIGS. 5A, 5B).

Variants of the disclosed nucleic acid sequences are typically characterized by possession of at least about 80%, at least 90%, at least 95%, at least 96%, at least 97%, at least 98% or at least 99% sequence identity counted over the full length alignment with the nucleic acid sequence using the NCBI Blast 2.0, gapped blastn set to default parameters. Thus, in some examples, a nucleic acid encoding a native CLV1 protein has at least about 80%, at least 90%, at least 95%, at least 96%, at least 97%, at least 98% or at least 99% sequence identity to SEQ ID NO: 1, 5, 7, 9, 11, 13, 15, or 17, and encodes a protein with a Ser at position 582 or equivalent thereof (e.g., a Ser to Asn substitution in the sequence SLT located between aa 500 and 900 of a native CLV1 sequence, such as between about aa 540 and 600 or about aa 540 to 860, see for example FIGS. 5A, 5B). In some examples, a nucleic acid encoding a mutant CLV1 protein with an S582N substitution has at least about 80%, at least 90%, at least 95%, at least 96%, at least 97%, at least 98% or at least 99% sequence identity to SEQ ID NO: 1, 3, 5, 7, 9, 11, 13, 15, or 17 and encodes an S582N substitution or equivalent thereof (e.g., a Ser to Asn substitution in the sequence SLT located between aa 500 and 900 of a native CLV1 sequence, such as between about aa 540 and 600 or about aa 540 to 860, see for example FIGS. 5A, 5B).

One of skill in the art will appreciate that these sequence identity ranges are provided for guidance only; it is possible that sequences coding for a CLV1 S582N mutation and CLV1 S582N protein sequences (or equivalent thereof) could be obtained that fall outside of the ranges provided.

Single locus converted (conversion) plant: Plants developed by backcrossing and/or by genetic transformation, wherein essentially all of the desired morphological and physiological characteristics of a particular variety (such as number of locules and/or seed production) are recovered in addition to the characteristics of the single locus transferred into the variety via the backcrossing technique and/or by genetic transformation.

Tissue culture: A composition that includes isolated cells of the same or a different type or a collection of such cells organized into parts of a plant. In some examples, the tissue culture includes a homogenous population of plant cells. In some examples, the tissue culture includes a callus tissue. In some examples, the tissue culture includes an anther culture. In some examples, the tissue culture includes a hairy root cultures.

Tolerance and resistance: These terms are used interchangeably to refer to any type of increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

Transformation: The introduction of exogenous genetic material (e.g., nucleic acids and vectors containing such) into cells, for example a plant cell. Exemplary mechanisms that can be used to transfer DNA into plant cells include (but not limited to) electroporation, microprojectile bombardment, *Agrobacterium*-mediated transformation and direct DNA uptake by protoplasts.

Transgene: An exogenous gene or other genetic material (e.g., nucleic acid molecules that encode a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B) and vectors containing such) that has been transferred into the genome of a plant or plant cell, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a Brassiceae plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

Under conditions sufficient for: A phrase that is used to describe any environment that permits a desired activity. In one example the desired activity is expression of a nucleic acid molecule that encode a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), in combination with other necessary elements, for example to increase locule number and or seed production.

Vector: A nucleic acid molecule into which a foreign nucleic acid molecule can be introduced without disrupting the ability of the vector to replicate and/or integrate in a host cell. In one example, a vector is not native to the cell into which it is introduced. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art.

A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes.

One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses).

Overview

Provided herein are mutant CLV1 nucleic acids and proteins that include or encode a S582N (or equivalent) substitution. In some examples such mutant CLV1 nucleic acids and proteins that include or encode a S582N (or equivalent) substitution are isolated or purified. Such mutant CLV1 nucleic acids and proteins can be introduced into a plant (or the mutation introduced into the plant, plant part or plant cell, for example by genetic engineering) to increase the number of locules and/or seed production in a plant, a plant part, or a plant cell. The methods can include introducing one or more exogenous nucleic acid molecules that encode a CLV1 S582N (or equivalent) substitution or introduce a CLV1 S582N (or equivalent) encoding substitution. This generates a plant, plant part, or plant cell comprising the exogenous nucleic acid (which in some examples are transgenic plants, transgenic plant parts, or transgenic plant cells that include an exogenous, non-native nucleic acid molecule).

One skilled in the art will appreciate that for the CLV1 sequence from some plant species, the position of the Ser to be mutated to an Asn might not be at position 582. However, nucleic acids encoding such, proteins containing such, and plants expressing such, are encompassed by this disclosure. For example, SEQ ID NO: 1 from *Brassica rapa* shows a native G at position 1745, which results in a Ser at position 582 in SEQ ID NO: 2. The resulting mutation of nt 1745 generating an Asn at position 582 is shown in SEQ ID NOS: 3 and 4. Although the specific location of the Ser to be mutated, can vary depending on the particular CLV1 sequence, the Ser to be mutated to Asn is located in the sequence SLT located between aa 500 and 900 of a native CLV1 sequence, such as between about aa 540 and 600 or about aa 540 to 860, see for example FIGS. 5A, 5B. For example, S582 of SEQ ID NO: 2 is equivalent to S577 of GenBank CAA0336861.1, S562 of SEQ ID NO: 6, S584 of SEQ ID NOs: 8 and 10, S589 of SEQ ID NO: 12 and 99, S590 of SEQ ID NO; 14, S857 of SEQ ID NO: 16, S586 of SEQ ID NO: 18, S541 of SEQ ID NO: 25, S571 of SEQ ID NO: 27 and 85, S570 of SEQ ID NO: 29, 41, and 51, S575 of SEQ ID NO: 31, 33, 35, 45, and 67, S578 of SEQ ID NO: 37 and 87, S580 of SEQ ID NO: 39 and 93, S568 of SEQ ID NO: 43, 57, and 65, S577 of SEQ ID NO: 47, 77 and 91, S592 of SEQ ID NO: 49, S572 of SEQ ID NO: 53, S573 of SEQ ID NO: 55, 59 and 75, S579 of SEQ ID NO: 61, 63 and 97, S596 of SEQ ID NO: 69, S574 of SEQ ID NO: 71 and 79, S581 of SEQ ID NO: 73, 81 and 89, S588 of SEQ ID NO: 83 and S565 of SEQ ID NO: 95.

Also provided are plants, plant parts, and plant cells (such as recombinant) having/containing one or more exogenous nucleic acids that express a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), such as one encoding a protein having at least 80%, at least 85%, at least 90%, at least 95%, at least 96%, at least 97%, at least 98%, at least 99%, or 100% identity to SEQ ID NO: 4 retaining the S582N mutation, such as a nucleic acid molecule having at least 80%, at least 85%, at least 90%, at least 95%, at least 96%, at least 97%, at least 98%, at least 99%, or 100% identity to SEQ ID NO: 3 retaining a codon at 582 (or equivalent thereof) that encodes N, wherein expression of the CLV1 S582N protein increases the number of locules and/or seed production by the plant in comparison to a wild type plant, wild type plant part, or wild type plant cell. In some examples such plants, plant parts, and plant cells are isolated or purified.

The provided plants, plant parts, and plant cells can further include one or more additional exogenous nucleic acid(s) encoding a protein(s) that confers upon the plant, plant part, or plant cell a desired trait, such as one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, abiotic stress tolerance, modified phosphorus characteristics, modified antioxidant characteristics, modified essential seed amino acid characteristics, decreased phytate, modified fatty acid metabolism, and modified carbohydrate metabolism.

Methods of producing a commodity plant product are provided. Such methods can include collecting or producing the commodity plant product from a plant, plant part, or plant cell provided herein (e.g., one that expresses a nucleic acid molecule that encodes a CLV1 S582N mutation (or equivalent thereof)). For example, such a method can include growing the plant, removing the harvestable parts (such as leaves, seeds, or oils) from the plant, and producing the product from or by the harvestable parts of the plant. Also provided are commodity plant product produced by such methods, wherein in come examples the commodity plant product includes the at least one exogenous nucleic acid molecule, a nucleic acid molecule that encodes a CLV1 S582N mutation, and/or a CLV1 S582N protein (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B). Exemplary commodity products include a protein concentrate, protein isolate, leaves, extract, and oil.

Methods of producing plant seed are provided herein. Such methods can include comprising crossing a plant provided herein (e.g., one that expresses a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B)) with itself or a second plant. In some examples, the second plant is recombinant. Also provided are $F_1$ seed produced by such a method, and a plant or part thereof produced by growing the seed. Such methods can further include (a) crossing a plant grown from said seed with itself or a different plant to produce a seed of a progeny plant of a subsequent generation; (b) growing a progeny plant of a subsequent generation from said seed of a progeny plant of a subsequent generation and crossing the progeny plant of a subsequent generation with itself or a second plant to produce a progeny plant of a further subsequent generation; and (c) repeating steps (a) and (b) using said progeny plant of a further subsequent generation from step (b) in place of the plant grown from said seed in step (a), wherein steps (a) and (b) are repeated with sufficient inbreeding to produce an inbred plant derived from the plant.

The disclosed plants, plant parts, and plant cells (e.g., one that expresses a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B)) can further include a single locus conversion, such as a transgene, for example a single locus that confers a desired trait. Examples of such traits include male sterility, herbicide tolerance, insect resistance, pest resistance, disease resistance, modified fatty acid metabolism, abiotic stress resistance, altered seed amino acid composition, and modified carbohydrate metabolism.

Methods for breeding a plant that expresses a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B) are provided. Such methods can include crossing a plant provided herein (e.g., one that expresses a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B)) with a second plant, thereby generating plants with increased number of locules and/or seed production. The method can further include obtaining seed from the crossing; planting the seeds and growing the seeds to plants; and selecting from said plants those with increased number of locules and/or seed production.

Also provided are containers (such as a paper, plastic or glass container, such as a bag, envelope, clamshell container, vial, or box), which includes dried, frozen, or fresh leaves (or sprouts or microgreens) of a plant provided herein (e.g., one that expresses a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B)); an oil extract of a plant provided herein, or combinations thereof.

In some examples, expression of CLV1 S582N (or equivalent thereof) in the plant, plant part, or plant cell increases number of locules and/or seed production by at least 10%, at least 20%, at least 30%, at least 40%, at least 50%, at least 60%, at least 70%, at least 80%, at least 90%, at least 95%, at least 96%, at least 97%, at least 98%, at least 99%, at least 100%, at least 200%, at least 300%, at least 400%, or at least 500%, for example as compared to a plant, cell, or plant part of the same plant type that expresses CLV1 S582 or equivalent thereof (e.g., wild type CLV1, such as a Ser in the sequence SLT located between aa 500 and 900 of a native CLV1 sequence, such as between about aa 540 and 600 or about aa 540 to 860, see for example FIGS. 5A, 5B).

In some examples, the plant is a flowering plant. In some examples, the plant is a member of the family Brassicaceae. In some examples, the plant, plant part, or plant cell is or is from the genus *Brassica*, the genus *Camelina*, or the genus *Thlaspi*. In some examples, the plant, plant part, or plant cell is or is *B. rapa, B. napus, B. oleracea, C. sativa, Thlaspi arvense*, or any other listed in FIGS. 3, 4, 5A, 5B. In some examples, the plant, plant part, or plant cell is or is from canola, camelina, pennycress, grape, cantaloupe, cucumber, pumpkin, squash, watermelon, hops, soybean, spinach, or sunflower. In some examples, the plant, plant part, or plant cell is or is from a monocot. In some examples, the plant, plant part, or plant cell is or is from a dicot.

In some examples, the plant part is a protoplast, leaf, stem, root, root tips, anther, pistil, stamen, seed, embryo, pollen, ovule, microspore, protoplast, sporophyte, gametophyte, cotyledon, hypocotyl, flower, shoot, tissue, petiole, or meristematic cell.

Multilocularity in oil seed-type Brassica crops is associated with increased seed production. The tetralocular phenotype in *B. rapa* R-o-18 (see Example 1) is caused by a recessive mutation in a secreted peptide produced from BraA.CLV3. CLV3 binds to the CLV1 receptor kinase to signal in meristem size control. A multilocular phenotype in the tetraploid *Brassica juncea* (an allotetraploid of *B. rapa* and *B. nigra*) is due to recessive mutations in homologs of the peptide receptor CLV1, but none are S582N.

Figure 8:
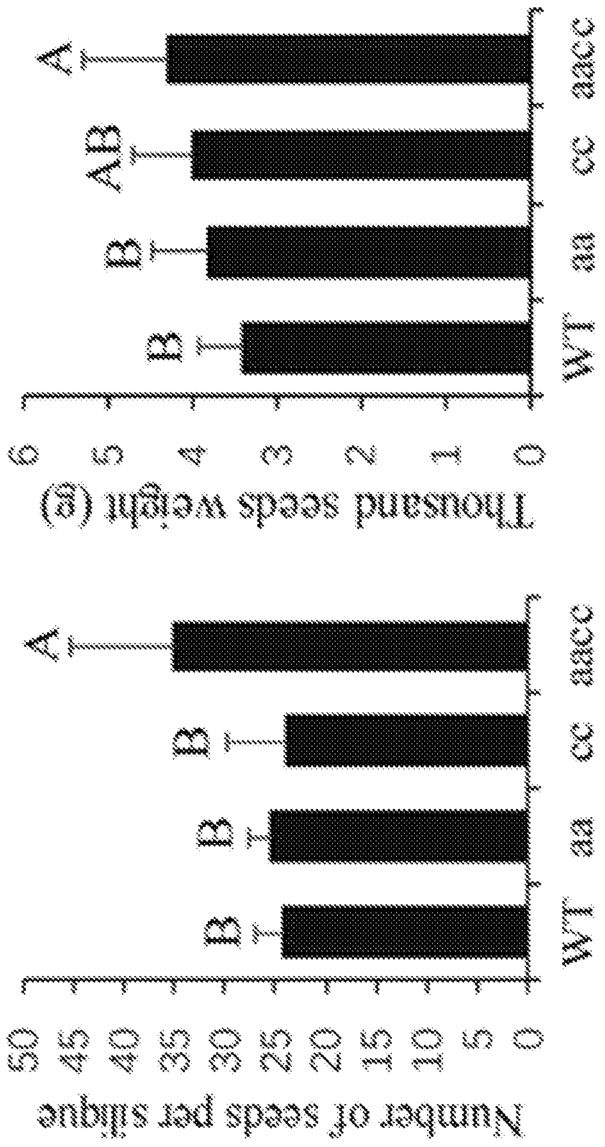
FIG. 8. are bar graphs from Yang, et al. (*Plant Biotechnology Journal* 16 (7): 1322-35, 2018) showing phenotypes of the BnCLV3 mutants. Statistical analysis of the number of seeds per silque and thousand seeds weight in the WT and single and double homozygous mutants of BnCLV3. The data and error bars represent the mean±SD (n≥15 plants for each genotype) are provided. Upper-case letters indicate a significant difference at the 0.01 probability level. aa, homozygous mutation of BnA04.CLV3; cc, homozygous mutation of BnC04.CLV3; aacc, double homozygous mutation of BnA04.CLV3 and BnC04.CLV3 (lines that are homozygous for clv3 mutations in both subgenomes of the allotetraploid).

Cas9-based mutation of CLAVATA genes by another group in the tetraploid *Brassica napus* (canola, an allotetraploid of *B. rapa* and *B. oleracea*) (Yang et al., Plant Biotechnology Journal 16 (7): 1322-35, 2018) resulted in created clv3 alleles producing increased seeds per silique and 1000 seed weight (FIG. 8). Total seed yield was not reported. The clv1 alleles created are reported in this publication to be "unstable" and result in only a proportion of siliques showing a multilocular phenotype. Therefore, the *B. rapa* clv1 allele disclosed herein can serve as germplasm for breeding multilocularity into *B. rapa* and other plants, and in breeding multilocular resynthesized *B. napus* and other plants.

Breeding New Varieties with Increase Number of Locules and/or Seed Production Methods for crossing one or more of the disclosed plants, such as a plant (e.g., Brassicaceae plant) expressing a nucleic acid molecule that encodes a CLV1 S582N mutation (or equivalent thereof), with itself or a second plant are provided, as are the seeds and plants produced by such methods. Such methods can be used for propagation of a new plant variety, or can be used to produce hybrid seeds and the plants grown therefrom. Hybrid plants can be used, for example, in the commercial production of commodity products (including leaves, fruit, biomass, oil, and extracts) or in breeding programs for the production of novel varieties. A hybrid plant can also be used as a recurrent parent at any given stage in a backcrossing protocol during the production of a single locus conversion (for example introduction of one or more desirable traits) of a plant provided herein.

Methods of producing plants and/or seed are provided. Such methods can include crossing one or more of the disclosed plants, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), with itself or a second plant and harvesting a resulting seed, such as an $F_1$ hybrid seed. The resulting plant can be grown, resulting in a plant or part thereof (such as an F1 plant).

In one example methods of producing an inbred plant derived from a plant provided herein, such as a plant e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B). In one example such methods include (a) generating a progeny plant derived from plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), by crossing such a plant with a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred plant derived from a plant provided herein.

The second plant crossed with a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), for the purpose of developing novel varieties, is typically a plant which either itself exhibits one or more desirable characteristics or which exhibits one or more desired characteristic(s) when in hybrid combination. In one example, the second plant is recombinant Exemplary desired characteristics include, but are not limited to: increased seed yield, increased seedling vigor, modified maturity date, desired plant height, high anthocyanin content, high phenolic content, herbicide tolerance or resistance, drought tolerance or resistance, heat tolerance or resistance, low or high soil pH level tolerance, salt tolerance or resistance, resistance to an insect, resistance to a bacterial disease, resistance to a viral disease, resistance to a fungal disease, resistance to a nematode, resistance to a pest, male sterility, abiotic stress tolerance, and increased number of locules and/or seed production.

When a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B) is crossed with another different variety, first generation ($F_1$) progeny are produced. The hybrid progeny are produced regardless of characteristics of the two varieties produced. As such, an $F_1$ hybrid plant can be produced by crossing a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), with any second plant. The second plant can be genetically homogeneous (e.g., inbred) or can itself be a hybrid. Therefore, the disclosure provides any $F_1$ hybrid plant produced by crossing a plant provided herein, such as a plant (e.g. Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), with a second plant (such as a plant having one or more genes that confer to the plant one or more desired characteristics).

Plants can be crossed by either natural or mechanical techniques. Natural pollination occurs by self-pollination or natural cross pollination, which typically is aided by pollinating organisms. In either natural or artificial crosses, flowering and flowering time can be a consideration.

Sensitivity to day length can be a consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting. Plants can be grown in winter nurseries located at sea level in tropical latitudes where day lengths are shorter than their critical photoperiod. The short day lengths and warm temperatures encourage early flowering and seed maturation. Early flowering can be useful for generation advance when only a few self-pollinated seeds per plant are desired, but usually not for artificial hybridization because the flowers self-pollinate before they are large enough to manipulate for hybridization. Artificial lighting can be used to extend the natural day length to about 14.5 hours to obtain flowers suitable for hybridization and to increase yields of self-pollinated seed. The effect of a short photoperiod on flowering and seed yield can be partly offset by altitude. At tropical latitudes, varieties adapted to the northern U.S. perform more like those adapted to the southern U.S. at high altitudes than they do at sea level. The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. *Bot. Gaz.* 108:1-26).

Temperature can also affect the flowering and development of plants. It can influence the time of flowering and suitability of flowers for hybridization. Artificial hybridization is typically successful between about 26° C. and about 32° C.

Self-pollination can occur naturally with no manipulation of the flowers. In some examples, the crossing of two plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated using known methods. Exemplary methods for emasculating the male parts of a flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, the parents of a cross can be planted adjacent to each other. Plants are typically grown in rows about 65 cm to about 100 cm apart, but plant densities for seed production fields can be significantly higher in density without compromising fertilization and seed quality. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less are commonly used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization. Grafting can be used to hasten the flowering of late flowering genotypes.

Plants Having One or More Heritable Traits

The disclosure provides plants (e.g., Brassicaceae plants) having increased number of locules and/or increased seed production relative to a native plant of the same species, which can be further modified to include one or more additional desired heritable traits. In some examples, such plants can be developed using backcrossing or genetic engineering (for example by introducing one or more transgenes into a plant provided herein, such as a plant (e.g., Brassicaceae plants) having increased number of locules and/or increased seed production relative to a native plant of the same species, wherein the transgenes encode one or more desired traits), wherein essentially all of the desired morphological and physiological characteristics of a disclosed plant are recovered (such as increased number of locules and/or seed production) in addition to a genetic locus transferred into the plant via the backcrossing technique. Plants developed using such methods can be referred to as a single locus converted plant.

In one example, the method of introducing one or more desired traits into one or more of the plants provided herein, such as a plant (e.g. Brassicaceae plant) expressing a nucleic acid molecule that encodes a CLV1 S582N mutation (or equivalent thereof), with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of the variety to produce backcross progeny plants; (d) selecting backcross progeny plants that have the one or more desired traits and physiological and morphological characteristics of the variety to produce selected backcross progeny plants; and (e) repeating steps (c) and (d) one or more times in succession to produce selected second or higher backcross progeny plants that have the one or more desired traits and the physiological and morphological characteristics of a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), when grown in the same environmental conditions.

Backcrossing methods can be used to improve or introduce a characteristic into a plant provided herein, such as a plant (e.g., Brassicaceae plant) expressing a nucleic acid molecule that encodes a CLV1 S582N mutation (or equivalent thereof). The parental plant, which contributes the locus for the desired characteristic, is termed the "nonrecurring" or "donor" parent. This terminology refers to the fact that the nonrecurring parent is used one time in the backcross protocol and therefore does not recur. The parental plant to which the locus or loci from the nonrecurring parent are transferred is known as the recurrent parent as it is used for several rounds in the backcrossing protocol (Poehlman and Sleper. 1995. "Breeding Field Crops" Ames, Iowa: Iowa State University Press; Sprague and Dudley, eds. 1988. Corn and Improvement, 3rd edition). In a typical backcross protocol, the original variety of interest (e.g., plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B)) is crossed to a second variety (nonrecurring parent) that carries the single locus of interest (such as a desirable trait) to be transferred. The resulting progeny from this cross are then crossed again to the recurrent parent and the process is repeated until a plant is obtained wherein essentially all of the desired morphological and physiological characteristics of the recurrent parent (e.g., a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B)) are recovered (such as increased number of locules and/or seed production) in the converted plant, in addition to the single transferred locus from the nonrecurring parent.

A backcross protocol alters or substitutes a single trait or characteristic in the original variety, such as a plant provided herein, such as a (e.g., Brassicaceae plant) expressing a nucleic acid molecule that encodes a CLV1 S582N mutation (or equivalent thereof). To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent can depend on the purpose of the backcross; for example, to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent can be composited without the usual replicated tests for traits such as yield, in the individual lines.

Varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, recombinant Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus characteristics, modified antioxidant characteristics, yield stability, and yield enhancement. These comprise genes generally inherited through the nucleus. Thus plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B) or progeny thereof, which include a single locus conversion (such as one that confers a desired trait, such as increased number of locules and/or seed production).

Direct selection can be applied where the single locus acts as a dominant trait. An example of a dominant trait is herbicide resistance (such as glyphosate resistance). For the selection process, the progeny of the initial cross are sprayed with an herbicide (such as RoundUp® herbicide) prior to the backcrossing. The spraying eliminates any plants which do not have the desired herbicide resistance characteristic; only those plants which have the herbicide resistance gene are used in the subsequent backcross. This process is then repeated for all additional backcross generations.

Selection of plants for breeding may not be dependent on the phenotype of a plant and instead can be based on genetic investigations. For example, a suitable genetic marker can be used which is genetically-linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to plant breeding are well known. Such methods can be useful in the case of recessive traits and variable phenotypes, or where conventional assays are more expensive, time consuming, or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, which is incorporated herein by reference in its entirety), and Single Nucleotide Polymorphisms (SNPs).

Qualitative characteristics can also be useful as phenotype-based genetic markers in plants; however, some or many may not differ among varieties commonly used as parents. Exemplary genetic markers include flower color, differences in maturity, height, and pest resistance.

Useful or desirable traits can be introduced by backcrossing, as well as directly into a plant by genetic transformation methods. Genetic transformation can therefore be used to insert a selected transgene into a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof, or can, alternatively, be used for the preparation of transgenes which can be introduced by backcrossing. Thus, the disclosure provides methods of producing a plant of a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof, that includes one or more added desired traits, for example that include introducing a transgene(s) conferring the one or more desired traits into a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof (for example by transformation with a transgene that confers upon the plant the desired trait), thereby producing a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof that includes the one or more added desired traits.

Exemplary methods for introducing a desired nucleic acid molecule (e.g., transgene), such as DNA or RNA, which can be employed for the genetic transformation of a plant include, but are not limited to, electroporation, microprojectile bombardment, *Agrobacterium*-mediated transformation and direct DNA uptake by protoplasts.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner Protoplasts can also be employed for electroporation transformation of plants (Bates. 1994. *Mol. Biotechnol.* 2(2):135-145; Lazzeri. 1995. *Methods Mol. Biol.* 49:95-106).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target plant cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large.

*Agrobacterium*-mediated transfer is a method for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. *Agrobacterium*-mediated plant integrating vectors can be used to introduce DNA into plant cells i (e.g., Fraley et al. 1985. *Bio. Tech.* 3(7):629-635; U.S. Pat. No. 5,563,055). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457).

In one example, such methods can also be used to introduce transgenes for the production of proteins in plant cells. The resulting produced protein can be harvested from the plant. The transgene can be harvested from the plants that are originated or are descended from a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), a seed of such a plant, or a hybrid progeny of such a plant.

Numerous different genes are known and can be introduced into a plant provided herein, such as a plant (e.g., Brassicaceae plant) expressing a nucleic acid molecule that encodes a CLV1 S582N mutation (or equivalent thereof), or progeny thereof. Non-limiting examples of particular genes and corresponding phenotypes that can be chosen for introduction into a plant are provided herein.

Included among various plant transformation techniques are methods permitting the site-specific modification of a plant genome. These modifications can include, but are not limited to, site-specific mutations, deletions, insertions, and replacements of nucleotides. These modifications can be made anywhere within the genome of a plant, for example, in genomic elements, including, among others, coding sequences, regulatory elements, and non-coding DNA sequences. Any number of such modifications can be made and the modifications may be made in any order or combination, for example, simultaneously, all together, or one after another. Such methods may be used to modify a particular trait conferred by a locus. Techniques for making such modifications by genome editing include, for example, use of CRISPR-Cas systems, zinc-finger nucleases (ZFNs), and transcription activator-like effector nucleases (TALENs), among others.

A transgene need not be directly transformed into a plant, as techniques for the production of stably transformed corn plants that pass single loci to progeny by Mendelian inheritance is known. Such loci may therefore be passed from parent plant to progeny plants by standard plant breeding techniques.

Herbicide Resistance

Herbicide resistance genes can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458). In one non-limiting example, the herbicide resistance gene is a gene that confers resistance to the sulfonylurea herbicide nicosulfuron.

Resistance genes for glyphosate (e.g., resistance conferred by mutant 5-enolpyruvl-3 phosphikimate synthase (EPSPS) enzyme and aroA genes) and other phosphono compounds such as glufosinate (phosphinothricin acetyl transferase (PAT) and *Streptomyces hygroscopicus* phosphinothricin-acetyl transferase (bar) genes) can be used (e.g., see U.S. Pat. No. 4,940,835). Examples of specific EPSP transformation events conferring glyphosate resistance are described, for example, in U.S. Pat. Nos. 6,040,497 and 7,632,985. The MON89788 event disclosed in U.S. Pat. No. 7,632,985 can be used to confer glyphosate tolerance in combination with an increase in average yield relative to prior events. Exemplary PAT sequences are provided in RE44962.

DNA molecules encoding a mutant aroA gene can be used with the methods and plants provided herein (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Exemplary genes conferring resistance to an herbicide that inhibits photosynthesis include triazine (psbA and gs+genes) and benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseuodmonas maltophilia*, which is involved in the conversion of a herbicidal form of the herbicide dicamba to a non-toxic 3,6-dichlorosalicylic acid and thus can be used for producing plants tolerant to this herbicide.

Genes or plasmids that contribute to the metabolism of chlorophenoxyacetic acids, such as, 2,4-D herbicide and which can be used with the methods and plants provided herein are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Genes are also known that confer resistance to herbicides that inhibit photosynthesis such as, for example, triazine herbicides (psbA and gs+ genes) and benzonitrile herbicides (nitrilase gene). In one non-limiting example, a gene confers resistance to the benzonitrile herbicide bromoxynil. Przibila et al. (*Plant Cell,* 3:169, 1991) describe the transformation of *Chlamydomonas* with plasmids encoding mutant psbA genes. Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes, et al. (*Biochem. J.,* 285:173, 1992). 4-hydroxyphenylpyruvate dioxygenase (HPPD) is a target of the HPPD-inhibiting herbicides, which deplete plant plastoquinone and vitamin E pools. Rippert, et al. (*Plant Physiol.,* 134:92, 2004) describes an HPPD-inhibitor resistant tobacco plant that was transformed with a yeast-derived prephenate dehydrogenase (PDH) gene. Protoporphyrinogen oxidase (PPO) is the target of the PPO-inhibitor class of herbicides; a PPO-inhibitor resistant PPO gene was recently identified in *Amaranthus tuberculatus* (Patzoldt, et al., *PNAS,* 103(33):12329, 2006). The herbicide methyl viologen inhibits $CO_2$ assimilation. Foyer, et al. (*Plant Physiol.,* 109:1047, 1995) describe a plant overexpressing glutathione reductase (GR) that is resistant to methyl viologen treatment.

Siminszky (*Phytochemistry Reviews,* 5:445, 2006) describes plant cytochrome P450-mediated detoxification of multiple, chemically unrelated classes of herbicides. Modified bacterial genes have been successfully demonstrated to confer resistance to atrazine, an herbicide that binds to the plastoquinone-binding membrane protein $Q_B$ in photosystem II to inhibit electron transport. For example, Cheung, et al. (*PNAS,* 85:391, 1988) describe tobacco plants expressing the chloroplast psbA gene from an atrazine-resistant biotype of *Amaranthus hybridus* fused to the regulatory sequences of a nuclear gene, and Wang, et al. (*Plant Biotech. J.,* 3:475, 2005) describe transgenic alfalfa, *Arabidopsis*, and tobacco plants expressing the atzA gene from *Pseudomonas* sp. that were able to detoxify atrazine.

Bayley, et al. (*Theor. Appl. Genet.,* 83:645, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a dicamba monooxygenase (DMO) gene from *Pseudomonas maltophilia* that is involved in the conversion of dicamba to a non-toxic 3,6-dichlorosalicylic acid and thus may be used for producing plants tolerant to this herbicide.

Other examples of herbicide resistance have been described, for example, in U.S. Pat. Nos. 6,803,501; 6,448,476; 6,248,876; 6,225,114; 6,107,549; 5,866,775; 5,804,425; 5,633,435; 5,463,175.

Disease Resistance

Plant defenses are often activated by specific interaction between the product of a disease resistance gene (R) in the plant and the product of a corresponding avirulence (Avr) gene in the pathogen. A plant, such as a plant provided herein, such as a plant (e.g., Brassicaceae plant) expressing a nucleic acid molecule that encodes a CLV1 S582N mutation (or equivalent thereof), or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium fulvum*); Martin et al. (1993. *Science* 262(5138):1432-1436) (tomato Pto gene for resistance to *Pseudomonas syringae pv.*); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance in a plant provided herein. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

A virus-specific antibody can also be used. See, for example, Tavladoraki et al. (1993. *Nature* 366:469-472), which shows that transgenic plants expressing recombinant antibody genes are protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production.

The barley ribosome-inactivating gene described by Logemann et al. (1992. *Bio/Technology* 10:305-308) can be used to increase resistance to fungal disease. Plant defensins may be used to provide resistance to fungal pathogens (Thomma et al., *Planta,* 216:193, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; 6,316,407; and 6,506,962.

Insect Resistance

One example of an insect resistance gene is one that encodes a *Bacillus thuringiensis* (Bt) protein (a Cry toxin), a derivative thereof or a synthetic polypeptide modeled thereon (e.g., see Geiser et al., 1986. Gene 48:109, discloses a Bt Δendotoxin gene) can be used with the methods and plants provided herein. Moreover, DNA molecules encoding Δ-endotoxin (e.g., ATCC Accession Nos. 40098, 67136, 31995 and 31998), or lectin (e.g., Van Damme et al. (1994. *Plant Mol Biol* 24(5):825-830), which discloses several *Clivia miniata* mannose-binding lectin genes) can be used with the methods and plants provided herein. Another example is a. A vitamin-binding protein can also be used with the methods and plants provided herein, such as avidin (e.g., WO 1994/000992, which teaches the use of avidin and avidin homologues as larvicides against insect pests). In one example, the *Bacillus thuringiensis* (Bt) protein is a member of the Cry1 class, and is active primarily against larval stages of the order Lepidoptera. Examples include Cr1Ab (Bt11), Cry1Ac, and Cry1F (e.g., Cry1Fa2 (TC1507)), as well as variants and truncations thereof that provide insect resistance. In one example, the *Bacillus thuringiensis* (Bt) protein is a member of the Cry2 class or the Cy3 class (such as Cy34Ab1, Cry35ab1).

In one example the insect resistance gene used with the methods and plants provided herein is an enzyme inhibitor, for example, a protease, proteinase inhibitor, or an α-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone, such as juvenile hormone esterase, can also be used with the methods and plants provided herein. See, for example, Hammock et al. (1990. *Nature* 344:458-461).

An insect-specific hormone or pheromone may also be used. For example, Hammock et al. (Nature, 344:458, 1990) describe baculovirus expression of cloned juvenile hormone esterase, an inactivator of juvenile hormone. Further, Gade and Goldsworthy (Eds., Physiological Systems in Insects, Elsevier Academic Press, Burlington, Mass., 2007) describe allostatins and their potential use in pest control, and Palli et al. (*Vitam. Horm.,* 73:59, 2005) describes the use of ecdysteroid and ecdysteroid receptor in agriculture. Additionally, Price et al., (*Insect Mol. Biol.,* 13:469, 2004) identified the diuretic hormone receptor (DHR) as a candidate target of insecticides.

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

Nematode resistance has been described, for example, in U.S. Pat. No. 6,228,992, and bacterial disease resistance has been described, for example, in U.S. Pat. No. 5,516,671.

Male Sterility

Genetic male sterility can increase the efficiency with which hybrids are made, in that it can eliminate the need to physically emasculate the plant used as a female in a given cross (Brim and Stuber. 1973. *Crop Sci.* 13:528-530). Herbicide-inducible male sterility systems (e.g., U.S. Pat. No. 6,762,344) can be used with the methods and plants provided herein.

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the plant is utilized. However, in many cases, the seeds are considered to be a valuable portion of the crop, thus, it is desirable to restore the fertility of the hybrids in these crops. Therefore, the disclosure provides a plant provided herein, such as a plant (e.g., Brassicaceae plant) expressing a nucleic acid molecule that encodes a CLV1 S582N mutation (or equivalent thereof), comprising a genetic locus capable of restoring male fertility in an otherwise male-sterile plant. Examples of male-sterility genes and corresponding restorers which can be employed are found in, e.g., U.S. Pat. Nos. 3,861,709, 3,710,511, 4,654,465, 4,727,219, 5,530,191 5,684,242 and 5,625,132.

Modified Fatty Acid, Phytate, and Carbohydrate Metabolism

Genes conferring modified fatty acid metabolism can be introduced into a plant provided herein, such as antisense stearoyl acyl carrier protein (ACP) desaturase genes (EC 1.14.99.6) (e.g., Knutzon et al. 1992. *PNAS* 89:2624-2628). Fatty acid desaturases can be introduced into a plant provided herein, such as *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., 1992. *J Biol Chem* 267(9):5931-5936); a gene encoding a stearoyl-acyl carrier protein-9 desaturase from castor (Fox et al. 1993. *PNAS* 90(6):2486-2490); Δ6- and Δ12-desaturases from the cyanobacteria *Synechocystis* responsible for the conversion of linoleic acid (18:2) to gamma-linolenic acid (18:3 gamma) (Reddy et al., 1993. *Plant Mol Biol* 22(2):293-300); a gene from *Arabidopsis thaliana* that encodes an omega-3 desaturase (Arondel et al. 1992. *Science* 258:1353-5); plant Δ9-desaturases (WIPO Publication No. WO 1991/013972) and corn and *Brassica* Δ15 desaturases (European Patent Application Publ. No. EP 0616644).

Phytate metabolism can also be modified by introduction of a phytase-encoding gene to enhance breakdown of phytate, adding more free phosphate to the transformed plant. For example, see Van Hartingsveldt et al. (1993. *Gene* 127:87-94), for an *Aspergillus niger* phytase gene. In corn, this, for example, could be accomplished by cloning and then reintroducing DNA associated with the single allele which is responsible for corn mutants characterized by low levels of phytic acid. See Raboy et al. (2000, *Plant Physiol.* 124(1):355-68).

A number of genes can be used to alter carbohydrate metabolism. For example, plants can be transformed with a gene coding for an enzyme that alters the branching pattern of starch. See Shiroza et al. (1988. *J Bacteriol* 170(2):810-816) (*Streptococcus* fructosyltransferase gene), Steinmetz et al. (1985. Mol Gen Genet. 200:220-228) (*Bacillus subtilis* levansucrase gene), Pen et al. (1992. *BioTechnology* 10:292) (*Bacillus lichenifonnis* α-amylase), Elliot et al. (1993. *Plant Mol. Biol* 21:515) (tomato invertase genes), Sergaard et al. (1993. *J. Biol. Chem.* 268:22480) (site-directed mutagenesis of barley α-amylase gene), and Fisher et al. (1993. *Plant Physiol* 102:1045) (maize endosperm starch branching enzyme II). The Z10 gene encoding a 10 kD zein storage protein from maize can also be used to alter the quantities of 10 kD zein in the cells relative to other components (Kirihara et al., 1988. *Mol Gen Genet.* 211:477-484).

U.S. Pat. No. 6,930,225 describes corn cellulose synthase genes and methods of use thereof.

Resistance to Abiotic Stress

Abiotic stress tolerance in a plant provided herein can include, but is not limited to, tolerance to stress induced by, for example, flowering, ear and seed development, enhancement of nitrogen utilization efficiency, altered nitrogen responsiveness, drought resistance or tolerance, cold resistance or tolerance, heat resistance or tolerance, low or high soil pH level resistance or tolerance, submergence tolerance, tolerance of exposure to heavy metals, oxidative stress tolerance, and salt resistance or tolerance. Such abiotic stress tolerance can increase yield under stress.

Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878.

Additional Traits

Additional traits can be introduced into the disclosed plants. A non-limiting example of such a trait is a coding sequence that decreases RNA and/or protein levels. The decreased RNA and/or protein levels may be achieved through RNAi methods, such as those described in U.S. Pat. No. 6,506,559.

Modifications can also include site-specific recombination; modified antioxidant characteristics; modified essential seed amino acid characteristics, or the like, or any combination thereof. Merely by way of example, FRT sites and/or Lox sites can be introduced into a plant. FRT sites can be used in the FLP/FRT system. Lox sites can be used in the Cre/Loxp system. Modifications can be made to a plant to introduce modified antioxidant characteristics (e.g., content or composition, such as alteration of tocopherol or tocotrienols) and/or modified essential seed amino acid characteristics (e.g., increasing accumulation of essential amino acids in seeds). Exemplary useful genes and traits for transgenic modification of the variety are disclosed in, for example, U.S. Pat. Nos. 7,687,686, 7,649,127 and 7,645,923.

In addition to the modification of oil, fatty acid, or phytate content described above, it may additionally be beneficial to modify the amounts or levels of other compounds. For example, the amount or composition of antioxidants can be altered. For example, U.S. Pat. Nos. 6,787,618 and 7,154,029 and International Patent Application Publication No. WO 00/68393 disclose manipulation of antioxidant levels, and International Patent Application Publication No. WO 03/082899 discloses manipulation of an antioxidant biosynthetic pathway.

Additionally, seed amino acid content may be manipulated. U.S. Pat. No. 5,850,016 and International Patent Application Publication No. WO 99/40209 disclose alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins in which the levels of essential amino acids can be manipulated. International Patent Application Publication No. WO 99/29882 discloses methods for altering amino acid content of proteins. International Patent Application Publication No. WO 98/20133 describes proteins with enhanced levels of essential amino acids. International Patent Application Publication No. WO 98/56935 and U.S. Pat. Nos. 6,346,403, 6,441,274, and 6,664,445 disclose plant amino acid biosynthetic enzymes. International Patent Application Publication No. WO 98/45458 describes synthetic seed proteins having a higher percentage of essential amino acids than wildtype.

U.S. Pat. No. 5,633,436 discloses plants comprising a higher content of sulfur-containing amino acids; U.S. Pat. No. 5,885,801 discloses plants comprising a high threonine content; U.S. Pat. No. 5,885,802 discloses plants comprising a high methionine content; U.S. Pat. No. 5,912,414 discloses plants comprising a high methionine content; U.S. Pat. No. 5,990,389 discloses plants comprising a high lysine content; U.S. Pat. No. 6,459,019 discloses plants comprising an increased lysine and threonine content; International Patent Application Publication No. WO 98/42831 discloses plants comprising a high lysine content; International Patent Application Publication No. WO 96/01905 discloses plants comprising a high threonine content; and International Patent Application Publication No. WO 95/15392 discloses plants comprising a high lysine content.

Tissue Cultures and In Vitro Regeneration of Plants

Tissue cultures of one or more of the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, petiole, stein, ovule, cotyledon, hypocotyl, shoot or stem, and the like. In a particular example, the tissue culture includes embryos, protoplasts, meristematic cells, pollen, leaves or anthers of the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B). Also provided are plants regenerated from such tissue cultures, wherein the regenerated plant expresses the physiological and morphological characteristics of a new plant disclosed herein.

Methods for preparing tissue cultures of regenerable plant cells and regenerating plants therefrom are known, such as those disclosed in U.S. Pat. Nos. 4,992,375; 5,015,580; 5,024,944, and 5,416,011. Tissue culture provides the capability to regenerate fertile plants. This can allow, for example, transformation of the tissue culture cells followed by regeneration of plants. For transformation to be efficient and successful, DNA can be introduced into cells that give rise to plants or germ-line tissue.

Plants can be regenerated using organogenesis or somatic embryogenesis. Organogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Organogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in organogenesis may not generate many somatic embryos, while lines that produce large numbers of embryos during an "induction" step (typically, exposure of the plant material to a specific regimen of plant growth regulators) may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Organogenesis is a system whereby shoots are obtained de novo from cotyledonary nodes of seedlings (Wright et al., 1986. *Plant Cell Reports* 5:150-154). The shoot meristems form subepidermally and morphogenic tissue can proliferate on a medium containing benzyl adenine (BA). This system can be used for transformation if the subepidermal, multicellular origin of the shoots is recognized and proliferative cultures are utilized. Tissue that can give rise to new shoots are targeted and proliferated within the meristematic tissue to lessen problems associated with chimerism.

Somatic embryogenesis is a system in which embryogenic tissue is obtained from the zygotic embryo axis (Christianson et al., 1983. *Science* 222:632-634). The embryogenic cultures are proliferative and the proliferative embryos are of apical or surface origin with a small number of cells contributing to embryo formation. The origin of primary embryos (the first embryos derived from the initial explant) is dependent on the explant tissue and the auxin levels in the induction medium (Hartweck et al., 1988. *In Vitro Cell. Develop. Bio.* 24:821-828). With proliferative embryonic cultures, single cells or small groups of surface cells of the "older" somatic embryos form the "newer", more recently developed somatic embryos.

Embryogenic cultures can also be used for regeneration, including regeneration of plants.

Methods of Making Plant Extracts

Extracts can be generated from the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof. Such extracts can be used, for example as a commodity, such as oil. In some examples, the extract includes genetic material, proteins, or both, from the plants provided herein, such as a plant (e.g., Brassicaceae plant) expressing a nucleic acid molecule that encodes a CLV1 S582N mutation (or equivalent thereof).

In one example, plants of the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or any above-ground part of the plant (such as seed), are harvested, for example, after at least 20 days, at least 30 days, at least 45 days, at least 60 days, at least 70 days, at least 90 days, at least 100 days, or at least 120 days of growth (such as after 45 to 100 days, 60 to 100 days, or 50 to 90 days, such as after 60 days or 90 days of growth). For example, canola oil is made by slightly heating and then crushing the seed, and can be extracted using hexane solvent which is recovered at the end of processing. Canola oil cam be refined using water precipitation and organic acid to remove gums and free fatty acids, filtering to remove color, and deodorizing using steam distillation.

The remainder of the seeds can be used for animal feed.

The plant from which an extract is generated can be field-grown, greenhouse grown or grown in pots, sacs and containers, and cut at any height above the soil, and the plant distilled fresh or partially dried to obtain the oil. Plants can be cut once per growing season, but can be harvested (or cut) once or twice or more per growing season, provided it is grown with ample water, nutrients and under environmental conditions that result in plant growth and development.

Products

The disclosure provides products obtained from one or more of the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof. Exemplary products include a biomass or part thereof, such as an extract, oil, protein isolate, protein concentrate, oil extract, or leaves. For example, a dried biomass and/or leaves of the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof can be used as part of food, beverage, or aroma-based product. In some examples, the product includes at least one cell, DNA, and/or protein of a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B).

The disclosure provides containers, such as a glass, paper, or plastic container, which includes seeds or oil of a plant provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B).

Provided herein are personal consumer items, which include leaves, oil extract, and/or biomass of one or more of the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B), or progeny thereof.

Oil extracts of one or more of the plants provided herein, such as a plant (e.g., Brassicaceae plant) expressing a nucleic acid molecule that encodes a CLV1 S582N mutation (or equivalent thereof, e.g., a Ser to Asn substitution in the sequence SLT located between aa 500 and 900 of a native CLV1 sequence, such as between about aa 540 and 600 or about aa 540 to 860, see for example FIGS. 5A, 5B) or progeny thereof are provided, and in one example are formulated into a spray.

Example 1

Identification of CLV1 S582N Mutation that Increases Locule Number

To understand factors linking epigenetic modification with seed production, a suppressor screen of the nrpd1 mutant, which produces virtually no seeds, was performed. One suppressor mutant that arose this mutant screen (sup-c) has increased number of locules (seed-containing compartments in the fruit/silique) and results in significantly higher seed production compared to the nrpd1 background. The mutant also has increased floral organs (FIGS. 6A-6D).

Genetic mapping was used to identify this mutation. The background containing the sup-c mutation is R-o-18, which normally has 4 locules due to a CLV3 mutation. The sup-c mutant was crossed to the R500 background, which has 2 locules. In the F2 mapping population, the following phenotypes were observed:

| Phenotype | number | conclusion |
|---|---|---|
| 2 locules | 221 (61%) | CLV3$^{R500}$; no sup-c phenotype |
| 4 locules | 64 (17.6%) | CLV3$^{R\text{-}o\text{-}18}$; no sup-c phenotype |
| 5-10 locules | 46 (12.6%) | sup-c phenotype |
| Failure to develop mature flowers | 33 (9.1%) | Likely effect of secondary mutation from original screen; cannot determine sup-c state |

This analysis confirmed that the sup-c mutation is recessive and heritable.

Because the CLV3 gene is associated with locule number, it was also confirmed that sup-c was segregating from the CLV3 gene in the F2 population. Among the 46 sup-c F2 plants, 9 CLV3$^{R500}$/CLV3$^{R500}$, 17 CLV3$^{R500}$/CLV3$^{R\text{-}o\text{-}18}$, and 20 CLV3$^{R\text{-}o\text{-}18}$/CLV3$^{R\text{-}o\text{-}18}$ were observed. This confirms that sup-c is not an allele of CLV3 and indicates that sup-c is linked to CLV3 (approximately 38 cM away).

It was determined whether the sup-c phenotype required the nrpd1 mutation, and observed 12 NRPD1/NRPD1, 27 NRPD1/nrpd1, and 7 nrpd1/nrpd1. This confirms that the multilocule phenotype of sup-c is independent from (and unlinked from) the nrpd1 mutation.

Figure 7:
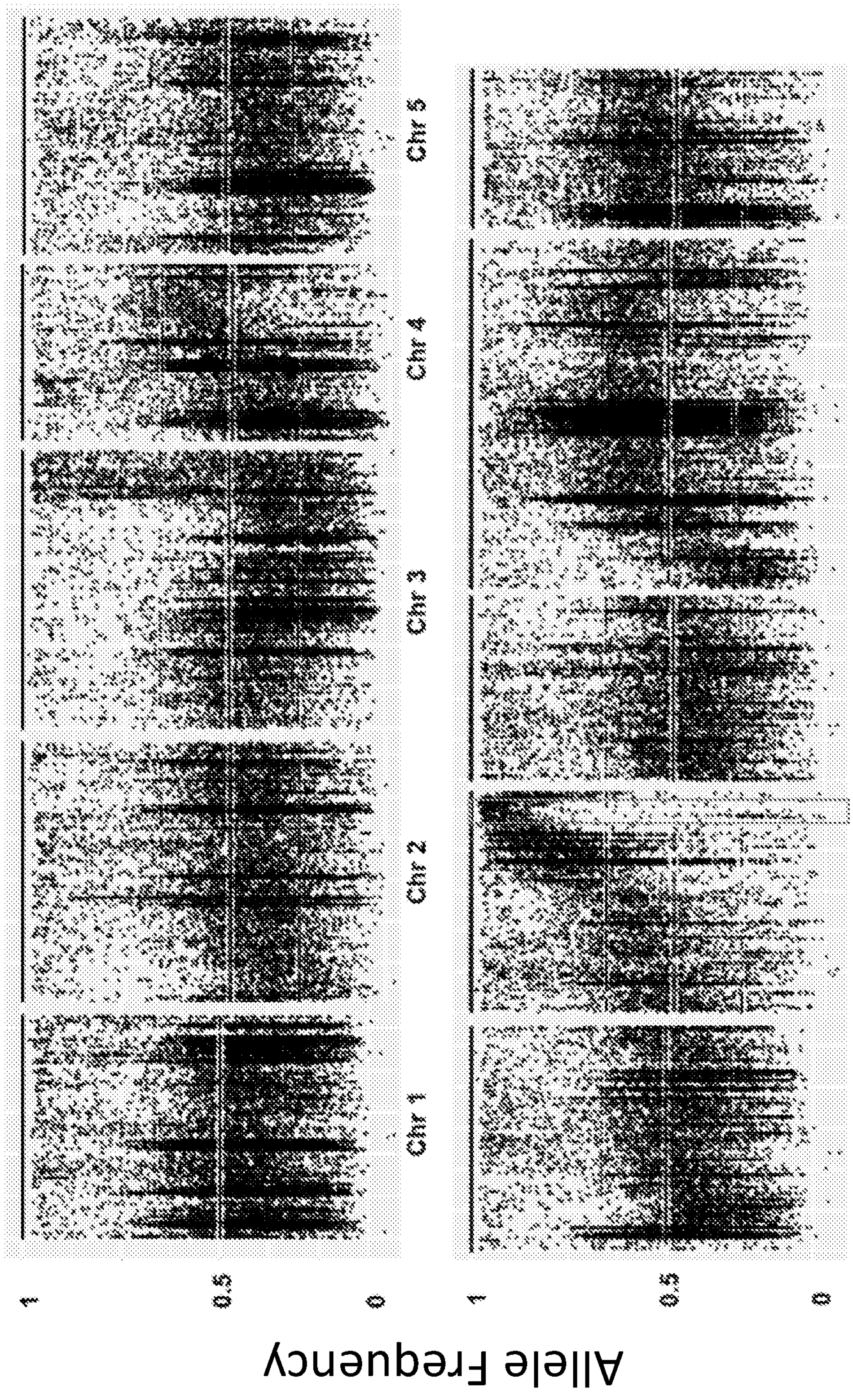
FIG. 7. SNP frequency when sup-c BSA-seq reads are mapped to the R500 reference genome.

Bulked Segregant Analysis sequencing (BSA-seq) was performed on the 46 F2 sup-c individuals. 207 million paired-end reads were obtained, of which 201 million mapped to the reference genomes. Analysis of SNP frequency indicates that the sup-c mutation is near the end of chromosome 7 (FIG. 7). This is consistent with its weak linkage to CLV3.

Reads were then aligned to the R-o-18 genome to identify putative mutations in a 4.15 Mb mapping interval. Various filtering steps narrowed the list to 2 putative mutations, one in a homolog of CLV1 and the second in a phosphoenolpyruvate carboxylase family protein.

Because of the role of CLAVATA (CLV) signaling in meristem size and locule number, it was concluded that the mutation in CLV1 is responsible for the multilocular phenotype of sup-c.

Example 2

An S582N Mutation in CLV1 Increases Locule Number in *Arabidopsis*

To determine whether the CLV1 S582N mutation conferred multilocularity in other Brassicaceae species, a transgene carrying this mutation was transformed into *Arabidopsis thaliana* that lacked functional CLV1. The *Brassica rapa* CLV1 genomic sequence (3.2 kb) with or without the S582N mutation was inserted between the Arabidopsis CLV1 promoter (4.0 kb) and the AtUBQ10 transcription terminator (0.4 kb) in a binary plasmid carrying an herbicide resistance gene (SEQ ID NOS: 102 and 103). These plasmids were independently transformed into *Agrobacterium*, and the resulting strains were used to transform the *Arabidopsis* clv1-11 T-DNA mutant via floral dip. Herbicide-resistant formants were selected and analyzed for silique morphology.

Figure 9:
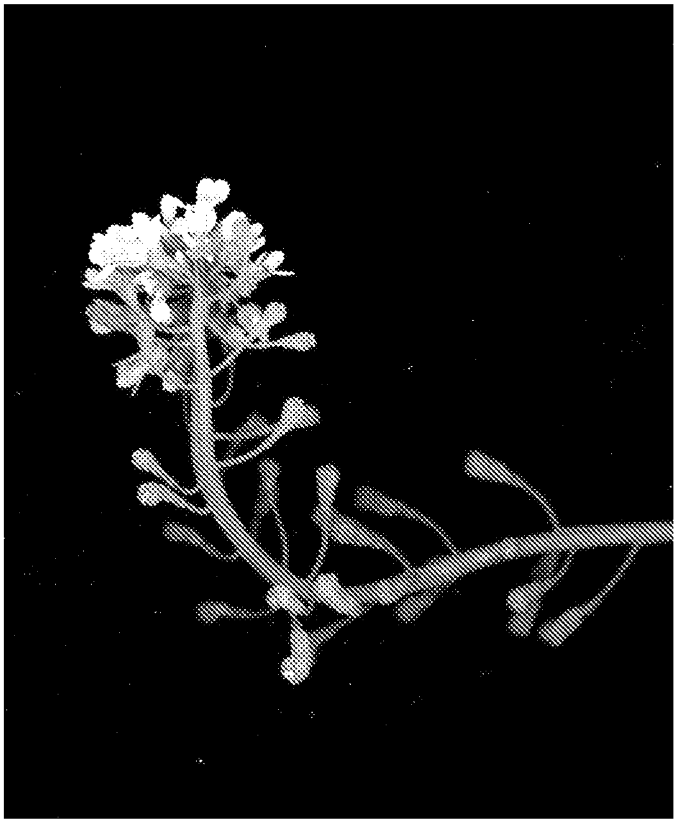
FIG. 9 is a digital image of an *Arabidopsis thaliana* plant expressing a CLV1 S582N transgene, showing this mutation confers multilocularity in other Brassicaceae species.

As shown in FIG. 9, plants carrying the CLV1-S582N transgene, but not the wild-type CLV1 transgene, had higher number of locules than the untransformed control. This confirms that the BrCLV1 with S582N mutation (or its equivalent) confers multilocularity to other Brassicaceae species.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. I therefore claim as my invention all that comes within the scope and spirit of these claims.

I claim:

1. An isolated mutant clavata 1 (CLV1) nucleic acid molecule, comprising a nucleic acid sequence encoding SEQ ID NO: 4.

2. A recombinant nucleic acid vector comprising the isolated mutant CLV1 nucleic acid molecule of claim 1.

3. A *Brassica rapa* cell or plant, comprising the isolated mutant CLV1 nucleic acid molecule of claim 1.

4. A recombinant plasmid, comprising:

the isolated nucleic acid molecule of claim 1, and a Cas9 coding sequence.

5. The isolated mutant CLV1 nucleic acid molecule of claim 1, comprising SEQ ID NO: 3.

6. The recombinant nucleic acid vector of claim 2, wherein the isolated mutant CLV1 nucleic acid molecule is operably linked to a promoter.

7. The recombinant nucleic acid vector of claim 2, wherein the vector is a plasmid or viral vector.

8. A plant cell or plant comprising the recombinant nucleic acid of claim 6, wherein the plant cell or plant is a species of Brassicaceae.

9. The plant cell or plant of claim 8, wherein the plant cell or plant is a species of *Brassica, Camelina*, or *Thlaspi* genus.

10. The plant cell or plant of claim 8, wherein the plant cell or plant is a crop plant.

11. The plant cell or plant of claim 10, wherein the crop plant is a fruit or vegetable.

12. The plant cell or plant of claim 11, wherein the vegetable is a canola, camelina, or pennycress.

13. The plant of claim 3, wherein the plant has increased locules as compared to a wild-type variety of the plant.

14. A bacterium comprising the isolated mutant CLV1 nucleic acid molecule of claim 1.

15. The bacterium of claim 14, wherein the bacterium is *Agrobacterium.*

16. The bacterium of claim 15, wherein the bacterium is *Agrobacterium tumefaciens.*

* * * * *

SEQUENCE LISTING

```
<160> NUMBER OF SEQ ID NOS: 103

<210> SEQ ID NO 1
<211> LENGTH: 2958
<212> TYPE: DNA
<213> ORGANISM: Brassica rapa
<220> FEATURE:
<221> NAME/KEY: CDS
<222> LOCATION: (1)..(2958)

<400> SEQUENCE: 1

atg aga ctt ctg aaa act cac ctt ctg ttt ctc cat ctt cat tac gtt        48
Met Arg Leu Leu Lys Thr His Leu Leu Phe Leu His Leu His Tyr Val
1               5                   10                  15

atc tcg att tcg ctt cta tgt ttc tca cca tgc ctc gct tcc act gac        96
Ile Ser Ile Ser Leu Leu Cys Phe Ser Pro Cys Leu Ala Ser Thr Asp
            20                  25                  30

atg gac cat ctc ctc aac ctc aaa tcc tcc atg att ggt ccc aac ggc       144
Met Asp His Leu Leu Asn Leu Lys Ser Ser Met Ile Gly Pro Asn Gly
        35                  40                  45

aac ggc ctc cac gac tgg gtt cac tcc cct tcc ccc aca gct cac tgt       192
Asn Gly Leu His Asp Trp Val His Ser Pro Ser Pro Thr Ala His Cys
    50                  55                  60

tct ttc tcc ggc gtt tcc tgc gac ggc gac gct cgt gtc atc tcc ctc       240
Ser Phe Ser Gly Val Ser Cys Asp Gly Asp Ala Arg Val Ile Ser Leu
65                  70                  75                  80

aac gtc tct ttc act cct ctc ttc gga acc atc tcc ccg gag att ggg       288
Asn Val Ser Phe Thr Pro Leu Phe Gly Thr Ile Ser Pro Glu Ile Gly
                85                  90                  95

atg ctg aac cgt ctt gtg aat ctc acg tta gct gct aat aac ttc tcc       336
Met Leu Asn Arg Leu Val Asn Leu Thr Leu Ala Ala Asn Asn Phe Ser
            100                 105                 110
```

-continued

```
ggt atg ttg ccg tta gag atg aag agt ctc act tct cta aag gtt ctc      384
Gly Met Leu Pro Leu Glu Met Lys Ser Leu Thr Ser Leu Lys Val Leu
        115                 120                 125

aac atc tcc aac aac gta aac ctc aac gga acg ttc ccc gga gag att      432
Asn Ile Ser Asn Asn Val Asn Leu Asn Gly Thr Phe Pro Gly Glu Ile
    130                 135                 140

ctc act ccc atg gtc gac ctc gaa gtc ctc gac gcg tac aac aac aac      480
Leu Thr Pro Met Val Asp Leu Glu Val Leu Asp Ala Tyr Asn Asn Asn
145                 150                 155                 160

ttc aca ggc cca tta ccg cca gag atc ccc ggg ctc aag aaa ctg aga      528
Phe Thr Gly Pro Leu Pro Pro Glu Ile Pro Gly Leu Lys Lys Leu Arg
                165                 170                 175

cac ctc tct ctc gga gga aac ttc tta acc gga gag atc cca gag agt      576
His Leu Ser Leu Gly Gly Asn Phe Leu Thr Gly Glu Ile Pro Glu Ser
            180                 185                 190

tac gga gat atc caa agc ttg gag tat ctc ggc ctc aac gga gcc gga      624
Tyr Gly Asp Ile Gln Ser Leu Glu Tyr Leu Gly Leu Asn Gly Ala Gly
        195                 200                 205

ctc tcc ggt gaa tct ccg gcg ttc ttg tca cgc ctc aag aat ctt aaa      672
Leu Ser Gly Glu Ser Pro Ala Phe Leu Ser Arg Leu Lys Asn Leu Lys
    210                 215                 220

gaa atg tac gtc ggc tac ttc aac agc tac acc ggc ggc gta ccg ccg      720
Glu Met Tyr Val Gly Tyr Phe Asn Ser Tyr Thr Gly Gly Val Pro Pro
225                 230                 235                 240

gag ttc ggt gaa ttg aca aac tta gaa gtc ctc gac atg gcg agc tgt      768
Glu Phe Gly Glu Leu Thr Asn Leu Glu Val Leu Asp Met Ala Ser Cys
                245                 250                 255

act ctc acc gga gag att ccg aca aca cta agt aat cta aaa cat ttg      816
Thr Leu Thr Gly Glu Ile Pro Thr Thr Leu Ser Asn Leu Lys His Leu
            260                 265                 270

cac act ttg ttt ctc cac atc aac aac tta acc gga aac atc cca ccc      864
His Thr Leu Phe Leu His Ile Asn Asn Leu Thr Gly Asn Ile Pro Pro
        275                 280                 285

gaa ctc tcc ggt tta atc agc tta aaa tct cta gac ctc tca ata aac      912
Glu Leu Ser Gly Leu Ile Ser Leu Lys Ser Leu Asp Leu Ser Ile Asn
    290                 295                 300

cag cta acc gga gag att cct cag agc ttc atc tcc cta ggg aac atc      960
Gln Leu Thr Gly Glu Ile Pro Gln Ser Phe Ile Ser Leu Gly Asn Ile
305                 310                 315                 320

act ctc atc aac ctc ttc cga aac aat ctc cac ggg ccg ata ccg gac     1008
Thr Leu Ile Asn Leu Phe Arg Asn Asn Leu His Gly Pro Ile Pro Asp
                325                 330                 335

ttc atc gga gac atg ccg aac ctc caa gtc ctc cag gtg tgg gag aac     1056
Phe Ile Gly Asp Met Pro Asn Leu Gln Val Leu Gln Val Trp Glu Asn
            340                 345                 350

aac ttc acg cta gag cta ccg gcg aat ctc ggc cgg aac ggg aat ctg     1104
Asn Phe Thr Leu Glu Leu Pro Ala Asn Leu Gly Arg Asn Gly Asn Leu
        355                 360                 365

aaa aag ctc gac gtc tct gat aac cat ctc acc gga ctc atc ccc atg     1152
Lys Lys Leu Asp Val Ser Asp Asn His Leu Thr Gly Leu Ile Pro Met
    370                 375                 380

gat ttg tgc aga ggc ggg aag ctg gag acg ctg gtg ctc tcc aac aac     1200
Asp Leu Cys Arg Gly Gly Lys Leu Glu Thr Leu Val Leu Ser Asn Asn
385                 390                 395                 400

ttc ttc ttc ggc tcg atc cct gag aag cta ggt caa tgc aaa tcg cta     1248
Phe Phe Phe Gly Ser Ile Pro Glu Lys Leu Gly Gln Cys Lys Ser Leu
                405                 410                 415

aac aag atc aga atc gtc aag aat ctc ctc aac ggc acg gtt ccg gag     1296
Asn Lys Ile Arg Ile Val Lys Asn Leu Leu Asn Gly Thr Val Pro Glu
            420                 425                 430
```

-continued

```
ggc tta ttc aat cta ccg ctc gta acg atc atc gag ctc acc gat aac      1344
Gly Leu Phe Asn Leu Pro Leu Val Thr Ile Ile Glu Leu Thr Asp Asn
        435                 440                 445

ttc ttc tcc ggg gag ctt ccg ggg gag atg tca ggc gac gtt ctc gat      1392
Phe Phe Ser Gly Glu Leu Pro Gly Glu Met Ser Gly Asp Val Leu Asp
    450                 455                 460

cat atc tac tta tct aac aat tgg ttt acc ggt tta atc ccc ccg gct      1440
His Ile Tyr Leu Ser Asn Asn Trp Phe Thr Gly Leu Ile Pro Pro Ala
465                 470                 475                 480

atc ggt aat ttt aaa aat cta cag gat tta ttc tta gac cgg aac cgg      1488
Ile Gly Asn Phe Lys Asn Leu Gln Asp Leu Phe Leu Asp Arg Asn Arg
                485                 490                 495

ttt agc ggg aat att ccg aga gaa gtt ttc gag ttg aag cat cta acg      1536
Phe Ser Gly Asn Ile Pro Arg Glu Val Phe Glu Leu Lys His Leu Thr
            500                 505                 510

aag atc aac acg agt gct aac aac cta acc ggc gat atc cct gac tca      1584
Lys Ile Asn Thr Ser Ala Asn Asn Leu Thr Gly Asp Ile Pro Asp Ser
        515                 520                 525

atc tca cgt tgc act tcc tta atc tcc gtc gat ctc agc cgt aac cga      1632
Ile Ser Arg Cys Thr Ser Leu Ile Ser Val Asp Leu Ser Arg Asn Arg
    530                 535                 540

atc ggc gga gat atc cct aaa gac atc cac gat gtg atc aat ctc gga      1680
Ile Gly Gly Asp Ile Pro Lys Asp Ile His Asp Val Ile Asn Leu Gly
545                 550                 555                 560

act cta aat ctc tcc ggg aat caa ctc acc ggc tcg atc ccg atc gga      1728
Thr Leu Asn Leu Ser Gly Asn Gln Leu Thr Gly Ser Ile Pro Ile Gly
                565                 570                 575

atc ggg aag atg acg agc tta acc act ctg gat ctc tcc ttc aac gac      1776
Ile Gly Lys Met Thr Ser Leu Thr Thr Leu Asp Leu Ser Phe Asn Asp
            580                 585                 590

ctc tcc ggg aga gtc cca ctc ggc ggc cag ttc cta gtc ttc aac gac      1824
Leu Ser Gly Arg Val Pro Leu Gly Gly Gln Phe Leu Val Phe Asn Asp
        595                 600                 605

act tcc ttc gcc gga aac cct tac ctc tgc ctc cct cac cac gtc tcg      1872
Thr Ser Phe Ala Gly Asn Pro Tyr Leu Cys Leu Pro His His Val Ser
    610                 615                 620

tgc ctt acg cgt ccg gaa caa acc tcc gat cgt atc cac acg gct ctc      1920
Cys Leu Thr Arg Pro Glu Gln Thr Ser Asp Arg Ile His Thr Ala Leu
625                 630                 635                 640

ttc tct ccg tcg agg atc gtt atc acg atc gtc gcg gcg ata acg gcg      1968
Phe Ser Pro Ser Arg Ile Val Ile Thr Ile Val Ala Ala Ile Thr Ala
                645                 650                 655

ttg atc ctc atc agc gtc gcg att cgt cag atg aac aag aag aaa cac      2016
Leu Ile Leu Ile Ser Val Ala Ile Arg Gln Met Asn Lys Lys Lys His
            660                 665                 670

gag agg tct ctc tcg tgg aag cta acc gcc ttc caa aga ctc gat ttc      2064
Glu Arg Ser Leu Ser Trp Lys Leu Thr Ala Phe Gln Arg Leu Asp Phe
        675                 680                 685

aaa gcg gaa gac gtc ctc gag tgt ctc cag gaa gag aac ata atc ggc      2112
Lys Ala Glu Asp Val Leu Glu Cys Leu Gln Glu Glu Asn Ile Ile Gly
    690                 695                 700

aaa ggc gga gct ggg atc gtc tac cgc gga tcc atg ccg aac aac gta      2160
Lys Gly Gly Ala Gly Ile Val Tyr Arg Gly Ser Met Pro Asn Asn Val
705                 710                 715                 720

gac gtc gcg atc aaa cgg tta gta gga cgc gga aca ggg agg agc gat      2208
Asp Val Ala Ile Lys Arg Leu Val Gly Arg Gly Thr Gly Arg Ser Asp
                725                 730                 735

cac gga ttc acg gcg gag ata caa act cta ggg aga atc cgc cac cgt      2256
His Gly Phe Thr Ala Glu Ile Gln Thr Leu Gly Arg Ile Arg His Arg
```

-continued

```
            740                 745                 750

cat ata gtg aga ctc ctc gga tac gtg gcg aac aag gac acg aac ctg      2304
His Ile Val Arg Leu Leu Gly Tyr Val Ala Asn Lys Asp Thr Asn Leu
        755                 760                 765

ctt ctc tac gag tac atg cct aac ggg agc ctc ggg gag ctt ttg cac      2352
Leu Leu Tyr Glu Tyr Met Pro Asn Gly Ser Leu Gly Glu Leu Leu His
    770                 775                 780

gga tct aaa gga ggt cat ctt cag tgg gag acg agg cac aga gta gcc      2400
Gly Ser Lys Gly Gly His Leu Gln Trp Glu Thr Arg His Arg Val Ala
785                 790                 795                 800

gtg gaa gcg gcg aaa gga ctg tgt tat ctt cat cat gac tgt tcg ccg      2448
Val Glu Ala Ala Lys Gly Leu Cys Tyr Leu His His Asp Cys Ser Pro
                805                 810                 815

ttg atc ttg cat aga gac gtt aag tcc aat aac ata cta ctg gac tct      2496
Leu Ile Leu His Arg Asp Val Lys Ser Asn Asn Ile Leu Leu Asp Ser
            820                 825                 830

gat ttt gag gcc cat gtt gct gat ttt ggg ctt gct aag ttc tta gtg      2544
Asp Phe Glu Ala His Val Ala Asp Phe Gly Leu Ala Lys Phe Leu Val
        835                 840                 845

gac ggt gct gct tct gag tgt atg tct tcg ata gct ggc tcc tat gga      2592
Asp Gly Ala Ala Ser Glu Cys Met Ser Ser Ile Ala Gly Ser Tyr Gly
    850                 855                 860

tac atc gct cca gag tat gct tac act ctc aaa gtg gac gag aag agt      2640
Tyr Ile Ala Pro Glu Tyr Ala Tyr Thr Leu Lys Val Asp Glu Lys Ser
865                 870                 875                 880

gat gtg tat agt ttc gga gtg gtg tta ttg gaa ctg ata gct ggg aag      2688
Asp Val Tyr Ser Phe Gly Val Val Leu Leu Glu Leu Ile Ala Gly Lys
                885                 890                 895

aaa ccg gtt ggt gag ttt ggg gaa gga gtg gat ata gtg agg tgg gtg      2736
Lys Pro Val Gly Glu Phe Gly Glu Gly Val Asp Ile Val Arg Trp Val
            900                 905                 910

agg aac acg gag ggt gag ata cct cag ccg tcg gat gca gct act gtt      2784
Arg Asn Thr Glu Gly Glu Ile Pro Gln Pro Ser Asp Ala Ala Thr Val
        915                 920                 925

gtg gcg atc gtt gac cag agg ttg act ggt tac ccg ttg act agt gtg      2832
Val Ala Ile Val Asp Gln Arg Leu Thr Gly Tyr Pro Leu Thr Ser Val
    930                 935                 940

att cac gtg ttc aag ata gcg atg atg tgt gtg gag gat gag gca gcg      2880
Ile His Val Phe Lys Ile Ala Met Met Cys Val Glu Asp Glu Ala Ala
945                 950                 955                 960

aca agg ccg acg atg agg gaa gtt gtg cac atg ctc act aac cct ccc      2928
Thr Arg Pro Thr Met Arg Glu Val Val His Met Leu Thr Asn Pro Pro
                965                 970                 975

aag tcc gtc act aac ttg atc gcc ttc tga                              2958
Lys Ser Val Thr Asn Leu Ile Ala Phe
            980                 985
```

<210> SEQ ID NO 2
<211> LENGTH: 985
<212> TYPE: PRT
<213> ORGANISM: Brassica rapa

<400> SEQUENCE: 2

```
Met Arg Leu Leu Lys Thr His Leu Leu Phe Leu His Leu His Tyr Val
1               5                   10                  15

Ile Ser Ile Ser Leu Leu Cys Phe Ser Pro Cys Leu Ala Ser Thr Asp
            20                  25                  30

Met Asp His Leu Leu Asn Leu Lys Ser Ser Met Ile Gly Pro Asn Gly
        35                  40                  45
```

-continued

```
Asn Gly Leu His Asp Trp Val His Ser Pro Ser Pro Thr Ala His Cys
    50                  55                  60

Ser Phe Ser Gly Val Ser Cys Asp Gly Asp Ala Arg Val Ile Ser Leu
65                  70                  75                  80

Asn Val Ser Phe Thr Pro Leu Phe Gly Thr Ile Ser Pro Glu Ile Gly
                85                  90                  95

Met Leu Asn Arg Leu Val Asn Leu Thr Leu Ala Ala Asn Asn Phe Ser
            100                 105                 110

Gly Met Leu Pro Leu Glu Met Lys Ser Leu Thr Ser Leu Lys Val Leu
        115                 120                 125

Asn Ile Ser Asn Asn Val Asn Leu Asn Gly Thr Phe Pro Gly Glu Ile
    130                 135                 140

Leu Thr Pro Met Val Asp Leu Glu Val Leu Asp Ala Tyr Asn Asn Asn
145                 150                 155                 160

Phe Thr Gly Pro Leu Pro Pro Glu Ile Pro Gly Leu Lys Lys Leu Arg
                165                 170                 175

His Leu Ser Leu Gly Gly Asn Phe Leu Thr Gly Glu Ile Pro Glu Ser
            180                 185                 190

Tyr Gly Asp Ile Gln Ser Leu Glu Tyr Leu Gly Leu Asn Gly Ala Gly
        195                 200                 205

Leu Ser Gly Glu Ser Pro Ala Phe Leu Ser Arg Leu Lys Asn Leu Lys
    210                 215                 220

Glu Met Tyr Val Gly Tyr Phe Asn Ser Tyr Thr Gly Gly Val Pro Pro
225                 230                 235                 240

Glu Phe Gly Glu Leu Thr Asn Leu Glu Val Leu Asp Met Ala Ser Cys
                245                 250                 255

Thr Leu Thr Gly Glu Ile Pro Thr Thr Leu Ser Asn Leu Lys His Leu
            260                 265                 270

His Thr Leu Phe Leu His Ile Asn Asn Leu Thr Gly Asn Ile Pro Pro
        275                 280                 285

Glu Leu Ser Gly Leu Ile Ser Leu Lys Ser Leu Asp Leu Ser Ile Asn
    290                 295                 300

Gln Leu Thr Gly Glu Ile Pro Gln Ser Phe Ile Ser Leu Gly Asn Ile
305                 310                 315                 320

Thr Leu Ile Asn Leu Phe Arg Asn Asn Leu His Gly Pro Ile Pro Asp
                325                 330                 335

Phe Ile Gly Asp Met Pro Asn Leu Gln Val Leu Gln Val Trp Glu Asn
            340                 345                 350

Asn Phe Thr Leu Glu Leu Pro Ala Asn Leu Gly Arg Asn Gly Asn Leu
        355                 360                 365

Lys Lys Leu Asp Val Ser Asp Asn His Leu Thr Gly Leu Ile Pro Met
    370                 375                 380

Asp Leu Cys Arg Gly Gly Lys Leu Glu Thr Leu Val Leu Ser Asn Asn
385                 390                 395                 400

Phe Phe Phe Gly Ser Ile Pro Glu Lys Leu Gly Gln Cys Lys Ser Leu
                405                 410                 415

Asn Lys Ile Arg Ile Val Lys Asn Leu Leu Asn Gly Thr Val Pro Glu
            420                 425                 430

Gly Leu Phe Asn Leu Pro Leu Val Thr Ile Ile Glu Leu Thr Asp Asn
        435                 440                 445

Phe Phe Ser Gly Glu Leu Pro Gly Glu Met Ser Gly Asp Val Leu Asp
    450                 455                 460

His Ile Tyr Leu Ser Asn Asn Trp Phe Thr Gly Leu Ile Pro Pro Ala
```

-continued

```
465                 470                 475                 480

Ile Gly Asn Phe Lys Asn Leu Gln Asp Leu Phe Leu Asp Arg Asn Arg
                485                 490                 495

Phe Ser Gly Asn Ile Pro Arg Glu Val Phe Glu Leu Lys His Leu Thr
            500                 505                 510

Lys Ile Asn Thr Ser Ala Asn Asn Leu Thr Gly Asp Ile Pro Asp Ser
        515                 520                 525

Ile Ser Arg Cys Thr Ser Leu Ile Ser Val Asp Leu Ser Arg Asn Arg
    530                 535                 540

Ile Gly Gly Asp Ile Pro Lys Asp Ile His Asp Val Ile Asn Leu Gly
545                 550                 555                 560

Thr Leu Asn Leu Ser Gly Asn Gln Leu Thr Gly Ser Ile Pro Ile Gly
                565                 570                 575

Ile Gly Lys Met Thr Ser Leu Thr Thr Leu Asp Leu Ser Phe Asn Asp
            580                 585                 590

Leu Ser Gly Arg Val Pro Leu Gly Gly Gln Phe Leu Val Phe Asn Asp
        595                 600                 605

Thr Ser Phe Ala Gly Asn Pro Tyr Leu Cys Leu Pro His His Val Ser
    610                 615                 620

Cys Leu Thr Arg Pro Glu Gln Thr Ser Asp Arg Ile His Thr Ala Leu
625                 630                 635                 640

Phe Ser Pro Ser Arg Ile Val Ile Thr Ile Val Ala Ala Ile Thr Ala
                645                 650                 655

Leu Ile Leu Ile Ser Val Ala Ile Arg Gln Met Asn Lys Lys Lys His
            660                 665                 670

Glu Arg Ser Leu Ser Trp Lys Leu Thr Ala Phe Gln Arg Leu Asp Phe
        675                 680                 685

Lys Ala Glu Asp Val Leu Glu Cys Leu Gln Glu Glu Asn Ile Ile Gly
    690                 695                 700

Lys Gly Gly Ala Gly Ile Val Tyr Arg Gly Ser Met Pro Asn Asn Val
705                 710                 715                 720

Asp Val Ala Ile Lys Arg Leu Val Gly Arg Gly Thr Gly Arg Ser Asp
                725                 730                 735

His Gly Phe Thr Ala Glu Ile Gln Thr Leu Gly Arg Ile Arg His Arg
            740                 745                 750

His Ile Val Arg Leu Leu Gly Tyr Val Ala Asn Lys Asp Thr Asn Leu
        755                 760                 765

Leu Leu Tyr Glu Tyr Met Pro Asn Gly Ser Leu Gly Glu Leu Leu His
    770                 775                 780

Gly Ser Lys Gly Gly His Leu Gln Trp Glu Thr Arg His Arg Val Ala
785                 790                 795                 800

Val Glu Ala Ala Lys Gly Leu Cys Tyr Leu His His Asp Cys Ser Pro
                805                 810                 815

Leu Ile Leu His Arg Asp Val Lys Ser Asn Asn Ile Leu Leu Asp Ser
            820                 825                 830

Asp Phe Glu Ala His Val Ala Asp Phe Gly Leu Ala Lys Phe Leu Val
        835                 840                 845

Asp Gly Ala Ala Ser Glu Cys Met Ser Ser Ile Ala Gly Ser Tyr Gly
    850                 855                 860

Tyr Ile Ala Pro Glu Tyr Ala Tyr Thr Leu Lys Val Asp Glu Lys Ser
865                 870                 875                 880

Asp Val Tyr Ser Phe Gly Val Val Leu Leu Glu Leu Ile Ala Gly Lys
                885                 890                 895
```

-continued

```
Lys Pro Val Gly Glu Phe Gly Glu Gly Val Asp Ile Val Arg Trp Val
            900                 905                 910

Arg Asn Thr Glu Gly Glu Ile Pro Gln Pro Ser Asp Ala Ala Thr Val
        915                 920                 925

Val Ala Ile Val Asp Gln Arg Leu Thr Gly Tyr Pro Leu Thr Ser Val
    930                 935                 940

Ile His Val Phe Lys Ile Ala Met Met Cys Val Glu Asp Glu Ala Ala
945                 950                 955                 960

Thr Arg Pro Thr Met Arg Glu Val Val His Met Leu Thr Asn Pro Pro
                965                 970                 975

Lys Ser Val Thr Asn Leu Ile Ala Phe
            980                 985


<210> SEQ ID NO 3
<211> LENGTH: 2958
<212> TYPE: DNA
<213> ORGANISM: Artificial Sequence
<220> FEATURE:
<223> OTHER INFORMATION: CLV1 S582N mutant
<220> FEATURE:
<221> NAME/KEY: CDS
<222> LOCATION: (1)..(2958)

<400> SEQUENCE: 3

atg aga ctt ctg aaa act cac ctt ctg ttt ctc cat ctt cat tac gtt       48
Met Arg Leu Leu Lys Thr His Leu Leu Phe Leu His Leu His Tyr Val
1               5                   10                  15

atc tcg att tcg ctt cta tgt ttc tca cca tgc ctc gct tcc act gac       96
Ile Ser Ile Ser Leu Leu Cys Phe Ser Pro Cys Leu Ala Ser Thr Asp
            20                  25                  30

atg gac cat ctc ctc aac ctc aaa tcc tcc atg att ggt ccc aac ggc      144
Met Asp His Leu Leu Asn Leu Lys Ser Ser Met Ile Gly Pro Asn Gly
        35                  40                  45

aac ggc ctc cac gac tgg gtt cac tcc cct tcc ccc aca gct cac tgt      192
Asn Gly Leu His Asp Trp Val His Ser Pro Ser Pro Thr Ala His Cys
    50                  55                  60

tct ttc tcc ggc gtt tcc tgc gac ggc gac gct cgt gtc atc tcc ctc      240
Ser Phe Ser Gly Val Ser Cys Asp Gly Asp Ala Arg Val Ile Ser Leu
65                  70                  75                  80

aac gtc tct ttc act cct ctc ttc gga acc atc tcc ccg gag att ggg      288
Asn Val Ser Phe Thr Pro Leu Phe Gly Thr Ile Ser Pro Glu Ile Gly
                85                  90                  95

atg ctg aac cgt ctt gtg aat ctc acg tta gct gct aat aac ttc tcc      336
Met Leu Asn Arg Leu Val Asn Leu Thr Leu Ala Ala Asn Asn Phe Ser
            100                 105                 110

ggt atg ttg ccg tta gag atg aag agt ctc act tct cta aag gtt ctc      384
Gly Met Leu Pro Leu Glu Met Lys Ser Leu Thr Ser Leu Lys Val Leu
        115                 120                 125

aac atc tcc aac aac gta aac ctc aac gga acg ttc ccc gga gag att      432
Asn Ile Ser Asn Asn Val Asn Leu Asn Gly Thr Phe Pro Gly Glu Ile
    130                 135                 140

ctc act ccc atg gtc gac ctc gaa gtc ctc gac gcg tac aac aac aac      480
Leu Thr Pro Met Val Asp Leu Glu Val Leu Asp Ala Tyr Asn Asn Asn
145                 150                 155                 160

ttc aca ggc cca tta ccg cca gag atc ccc ggg ctc aag aaa ctg aga      528
Phe Thr Gly Pro Leu Pro Pro Glu Ile Pro Gly Leu Lys Lys Leu Arg
                165                 170                 175

cac ctc tct ctc gga gga aac ttc tta acc gga gag atc cca gag agt      576
His Leu Ser Leu Gly Gly Asn Phe Leu Thr Gly Glu Ile Pro Glu Ser
            180                 185                 190
```

-continued

```
tac gga gat atc caa agc ttg gag tat ctc ggc ctc aac gga gcc gga      624
Tyr Gly Asp Ile Gln Ser Leu Glu Tyr Leu Gly Leu Asn Gly Ala Gly
        195                 200                 205

ctc tcc ggt gaa tct ccg gcg ttc ttg tca cgc ctc aag aat ctt aaa      672
Leu Ser Gly Glu Ser Pro Ala Phe Leu Ser Arg Leu Lys Asn Leu Lys
    210                 215                 220

gaa atg tac gtc ggc tac ttc aac agc tac acc ggc ggc gta ccg ccg      720
Glu Met Tyr Val Gly Tyr Phe Asn Ser Tyr Thr Gly Gly Val Pro Pro
225                 230                 235                 240

gag ttc ggt gaa ttg aca aac tta gaa gtc ctc gac atg gcg agc tgt      768
Glu Phe Gly Glu Leu Thr Asn Leu Glu Val Leu Asp Met Ala Ser Cys
                245                 250                 255

act ctc acc gga gag att ccg aca aca cta agt aat cta aaa cat ttg      816
Thr Leu Thr Gly Glu Ile Pro Thr Thr Leu Ser Asn Leu Lys His Leu
            260                 265                 270

cac act ttg ttt ctc cac atc aac aac tta acc gga aac atc cca ccc      864
His Thr Leu Phe Leu His Ile Asn Asn Leu Thr Gly Asn Ile Pro Pro
        275                 280                 285

gaa ctc tcc ggt tta atc agc tta aaa tct cta gac ctc tca ata aac      912
Glu Leu Ser Gly Leu Ile Ser Leu Lys Ser Leu Asp Leu Ser Ile Asn
    290                 295                 300

cag cta acc gga gag att cct cag agc ttc atc tcc cta ggg aac atc      960
Gln Leu Thr Gly Glu Ile Pro Gln Ser Phe Ile Ser Leu Gly Asn Ile
305                 310                 315                 320

act ctc atc aac ctc ttc cga aac aat ctc cac ggg ccg ata ccg gac     1008
Thr Leu Ile Asn Leu Phe Arg Asn Asn Leu His Gly Pro Ile Pro Asp
                325                 330                 335

ttc atc gga gac atg ccg aac ctc caa gtc ctc cag gtg tgg gag aac     1056
Phe Ile Gly Asp Met Pro Asn Leu Gln Val Leu Gln Val Trp Glu Asn
            340                 345                 350

aac ttc acg cta gag cta ccg gcg aat ctc ggc cgg aac ggg aat ctg     1104
Asn Phe Thr Leu Glu Leu Pro Ala Asn Leu Gly Arg Asn Gly Asn Leu
        355                 360                 365

aaa aag ctc gac gtc tct gat aac cat ctc acc gga ctc atc ccc atg     1152
Lys Lys Leu Asp Val Ser Asp Asn His Leu Thr Gly Leu Ile Pro Met
    370                 375                 380

gat ttg tgc aga ggc ggg aag ctg gag acg ctg gtg ctc tcc aac aac     1200
Asp Leu Cys Arg Gly Gly Lys Leu Glu Thr Leu Val Leu Ser Asn Asn
385                 390                 395                 400

ttc ttc ttc ggc tcg atc cct gag aag cta ggt caa tgc aaa tcg cta     1248
Phe Phe Phe Gly Ser Ile Pro Glu Lys Leu Gly Gln Cys Lys Ser Leu
                405                 410                 415

aac aag atc aga atc gtc aag aat ctc ctc aac ggc acg gtt ccg gag     1296
Asn Lys Ile Arg Ile Val Lys Asn Leu Leu Asn Gly Thr Val Pro Glu
            420                 425                 430

ggc tta ttc aat cta ccg ctc gta acg atc atc gag ctc acc gat aac     1344
Gly Leu Phe Asn Leu Pro Leu Val Thr Ile Ile Glu Leu Thr Asp Asn
        435                 440                 445

ttc ttc tcc ggg gag ctt ccg ggg gag atg tca ggc gac gtt ctc gat     1392
Phe Phe Ser Gly Glu Leu Pro Gly Glu Met Ser Gly Asp Val Leu Asp
    450                 455                 460

cat atc tac tta tct aac aat tgg ttt acc ggt tta atc ccc ccg gct     1440
His Ile Tyr Leu Ser Asn Asn Trp Phe Thr Gly Leu Ile Pro Pro Ala
465                 470                 475                 480

atc ggt aat ttt aaa aat cta cag gat tta ttc tta gac cgg aac cgg     1488
Ile Gly Asn Phe Lys Asn Leu Gln Asp Leu Phe Leu Asp Arg Asn Arg
                485                 490                 495

ttt agc ggg aat att ccg aga gaa gtt ttc gag ttg aag cat cta acg     1536
Phe Ser Gly Asn Ile Pro Arg Glu Val Phe Glu Leu Lys His Leu Thr
```

```
            500                 505                 510

aag atc aac acg agt gct aac aac cta acc ggc gat atc cct gac tca     1584
Lys Ile Asn Thr Ser Ala Asn Asn Leu Thr Gly Asp Ile Pro Asp Ser
        515                 520                 525

atc tca cgt tgc act tcc tta atc tcc gtc gat ctc agc cgt aac cga     1632
Ile Ser Arg Cys Thr Ser Leu Ile Ser Val Asp Leu Ser Arg Asn Arg
    530                 535                 540

atc ggc gga gat atc cct aaa gac atc cac gat gtg atc aat ctc gga     1680
Ile Gly Gly Asp Ile Pro Lys Asp Ile His Asp Val Ile Asn Leu Gly
545                 550                 555                 560

act cta aat ctc tcc ggg aat caa ctc acc ggc tcg atc ccg atc gga     1728
Thr Leu Asn Leu Ser Gly Asn Gln Leu Thr Gly Ser Ile Pro Ile Gly
                565                 570                 575

atc ggg aag atg acg aac tta acc act ctg gat ctc tcc ttc aac gac     1776
Ile Gly Lys Met Thr Asn Leu Thr Thr Leu Asp Leu Ser Phe Asn Asp
            580                 585                 590

ctc tcc ggg aga gtc cca ctc ggc ggc cag ttc cta gtc ttc aac gac     1824
Leu Ser Gly Arg Val Pro Leu Gly Gly Gln Phe Leu Val Phe Asn Asp
        595                 600                 605

act tcc ttc gcc gga aac cct tac ctc tgc ctc cct cac cac gtc tcg     1872
Thr Ser Phe Ala Gly Asn Pro Tyr Leu Cys Leu Pro His His Val Ser
    610                 615                 620

tgc ctt acg cgt ccg gaa caa acc tcc gat cgt atc cac acg gct ctc     1920
Cys Leu Thr Arg Pro Glu Gln Thr Ser Asp Arg Ile His Thr Ala Leu
625                 630                 635                 640

ttc tct ccg tcg agg atc gtt atc acg atc gtc gcg gcg ata acg gcg     1968
Phe Ser Pro Ser Arg Ile Val Ile Thr Ile Val Ala Ala Ile Thr Ala
                645                 650                 655

ttg atc ctc atc agc gtc gcg att cgt cag atg aac aag aag aaa cac     2016
Leu Ile Leu Ile Ser Val Ala Ile Arg Gln Met Asn Lys Lys Lys His
            660                 665                 670

gag agg tct ctc tcg tgg aag cta acc gcc ttc caa aga ctc gat ttc     2064
Glu Arg Ser Leu Ser Trp Lys Leu Thr Ala Phe Gln Arg Leu Asp Phe
        675                 680                 685

aaa gcg gaa gac gtc ctc gag tgt ctc cag gaa gag aac ata atc ggc     2112
Lys Ala Glu Asp Val Leu Glu Cys Leu Gln Glu Glu Asn Ile Ile Gly
    690                 695                 700

aaa ggc gga gct ggg atc gtc tac cgc gga tcc atg ccg aac aac gta     2160
Lys Gly Gly Ala Gly Ile Val Tyr Arg Gly Ser Met Pro Asn Asn Val
705                 710                 715                 720

gac gtc gcg atc aaa cgg tta gta gga cgc gga aca ggg agg agc gat     2208
Asp Val Ala Ile Lys Arg Leu Val Gly Arg Gly Thr Gly Arg Ser Asp
                725                 730                 735

cac gga ttc acg gcg gag ata caa act cta ggg aga atc cgc cac cgt     2256
His Gly Phe Thr Ala Glu Ile Gln Thr Leu Gly Arg Ile Arg His Arg
            740                 745                 750

cat ata gtg aga ctc ctc gga tac gtg gcg aac aag gac acg aac ctg     2304
His Ile Val Arg Leu Leu Gly Tyr Val Ala Asn Lys Asp Thr Asn Leu
        755                 760                 765

ctt ctc tac gag tac atg cct aac ggg agc ctc ggg gag ctt ttg cac     2352
Leu Leu Tyr Glu Tyr Met Pro Asn Gly Ser Leu Gly Glu Leu Leu His
    770                 775                 780

gga tct aaa gga ggt cat ctt cag tgg gag acg agg cac aga gta gcc     2400
Gly Ser Lys Gly Gly His Leu Gln Trp Glu Thr Arg His Arg Val Ala
785                 790                 795                 800

gtg gaa gcg gcg aaa gga ctg tgt tat ctt cat cat gac tgt tcg ccg     2448
Val Glu Ala Ala Lys Gly Leu Cys Tyr Leu His His Asp Cys Ser Pro
                805                 810                 815

ttg atc ttg cat aga gac gtt aag tcc aat aac ata cta ctg gac tct     2496
```

```
Leu Ile Leu His Arg Asp Val Lys Ser Asn Asn Ile Leu Leu Asp Ser
            820                 825                 830

gat ttt gag gcc cat gtt gct gat ttt ggg ctt gct aag ttc tta gtg     2544
Asp Phe Glu Ala His Val Ala Asp Phe Gly Leu Ala Lys Phe Leu Val
        835                 840                 845

gac ggt gct gct tct gag tgt atg tct tcg ata gct ggc tcc tat gga     2592
Asp Gly Ala Ala Ser Glu Cys Met Ser Ser Ile Ala Gly Ser Tyr Gly
    850                 855                 860

tac atc gct cca gag tat gct tac act ctc aaa gtg gac gag aag agt     2640
Tyr Ile Ala Pro Glu Tyr Ala Tyr Thr Leu Lys Val Asp Glu Lys Ser
865                 870                 875                 880

gat gtg tat agt ttc gga gtg gtg tta ttg gaa ctg ata gct ggg aag     2688
Asp Val Tyr Ser Phe Gly Val Val Leu Leu Glu Leu Ile Ala Gly Lys
                885                 890                 895

aaa ccg gtt ggt gag ttt ggg gaa gga gtg gat ata gtg agg tgg gtg     2736
Lys Pro Val Gly Glu Phe Gly Glu Gly Val Asp Ile Val Arg Trp Val
            900                 905                 910

agg aac acg gag ggt gag ata cct cag ccg tcg gat gca gct act gtt     2784
Arg Asn Thr Glu Gly Glu Ile Pro Gln Pro Ser Asp Ala Ala Thr Val
        915                 920                 925

gtg gcg atc gtt gac cag agg ttg act ggt tac ccg ttg act agt gtg     2832
Val Ala Ile Val Asp Gln Arg Leu Thr Gly Tyr Pro Leu Thr Ser Val
    930                 935                 940

att cac gtg ttc aag ata gcg atg atg tgt gtg gag gat gag gca gcg     2880
Ile His Val Phe Lys Ile Ala Met Met Cys Val Glu Asp Glu Ala Ala
945                 950                 955                 960

aca agg ccg acg atg agg gaa gtt gtg cac atg ctc act aac cct ccc     2928
Thr Arg Pro Thr Met Arg Glu Val Val His Met Leu Thr Asn Pro Pro
                965                 970                 975

aag tcc gtc act aac ttg atc gcc ttc tga                             2958
Lys Ser Val Thr Asn Leu Ile Ala Phe
            980                 985


<210> SEQ ID NO 4
<211> LENGTH: 985
<212> TYPE: PRT
<213> ORGANISM: Artificial Sequence
<220> FEATURE:
<223> OTHER INFORMATION: Synthetic Construct

<400> SEQUENCE: 4

Met Arg Leu Leu Lys Thr His Leu Leu Phe Leu His Leu His Tyr Val
1               5                   10                  15

Ile Ser Ile Ser Leu Leu Cys Phe Ser Pro Cys Leu Ala Ser Thr Asp
            20                  25                  30

Met Asp His Leu Leu Asn Leu Lys Ser Ser Met Ile Gly Pro Asn Gly
        35                  40                  45

Asn Gly Leu His Asp Trp Val His Ser Pro Ser Pro Thr Ala His Cys
    50                  55                  60

Ser Phe Ser Gly Val Ser Cys Asp Gly Asp Ala Arg Val Ile Ser Leu
65                  70                  75                  80

Asn Val Ser Phe Thr Pro Leu Phe Gly Thr Ile Ser Pro Glu Ile Gly
                85                  90                  95

Met Leu Asn Arg Leu Val Asn Leu Thr Leu Ala Ala Asn Asn Phe Ser
            100                 105                 110

Gly Met Leu Pro Leu Glu Met Lys Ser Leu Thr Ser Leu Lys Val Leu
        115                 120                 125

Asn Ile Ser Asn Asn Val Asn Leu Asn Gly Thr Phe Pro Gly Glu Ile
    130                 135                 140
```

-continued

```
Leu Thr Pro Met Val Asp Leu Glu Val Leu Asp Ala Tyr Asn Asn Asn
145                 150                 155                 160

Phe Thr Gly Pro Leu Pro Pro Glu Ile Pro Gly Leu Lys Lys Leu Arg
                165                 170                 175

His Leu Ser Leu Gly Gly Asn Phe Leu Thr Gly Glu Ile Pro Glu Ser
            180                 185                 190

Tyr Gly Asp Ile Gln Ser Leu Glu Tyr Leu Gly Leu Asn Gly Ala Gly
        195                 200                 205

Leu Ser Gly Glu Ser Pro Ala Phe Leu Ser Arg Leu Lys Asn Leu Lys
    210                 215                 220

Glu Met Tyr Val Gly Tyr Phe Asn Ser Tyr Thr Gly Gly Val Pro Pro
225                 230                 235                 240

Glu Phe Gly Glu Leu Thr Asn Leu Glu Val Leu Asp Met Ala Ser Cys
                245                 250                 255

Thr Leu Thr Gly Glu Ile Pro Thr Thr Leu Ser Asn Leu Lys His Leu
            260                 265                 270

His Thr Leu Phe Leu His Ile Asn Asn Leu Thr Gly Asn Ile Pro Pro
        275                 280                 285

Glu Leu Ser Gly Leu Ile Ser Leu Lys Ser Leu Asp Leu Ser Ile Asn
    290                 295                 300

Gln Leu Thr Gly Glu Ile Pro Gln Ser Phe Ile Ser Leu Gly Asn Ile
305                 310                 315                 320

Thr Leu Ile Asn Leu Phe Arg Asn Asn Leu His Gly Pro Ile Pro Asp
                325                 330                 335

Phe Ile Gly Asp Met Pro Asn Leu Gln Val Leu Gln Val Trp Glu Asn
            340                 345                 350

Asn Phe Thr Leu Glu Leu Pro Ala Asn Leu Gly Arg Asn Gly Asn Leu
        355                 360                 365

Lys Lys Leu Asp Val Ser Asp Asn His Leu Thr Gly Leu Ile Pro Met
    370                 375                 380

Asp Leu Cys Arg Gly Gly Lys Leu Glu Thr Leu Val Leu Ser Asn Asn
385                 390                 395                 400

Phe Phe Phe Gly Ser Ile Pro Glu Lys Leu Gly Gln Cys Lys Ser Leu
                405                 410                 415

Asn Lys Ile Arg Ile Val Lys Asn Leu Leu Asn Gly Thr Val Pro Glu
            420                 425                 430

Gly Leu Phe Asn Leu Pro Leu Val Thr Ile Ile Glu Leu Thr Asp Asn
        435                 440                 445

Phe Phe Ser Gly Glu Leu Pro Gly Glu Met Ser Gly Asp Val Leu Asp
    450                 455                 460

His Ile Tyr Leu Ser Asn Asn Trp Phe Thr Gly Leu Ile Pro Pro Ala
465                 470                 475                 480

Ile Gly Asn Phe Lys Asn Leu Gln Asp Leu Phe Leu Asp Arg Asn Arg
                485                 490                 495

Phe Ser Gly Asn Ile Pro Arg Glu Val Phe Glu Leu Lys His Leu Thr
            500                 505                 510

Lys Ile Asn Thr Ser Ala Asn Asn Leu Thr Gly Asp Ile Pro Asp Ser
        515                 520                 525

Ile Ser Arg Cys Thr Ser Leu Ile Ser Val Asp Leu Ser Arg Asn Arg
    530                 535                 540

Ile Gly Gly Asp Ile Pro Lys Asp Ile His Asp Val Ile Asn Leu Gly
545                 550                 555                 560
```

-continued

```
Thr Leu Asn Leu Ser Gly Asn Gln Leu Thr Gly Ser Ile Pro Ile Gly
                565                 570                 575

Ile Gly Lys Met Thr Asn Leu Thr Thr Leu Asp Leu Ser Phe Asn Asp
            580                 585                 590

Leu Ser Gly Arg Val Pro Leu Gly Gly Gln Phe Leu Val Phe Asn Asp
        595                 600                 605

Thr Ser Phe Ala Gly Asn Pro Tyr Leu Cys Leu Pro His His Val Ser
    610                 615                 620

Cys Leu Thr Arg Pro Glu Gln Thr Ser Asp Arg Ile His Thr Ala Leu
625                 630                 635                 640

Phe Ser Pro Ser Arg Ile Val Ile Thr Ile Val Ala Ala Ile Thr Ala
                645                 650                 655

Leu Ile Leu Ile Ser Val Ala Ile Arg Gln Met Asn Lys Lys Lys His
            660                 665                 670

Glu Arg Ser Leu Ser Trp Lys Leu Thr Ala Phe Gln Arg Leu Asp Phe
        675                 680                 685

Lys Ala Glu Asp Val Leu Glu Cys Leu Gln Glu Glu Asn Ile Ile Gly
    690                 695                 700

Lys Gly Gly Ala Gly Ile Val Tyr Arg Gly Ser Met Pro Asn Asn Val
705                 710                 715                 720

Asp Val Ala Ile Lys Arg Leu Val Gly Arg Gly Thr Gly Arg Ser Asp
                725                 730                 735

His Gly Phe Thr Ala Glu Ile Gln Thr Leu Gly Arg Ile Arg His Arg
            740                 745                 750

His Ile Val Arg Leu Leu Gly Tyr Val Ala Asn Lys Asp Thr Asn Leu
        755                 760                 765

Leu Leu Tyr Glu Tyr Met Pro Asn Gly Ser Leu Gly Glu Leu Leu His
    770                 775                 780

Gly Ser Lys Gly Gly His Leu Gln Trp Glu Thr Arg His Arg Val Ala
785                 790                 795                 800

Val Glu Ala Ala Lys Gly Leu Cys Tyr Leu His His Asp Cys Ser Pro
                805                 810                 815

Leu Ile Leu His Arg Asp Val Lys Ser Asn Asn Ile Leu Leu Asp Ser
            820                 825                 830

Asp Phe Glu Ala His Val Ala Asp Phe Gly Leu Ala Lys Phe Leu Val
        835                 840                 845

Asp Gly Ala Ala Ser Glu Cys Met Ser Ser Ile Ala Gly Ser Tyr Gly
    850                 855                 860

Tyr Ile Ala Pro Glu Tyr Ala Tyr Thr Leu Lys Val Asp Glu Lys Ser
865                 870                 875                 880

Asp Val Tyr Ser Phe Gly Val Val Leu Leu Glu Leu Ile Ala Gly Lys
                885                 890                 895

Lys Pro Val Gly Glu Phe Gly Glu Gly Val Asp Ile Val Arg Trp Val
            900                 905                 910

Arg Asn Thr Glu Gly Glu Ile Pro Gln Pro Ser Asp Ala Ala Thr Val
        915                 920                 925

Val Ala Ile Val Asp Gln Arg Leu Thr Gly Tyr Pro Leu Thr Ser Val
    930                 935                 940

Ile His Val Phe Lys Ile Ala Met Met Cys Val Glu Asp Glu Ala Ala
945                 950                 955                 960

Thr Arg Pro Thr Met Arg Glu Val Val His Met Leu Thr Asn Pro Pro
                965                 970                 975

Lys Ser Val Thr Asn Leu Ile Ala Phe
```

```
        980                 985


<210> SEQ ID NO 5
<211> LENGTH: 2898
<212> TYPE: DNA
<213> ORGANISM: Brassica napus
<220> FEATURE:
<221> NAME/KEY: CDS
<222> LOCATION: (1)..(2898)

<400> SEQUENCE: 5

atg gag atg aga ctt ctg aaa act cac ctt ctg ttt ctc cat ctt cat       48
Met Glu Met Arg Leu Leu Lys Thr His Leu Leu Phe Leu His Leu His
1               5                   10                  15

tac gtt atc tcg att tcg ctt cta tgt ttc gca cca tgc ctc gct tcc       96
Tyr Val Ile Ser Ile Ser Leu Leu Cys Phe Ala Pro Cys Leu Ala Ser
            20                  25                  30

act gac atg gac cat ctc ctc acc ctc aaa tcg tcc atg gtc ggt ccc      144
Thr Asp Met Asp His Leu Leu Thr Leu Lys Ser Ser Met Val Gly Pro
        35                  40                  45

aac ggc aac ggc ctc cac gac tgg gtt cac tcc cct tcc ccc aca gct      192
Asn Gly Asn Gly Leu His Asp Trp Val His Ser Pro Ser Pro Thr Ala
    50                  55                  60

cac tgt tct ttc tcc ggc gtt tcc tgc gac ggc gac gct cgt gtc atc      240
His Cys Ser Phe Ser Gly Val Ser Cys Asp Gly Asp Ala Arg Val Ile
65                  70                  75                  80

tcc ctc aac gtc tct ttc act cct ctc ttc gga acc atc tcc ccg gag      288
Ser Leu Asn Val Ser Phe Thr Pro Leu Phe Gly Thr Ile Ser Pro Glu
                85                  90                  95

att ggg atg ctg aac cgt ctt gtg aat ctc acg tta gct gct aat aac      336
Ile Gly Met Leu Asn Arg Leu Val Asn Leu Thr Leu Ala Ala Asn Asn
            100                 105                 110

ttc tcc ggt atg ttg ccg ctg gag atg aag agt ctc act tct cta aag      384
Phe Ser Gly Met Leu Pro Leu Glu Met Lys Ser Leu Thr Ser Leu Lys
        115                 120                 125

gtt ctc aac atc tcc aac aac gtg aac ctc aac ggg acc ttc ccc gga      432
Val Leu Asn Ile Ser Asn Asn Val Asn Leu Asn Gly Thr Phe Pro Gly
    130                 135                 140

gag att ctc act ccc atg gtg gac ctc gaa gtc ctc gac gcg tac aac      480
Glu Ile Leu Thr Pro Met Val Asp Leu Glu Val Leu Asp Ala Tyr Asn
145                 150                 155                 160

aac aac ttc aca ggc cca tta ccc ccg gag atc ccc ggg ctc aag aag      528
Asn Asn Phe Thr Gly Pro Leu Pro Pro Glu Ile Pro Gly Leu Lys Lys
                165                 170                 175

ctg aga cac ctc tct ctc gga ggt aac ttc tta acc gga gag atc cca      576
Leu Arg His Leu Ser Leu Gly Gly Asn Phe Leu Thr Gly Glu Ile Pro
            180                 185                 190

gag agt tac gga gat atc caa agc ttg gag tat ctt ggc ctc aac gga      624
Glu Ser Tyr Gly Asp Ile Gln Ser Leu Glu Tyr Leu Gly Leu Asn Gly
        195                 200                 205

gcc gga ctc tcc ggt gaa tct ccg gcg ttc ttg tca cgc ctc aag aat      672
Ala Gly Leu Ser Gly Glu Ser Pro Ala Phe Leu Ser Arg Leu Lys Asn
    210                 215                 220

ctt aaa gaa atg tac gtc ggc tac ttc aac agc tac acc ggc ggc gta      720
Leu Lys Glu Met Tyr Val Gly Tyr Phe Asn Ser Tyr Thr Gly Gly Val
225                 230                 235                 240

ccg ccg gag ttc ggt gaa ttg tca aac cta gag gtt ctc gac atg gcg      768
Pro Pro Glu Phe Gly Glu Leu Ser Asn Leu Glu Val Leu Asp Met Ala
                245                 250                 255

agc tgt act ctc acc gga gag att ccg aca aca cta agt aat cta aaa      816
Ser Cys Thr Leu Thr Gly Glu Ile Pro Thr Thr Leu Ser Asn Leu Lys
```

-continued

```
            260                 265                 270

cat ttg cac act ttg ttt ctc cac atc aac aac tta acc gga aac atc      864
His Leu His Thr Leu Phe Leu His Ile Asn Asn Leu Thr Gly Asn Ile
        275                 280                 285

cca ccc gaa ctc tcc ggt tta atc agc tta aaa tct cta gac ctc tca      912
Pro Pro Glu Leu Ser Gly Leu Ile Ser Leu Lys Ser Leu Asp Leu Ser
    290                 295                 300

ata aac cag cta acc gga gag att cct cag agc ttc atc tcc cta ggg      960
Ile Asn Gln Leu Thr Gly Glu Ile Pro Gln Ser Phe Ile Ser Leu Gly
305                 310                 315                 320

aac atc act ctc atc aac ctc ttc cga aac aat ctc cac ggg ccg ata     1008
Asn Ile Thr Leu Ile Asn Leu Phe Arg Asn Asn Leu His Gly Pro Ile
                325                 330                 335

ccg gac ttc atc gga gac atg ccg aac ctc caa gtc ctc caa ctc gac     1056
Pro Asp Phe Ile Gly Asp Met Pro Asn Leu Gln Val Leu Gln Leu Asp
            340                 345                 350

gtc tct gat aac cat ctc acc gga ctc atc ccc atg gat tta tgc aga     1104
Val Ser Asp Asn His Leu Thr Gly Leu Ile Pro Met Asp Leu Cys Arg
        355                 360                 365

ggc ggg aag ctg gag acg ctg gtg ctc tcc aac aac ttc ttc ttc ggc     1152
Gly Gly Lys Leu Glu Thr Leu Val Leu Ser Asn Asn Phe Phe Phe Gly
    370                 375                 380

tcg atc cct gag aag cta ggt caa tgc aaa tcg cta aac aag atc aga     1200
Ser Ile Pro Glu Lys Leu Gly Gln Cys Lys Ser Leu Asn Lys Ile Arg
385                 390                 395                 400

atc gtc aag aat ctc ctc aac ggt acg gtt ccg gag gga tta ttc aat     1248
Ile Val Lys Asn Leu Leu Asn Gly Thr Val Pro Glu Gly Leu Phe Asn
                405                 410                 415

cta ccg ctc gtt acg atc atc gag ctc acc gat aac ttc ttc tcc gga     1296
Leu Pro Leu Val Thr Ile Ile Glu Leu Thr Asp Asn Phe Phe Ser Gly
            420                 425                 430

gag ctt ccg ggg gag atg tca ggc gac gtt ctc gat cat atc tac tta     1344
Glu Leu Pro Gly Glu Met Ser Gly Asp Val Leu Asp His Ile Tyr Leu
        435                 440                 445

tct aac aat tgg ttt tcc ggt tta atc cct ccg gct atc ggt aat ttt     1392
Ser Asn Asn Trp Phe Ser Gly Leu Ile Pro Pro Ala Ile Gly Asn Phe
    450                 455                 460

aaa aat cta cag gat tta ttc tta gac cgg aac cgg ttt agc ggg aat     1440
Lys Asn Leu Gln Asp Leu Phe Leu Asp Arg Asn Arg Phe Ser Gly Asn
465                 470                 475                 480

att ccg agg gaa gtt ttc gag tta aag cat cta acg aag atc aac acg     1488
Ile Pro Arg Glu Val Phe Glu Leu Lys His Leu Thr Lys Ile Asn Thr
                485                 490                 495

agt gct aac aac cta acc ggc gac atc cct gac tca atc tca cgt tgc     1536
Ser Ala Asn Asn Leu Thr Gly Asp Ile Pro Asp Ser Ile Ser Arg Cys
            500                 505                 510

act tcc tta atc tcc gtc gat ctc agc cgt aac cga atc ggc gga gat     1584
Thr Ser Leu Ile Ser Val Asp Leu Ser Arg Asn Arg Ile Gly Gly Asp
        515                 520                 525

atc cct aaa gac atc cac gat gtg atg aat ctc gga act cta aat ctc     1632
Ile Pro Lys Asp Ile His Asp Val Met Asn Leu Gly Thr Leu Asn Leu
    530                 535                 540

tcc ggg aat caa ctc acc ggc tcg atc ccg atc gga atc ggg aag atg     1680
Ser Gly Asn Gln Leu Thr Gly Ser Ile Pro Ile Gly Ile Gly Lys Met
545                 550                 555                 560

acg agc tta acc act ctg gat ctc tcc ttc aac gac ctc tcc ggg aga     1728
Thr Ser Leu Thr Thr Leu Asp Leu Ser Phe Asn Asp Leu Ser Gly Arg
                565                 570                 575

gtc cca ctc ggc ggc cag ttc cta gtc ttc aac gac act tcc ttc gcc     1776
```

-continued

```
Val Pro Leu Gly Gly Gln Phe Leu Val Phe Asn Asp Thr Ser Phe Ala
            580                 585                 590

gga aac cct tac ctc tgc ctc cct cac cac gtc tcg tgc ctt acg cgt      1824
Gly Asn Pro Tyr Leu Cys Leu Pro His His Val Ser Cys Leu Thr Arg
        595                 600                 605

ccg gaa caa acc tcc gat cgt atc cac acg gct ctc ttc tct ccg tcg      1872
Pro Glu Gln Thr Ser Asp Arg Ile His Thr Ala Leu Phe Ser Pro Ser
    610                 615                 620

agg atc gtt atc acg atc gtc gcg gcg ata acg gcg ttg atc ctc atc      1920
Arg Ile Val Ile Thr Ile Val Ala Ala Ile Thr Ala Leu Ile Leu Ile
625                 630                 635                 640

agc gtc gcg att cgt cag atg aac aag aag aag cac gag aga tct ctc      1968
Ser Val Ala Ile Arg Gln Met Asn Lys Lys Lys His Glu Arg Ser Leu
                645                 650                 655

tcc tgg aag cta acc gcc ttc caa aga ctc gat ttc aaa gcc gaa gac      2016
Ser Trp Lys Leu Thr Ala Phe Gln Arg Leu Asp Phe Lys Ala Glu Asp
            660                 665                 670

gtc ctc gag tgc ctc caa gag gaa aac atc atc ggc aaa ggc gga gcg      2064
Val Leu Glu Cys Leu Gln Glu Glu Asn Ile Ile Gly Lys Gly Gly Ala
        675                 680                 685

ggg atc gtc tac cgc gga tcc atg ccg aac aat gtc gac gtc gcg atc      2112
Gly Ile Val Tyr Arg Gly Ser Met Pro Asn Asn Val Asp Val Ala Ile
    690                 695                 700

aaa cgc ctt gtg gga cgc gga aca ggg agg agc gat cac gga ttc acg      2160
Lys Arg Leu Val Gly Arg Gly Thr Gly Arg Ser Asp His Gly Phe Thr
705                 710                 715                 720

gcg gag ata caa act cta ggg aga atc cgc cac cgt cat ata gtt aga      2208
Ala Glu Ile Gln Thr Leu Gly Arg Ile Arg His Arg His Ile Val Arg
                725                 730                 735

ctc ctc gga tac gtg gcg aac aag gac acg aac ctg ctt ctc tac gag      2256
Leu Leu Gly Tyr Val Ala Asn Lys Asp Thr Asn Leu Leu Leu Tyr Glu
            740                 745                 750

tac atg cct aac ggg agc ctc ggc gag ctt ttg cac ggt tct aaa gga      2304
Tyr Met Pro Asn Gly Ser Leu Gly Glu Leu Leu His Gly Ser Lys Gly
        755                 760                 765

ggt cat ctt cag tgg gag acg agg cac aga gta gcc gtt gaa gcg gcg      2352
Gly His Leu Gln Trp Glu Thr Arg His Arg Val Ala Val Glu Ala Ala
    770                 775                 780

aaa gga ctg tgt tat ctt cat cat gac tgt tcg ccg ttg atc ttg cat      2400
Lys Gly Leu Cys Tyr Leu His His Asp Cys Ser Pro Leu Ile Leu His
785                 790                 795                 800

aga gac gtt aag tcc aat aac att tta ctg gac tct gat ttt gag gcc      2448
Arg Asp Val Lys Ser Asn Asn Ile Leu Leu Asp Ser Asp Phe Glu Ala
                805                 810                 815

cat gtt gct gat ttt ggg ctt gct aag ttc tta gtg gac ggt gct gct      2496
His Val Ala Asp Phe Gly Leu Ala Lys Phe Leu Val Asp Gly Ala Ala
            820                 825                 830

tct gag tgt atg tct tcg ata gct ggc tcc tat gga tac atc gct cca      2544
Ser Glu Cys Met Ser Ser Ile Ala Gly Ser Tyr Gly Tyr Ile Ala Pro
        835                 840                 845

gag tat gct tac act ctc aaa gtg gat gag aag agt gat gtg tat agt      2592
Glu Tyr Ala Tyr Thr Leu Lys Val Asp Glu Lys Ser Asp Val Tyr Ser
    850                 855                 860

ttc gga gtg gtg tta ttg gag ctg ata gct ggg aag aaa ccg gtt ggt      2640
Phe Gly Val Val Leu Leu Glu Leu Ile Ala Gly Lys Lys Pro Val Gly
865                 870                 875                 880

gag ttt ggg gaa gga gtg gat ata gtt agg tgg gtg agg aac acg gag      2688
Glu Phe Gly Glu Gly Val Asp Ile Val Arg Trp Val Arg Asn Thr Glu
                885                 890                 895
```

-continued

```
ggt gag ata cct cag ccg tcg gat gca gct act gtt gtg gcg atc gtt      2736
Gly Glu Ile Pro Gln Pro Ser Asp Ala Ala Thr Val Val Ala Ile Val
            900                 905                 910

gac cag agg ttg act ggt tac ccg ttg act agt gtg att cac gtg ttc      2784
Asp Gln Arg Leu Thr Gly Tyr Pro Leu Thr Ser Val Ile His Val Phe
        915                 920                 925

aag ata gcg atg atg tgt gtg gag gat gag gca gcg aca agg ccg acg      2832
Lys Ile Ala Met Met Cys Val Glu Asp Glu Ala Ala Thr Arg Pro Thr
    930                 935                 940

atg agg gaa gtt gtg cac atg ctc act aac cct ccc aag tcc gtc act      2880
Met Arg Glu Val Val His Met Leu Thr Asn Pro Pro Lys Ser Val Thr
945                 950                 955                 960

aac ttg atc gcc ttc tga                                              2898
Asn Leu Ile Ala Phe
                965


<210> SEQ ID NO 6
<211> LENGTH: 965
<212> TYPE: PRT
<213> ORGANISM: Brassica napus

<400> SEQUENCE: 6

Met Glu Met Arg Leu Leu Lys Thr His Leu Leu Phe Leu His Leu His
1               5                   10                  15

Tyr Val Ile Ser Ile Ser Leu Leu Cys Phe Ala Pro Cys Leu Ala Ser
            20                  25                  30

Thr Asp Met Asp His Leu Leu Thr Leu Lys Ser Ser Met Val Gly Pro
        35                  40                  45

Asn Gly Asn Gly Leu His Asp Trp Val His Ser Pro Ser Pro Thr Ala
    50                  55                  60

His Cys Ser Phe Ser Gly Val Ser Cys Asp Gly Asp Ala Arg Val Ile
65                  70                  75                  80

Ser Leu Asn Val Ser Phe Thr Pro Leu Phe Gly Thr Ile Ser Pro Glu
                85                  90                  95

Ile Gly Met Leu Asn Arg Leu Val Asn Leu Thr Leu Ala Ala Asn Asn
            100                 105                 110

Phe Ser Gly Met Leu Pro Leu Glu Met Lys Ser Leu Thr Ser Leu Lys
        115                 120                 125

Val Leu Asn Ile Ser Asn Asn Val Asn Leu Asn Gly Thr Phe Pro Gly
    130                 135                 140

Glu Ile Leu Thr Pro Met Val Asp Leu Glu Val Leu Asp Ala Tyr Asn
145                 150                 155                 160

Asn Asn Phe Thr Gly Pro Leu Pro Pro Glu Ile Pro Gly Leu Lys Lys
                165                 170                 175

Leu Arg His Leu Ser Leu Gly Gly Asn Phe Leu Thr Gly Glu Ile Pro
            180                 185                 190

Glu Ser Tyr Gly Asp Ile Gln Ser Leu Glu Tyr Leu Gly Leu Asn Gly
        195                 200                 205

Ala Gly Leu Ser Gly Glu Ser Pro Ala Phe Leu Ser Arg Leu Lys Asn
    210                 215                 220

Leu Lys Glu Met Tyr Val Gly Tyr Phe Asn Ser Tyr Thr Gly Gly Val
225                 230                 235                 240

Pro Pro Glu Phe Gly Glu Leu Ser Asn Leu Glu Val Leu Asp Met Ala
                245                 250                 255

Ser Cys Thr Leu Thr Gly Glu Ile Pro Thr Thr Leu Ser Asn Leu Lys
            260                 265                 270
```

-continued

```
His Leu His Thr Leu Phe Leu His Ile Asn Asn Leu Thr Gly Asn Ile
        275                 280                 285

Pro Pro Glu Leu Ser Gly Leu Ile Ser Leu Lys Ser Leu Asp Leu Ser
    290                 295                 300

Ile Asn Gln Leu Thr Gly Glu Ile Pro Gln Ser Phe Ile Ser Leu Gly
305                 310                 315                 320

Asn Ile Thr Leu Ile Asn Leu Phe Arg Asn Asn Leu His Gly Pro Ile
                325                 330                 335

Pro Asp Phe Ile Gly Asp Met Pro Asn Leu Gln Val Leu Gln Leu Asp
            340                 345                 350

Val Ser Asp Asn His Leu Thr Gly Leu Ile Pro Met Asp Leu Cys Arg
        355                 360                 365

Gly Gly Lys Leu Glu Thr Leu Val Leu Ser Asn Asn Phe Phe Phe Gly
    370                 375                 380

Ser Ile Pro Glu Lys Leu Gly Gln Cys Lys Ser Leu Asn Lys Ile Arg
385                 390                 395                 400

Ile Val Lys Asn Leu Leu Asn Gly Thr Val Pro Glu Gly Leu Phe Asn
                405                 410                 415

Leu Pro Leu Val Thr Ile Ile Glu Leu Thr Asp Asn Phe Phe Ser Gly
            420                 425                 430

Glu Leu Pro Gly Glu Met Ser Gly Asp Val Leu Asp His Ile Tyr Leu
        435                 440                 445

Ser Asn Asn Trp Phe Ser Gly Leu Ile Pro Pro Ala Ile Gly Asn Phe
    450                 455                 460

Lys Asn Leu Gln Asp Leu Phe Leu Asp Arg Asn Arg Phe Ser Gly Asn
465                 470                 475                 480

Ile Pro Arg Glu Val Phe Glu Leu Lys His Leu Thr Lys Ile Asn Thr
                485                 490                 495

Ser Ala Asn Asn Leu Thr Gly Asp Ile Pro Asp Ser Ile Ser Arg Cys
            500                 505                 510

Thr Ser Leu Ile Ser Val Asp Leu Ser Arg Asn Arg Ile Gly Gly Asp
        515                 520                 525

Ile Pro Lys Asp Ile His Asp Val Met Asn Leu Gly Thr Leu Asn Leu
    530                 535                 540

Ser Gly Asn Gln Leu Thr Gly Ser Ile Pro Ile Gly Ile Gly Lys Met
545                 550                 555                 560

Thr Ser Leu Thr Thr Leu Asp Leu Ser Phe Asn Asp Leu Ser Gly Arg
                565                 570                 575

Val Pro Leu Gly Gly Gln Phe Leu Val Phe Asn Asp Thr Ser Phe Ala
            580                 585                 590

Gly Asn Pro Tyr Leu Cys Leu Pro His His Val Ser Cys Leu Thr Arg
        595                 600                 605

Pro Glu Gln Thr Ser Asp Arg Ile His Thr Ala Leu Phe Ser Pro Ser
    610                 615                 620

Arg Ile Val Ile Thr Ile Val Ala Ala Ile Thr Ala Leu Ile Leu Ile
625                 630                 635                 640

Ser Val Ala Ile Arg Gln Met Asn Lys Lys Lys His Glu Arg Ser Leu
                645                 650                 655

Ser Trp Lys Leu Thr Ala Phe Gln Arg Leu Asp Phe Lys Ala Glu Asp
            660                 665                 670

Val Leu Glu Cys Leu Gln Glu Glu Asn Ile Ile Gly Lys Gly Gly Ala
        675                 680                 685

Gly Ile Val Tyr Arg Gly Ser Met Pro Asn Asn Val Asp Val Ala Ile
```

-continued

```
    690                 695                 700

Lys Arg Leu Val Gly Arg Gly Thr Gly Arg Ser Asp His Gly Phe Thr
705                 710                 715                 720

Ala Glu Ile Gln Thr Leu Gly Arg Ile Arg His Arg His Ile Val Arg
                725                 730                 735

Leu Leu Gly Tyr Val Ala Asn Lys Asp Thr Asn Leu Leu Leu Tyr Glu
            740                 745                 750

Tyr Met Pro Asn Gly Ser Leu Gly Glu Leu Leu His Gly Ser Lys Gly
        755                 760                 765

Gly His Leu Gln Trp Glu Thr Arg His Arg Val Ala Val Glu Ala Ala
    770                 775                 780

Lys Gly Leu Cys Tyr Leu His His Asp Cys Ser Pro Leu Ile Leu His
785                 790                 795                 800

Arg Asp Val Lys Ser Asn Asn Ile Leu Leu Asp Ser Asp Phe Glu Ala
                805                 810                 815

His Val Ala Asp Phe Gly Leu Ala Lys Phe Leu Val Asp Gly Ala Ala
            820                 825                 830

Ser Glu Cys Met Ser Ser Ile Ala Gly Ser Tyr Gly Tyr Ile Ala Pro
        835                 840                 845

Glu Tyr Ala Tyr Thr Leu Lys Val Asp Glu Lys Ser Asp Val Tyr Ser
    850                 855                 860

Phe Gly Val Val Leu Leu Glu Leu Ile Ala Gly Lys Lys Pro Val Gly
865                 870                 875                 880

Glu Phe Gly Glu Gly Val Asp Ile Val Arg Trp Val Arg Asn Thr Glu
                885                 890                 895

Gly Glu Ile Pro Gln Pro Ser Asp Ala Ala Thr Val Val Ala Ile Val
            900                 905                 910

Asp Gln Arg Leu Thr Gly Tyr Pro Leu Thr Ser Val Ile His Val Phe
        915                 920                 925

Lys Ile Ala Met Met Cys Val Glu Asp Glu Ala Ala Thr Arg Pro Thr
    930                 935                 940

Met Arg Glu Val Val His Met Leu Thr Asn Pro Pro Lys Ser Val Thr
945                 950                 955                 960

Asn Leu Ile Ala Phe
                965


<210> SEQ ID NO 7
<211> LENGTH: 2964
<212> TYPE: DNA
<213> ORGANISM: Brassica rapa
<220> FEATURE:
<221> NAME/KEY: CDS
<222> LOCATION: (1)..(2964)

<400> SEQUENCE: 7

atg gag atg aga ctt ttg aaa act cac ctt ctg ttt ctc cat ctt cat       48
Met Glu Met Arg Leu Leu Lys Thr His Leu Leu Phe Leu His Leu His
1               5                   10                  15

tac gtt atc tcg att ttg ctt ctg tct ttc tca cca tgc ttc gct tcc       96
Tyr Val Ile Ser Ile Leu Leu Leu Ser Phe Ser Pro Cys Phe Ala Ser
            20                  25                  30

act gac atg gac cat ctc ctc acc ctc aaa tcc tcc atg gtc ggc ccc      144
Thr Asp Met Asp His Leu Leu Thr Leu Lys Ser Ser Met Val Gly Pro
        35                  40                  45

aac ggc cac ggc ctc cac gac tgg gtt cac tcc act tct ccc tca gct      192
Asn Gly His Gly Leu His Asp Trp Val His Ser Thr Ser Pro Ser Ala
    50                  55                  60
```

-continued

```
cac tgt tct ttc tcc ggc gtt tcc tgc gac ggc gac gct cgt gtc atc      240
His Cys Ser Phe Ser Gly Val Ser Cys Asp Gly Asp Ala Arg Val Ile
65                  70                  75                  80

tcc ctc aac gtc tct ttc act cct ctc ttc gga acc atc tcc ccg gag      288
Ser Leu Asn Val Ser Phe Thr Pro Leu Phe Gly Thr Ile Ser Pro Glu
                85                  90                  95

att ggg atg ctg gac cgt ctc gtg aat ctg acg tta gct gct aat aat      336
Ile Gly Met Leu Asp Arg Leu Val Asn Leu Thr Leu Ala Ala Asn Asn
            100                 105                 110

ttc tcc ggt atg ctc ccg ttg gag atg aag agt ctc act tct cta aag      384
Phe Ser Gly Met Leu Pro Leu Glu Met Lys Ser Leu Thr Ser Leu Lys
        115                 120                 125

gtt ctc aac atc tcc aac aac gtg aac ctc aac gga acc ttc ccc gga      432
Val Leu Asn Ile Ser Asn Asn Val Asn Leu Asn Gly Thr Phe Pro Gly
    130                 135                 140

gag att ctc act ccc atg gtc gac ctc gaa gtc ctc gac gcg tac aac      480
Glu Ile Leu Thr Pro Met Val Asp Leu Glu Val Leu Asp Ala Tyr Asn
145                 150                 155                 160

aac aac ttc aca ggc cca cta ccg ccg gag atc ccc ggg ctc aag aag      528
Asn Asn Phe Thr Gly Pro Leu Pro Pro Glu Ile Pro Gly Leu Lys Lys
                165                 170                 175

ctg aga cac ctc tct ctc gga gga aac ttc tta acc gga gaa atc cca      576
Leu Arg His Leu Ser Leu Gly Gly Asn Phe Leu Thr Gly Glu Ile Pro
            180                 185                 190

gag agt tac gga gat atc cag agc ttg gag tat ctt ggc ctc aac gga      624
Glu Ser Tyr Gly Asp Ile Gln Ser Leu Glu Tyr Leu Gly Leu Asn Gly
        195                 200                 205

gcc gga ctc tcc ggc gaa tct ccg gcg ttc ttg tct cgc ctc aag aat      672
Ala Gly Leu Ser Gly Glu Ser Pro Ala Phe Leu Ser Arg Leu Lys Asn
    210                 215                 220

ctt aaa gaa atg tac gtc ggc tac ttc aac agc tac acc ggc ggc gta      720
Leu Lys Glu Met Tyr Val Gly Tyr Phe Asn Ser Tyr Thr Gly Gly Val
225                 230                 235                 240

ccg ccg gag ttc ggt gaa ttg aca aac cta gag gtt ctc gac atg gcg      768
Pro Pro Glu Phe Gly Glu Leu Thr Asn Leu Glu Val Leu Asp Met Ala
                245                 250                 255

agc tgt aca ctc acg gga gag att ccg acg act ctg agt aat cta aaa      816
Ser Cys Thr Leu Thr Gly Glu Ile Pro Thr Thr Leu Ser Asn Leu Lys
            260                 265                 270

cat ttg cac act ttg ttt ctc cac atc aac aac tta acc gga aac atc      864
His Leu His Thr Leu Phe Leu His Ile Asn Asn Leu Thr Gly Asn Ile
        275                 280                 285

cca ccg gaa ctc tcc ggt tta atc agc tta aaa tct cta gac ctc tca      912
Pro Pro Glu Leu Ser Gly Leu Ile Ser Leu Lys Ser Leu Asp Leu Ser
    290                 295                 300

ata aac cag cta acc gga gag att cct cag agc ttc atc tcc ctc tgg      960
Ile Asn Gln Leu Thr Gly Glu Ile Pro Gln Ser Phe Ile Ser Leu Trp
305                 310                 315                 320

aac atc act ctc atc aac ctc ttc aga aac aat ctc cac ggg ccc ata     1008
Asn Ile Thr Leu Ile Asn Leu Phe Arg Asn Asn Leu His Gly Pro Ile
                325                 330                 335

cct gag ttc atc gga gac atg ccg aac ctc caa gtc ctc cag gtg tgg     1056
Pro Glu Phe Ile Gly Asp Met Pro Asn Leu Gln Val Leu Gln Val Trp
            340                 345                 350

gag aac aac ttc acg cta gag cta ccg gcg aat ctc ggc cgg aac ggg     1104
Glu Asn Asn Phe Thr Leu Glu Leu Pro Ala Asn Leu Gly Arg Asn Gly
        355                 360                 365

aat ctg aaa aag ctc gac gtc tct gat aac cat ctc acc gga ctc atc     1152
Asn Leu Lys Lys Leu Asp Val Ser Asp Asn His Leu Thr Gly Leu Ile
```

```
    370                 375                 380

ccc atg gat ttg tgc aga ggc ggg aag ctg gag acg ctg gtg ctc tcc      1200
Pro Met Asp Leu Cys Arg Gly Gly Lys Leu Glu Thr Leu Val Leu Ser
385                 390                 395                 400

gac aac ttc ttc ttc ggc tcg atc cct gag aag cta ggt cga tgc aaa      1248
Asp Asn Phe Phe Phe Gly Ser Ile Pro Glu Lys Leu Gly Arg Cys Lys
                405                 410                 415

tcg cta aac aag atc aga atc gtc aag aat ctc ctc aac ggt acg gtt      1296
Ser Leu Asn Lys Ile Arg Ile Val Lys Asn Leu Leu Asn Gly Thr Val
            420                 425                 430

ccg gcg gga cta ttc act cta ccg ctc gtt acc atc atc gag ctc acc      1344
Pro Ala Gly Leu Phe Thr Leu Pro Leu Val Thr Ile Ile Glu Leu Thr
        435                 440                 445

gat aac ttc ttc tcc ggg gag ctt ccg ggg gag atg tca ggc gac ctt      1392
Asp Asn Phe Phe Ser Gly Glu Leu Pro Gly Glu Met Ser Gly Asp Leu
    450                 455                 460

ctc gat cat atc tac tta tct aac aat tgg ttt acc ggt tta atc ccc      1440
Leu Asp His Ile Tyr Leu Ser Asn Asn Trp Phe Thr Gly Leu Ile Pro
465                 470                 475                 480

ccg gct atc ggt aat ttt aaa aat cta cag gat tta ttc tta gac cgg      1488
Pro Ala Ile Gly Asn Phe Lys Asn Leu Gln Asp Leu Phe Leu Asp Arg
                485                 490                 495

aac cgg ttt agc ggg aat att ccg aga gaa gtt ttc gag tta aag cat      1536
Asn Arg Phe Ser Gly Asn Ile Pro Arg Glu Val Phe Glu Leu Lys His
            500                 505                 510

ctc act aag atc aac acg agt gct aac aac ctc acc ggc gac atc cct      1584
Leu Thr Lys Ile Asn Thr Ser Ala Asn Asn Leu Thr Gly Asp Ile Pro
        515                 520                 525

gac tcg atc tcg cga tgc act tcc tta atc tcc gtc gat ctc agc cgt      1632
Asp Ser Ile Ser Arg Cys Thr Ser Leu Ile Ser Val Asp Leu Ser Arg
    530                 535                 540

aac cga atc ggc gga gat atc ccg aaa gac atc cac gac gtg att aac      1680
Asn Arg Ile Gly Gly Asp Ile Pro Lys Asp Ile His Asp Val Ile Asn
545                 550                 555                 560

tta gga act ctc aat ctc tcc ggg aat caa ctc acc ggc tcg atc ccg      1728
Leu Gly Thr Leu Asn Leu Ser Gly Asn Gln Leu Thr Gly Ser Ile Pro
                565                 570                 575

atc gga atc ggg aag atg acg agc tta acc act ctc gat ctc tcc ttc      1776
Ile Gly Ile Gly Lys Met Thr Ser Leu Thr Thr Leu Asp Leu Ser Phe
            580                 585                 590

aac gac ctc tcg ggg cga gtc cca ctc ggc ggc cag ttc cta gtc ttc      1824
Asn Asp Leu Ser Gly Arg Val Pro Leu Gly Gly Gln Phe Leu Val Phe
        595                 600                 605

aac gac act tcc ttc gcc gga aac cct tac ctc tgc ctc cct cgc cac      1872
Asn Asp Thr Ser Phe Ala Gly Asn Pro Tyr Leu Cys Leu Pro Arg His
    610                 615                 620

gtc tcg tgc ctc acg cgt ccc ggc caa acc tcc gat cgc atc cac acg      1920
Val Ser Cys Leu Thr Arg Pro Gly Gln Thr Ser Asp Arg Ile His Thr
625                 630                 635                 640

gcg ctg ttc tcg ccg tcg agg atc gcc atc acg ata atc gca gcg gtc      1968
Ala Leu Phe Ser Pro Ser Arg Ile Ala Ile Thr Ile Ile Ala Ala Val
                645                 650                 655

acg gcg ctg atc ctc atc agc gtc gcg att cgt cag atg aac aag aag      2016
Thr Ala Leu Ile Leu Ile Ser Val Ala Ile Arg Gln Met Asn Lys Lys
            660                 665                 670

aag cac gag aga tcc ctc tcc tgg aag cta acc gcc ttc cag cgg ctc      2064
Lys His Glu Arg Ser Leu Ser Trp Lys Leu Thr Ala Phe Gln Arg Leu
        675                 680                 685

gat ttc aag gcg gaa gac gtc ctc gag tgc ctc caa gag gag aac ata      2112
```

-continued

```
Asp Phe Lys Ala Glu Asp Val Leu Glu Cys Leu Gln Glu Glu Asn Ile
    690                 695                 700

atc ggc aaa ggc gga gcg ggg atc gtc tac cgc gga tcc atg ccg aac      2160
Ile Gly Lys Gly Gly Ala Gly Ile Val Tyr Arg Gly Ser Met Pro Asn
705                 710                 715                 720

aac gta gac gtc gcg atc aaa cgc ctc gtg gga cgc gga aca ggg agg      2208
Asn Val Asp Val Ala Ile Lys Arg Leu Val Gly Arg Gly Thr Gly Arg
                725                 730                 735

agc gat cac gga ttc acg gcg gag att cag acg cta ggg agg atc cgc      2256
Ser Asp His Gly Phe Thr Ala Glu Ile Gln Thr Leu Gly Arg Ile Arg
            740                 745                 750

cac cgt cac atc gtg aga ctc ctc gga tac gtg gcg aac aag gac acg      2304
His Arg His Ile Val Arg Leu Leu Gly Tyr Val Ala Asn Lys Asp Thr
        755                 760                 765

aac ctg ctt ctc tac gag tac atg cct aac ggg agc ctc ggc gag ctt      2352
Asn Leu Leu Leu Tyr Glu Tyr Met Pro Asn Gly Ser Leu Gly Glu Leu
    770                 775                 780

ttg cac ggg tct aaa gga ggt cat ctt cag tgg gag acg agg cac aga      2400
Leu His Gly Ser Lys Gly Gly His Leu Gln Trp Glu Thr Arg His Arg
785                 790                 795                 800

gta gcc gtt gaa gcg gcg aaa gga ctg tgt tat ctt cac cat gac tgt      2448
Val Ala Val Glu Ala Ala Lys Gly Leu Cys Tyr Leu His His Asp Cys
                805                 810                 815

tcg ccg ttg atc ttg cat aga gac gtt aag tcc aat aac att tta ctg      2496
Ser Pro Leu Ile Leu His Arg Asp Val Lys Ser Asn Asn Ile Leu Leu
            820                 825                 830

gac tct gat ttt gag gcc cat gtt gct gat ttt ggg ctt gct aag ttc      2544
Asp Ser Asp Phe Glu Ala His Val Ala Asp Phe Gly Leu Ala Lys Phe
        835                 840                 845

tta gtg gac ggt gct gct tcc gag tgt atg tct tcg ata gct gga tcc      2592
Leu Val Asp Gly Ala Ala Ser Glu Cys Met Ser Ser Ile Ala Gly Ser
    850                 855                 860

tat gga tac atc gct cca gag tat gct tac act ctc aaa gtg gat gag      2640
Tyr Gly Tyr Ile Ala Pro Glu Tyr Ala Tyr Thr Leu Lys Val Asp Glu
865                 870                 875                 880

aag agt gat gtt tat agt ttt gga gtg gtg tta ttg gag ctg ata gct      2688
Lys Ser Asp Val Tyr Ser Phe Gly Val Val Leu Leu Glu Leu Ile Ala
                885                 890                 895

ggg aag aaa ccg gtt ggt gag ttt ggg gaa gga gtg gat ata gtg agg      2736
Gly Lys Lys Pro Val Gly Glu Phe Gly Glu Gly Val Asp Ile Val Arg
            900                 905                 910

tgg gtg agg aac acg gag ggt gag ata cct cag ccg tcg gat gca gct      2784
Trp Val Arg Asn Thr Glu Gly Glu Ile Pro Gln Pro Ser Asp Ala Ala
        915                 920                 925

act gtt gtt gcg atc gtc gac cag agg ttg act ggt tac ccg ttg act      2832
Thr Val Val Ala Ile Val Asp Gln Arg Leu Thr Gly Tyr Pro Leu Thr
    930                 935                 940

agt gtg att cac gtg ttc aag ata gcg atg atg tgt gtg gag gat gag      2880
Ser Val Ile His Val Phe Lys Ile Ala Met Met Cys Val Glu Asp Glu
945                 950                 955                 960

gca acg aca agg ccg acg atg agg gaa gtt gtg cac atg ctc act aac      2928
Ala Thr Thr Arg Pro Thr Met Arg Glu Val Val His Met Leu Thr Asn
                965                 970                 975

cct cct aag tcc gtg act aac ttg atc gcc ttc tga                      2964
Pro Pro Lys Ser Val Thr Asn Leu Ile Ala Phe
            980                 985
```

<210> SEQ ID NO 8
<211> LENGTH: 987
<212> TYPE: PRT

-continued

```
<213> ORGANISM: Brassica rapa

<400> SEQUENCE: 8

Met Glu Met Arg Leu Leu Lys Thr His Leu Leu Phe Leu His Leu His
1               5                   10                  15

Tyr Val Ile Ser Ile Leu Leu Leu Ser Phe Ser Pro Cys Phe Ala Ser
            20                  25                  30

Thr Asp Met Asp His Leu Leu Thr Leu Lys Ser Ser Met Val Gly Pro
        35                  40                  45

Asn Gly His Gly Leu His Asp Trp Val His Ser Thr Ser Pro Ser Ala
    50                  55                  60

His Cys Ser Phe Ser Gly Val Ser Cys Asp Gly Asp Ala Arg Val Ile
65                  70                  75                  80

Ser Leu Asn Val Ser Phe Thr Pro Leu Phe Gly Thr Ile Ser Pro Glu
                85                  90                  95

Ile Gly Met Leu Asp Arg Leu Val Asn Leu Thr Leu Ala Ala Asn Asn
            100                 105                 110

Phe Ser Gly Met Leu Pro Leu Glu Met Lys Ser Leu Thr Ser Leu Lys
        115                 120                 125

Val Leu Asn Ile Ser Asn Asn Val Asn Leu Asn Gly Thr Phe Pro Gly
    130                 135                 140

Glu Ile Leu Thr Pro Met Val Asp Leu Glu Val Leu Asp Ala Tyr Asn
145                 150                 155                 160

Asn Asn Phe Thr Gly Pro Leu Pro Pro Glu Ile Pro Gly Leu Lys Lys
                165                 170                 175

Leu Arg His Leu Ser Leu Gly Gly Asn Phe Leu Thr Gly Glu Ile Pro
            180                 185                 190

Glu Ser Tyr Gly Asp Ile Gln Ser Leu Glu Tyr Leu Gly Leu Asn Gly
        195                 200                 205

Ala Gly Leu Ser Gly Glu Ser Pro Ala Phe Leu Ser Arg Leu Lys Asn
    210                 215                 220

Leu Lys Glu Met Tyr Val Gly Tyr Phe Asn Ser Tyr Thr Gly Gly Val
225                 230                 235                 240

Pro Pro Glu Phe Gly Glu Leu Thr Asn Leu Glu Val Leu Asp Met Ala
                245                 250                 255

Ser Cys Thr Leu Thr Gly Glu Ile Pro Thr Thr Leu Ser Asn Leu Lys
            260                 265                 270

His Leu His Thr Leu Phe Leu His Ile Asn Asn Leu Thr Gly Asn Ile
        275                 280                 285

Pro Pro Glu Leu Ser Gly Leu Ile Ser Leu Lys Ser Leu Asp Leu Ser
    290                 295                 300

Ile Asn Gln Leu Thr Gly Glu Ile Pro Gln Ser Phe Ile Ser Leu Trp
305                 310                 315                 320

Asn Ile Thr Leu Ile Asn Leu Phe Arg Asn Asn Leu His Gly Pro Ile
                325                 330                 335

Pro Glu Phe Ile Gly Asp Met Pro Asn Leu Gln Val Leu Gln Val Trp
            340                 345                 350

Glu Asn Asn Phe Thr Leu Glu Leu Pro Ala Asn Leu Gly Arg Asn Gly
        355                 360                 365

Asn Leu Lys Lys Leu Asp Val Ser Asp Asn His Leu Thr Gly Leu Ile
    370                 375                 380

Pro Met Asp Leu Cys Arg Gly Gly Lys Leu Glu Thr Leu Val Leu Ser
385                 390                 395                 400
```

-continued

```
Asp Asn Phe Phe Phe Gly Ser Ile Pro Glu Lys Leu Gly Arg Cys Lys
                405                 410                 415

Ser Leu Asn Lys Ile Arg Ile Val Lys Asn Leu Leu Asn Gly Thr Val
            420                 425                 430

Pro Ala Gly Leu Phe Thr Leu Pro Leu Val Thr Ile Ile Glu Leu Thr
        435                 440                 445

Asp Asn Phe Phe Ser Gly Glu Leu Pro Gly Glu Met Ser Gly Asp Leu
    450                 455                 460

Leu Asp His Ile Tyr Leu Ser Asn Asn Trp Phe Thr Gly Leu Ile Pro
465                 470                 475                 480

Pro Ala Ile Gly Asn Phe Lys Asn Leu Gln Asp Leu Phe Leu Asp Arg
                485                 490                 495

Asn Arg Phe Ser Gly Asn Ile Pro Arg Glu Val Phe Glu Leu Lys His
            500                 505                 510

Leu Thr Lys Ile Asn Thr Ser Ala Asn Asn Leu Thr Gly Asp Ile Pro
        515                 520                 525

Asp Ser Ile Ser Arg Cys Thr Ser Leu Ile Ser Val Asp Leu Ser Arg
    530                 535                 540

Asn Arg Ile Gly Gly Asp Ile Pro Lys Asp Ile His Asp Val Ile Asn
545                 550                 555                 560

Leu Gly Thr Leu Asn Leu Ser Gly Asn Gln Leu Thr Gly Ser Ile Pro
                565                 570                 575

Ile Gly Ile Gly Lys Met Thr Ser Leu Thr Thr Leu Asp Leu Ser Phe
            580                 585                 590

Asn Asp Leu Ser Gly Arg Val Pro Leu Gly Gly Gln Phe Leu Val Phe
        595                 600                 605

Asn Asp Thr Ser Phe Ala Gly Asn Pro Tyr Leu Cys Leu Pro Arg His
    610                 615                 620

Val Ser Cys Leu Thr Arg Pro Gly Gln Thr Ser Asp Arg Ile His Thr
625                 630                 635                 640

Ala Leu Phe Ser Pro Ser Arg Ile Ala Ile Thr Ile Ile Ala Ala Val
                645                 650                 655

Thr Ala Leu Ile Leu Ile Ser Val Ala Ile Arg Gln Met Asn Lys Lys
            660                 665                 670

Lys His Glu Arg Ser Leu Ser Trp Lys Leu Thr Ala Phe Gln Arg Leu
        675                 680                 685

Asp Phe Lys Ala Glu Asp Val Leu Glu Cys Leu Gln Glu Glu Asn Ile
    690                 695                 700

Ile Gly Lys Gly Gly Ala Gly Ile Val Tyr Arg Gly Ser Met Pro Asn
705                 710                 715                 720

Asn Val Asp Val Ala Ile Lys Arg Leu Val Gly Arg Gly Thr Gly Arg
                725                 730                 735

Ser Asp His Gly Phe Thr Ala Glu Ile Gln Thr Leu Gly Arg Ile Arg
            740                 745                 750

His Arg His Ile Val Arg Leu Leu Gly Tyr Val Ala Asn Lys Asp Thr
        755                 760                 765

Asn Leu Leu Leu Tyr Glu Tyr Met Pro Asn Gly Ser Leu Gly Glu Leu
    770                 775                 780

Leu His Gly Ser Lys Gly Gly His Leu Gln Trp Glu Thr Arg His Arg
785                 790                 795                 800

Val Ala Val Glu Ala Ala Lys Gly Leu Cys Tyr Leu His His Asp Cys
                805                 810                 815

Ser Pro Leu Ile Leu His Arg Asp Val Lys Ser Asn Asn Ile Leu Leu
```

-continued

```
            820                 825                 830

Asp Ser Asp Phe Glu Ala His Val Ala Asp Phe Gly Leu Ala Lys Phe
        835                 840                 845

Leu Val Asp Gly Ala Ala Ser Glu Cys Met Ser Ser Ile Ala Gly Ser
    850                 855                 860

Tyr Gly Tyr Ile Ala Pro Glu Tyr Ala Tyr Thr Leu Lys Val Asp Glu
865                 870                 875                 880

Lys Ser Asp Val Tyr Ser Phe Gly Val Val Leu Leu Glu Leu Ile Ala
                885                 890                 895

Gly Lys Lys Pro Val Gly Glu Phe Gly Glu Gly Val Asp Ile Val Arg
            900                 905                 910

Trp Val Arg Asn Thr Glu Gly Glu Ile Pro Gln Pro Ser Asp Ala Ala
        915                 920                 925

Thr Val Val Ala Ile Val Asp Gln Arg Leu Thr Gly Tyr Pro Leu Thr
    930                 935                 940

Ser Val Ile His Val Phe Lys Ile Ala Met Met Cys Val Glu Asp Glu
945                 950                 955                 960

Ala Thr Thr Arg Pro Thr Met Arg Glu Val Val His Met Leu Thr Asn
                965                 970                 975

Pro Pro Lys Ser Val Thr Asn Leu Ile Ala Phe
            980                 985


<210> SEQ ID NO 9
<211> LENGTH: 2964
<212> TYPE: DNA
<213> ORGANISM: Brassica oleracea
<220> FEATURE:
<221> NAME/KEY: CDS
<222> LOCATION: (1)..(2964)

<400> SEQUENCE: 9

atg gag atg aga ctt ttg aaa act cac ctt ctg ttt ctc cat ctt cat       48
Met Glu Met Arg Leu Leu Lys Thr His Leu Leu Phe Leu His Leu His
1               5                   10                  15

tac gtt atc tcg att ttg ctt ctg tct ttc tca cca tgc ttc gct tcc       96
Tyr Val Ile Ser Ile Leu Leu Leu Ser Phe Ser Pro Cys Phe Ala Ser
            20                  25                  30

act gac atg gac cat ctc ctc acc ctc aaa tcc tcc atg gtc ggc ccc      144
Thr Asp Met Asp His Leu Leu Thr Leu Lys Ser Ser Met Val Gly Pro
        35                  40                  45

aac ggc cac ggc ctc cac gac tgg gtt cac tcc act tct ccc tca gct      192
Asn Gly His Gly Leu His Asp Trp Val His Ser Thr Ser Pro Ser Ala
    50                  55                  60

cac tgt tct ttc tcc ggc gtt tcc tgc gac ggc gac gct cgt gtc atc      240
His Cys Ser Phe Ser Gly Val Ser Cys Asp Gly Asp Ala Arg Val Ile
65                  70                  75                  80

tcc ctc aac gtc tct ttc act cct ctc ttc gga acc atc tcc ccg gag      288
Ser Leu Asn Val Ser Phe Thr Pro Leu Phe Gly Thr Ile Ser Pro Glu
                85                  90                  95

att ggg atg ctg gac cgt ctc gtg aat ctg acg tta gct gct aat aat      336
Ile Gly Met Leu Asp Arg Leu Val Asn Leu Thr Leu Ala Ala Asn Asn
            100                 105                 110

ttc tcc ggt atg ctc ccg ttg gag atg aag agt ctc act tct cta aag      384
Phe Ser Gly Met Leu Pro Leu Glu Met Lys Ser Leu Thr Ser Leu Lys
        115                 120                 125

gtt ctc aac atc tcc aac aac gtg aac ctc aac gga acc ttc ccc gga      432
Val Leu Asn Ile Ser Asn Asn Val Asn Leu Asn Gly Thr Phe Pro Gly
    130                 135                 140
```

-continued

```
gag att ctc act ccc atg gtc gac ctc gaa gtc ctc gac gcg tac aac      480
Glu Ile Leu Thr Pro Met Val Asp Leu Glu Val Leu Asp Ala Tyr Asn
145                 150                 155                 160

aac aac ttc aca ggc cca cta ccg ccg gag atc ccc ggg ctc aag aag      528
Asn Asn Phe Thr Gly Pro Leu Pro Pro Glu Ile Pro Gly Leu Lys Lys
                165                 170                 175

ctg aga cac ctc tct ctc gga gga aac ttc tta acc gga gag atc ccg      576
Leu Arg His Leu Ser Leu Gly Gly Asn Phe Leu Thr Gly Glu Ile Pro
            180                 185                 190

gag agt tac gga gat atc cag agc ttg gag tat ctc ggc ctc aac gga      624
Glu Ser Tyr Gly Asp Ile Gln Ser Leu Glu Tyr Leu Gly Leu Asn Gly
        195                 200                 205

gcc gga ctc tcc ggc gaa tct ccg gcg ttc ttg tca cgc ctc aag aat      672
Ala Gly Leu Ser Gly Glu Ser Pro Ala Phe Leu Ser Arg Leu Lys Asn
    210                 215                 220

ctt aaa gaa atg tac gtc ggc tac ttc aac agc tac acc ggc ggc gta      720
Leu Lys Glu Met Tyr Val Gly Tyr Phe Asn Ser Tyr Thr Gly Gly Val
225                 230                 235                 240

ccg ccg gag ttc ggt gaa ttg aca aac cta gag gtt ctc gac atg gcg      768
Pro Pro Glu Phe Gly Glu Leu Thr Asn Leu Glu Val Leu Asp Met Ala
                245                 250                 255

agc tgt aca ctc acg gga gag att ccg acg act ctg agt aat cta aaa      816
Ser Cys Thr Leu Thr Gly Glu Ile Pro Thr Thr Leu Ser Asn Leu Lys
            260                 265                 270

cat ttg cac act ttg ttt ctc cac atc aac aac tta acc gga aac atc      864
His Leu His Thr Leu Phe Leu His Ile Asn Asn Leu Thr Gly Asn Ile
        275                 280                 285

cca ccc gaa ctc tcc ggt tta atc agc tta aaa tct cta gac ctc tca      912
Pro Pro Glu Leu Ser Gly Leu Ile Ser Leu Lys Ser Leu Asp Leu Ser
    290                 295                 300

ata aac cag cta acc gga gag att cct cag agc ttc atc tcc tta gca      960
Ile Asn Gln Leu Thr Gly Glu Ile Pro Gln Ser Phe Ile Ser Leu Ala
305                 310                 315                 320

aac atc act ctc atc aac ctc ttc cga aac aat ctc cac ggg ccc ata     1008
Asn Ile Thr Leu Ile Asn Leu Phe Arg Asn Asn Leu His Gly Pro Ile
                325                 330                 335

cct gag ttc atc gga gac atg ccg aac ctc caa gtc ctc cag gtg tgg     1056
Pro Glu Phe Ile Gly Asp Met Pro Asn Leu Gln Val Leu Gln Val Trp
            340                 345                 350

gag aac aac ttc acg cta gag cta ccg gcg aat ctc ggc cgg aac ggg     1104
Glu Asn Asn Phe Thr Leu Glu Leu Pro Ala Asn Leu Gly Arg Asn Gly
        355                 360                 365

aat ctg aaa aag ctc gac gtc tct gat aac cat ctc acc gga ctc atc     1152
Asn Leu Lys Lys Leu Asp Val Ser Asp Asn His Leu Thr Gly Leu Ile
    370                 375                 380

ccc gtg gat ttg tgc aga ggc ggg aag ctg gag acg ctg gtg ctc tcc     1200
Pro Val Asp Leu Cys Arg Gly Gly Lys Leu Glu Thr Leu Val Leu Ser
385                 390                 395                 400

aac aac ttc ttc ttc ggc tcc atc cct gag aag cta ggt caa tgc aaa     1248
Asn Asn Phe Phe Phe Gly Ser Ile Pro Glu Lys Leu Gly Gln Cys Lys
                405                 410                 415

tcg cta aac aag atc cga atc gtc aag aat ctc ctc aac ggt acg gtt     1296
Ser Leu Asn Lys Ile Arg Ile Val Lys Asn Leu Leu Asn Gly Thr Val
            420                 425                 430

ccg gag gga tta ttc aat cta ccg ctc gtt acg atc atc gag ctc acc     1344
Pro Glu Gly Leu Phe Asn Leu Pro Leu Val Thr Ile Ile Glu Leu Thr
        435                 440                 445

gat aac ttc ttc tcc gga gat ctt ccg ggg gag atg tca ggc gac gtt     1392
Asp Asn Phe Phe Ser Gly Asp Leu Pro Gly Glu Met Ser Gly Asp Val
    450                 455                 460
```

-continued

```
ctc gat cat atc tac tta tct aac aat tgg ttt acc ggt tta atc ccc      1440
Leu Asp His Ile Tyr Leu Ser Asn Asn Trp Phe Thr Gly Leu Ile Pro
465                 470                 475                 480

ccg gct atc ggt aat ttt aaa aat cta cag gat tta ttc tta gac cgg      1488
Pro Ala Ile Gly Asn Phe Lys Asn Leu Gln Asp Leu Phe Leu Asp Arg
                485                 490                 495

aac cgg ttt agc ggg aat att ccg aga gaa gtt ttc gag tta aag cat      1536
Asn Arg Phe Ser Gly Asn Ile Pro Arg Glu Val Phe Glu Leu Lys His
            500                 505                 510

ctc act aag atc aac acg agt gct aac aac ctc acc ggc gac atc cct      1584
Leu Thr Lys Ile Asn Thr Ser Ala Asn Asn Leu Thr Gly Asp Ile Pro
        515                 520                 525

gac tcg atc tcg cga tgc act tcc tta atc tcc gtc gat ctc agc cgt      1632
Asp Ser Ile Ser Arg Cys Thr Ser Leu Ile Ser Val Asp Leu Ser Arg
    530                 535                 540

aac cga atc ggc ggc gat atc ccg aaa gac atc cac gac gtg att aac      1680
Asn Arg Ile Gly Gly Asp Ile Pro Lys Asp Ile His Asp Val Ile Asn
545                 550                 555                 560

tta gga act ctc aat ctc tcc ggg aat caa ctc acc ggc tcg atc ccg      1728
Leu Gly Thr Leu Asn Leu Ser Gly Asn Gln Leu Thr Gly Ser Ile Pro
                565                 570                 575

atc gga atc ggg aag atg acg agc tta acc act ctc gat ctc tcc ttc      1776
Ile Gly Ile Gly Lys Met Thr Ser Leu Thr Thr Leu Asp Leu Ser Phe
            580                 585                 590

aac gac ctc tcg ggg aga gtc cca ctc ggc ggc cag ttc cta gtc ttc      1824
Asn Asp Leu Ser Gly Arg Val Pro Leu Gly Gly Gln Phe Leu Val Phe
        595                 600                 605

aac gac act tcc ttc gcc gga aac cct tac ctc tgc ctc cct cgc cac      1872
Asn Asp Thr Ser Phe Ala Gly Asn Pro Tyr Leu Cys Leu Pro Arg His
    610                 615                 620

gtc tcg tgc cta acg cgt ccc ggc caa acc tcc gat cgc atc cac acg      1920
Val Ser Cys Leu Thr Arg Pro Gly Gln Thr Ser Asp Arg Ile His Thr
625                 630                 635                 640

gcg ctg ttc tcg ccg tcg agg atc gcc atc acg ata atc gca gcg gtc      1968
Ala Leu Phe Ser Pro Ser Arg Ile Ala Ile Thr Ile Ile Ala Ala Val
                645                 650                 655

acg gcg ctg atc ctc atc agc gtc gcg att cgt cag atg aac aag aag      2016
Thr Ala Leu Ile Leu Ile Ser Val Ala Ile Arg Gln Met Asn Lys Lys
            660                 665                 670

aag cac gag aga tcc ctc tcg tgg aag cta acc gcc ttc cag cgg ctc      2064
Lys His Glu Arg Ser Leu Ser Trp Lys Leu Thr Ala Phe Gln Arg Leu
        675                 680                 685

gat ttc aaa gcg gaa gac gtc ctc gag tgc ctc caa gag gag aac ata      2112
Asp Phe Lys Ala Glu Asp Val Leu Glu Cys Leu Gln Glu Glu Asn Ile
    690                 695                 700

atc ggg aaa ggc gga gcg ggg atc gtc tac cgc gga tcc atg ccg aac      2160
Ile Gly Lys Gly Gly Ala Gly Ile Val Tyr Arg Gly Ser Met Pro Asn
705                 710                 715                 720

aac gtc gac gtc gcg atc aaa cgc ttg gtg gga cgc gga aca ggg agg      2208
Asn Val Asp Val Ala Ile Lys Arg Leu Val Gly Arg Gly Thr Gly Arg
                725                 730                 735

agc gat cac gga ttc acg gcg gag ata caa act cta ggg aga atc cgc      2256
Ser Asp His Gly Phe Thr Ala Glu Ile Gln Thr Leu Gly Arg Ile Arg
            740                 745                 750

cac cgt cat ata gtt aga cta ttt gga tac gtg gcg aac aag gac acg      2304
His Arg His Ile Val Arg Leu Phe Gly Tyr Val Ala Asn Lys Asp Thr
        755                 760                 765

aac ctg ctt ctc tac gag tac atg cct aac ggg agc ctc ggc gag ctt      2352
Asn Leu Leu Leu Tyr Glu Tyr Met Pro Asn Gly Ser Leu Gly Glu Leu
```

-continued

```
    770                 775                 780

ttg cac ggg tct aaa gga ggt cat ctt cag tgg gag acg agg cac aga      2400
Leu His Gly Ser Lys Gly Gly His Leu Gln Trp Glu Thr Arg His Arg
785                 790                 795                 800

gta gcc ctt gaa gcg gcg aaa gga ctg tgt tat ctt cat cat gac tgt      2448
Val Ala Leu Glu Ala Ala Lys Gly Leu Cys Tyr Leu His His Asp Cys
                805                 810                 815

tcg ccg ttg atc ttg cat aga gac gtt aag tcc aat aac att ctt ctg      2496
Ser Pro Leu Ile Leu His Arg Asp Val Lys Ser Asn Asn Ile Leu Leu
            820                 825                 830

gac tct gat ttt gag gcc cat gtt gct gat ttt ggg ctt gct aag ttc      2544
Asp Ser Asp Phe Glu Ala His Val Ala Asp Phe Gly Leu Ala Lys Phe
        835                 840                 845

tta gtg gac ggt gct gct tct gag tgt atg tct tca ata gct ggg tcc      2592
Leu Val Asp Gly Ala Ala Ser Glu Cys Met Ser Ser Ile Ala Gly Ser
    850                 855                 860

tat gga tac atc gct cca gag tat gct tac act ctc aaa gtg gat gag      2640
Tyr Gly Tyr Ile Ala Pro Glu Tyr Ala Tyr Thr Leu Lys Val Asp Glu
865                 870                 875                 880

aag agt gat gtg tat agt ttt gga gtg gtg tta ttg gag ctg ata gct      2688
Lys Ser Asp Val Tyr Ser Phe Gly Val Val Leu Leu Glu Leu Ile Ala
                885                 890                 895

ggg aag aaa ccg gtt ggt gag ttt ggg gaa gga gtg gat ata gtg agg      2736
Gly Lys Lys Pro Val Gly Glu Phe Gly Glu Gly Val Asp Ile Val Arg
            900                 905                 910

tgg gtg agg aac acg gag ggt gag ata cct cag ccg tcg gat gca gct      2784
Trp Val Arg Asn Thr Glu Gly Glu Ile Pro Gln Pro Ser Asp Ala Ala
        915                 920                 925

act gtt gtt gcg atc gtt gac cag agg ttg act ggt tac ccg ttg act      2832
Thr Val Val Ala Ile Val Asp Gln Arg Leu Thr Gly Tyr Pro Leu Thr
    930                 935                 940

agt gtg att cac gtg ttc aag ata gcg atg atg tgt gtg gag gat gag      2880
Ser Val Ile His Val Phe Lys Ile Ala Met Met Cys Val Glu Asp Glu
945                 950                 955                 960

gca gcg aca agg ccg acg atg agg gaa gtt gtg cac atg ctc act aac      2928
Ala Ala Thr Arg Pro Thr Met Arg Glu Val Val His Met Leu Thr Asn
                965                 970                 975

cct ccc aag tcc gtc act aac ttg atc gcc ttc tga                      2964
Pro Pro Lys Ser Val Thr Asn Leu Ile Ala Phe
            980                 985


<210> SEQ ID NO 10
<211> LENGTH: 987
<212> TYPE: PRT
<213> ORGANISM: Brassica oleracea

<400> SEQUENCE: 10

Met Glu Met Arg Leu Leu Lys Thr His Leu Leu Phe Leu His Leu His
1               5                   10                  15

Tyr Val Ile Ser Ile Leu Leu Leu Ser Phe Ser Pro Cys Phe Ala Ser
            20                  25                  30

Thr Asp Met Asp His Leu Leu Thr Leu Lys Ser Ser Met Val Gly Pro
        35                  40                  45

Asn Gly His Gly Leu His Asp Trp Val His Ser Thr Ser Pro Ser Ala
    50                  55                  60

His Cys Ser Phe Ser Gly Val Ser Cys Asp Gly Asp Ala Arg Val Ile
65                  70                  75                  80

Ser Leu Asn Val Ser Phe Thr Pro Leu Phe Gly Thr Ile Ser Pro Glu
                85                  90                  95
```

-continued

```
Ile Gly Met Leu Asp Arg Leu Val Asn Leu Thr Leu Ala Ala Asn Asn
            100                 105                 110

Phe Ser Gly Met Leu Pro Leu Glu Met Lys Ser Leu Thr Ser Leu Lys
        115                 120                 125

Val Leu Asn Ile Ser Asn Asn Val Asn Leu Asn Gly Thr Phe Pro Gly
    130                 135                 140

Glu Ile Leu Thr Pro Met Val Asp Leu Glu Val Leu Asp Ala Tyr Asn
145                 150                 155                 160

Asn Asn Phe Thr Gly Pro Leu Pro Pro Glu Ile Pro Gly Leu Lys Lys
                165                 170                 175

Leu Arg His Leu Ser Leu Gly Gly Asn Phe Leu Thr Gly Glu Ile Pro
            180                 185                 190

Glu Ser Tyr Gly Asp Ile Gln Ser Leu Glu Tyr Leu Gly Leu Asn Gly
        195                 200                 205

Ala Gly Leu Ser Gly Glu Ser Pro Ala Phe Leu Ser Arg Leu Lys Asn
    210                 215                 220

Leu Lys Glu Met Tyr Val Gly Tyr Phe Asn Ser Tyr Thr Gly Gly Val
225                 230                 235                 240

Pro Pro Glu Phe Gly Glu Leu Thr Asn Leu Glu Val Leu Asp Met Ala
                245                 250                 255

Ser Cys Thr Leu Thr Gly Glu Ile Pro Thr Thr Leu Ser Asn Leu Lys
            260                 265                 270

His Leu His Thr Leu Phe Leu His Ile Asn Asn Leu Thr Gly Asn Ile
        275                 280                 285

Pro Pro Glu Leu Ser Gly Leu Ile Ser Leu Lys Ser Leu Asp Leu Ser
    290                 295                 300

Ile Asn Gln Leu Thr Gly Glu Ile Pro Gln Ser Phe Ile Ser Leu Ala
305                 310                 315                 320

Asn Ile Thr Leu Ile Asn Leu Phe Arg Asn Asn Leu His Gly Pro Ile
                325                 330                 335

Pro Glu Phe Ile Gly Asp Met Pro Asn Leu Gln Val Leu Gln Val Trp
            340                 345                 350

Glu Asn Asn Phe Thr Leu Glu Leu Pro Ala Asn Leu Gly Arg Asn Gly
        355                 360                 365

Asn Leu Lys Lys Leu Asp Val Ser Asp Asn His Leu Thr Gly Leu Ile
    370                 375                 380

Pro Val Asp Leu Cys Arg Gly Gly Lys Leu Glu Thr Leu Val Leu Ser
385                 390                 395                 400

Asn Asn Phe Phe Phe Gly Ser Ile Pro Glu Lys Leu Gly Gln Cys Lys
                405                 410                 415

Ser Leu Asn Lys Ile Arg Ile Val Lys Asn Leu Leu Asn Gly Thr Val
            420                 425                 430

Pro Glu Gly Leu Phe Asn Leu Pro Leu Val Thr Ile Ile Glu Leu Thr
        435                 440                 445

Asp Asn Phe Phe Ser Gly Asp Leu Pro Gly Glu Met Ser Gly Asp Val
    450                 455                 460

Leu Asp His Ile Tyr Leu Ser Asn Asn Trp Phe Thr Gly Leu Ile Pro
465                 470                 475                 480

Pro Ala Ile Gly Asn Phe Lys Asn Leu Gln Asp Leu Phe Leu Asp Arg
                485                 490                 495

Asn Arg Phe Ser Gly Asn Ile Pro Arg Glu Val Phe Glu Leu Lys His
            500                 505                 510
```

```
Leu Thr Lys Ile Asn Thr Ser Ala Asn Asn Leu Thr Gly Asp Ile Pro
        515                 520                 525

Asp Ser Ile Ser Arg Cys Thr Ser Leu Ile Ser Val Asp Leu Ser Arg
    530                 535                 540

Asn Arg Ile Gly Gly Asp Ile Pro Lys Asp Ile His Asp Val Ile Asn
545                 550                 555                 560

Leu Gly Thr Leu Asn Leu Ser Gly Asn Gln Leu Thr Gly Ser Ile Pro
                565                 570                 575

Ile Gly Ile Gly Lys Met Thr Ser Leu Thr Thr Leu Asp Leu Ser Phe
            580                 585                 590

Asn Asp Leu Ser Gly Arg Val Pro Leu Gly Gly Gln Phe Leu Val Phe
        595                 600                 605

Asn Asp Thr Ser Phe Ala Gly Asn Pro Tyr Leu Cys Leu Pro Arg His
    610                 615                 620

Val Ser Cys Leu Thr Arg Pro Gly Gln Thr Ser Asp Arg Ile His Thr
625                 630                 635                 640

Ala Leu Phe Ser Pro Ser Arg Ile Ala Ile Thr Ile Ile Ala Ala Val
                645                 650                 655

Thr Ala Leu Ile Leu Ile Ser Val Ala Ile Arg Gln Met Asn Lys Lys
            660                 665                 670

Lys His Glu Arg Ser Leu Ser Trp Lys Leu Thr Ala Phe Gln Arg Leu
        675                 680                 685

Asp Phe Lys Ala Glu Asp Val Leu Glu Cys Leu Gln Glu Glu Asn Ile
    690                 695                 700

Ile Gly Lys Gly Gly Ala Gly Ile Val Tyr Arg Gly Ser Met Pro Asn
705                 710                 715                 720

Asn Val Asp Val Ala Ile Lys Arg Leu Val Gly Arg Gly Thr Gly Arg
                725                 730                 735

Ser Asp His Gly Phe Thr Ala Glu Ile Gln Thr Leu Gly Arg Ile Arg
            740                 745                 750

His Arg His Ile Val Arg Leu Phe Gly Tyr Val Ala Asn Lys Asp Thr
        755                 760                 765

Asn Leu Leu Leu Tyr Glu Tyr Met Pro Asn Gly Ser Leu Gly Glu Leu
    770                 775                 780

Leu His Gly Ser Lys Gly Gly His Leu Gln Trp Glu Thr Arg His Arg
785                 790                 795                 800

Val Ala Leu Glu Ala Ala Lys Gly Leu Cys Tyr Leu His His Asp Cys
                805                 810                 815

Ser Pro Leu Ile Leu His Arg Asp Val Lys Ser Asn Asn Ile Leu Leu
            820                 825                 830

Asp Ser Asp Phe Glu Ala His Val Ala Asp Phe Gly Leu Ala Lys Phe
        835                 840                 845

Leu Val Asp Gly Ala Ala Ser Glu Cys Met Ser Ser Ile Ala Gly Ser
    850                 855                 860

Tyr Gly Tyr Ile Ala Pro Glu Tyr Ala Tyr Thr Leu Lys Val Asp Glu
865                 870                 875                 880

Lys Ser Asp Val Tyr Ser Phe Gly Val Val Leu Leu Glu Leu Ile Ala
                885                 890                 895

Gly Lys Lys Pro Val Gly Glu Phe Gly Glu Gly Val Asp Ile Val Arg
            900                 905                 910

Trp Val Arg Asn Thr Glu Gly Glu Ile Pro Gln Pro Ser Asp Ala Ala
        915                 920                 925

Thr Val Val Ala Ile Val Asp Gln Arg Leu Thr Gly Tyr Pro Leu Thr
```

```
    930                 935                 940

Ser Val Ile His Val Phe Lys Ile Ala Met Met Cys Val Glu Asp Glu
945                 950                 955                 960

Ala Ala Thr Arg Pro Thr Met Arg Glu Val Val His Met Leu Thr Asn
                965                 970                 975

Pro Pro Lys Ser Val Thr Asn Leu Ile Ala Phe
            980                 985


<210> SEQ ID NO 11
<211> LENGTH: 2979
<212> TYPE: DNA
<213> ORGANISM: Cannabis sativa
<220> FEATURE:
<221> NAME/KEY: CDS
<222> LOCATION: (1)..(2979)

<400> SEQUENCE: 11

atg gcg atg aga ctt ttg aac act cat ctt ctg ttt ctg cat ctg tat       48
Met Ala Met Arg Leu Leu Asn Thr His Leu Leu Phe Leu His Leu Tyr
1               5                   10                  15

act act cag ctt tac gtt atc tcc ttc ttc att cta ttc ttc tca cca       96
Thr Thr Gln Leu Tyr Val Ile Ser Phe Phe Ile Leu Phe Phe Ser Pro
            20                  25                  30

tgc tta gct tac act act gac atg gat gtt ctc ctt act ctc aaa tcc      144
Cys Leu Ala Tyr Thr Thr Asp Met Asp Val Leu Leu Thr Leu Lys Ser
        35                  40                  45

tct atg att ggt cct aac ggc gac ggt ctc cac gac tgg att cac aca      192
Ser Met Ile Gly Pro Asn Gly Asp Gly Leu His Asp Trp Ile His Thr
    50                  55                  60

cct tct ccg gcg gct cac tgc tct ttc acc ggc gtt tca tgt gac ggc      240
Pro Ser Pro Ala Ala His Cys Ser Phe Thr Gly Val Ser Cys Asp Gly
65                  70                  75                  80

gaa tct cgt gtc atc tct ctc aac gtc tcc ttt act cct ttg ttc gga      288
Glu Ser Arg Val Ile Ser Leu Asn Val Ser Phe Thr Pro Leu Phe Gly
                85                  90                  95

aaa atc tca ccg gag att ggg atg tta aac cgt ctg gtg aat cta aca      336
Lys Ile Ser Pro Glu Ile Gly Met Leu Asn Arg Leu Val Asn Leu Thr
            100                 105                 110

tta gct gcc aac aat ttc tcc ggt gaa tta cca ttg gag atg aag agt      384
Leu Ala Ala Asn Asn Phe Ser Gly Glu Leu Pro Leu Glu Met Lys Ser
        115                 120                 125

cta act tca cta aag gtt ttg aac att tcc aac aat gtt aac ctc aac      432
Leu Thr Ser Leu Lys Val Leu Asn Ile Ser Asn Asn Val Asn Leu Asn
    130                 135                 140

gga agc ttc cct gga gag att ctt aaa gcc atg ctt gat ctt gaa gtt      480
Gly Ser Phe Pro Gly Glu Ile Leu Lys Ala Met Leu Asp Leu Glu Val
145                 150                 155                 160

ctt gac gct tac aac aac aat ttc acg ggt acg tta cca ctt gag att      528
Leu Asp Ala Tyr Asn Asn Asn Phe Thr Gly Thr Leu Pro Leu Glu Ile
                165                 170                 175

tca gag ctc aag aac ctc aaa cat ctc tct ctc ggt gga aac ttc ttc      576
Ser Glu Leu Lys Asn Leu Lys His Leu Ser Leu Gly Gly Asn Phe Phe
            180                 185                 190

acc ggc gag att cct gag agt tac gga gat atc caa agc cta gag tat      624
Thr Gly Glu Ile Pro Glu Ser Tyr Gly Asp Ile Gln Ser Leu Glu Tyr
        195                 200                 205

ctc gga ctc aac gga gct gga ctc tcc ggt aaa tca ccg gcg ttt cta      672
Leu Gly Leu Asn Gly Ala Gly Leu Ser Gly Lys Ser Pro Ala Phe Leu
    210                 215                 220

tct cgc ctc aag aac ttg aga gaa atg tat gtc gga tac ttc aac agc      720
```

-continued

```
Ser Arg Leu Lys Asn Leu Arg Glu Met Tyr Val Gly Tyr Phe Asn Ser
225                 230                 235                 240

tac acc ggt ggt gtt ccc ccg gag ttc ggt ggt tta acc aac ctt cag      768
Tyr Thr Gly Gly Val Pro Pro Glu Phe Gly Gly Leu Thr Asn Leu Gln
                245                 250                 255

atc ctc gac atg gcg agt tgt aca ctc acc gga gag atc cca acg agt      816
Ile Leu Asp Met Ala Ser Cys Thr Leu Thr Gly Glu Ile Pro Thr Ser
            260                 265                 270

tta agt aac ctg aaa cat tta cac aca ctg ttc ctt cac atc aac aac      864
Leu Ser Asn Leu Lys His Leu His Thr Leu Phe Leu His Ile Asn Asn
        275                 280                 285

tta acc gga cac ata cca cca gaa ctc tcc ggt tta atc agc ctc aaa      912
Leu Thr Gly His Ile Pro Pro Glu Leu Ser Gly Leu Ile Ser Leu Lys
    290                 295                 300

tca ctc gat tta tca atc aac cag tta acc gga gaa ata cct caa agc      960
Ser Leu Asp Leu Ser Ile Asn Gln Leu Thr Gly Glu Ile Pro Gln Ser
305                 310                 315                 320

ttc atc gac ctc gga aac atc act ctc atc aac ctc ttc aga aac aaa     1008
Phe Ile Asp Leu Gly Asn Ile Thr Leu Ile Asn Leu Phe Arg Asn Lys
                325                 330                 335

ctc tac ggt cca ata cca gag ttc atc gga gag tta cca aaa ctc caa     1056
Leu Tyr Gly Pro Ile Pro Glu Phe Ile Gly Glu Leu Pro Lys Leu Gln
            340                 345                 350

gtc ttc gaa gtc tgg gag aac aac ttc acc tta cag cta cct tcg aat     1104
Val Phe Glu Val Trp Glu Asn Asn Phe Thr Leu Gln Leu Pro Ser Asn
        355                 360                 365

ctt gga cgg aac ggg aat ctg aaa aag ctc gac gtc tct tac aac cac     1152
Leu Gly Arg Asn Gly Asn Leu Lys Lys Leu Asp Val Ser Tyr Asn His
    370                 375                 380

ctc acc ggg ctt atc ccc atg gat tta tgc aga ggc gag aag cta gag     1200
Leu Thr Gly Leu Ile Pro Met Asp Leu Cys Arg Gly Glu Lys Leu Glu
385                 390                 395                 400

atg ttg ata ctc tca aac aac ttc ttc ttc ggt cca atc cca gaa gag     1248
Met Leu Ile Leu Ser Asn Asn Phe Phe Phe Gly Pro Ile Pro Glu Glu
                405                 410                 415

ctt ggt aaa tgc aag tcc tta aac aaa atc aga atc atc aag aat ctt     1296
Leu Gly Lys Cys Lys Ser Leu Asn Lys Ile Arg Ile Ile Lys Asn Leu
            420                 425                 430

ctc aac gga act gta ccg gcg ggg ctt ttc aat cta ccg ctc gtt acg     1344
Leu Asn Gly Thr Val Pro Ala Gly Leu Phe Asn Leu Pro Leu Val Thr
        435                 440                 445

att atc gaa ctc acc gat aat ttc ttc tcc ggt gaa ctc ccg acg acg     1392
Ile Ile Glu Leu Thr Asp Asn Phe Phe Ser Gly Glu Leu Pro Thr Thr
    450                 455                 460

atg tcc gga gct gtt gcc gac cag att tac ctc tct aac aat tgg ttc     1440
Met Ser Gly Ala Val Ala Asp Gln Ile Tyr Leu Ser Asn Asn Trp Phe
465                 470                 475                 480

tcc ggc gag att cct ccg gcg atc ggt aat ttc cct att ttg cag act     1488
Ser Gly Glu Ile Pro Pro Ala Ile Gly Asn Phe Pro Ile Leu Gln Thr
                485                 490                 495

ctg ttc tta gat cgg aac cga ttc cgc ggg agt atc ccg aga gag atc     1536
Leu Phe Leu Asp Arg Asn Arg Phe Arg Gly Ser Ile Pro Arg Glu Ile
            500                 505                 510

ttc gaa ttg aag cat cta tcg aag atc aac aca agt gcg aac aac atc     1584
Phe Glu Leu Lys His Leu Ser Lys Ile Asn Thr Ser Ala Asn Asn Ile
        515                 520                 525

acc ggc gtt atc cca gat tca atc tca cgc tgc act act cta atc tcc     1632
Thr Gly Val Ile Pro Asp Ser Ile Ser Arg Cys Thr Thr Leu Ile Ser
    530                 535                 540
```

-continued

```
gtc gat ctc agc cgt aac cga atc aac gga gat ata cct aaa gag atc      1680
Val Asp Leu Ser Arg Asn Arg Ile Asn Gly Asp Ile Pro Lys Glu Ile
545                 550                 555                 560

aac aac gtg att aac ctc ggt aca ctt aat ctc tcc ggt aac caa cta      1728
Asn Asn Val Ile Asn Leu Gly Thr Leu Asn Leu Ser Gly Asn Gln Leu
                565                 570                 575

acc ggt tcg atc cca acc gga atc gga aac atg acg agt tta aca acg      1776
Thr Gly Ser Ile Pro Thr Gly Ile Gly Asn Met Thr Ser Leu Thr Thr
            580                 585                 590

cta gat ctc tct ttc aac gat ctc tcc ggg aga gta cca cta ggt ggt      1824
Leu Asp Leu Ser Phe Asn Asp Leu Ser Gly Arg Val Pro Leu Gly Gly
        595                 600                 605

caa ttc atg gtg ttc aac gac act tcc ttc gcc gga aac act tac ctc      1872
Gln Phe Met Val Phe Asn Asp Thr Ser Phe Ala Gly Asn Thr Tyr Leu
    610                 615                 620

tgt tta cct ccc cac gtc tca tgt cca aca cgg cca gga caa acc tcc      1920
Cys Leu Pro Pro His Val Ser Cys Pro Thr Arg Pro Gly Gln Thr Ser
625                 630                 635                 640

gat cgc aac ccc acg gcg ttg ttc tca ccg tca agg atc gta atc acg      1968
Asp Arg Asn Pro Thr Ala Leu Phe Ser Pro Ser Arg Ile Val Ile Thr
                645                 650                 655

gtt atc gca gcg atc acg gcg ttg atc cta atc agc gta gcg att cgt      2016
Val Ile Ala Ala Ile Thr Ala Leu Ile Leu Ile Ser Val Ala Ile Arg
            660                 665                 670

cag atg aac aag aag aag aac cag aaa tct ctc gcc tgg aag cta acc      2064
Gln Met Asn Lys Lys Lys Asn Gln Lys Ser Leu Ala Trp Lys Leu Thr
        675                 680                 685

gcc ttc cgg aaa ctg gat ttc aaa tca gaa gac gtc ctc gag tgt ttg      2112
Ala Phe Arg Lys Leu Asp Phe Lys Ser Glu Asp Val Leu Glu Cys Leu
    690                 695                 700

aaa gaa gag aac ata atc ggc aaa gga gga gct gga atc gtt tac cgt      2160
Lys Glu Glu Asn Ile Ile Gly Lys Gly Gly Ala Gly Ile Val Tyr Arg
705                 710                 715                 720

gga tct atg cca aac aac gtc gac gtc gcg atc aaa cga ctc gtt ggt      2208
Gly Ser Met Pro Asn Asn Val Asp Val Ala Ile Lys Arg Leu Val Gly
                725                 730                 735

cgt ggc act ggg agg agc gat cat gga ttc acg gcg gag att caa act      2256
Arg Gly Thr Gly Arg Ser Asp His Gly Phe Thr Ala Glu Ile Gln Thr
            740                 745                 750

ttg gga agg att cga cac cgt cac atc gtg agg ctt cta ggt tac gta      2304
Leu Gly Arg Ile Arg His Arg His Ile Val Arg Leu Leu Gly Tyr Val
        755                 760                 765

gcg aac aag gac acg aac ttg ctt ctc tat gag tac atg cct aat gga      2352
Ala Asn Lys Asp Thr Asn Leu Leu Leu Tyr Glu Tyr Met Pro Asn Gly
    770                 775                 780

agc ctt gga gag ctt ttg cat gga tct aaa ggt ggt cat ctt caa tgg      2400
Ser Leu Gly Glu Leu Leu His Gly Ser Lys Gly Gly His Leu Gln Trp
785                 790                 795                 800

gag acg aga cat aga gta gcc gtg gaa gca gcc aag ggc ttg tgt tat      2448
Glu Thr Arg His Arg Val Ala Val Glu Ala Ala Lys Gly Leu Cys Tyr
                805                 810                 815

ctt cac cat gac tgt tca ccg ttg atc ttg cat aga gat gtt aag tcc      2496
Leu His His Asp Cys Ser Pro Leu Ile Leu His Arg Asp Val Lys Ser
            820                 825                 830

aat aac att ctt ttg gac tct gat ttt gaa gcc cat gtt gct gat ttt      2544
Asn Asn Ile Leu Leu Asp Ser Asp Phe Glu Ala His Val Ala Asp Phe
        835                 840                 845

ggg ctt gct aag ttc tta gtg gac ggt gct gct tct gag tgt atg tct      2592
Gly Leu Ala Lys Phe Leu Val Asp Gly Ala Ala Ser Glu Cys Met Ser
    850                 855                 860
```

```
tcg att gct ggc tct tat gga tac atc gcc cca gag tat gca tat acc      2640
Ser Ile Ala Gly Ser Tyr Gly Tyr Ile Ala Pro Glu Tyr Ala Tyr Thr
865                 870                 875                 880

ttg aaa gtg gac gag aaa agt gat gta tat agt ttc gga gtg gtt tta      2688
Leu Lys Val Asp Glu Lys Ser Asp Val Tyr Ser Phe Gly Val Val Leu
                885                 890                 895

ttg gag cta ata gcc ggg aag aaa ccg gtt ggt gaa ttt gga gaa gga      2736
Leu Glu Leu Ile Ala Gly Lys Lys Pro Val Gly Glu Phe Gly Glu Gly
            900                 905                 910

gtc gat ata gtt agg tgg gtg agg aac acg gaa gaa gag atg tct cag      2784
Val Asp Ile Val Arg Trp Val Arg Asn Thr Glu Glu Glu Met Ser Gln
        915                 920                 925

ccg tcg gat gct gct att gtt gtt gcg atc gtt gac tcg agg ttg act      2832
Pro Ser Asp Ala Ala Ile Val Val Ala Ile Val Asp Ser Arg Leu Thr
    930                 935                 940

ggt tat ccg ttg acc agc gtg gtt cat gtg ttc aag att gca atg atg      2880
Gly Tyr Pro Leu Thr Ser Val Val His Val Phe Lys Ile Ala Met Met
945                 950                 955                 960

tgt gtg gag gat gag gcc gca aca agg cct acg atg agg gag gtt gtg      2928
Cys Val Glu Asp Glu Ala Ala Thr Arg Pro Thr Met Arg Glu Val Val
                965                 970                 975

cac atg ctc act aac cct ccg aaa tcc gtg gct aac ttg att gcg ttc      2976
His Met Leu Thr Asn Pro Pro Lys Ser Val Ala Asn Leu Ile Ala Phe
            980                 985                 990

taa                                                                  2979


<210> SEQ ID NO 12
<211> LENGTH: 992
<212> TYPE: PRT
<213> ORGANISM: Cannabis sativa

<400> SEQUENCE: 12

Met Ala Met Arg Leu Leu Asn Thr His Leu Leu Phe Leu His Leu Tyr
1               5                   10                  15

Thr Thr Gln Leu Tyr Val Ile Ser Phe Phe Ile Leu Phe Phe Ser Pro
            20                  25                  30

Cys Leu Ala Tyr Thr Thr Asp Met Asp Val Leu Leu Thr Leu Lys Ser
        35                  40                  45

Ser Met Ile Gly Pro Asn Gly Asp Gly Leu His Asp Trp Ile His Thr
    50                  55                  60

Pro Ser Pro Ala Ala His Cys Ser Phe Thr Gly Val Ser Cys Asp Gly
65                  70                  75                  80

Glu Ser Arg Val Ile Ser Leu Asn Val Ser Phe Thr Pro Leu Phe Gly
                85                  90                  95

Lys Ile Ser Pro Glu Ile Gly Met Leu Asn Arg Leu Val Asn Leu Thr
            100                 105                 110

Leu Ala Ala Asn Asn Phe Ser Gly Glu Leu Pro Leu Glu Met Lys Ser
        115                 120                 125

Leu Thr Ser Leu Lys Val Leu Asn Ile Ser Asn Asn Val Asn Leu Asn
    130                 135                 140

Gly Ser Phe Pro Gly Glu Ile Leu Lys Ala Met Leu Asp Leu Glu Val
145                 150                 155                 160

Leu Asp Ala Tyr Asn Asn Asn Phe Thr Gly Thr Leu Pro Leu Glu Ile
                165                 170                 175

Ser Glu Leu Lys Asn Leu Lys His Leu Ser Leu Gly Gly Asn Phe Phe
            180                 185                 190
```

-continued

```
Thr Gly Glu Ile Pro Glu Ser Tyr Gly Asp Ile Gln Ser Leu Glu Tyr
        195                 200                 205

Leu Gly Leu Asn Gly Ala Gly Leu Ser Gly Lys Ser Pro Ala Phe Leu
    210                 215                 220

Ser Arg Leu Lys Asn Leu Arg Glu Met Tyr Val Gly Tyr Phe Asn Ser
225                 230                 235                 240

Tyr Thr Gly Gly Val Pro Pro Glu Phe Gly Gly Leu Thr Asn Leu Gln
                245                 250                 255

Ile Leu Asp Met Ala Ser Cys Thr Leu Thr Gly Glu Ile Pro Thr Ser
            260                 265                 270

Leu Ser Asn Leu Lys His Leu His Thr Leu Phe Leu His Ile Asn Asn
        275                 280                 285

Leu Thr Gly His Ile Pro Pro Glu Leu Ser Gly Leu Ile Ser Leu Lys
    290                 295                 300

Ser Leu Asp Leu Ser Ile Asn Gln Leu Thr Gly Glu Ile Pro Gln Ser
305                 310                 315                 320

Phe Ile Asp Leu Gly Asn Ile Thr Leu Ile Asn Leu Phe Arg Asn Lys
                325                 330                 335

Leu Tyr Gly Pro Ile Pro Glu Phe Ile Gly Glu Leu Pro Lys Leu Gln
            340                 345                 350

Val Phe Glu Val Trp Glu Asn Asn Phe Thr Leu Gln Leu Pro Ser Asn
        355                 360                 365

Leu Gly Arg Asn Gly Asn Leu Lys Lys Leu Asp Val Ser Tyr Asn His
    370                 375                 380

Leu Thr Gly Leu Ile Pro Met Asp Leu Cys Arg Gly Glu Lys Leu Glu
385                 390                 395                 400

Met Leu Ile Leu Ser Asn Asn Phe Phe Phe Gly Pro Ile Pro Glu Glu
                405                 410                 415

Leu Gly Lys Cys Lys Ser Leu Asn Lys Ile Arg Ile Ile Lys Asn Leu
            420                 425                 430

Leu Asn Gly Thr Val Pro Ala Gly Leu Phe Asn Leu Pro Leu Val Thr
        435                 440                 445

Ile Ile Glu Leu Thr Asp Asn Phe Phe Ser Gly Glu Leu Pro Thr Thr
    450                 455                 460

Met Ser Gly Ala Val Ala Asp Gln Ile Tyr Leu Ser Asn Asn Trp Phe
465                 470                 475                 480

Ser Gly Glu Ile Pro Pro Ala Ile Gly Asn Phe Pro Ile Leu Gln Thr
                485                 490                 495

Leu Phe Leu Asp Arg Asn Arg Phe Arg Gly Ser Ile Pro Arg Glu Ile
            500                 505                 510

Phe Glu Leu Lys His Leu Ser Lys Ile Asn Thr Ser Ala Asn Asn Ile
        515                 520                 525

Thr Gly Val Ile Pro Asp Ser Ile Ser Arg Cys Thr Thr Leu Ile Ser
    530                 535                 540

Val Asp Leu Ser Arg Asn Arg Ile Asn Gly Asp Ile Pro Lys Glu Ile
545                 550                 555                 560

Asn Asn Val Ile Asn Leu Gly Thr Leu Asn Leu Ser Gly Asn Gln Leu
                565                 570                 575

Thr Gly Ser Ile Pro Thr Gly Ile Gly Asn Met Thr Ser Leu Thr Thr
            580                 585                 590

Leu Asp Leu Ser Phe Asn Asp Leu Ser Gly Arg Val Pro Leu Gly Gly
        595                 600                 605

Gln Phe Met Val Phe Asn Asp Thr Ser Phe Ala Gly Asn Thr Tyr Leu
```

```
    610                 615                 620

Cys Leu Pro Pro His Val Ser Cys Pro Thr Arg Pro Gly Gln Thr Ser
625                 630                 635                 640

Asp Arg Asn Pro Thr Ala Leu Phe Ser Pro Ser Arg Ile Val Ile Thr
                645                 650                 655

Val Ile Ala Ala Ile Thr Ala Leu Ile Leu Ile Ser Val Ala Ile Arg
            660                 665                 670

Gln Met Asn Lys Lys Lys Asn Gln Lys Ser Leu Ala Trp Lys Leu Thr
        675                 680                 685

Ala Phe Arg Lys Leu Asp Phe Lys Ser Glu Asp Val Leu Glu Cys Leu
    690                 695                 700

Lys Glu Glu Asn Ile Ile Gly Lys Gly Gly Ala Gly Ile Val Tyr Arg
705                 710                 715                 720

Gly Ser Met Pro Asn Asn Val Asp Val Ala Ile Lys Arg Leu Val Gly
                725                 730                 735

Arg Gly Thr Gly Arg Ser Asp His Gly Phe Thr Ala Glu Ile Gln Thr
            740                 745                 750

Leu Gly Arg Ile Arg His Arg His Ile Val Arg Leu Leu Gly Tyr Val
        755                 760                 765

Ala Asn Lys Asp Thr Asn Leu Leu Leu Tyr Glu Tyr Met Pro Asn Gly
    770                 775                 780

Ser Leu Gly Glu Leu Leu His Gly Ser Lys Gly Gly His Leu Gln Trp
785                 790                 795                 800

Glu Thr Arg His Arg Val Ala Val Glu Ala Ala Lys Gly Leu Cys Tyr
                805                 810                 815

Leu His His Asp Cys Ser Pro Leu Ile Leu His Arg Asp Val Lys Ser
            820                 825                 830

Asn Asn Ile Leu Leu Asp Ser Asp Phe Glu Ala His Val Ala Asp Phe
        835                 840                 845

Gly Leu Ala Lys Phe Leu Val Asp Gly Ala Ala Ser Glu Cys Met Ser
    850                 855                 860

Ser Ile Ala Gly Ser Tyr Gly Tyr Ile Ala Pro Glu Tyr Ala Tyr Thr
865                 870                 875                 880

Leu Lys Val Asp Glu Lys Ser Asp Val Tyr Ser Phe Gly Val Val Leu
                885                 890                 895

Leu Glu Leu Ile Ala Gly Lys Lys Pro Val Gly Glu Phe Gly Glu Gly
            900                 905                 910

Val Asp Ile Val Arg Trp Val Arg Asn Thr Glu Glu Glu Met Ser Gln
        915                 920                 925

Pro Ser Asp Ala Ala Ile Val Val Ala Ile Val Asp Ser Arg Leu Thr
    930                 935                 940

Gly Tyr Pro Leu Thr Ser Val Val His Val Phe Lys Ile Ala Met Met
945                 950                 955                 960

Cys Val Glu Asp Glu Ala Ala Thr Arg Pro Thr Met Arg Glu Val Val
                965                 970                 975

His Met Leu Thr Asn Pro Pro Lys Ser Val Ala Asn Leu Ile Ala Phe
            980                 985                 990
```

<210> SEQ ID NO 13
<211> LENGTH: 2982
<212> TYPE: DNA
<213> ORGANISM: Cannabis sativa
<220> FEATURE:
<221> NAME/KEY: CDS
<222> LOCATION: (1)..(2982)

<400> SEQUENCE: 13

```
atg gcg atg aga ctt ttg aag act cat ctt ctg ttt ctg cat ctg tat       48
Met Ala Met Arg Leu Leu Lys Thr His Leu Leu Phe Leu His Leu Tyr
1               5                   10                  15

act act cag ctt tac gtt atc tct ttc ttc ttt cta ttc ttc tca cca       96
Thr Thr Gln Leu Tyr Val Ile Ser Phe Phe Phe Leu Phe Phe Ser Pro
            20                  25                  30

tgc tta tta gct tac act act gac atg gat gtt ctt ctc act ctc aaa      144
Cys Leu Leu Ala Tyr Thr Thr Asp Met Asp Val Leu Leu Thr Leu Lys
        35                  40                  45

tcc tct atg att ggt cct aac ggc gac ggt ctc cac gac tgg att cac      192
Ser Ser Met Ile Gly Pro Asn Gly Asp Gly Leu His Asp Trp Ile His
    50                  55                  60

tca cct tct ccg gca gct cac tgc tct ttc aca ggc gtt tca tgt gac      240
Ser Pro Ser Pro Ala Ala His Cys Ser Phe Thr Gly Val Ser Cys Asp
65                  70                  75                  80

ggc gaa gca cgt gtc atc tct ctc aac gtc tcc ttt act cct ttg ttc      288
Gly Glu Ala Arg Val Ile Ser Leu Asn Val Ser Phe Thr Pro Leu Phe
                85                  90                  95

gga aaa atc tca ccg gag att ggg atg tta aac cgt ctg gtg aat cta      336
Gly Lys Ile Ser Pro Glu Ile Gly Met Leu Asn Arg Leu Val Asn Leu
            100                 105                 110

acg tta gct gcc aac aat ttc acc ggt gaa tta cca ttg gag atg aag      384
Thr Leu Ala Ala Asn Asn Phe Thr Gly Glu Leu Pro Leu Glu Met Lys
        115                 120                 125

agt cta act tca ctc aag gtt ttg aat atc tcc aac aat gtt aac ctc      432
Ser Leu Thr Ser Leu Lys Val Leu Asn Ile Ser Asn Asn Val Asn Leu
    130                 135                 140

agc gga agc ttc cct gga gag att gtt ata gcc atg gtt gat ctt gaa      480
Ser Gly Ser Phe Pro Gly Glu Ile Val Ile Ala Met Val Asp Leu Glu
145                 150                 155                 160

gtt ctt gac gct tac aac aac aat ttc acc ggt acg tta cca ctg gag      528
Val Leu Asp Ala Tyr Asn Asn Asn Phe Thr Gly Thr Leu Pro Leu Glu
                165                 170                 175

att gca aag ctc aag aac ctc aaa cat ctc tct ctc ggt gga aac ttc      576
Ile Ala Lys Leu Lys Asn Leu Lys His Leu Ser Leu Gly Gly Asn Phe
            180                 185                 190

ttc acc ggc gag att ccc gag agt tac gga gat atc caa agc cta gag      624
Phe Thr Gly Glu Ile Pro Glu Ser Tyr Gly Asp Ile Gln Ser Leu Glu
        195                 200                 205

tat ctc gga ctc aac gga gca gga ctc tcc ggt aaa tct ccg gcg ttt      672
Tyr Leu Gly Leu Asn Gly Ala Gly Leu Ser Gly Lys Ser Pro Ala Phe
    210                 215                 220

cta tct cgc ctc aag aac ttg aga gaa atg tat gtc gga tac ttc aac      720
Leu Ser Arg Leu Lys Asn Leu Arg Glu Met Tyr Val Gly Tyr Phe Asn
225                 230                 235                 240

agc tac acc ggt ggt gtt ccc ccg gag ttc ggt ggt tta aca aac ctt      768
Ser Tyr Thr Gly Gly Val Pro Pro Glu Phe Gly Gly Leu Thr Asn Leu
                245                 250                 255

cag atc ctc gac atg gcg agt tgt aca ctc acc gga gag atc cca acg      816
Gln Ile Leu Asp Met Ala Ser Cys Thr Leu Thr Gly Glu Ile Pro Thr
            260                 265                 270

agt tta agc aat ctg aaa cat tta cac act ctg ttc ctt cac atc aac      864
Ser Leu Ser Asn Leu Lys His Leu His Thr Leu Phe Leu His Ile Asn
        275                 280                 285

aac tta acc gga cac att cca cca gaa ctc tcc ggt tta atc agc ctc      912
Asn Leu Thr Gly His Ile Pro Pro Glu Leu Ser Gly Leu Ile Ser Leu
    290                 295                 300
```

-continued

```
aaa tct ctc gat tta tca atc aac cag tta acc gga gaa ata cct caa      960
Lys Ser Leu Asp Leu Ser Ile Asn Gln Leu Thr Gly Glu Ile Pro Gln
305                 310                 315                 320

agc ttc atc gac ctc gga aac atc act ctc atc aac ctc ttc aga aac     1008
Ser Phe Ile Asp Leu Gly Asn Ile Thr Leu Ile Asn Leu Phe Arg Asn
                325                 330                 335

aac ctc tac ggt cca ata cca gag ttc atc gga gag tta cca aaa cta     1056
Asn Leu Tyr Gly Pro Ile Pro Glu Phe Ile Gly Glu Leu Pro Lys Leu
            340                 345                 350

caa gtc ttc gaa gtc tgg gag aac aac ttc acc tta cag tta ccg gca     1104
Gln Val Phe Glu Val Trp Glu Asn Asn Phe Thr Leu Gln Leu Pro Ala
        355                 360                 365

aat ctt gga cgg aac ggg aat ctg aaa aag ctc gac gtc tct tac aac     1152
Asn Leu Gly Arg Asn Gly Asn Leu Lys Lys Leu Asp Val Ser Tyr Asn
    370                 375                 380

cac ctc acc gga ctc atc ccc atg gat tta tgc aga ggc gag aaa ctg     1200
His Leu Thr Gly Leu Ile Pro Met Asp Leu Cys Arg Gly Glu Lys Leu
385                 390                 395                 400

gag atg tta ata ctc tct aac aac ttc ttc ttc ggt cca atc cca gaa     1248
Glu Met Leu Ile Leu Ser Asn Asn Phe Phe Phe Gly Pro Ile Pro Glu
                405                 410                 415

gag ctt ggt aaa tgc aaa tcg tta aac aaa atc aga atc gtc aag aat     1296
Glu Leu Gly Lys Cys Lys Ser Leu Asn Lys Ile Arg Ile Val Lys Asn
            420                 425                 430

cta ctc aac gga act gta ccg gcg ggg ctt ttc aat cta ccg cta gta     1344
Leu Leu Asn Gly Thr Val Pro Ala Gly Leu Phe Asn Leu Pro Leu Val
        435                 440                 445

acg att atc gaa ctc acc gat aat atc ttc tcc ggc gaa ctt ccg acg     1392
Thr Ile Ile Glu Leu Thr Asp Asn Ile Phe Ser Gly Glu Leu Pro Thr
    450                 455                 460

aag atg tcc ggc gct gtt gcc gac cag att tac ctc tct aac aac tgg     1440
Lys Met Ser Gly Ala Val Ala Asp Gln Ile Tyr Leu Ser Asn Asn Trp
465                 470                 475                 480

ttc tcc ggc gag att cct ccg gcg atc ggt aat ttc cct aat ttg cag     1488
Phe Ser Gly Glu Ile Pro Pro Ala Ile Gly Asn Phe Pro Asn Leu Gln
                485                 490                 495

act ctc ttc tta gat cgg aac cga ttc cgc ggc agc atc ccg aga gag     1536
Thr Leu Phe Leu Asp Arg Asn Arg Phe Arg Gly Ser Ile Pro Arg Glu
            500                 505                 510

atc ttc gag ttg aag cat cta tcg aag atc aac aca agt gcg aac aac     1584
Ile Phe Glu Leu Lys His Leu Ser Lys Ile Asn Thr Ser Ala Asn Asn
        515                 520                 525

atc acc ggc gtt atc cca gat tca atc tcg cgc tgc act act tta atc     1632
Ile Thr Gly Val Ile Pro Asp Ser Ile Ser Arg Cys Thr Thr Leu Ile
    530                 535                 540

tcc gtc gat ctc agc cgt aac cga atc aac gga gag ata cct aaa gag     1680
Ser Val Asp Leu Ser Arg Asn Arg Ile Asn Gly Glu Ile Pro Lys Glu
545                 550                 555                 560

atc aac aac gtg att aac ctc ggt aca ctt aat ctc tcc ggt aat caa     1728
Ile Asn Asn Val Ile Asn Leu Gly Thr Leu Asn Leu Ser Gly Asn Gln
                565                 570                 575

cta acc ggt tca atc cca acc gga atc gga aac atg acg agt cta aca     1776
Leu Thr Gly Ser Ile Pro Thr Gly Ile Gly Asn Met Thr Ser Leu Thr
            580                 585                 590

acg cta gat ctc tct ttc aac gat ctc tca gga aga gta cca cta ggt     1824
Thr Leu Asp Leu Ser Phe Asn Asp Leu Ser Gly Arg Val Pro Leu Gly
        595                 600                 605

ggt caa ttc atg gtg ttc aac gac act tct ttc gcc gga aac act tac     1872
Gly Gln Phe Met Val Phe Asn Asp Thr Ser Phe Ala Gly Asn Thr Tyr
    610                 615                 620
```

-continued ctc tgt tta cct cac cac gtc tca tgt cca aca cgg cca gga caa acc 1920
Leu Cys Leu Pro His His Val Ser Cys Pro Thr Arg Pro Gly Gln Thr
625 630 635 640 tcc gat cgc aac ccc acg gcg ttg ttc tca ccg tca agg atc gta atc 1968
Ser Asp Arg Asn Pro Thr Ala Leu Phe Ser Pro Ser Arg Ile Val Ile
645 650 655 acg gtt atc gca gcg atc acg gcg ttg atc cta atc agc gta gcg att 2016
Thr Val Ile Ala Ala Ile Thr Ala Leu Ile Leu Ile Ser Val Ala Ile
660 665 670 cgt cag atg aac aag aag aag aac cag aaa tct ctc gcc tgg aag cta 2064
Arg Gln Met Asn Lys Lys Lys Asn Gln Lys Ser Leu Ala Trp Lys Leu
675 680 685 acc gcc ttc cag aaa ctc gat ttc aaa tcc gaa gac gta ctc gag tgt 2112
Thr Ala Phe Gln Lys Leu Asp Phe Lys Ser Glu Asp Val Leu Glu Cys
690 695 700 ttg aaa gaa gag aat ata atc ggc aaa ggc gga gct gga atc gtt tac 2160
Leu Lys Glu Glu Asn Ile Ile Gly Lys Gly Gly Ala Gly Ile Val Tyr
705 710 715 720 cgt gga tct atg cca aac aac gtt gac gtc gcg atc aaa cga ctc gtt 2208
Arg Gly Ser Met Pro Asn Asn Val Asp Val Ala Ile Lys Arg Leu Val
725 730 735 ggt cgt ggc aca ggg agg agc gat cat gga ttc acg gcg gag att caa 2256
Gly Arg Gly Thr Gly Arg Ser Asp His Gly Phe Thr Ala Glu Ile Gln
740 745 750 act ttg gga agg att cga cac cgt cac atc gtg agg ctt ctc ggt tac 2304
Thr Leu Gly Arg Ile Arg His Arg His Ile Val Arg Leu Leu Gly Tyr
755 760 765 gta gcg aac aag gac acg aac ttg ctt ctc tat gag tac atg cct aat 2352
Val Ala Asn Lys Asp Thr Asn Leu Leu Leu Tyr Glu Tyr Met Pro Asn
770 775 780 gga agc ctt gga gag ctt ttg cat gga tct aaa ggt ggt cac ctc caa 2400
Gly Ser Leu Gly Glu Leu Leu His Gly Ser Lys Gly Gly His Leu Gln
785 790 795 800 tgg gag acg aga cat aga gta gcc gtg gaa gca gcg aaa ggc ttg tgt 2448
Trp Glu Thr Arg His Arg Val Ala Val Glu Ala Ala Lys Gly Leu Cys
805 810 815 tat ctt cac cat gac tgt tca ccg ttg atc ttg cac aga gat gtg aag 2496
Tyr Leu His His Asp Cys Ser Pro Leu Ile Leu His Arg Asp Val Lys
820 825 830 tcc aat aac att ctt ttg gac tct gat ttt gaa gcc cat gtt gct gat 2544
Ser Asn Asn Ile Leu Leu Asp Ser Asp Phe Glu Ala His Val Ala Asp
835 840 845 ttt ggg ctt gct aag ttc ttg gtg gac ggt gct gct tct gag tgt atg 2592
Phe Gly Leu Ala Lys Phe Leu Val Asp Gly Ala Ala Ser Glu Cys Met
850 855 860 tct tca att gct ggc tct tat gga tac atc gcc cca gag tat gca tat 2640
Ser Ser Ile Ala Gly Ser Tyr Gly Tyr Ile Ala Pro Glu Tyr Ala Tyr
865 870 875 880 acc ttg aaa gtg gac gag aag agt gat gtg tat agt ttt gga gtg gtt 2688
Thr Leu Lys Val Asp Glu Lys Ser Asp Val Tyr Ser Phe Gly Val Val
885 890 895 tta ttg gag cta ata gcc ggg aag aaa ccg gtt ggt gaa ttt gga gaa 2736
Leu Leu Glu Leu Ile Ala Gly Lys Lys Pro Val Gly Glu Phe Gly Glu
900 905 910 gga gtc gat ata gtt agg tgg gtg agg aac acg gaa gaa gag ata tct 2784
Gly Val Asp Ile Val Arg Trp Val Arg Asn Thr Glu Glu Glu Ile Ser
915 920 925 cag ccg tcg gat gct gct att gtt gtt gct atc gtt gac tcg agg ttg 2832
Gln Pro Ser Asp Ala Ala Ile Val Val Ala Ile Val Asp Ser Arg Leu

```
    930                 935                 940

act ggt tat acg ttg acc agt gtg gtt cat gtg ttt aag att gca atg     2880
Thr Gly Tyr Thr Leu Thr Ser Val Val His Val Phe Lys Ile Ala Met
945                 950                 955                 960

atg tgt gta gag gat gaa gcc gcg acg agg cct acg atg agg gag gtt     2928
Met Cys Val Glu Asp Glu Ala Ala Thr Arg Pro Thr Met Arg Glu Val
                965                 970                 975

gtg cac atg ctc act aac cct cct aaa tcc gtg gct aac ttg atc gcg     2976
Val His Met Leu Thr Asn Pro Pro Lys Ser Val Ala Asn Leu Ile Ala
            980                 985                 990

ttc tga                                                             2982
Phe


<210> SEQ ID NO 14
<211> LENGTH: 993
<212> TYPE: PRT
<213> ORGANISM: Cannabis sativa

<400> SEQUENCE: 14

Met Ala Met Arg Leu Leu Lys Thr His Leu Leu Phe Leu His Leu Tyr
1               5                   10                  15

Thr Thr Gln Leu Tyr Val Ile Ser Phe Phe Phe Leu Phe Phe Ser Pro
            20                  25                  30

Cys Leu Leu Ala Tyr Thr Thr Asp Met Asp Val Leu Leu Thr Leu Lys
        35                  40                  45

Ser Ser Met Ile Gly Pro Asn Gly Asp Gly Leu His Asp Trp Ile His
    50                  55                  60

Ser Pro Ser Pro Ala Ala His Cys Ser Phe Thr Gly Val Ser Cys Asp
65                  70                  75                  80

Gly Glu Ala Arg Val Ile Ser Leu Asn Val Ser Phe Thr Pro Leu Phe
                85                  90                  95

Gly Lys Ile Ser Pro Glu Ile Gly Met Leu Asn Arg Leu Val Asn Leu
            100                 105                 110

Thr Leu Ala Ala Asn Asn Phe Thr Gly Glu Leu Pro Leu Glu Met Lys
        115                 120                 125

Ser Leu Thr Ser Leu Lys Val Leu Asn Ile Ser Asn Asn Val Asn Leu
    130                 135                 140

Ser Gly Ser Phe Pro Gly Glu Ile Val Ile Ala Met Val Asp Leu Glu
145                 150                 155                 160

Val Leu Asp Ala Tyr Asn Asn Asn Phe Thr Gly Thr Leu Pro Leu Glu
                165                 170                 175

Ile Ala Lys Leu Lys Asn Leu Lys His Leu Ser Leu Gly Gly Asn Phe
            180                 185                 190

Phe Thr Gly Glu Ile Pro Glu Ser Tyr Gly Asp Ile Gln Ser Leu Glu
        195                 200                 205

Tyr Leu Gly Leu Asn Gly Ala Gly Leu Ser Gly Lys Ser Pro Ala Phe
    210                 215                 220

Leu Ser Arg Leu Lys Asn Leu Arg Glu Met Tyr Val Gly Tyr Phe Asn
225                 230                 235                 240

Ser Tyr Thr Gly Gly Val Pro Pro Glu Phe Gly Gly Leu Thr Asn Leu
                245                 250                 255

Gln Ile Leu Asp Met Ala Ser Cys Thr Leu Thr Gly Glu Ile Pro Thr
            260                 265                 270

Ser Leu Ser Asn Leu Lys His Leu His Thr Leu Phe Leu His Ile Asn
        275                 280                 285
```

-continued

```
Asn Leu Thr Gly His Ile Pro Pro Glu Leu Ser Gly Leu Ile Ser Leu
    290                 295                 300

Lys Ser Leu Asp Leu Ser Ile Asn Gln Leu Thr Gly Glu Ile Pro Gln
305                 310                 315                 320

Ser Phe Ile Asp Leu Gly Asn Ile Thr Leu Ile Asn Leu Phe Arg Asn
                325                 330                 335

Asn Leu Tyr Gly Pro Ile Pro Glu Phe Ile Gly Glu Leu Pro Lys Leu
            340                 345                 350

Gln Val Phe Glu Val Trp Glu Asn Asn Phe Thr Leu Gln Leu Pro Ala
        355                 360                 365

Asn Leu Gly Arg Asn Gly Asn Leu Lys Lys Leu Asp Val Ser Tyr Asn
    370                 375                 380

His Leu Thr Gly Leu Ile Pro Met Asp Leu Cys Arg Gly Glu Lys Leu
385                 390                 395                 400

Glu Met Leu Ile Leu Ser Asn Asn Phe Phe Gly Pro Ile Pro Glu
                405                 410                 415

Glu Leu Gly Lys Cys Lys Ser Leu Asn Lys Ile Arg Ile Val Lys Asn
            420                 425                 430

Leu Leu Asn Gly Thr Val Pro Ala Gly Leu Phe Asn Leu Pro Leu Val
        435                 440                 445

Thr Ile Ile Glu Leu Thr Asp Asn Ile Phe Ser Gly Glu Leu Pro Thr
    450                 455                 460

Lys Met Ser Gly Ala Val Ala Asp Gln Ile Tyr Leu Ser Asn Asn Trp
465                 470                 475                 480

Phe Ser Gly Glu Ile Pro Pro Ala Ile Gly Asn Phe Pro Asn Leu Gln
                485                 490                 495

Thr Leu Phe Leu Asp Arg Asn Arg Phe Arg Gly Ser Ile Pro Arg Glu
            500                 505                 510

Ile Phe Glu Leu Lys His Leu Ser Lys Ile Asn Thr Ser Ala Asn Asn
        515                 520                 525

Ile Thr Gly Val Ile Pro Asp Ser Ile Ser Arg Cys Thr Thr Leu Ile
    530                 535                 540

Ser Val Asp Leu Ser Arg Asn Arg Ile Asn Gly Glu Ile Pro Lys Glu
545                 550                 555                 560

Ile Asn Asn Val Ile Asn Leu Gly Thr Leu Asn Leu Ser Gly Asn Gln
                565                 570                 575

Leu Thr Gly Ser Ile Pro Thr Gly Ile Gly Asn Met Thr Ser Leu Thr
            580                 585                 590

Thr Leu Asp Leu Ser Phe Asn Asp Leu Ser Gly Arg Val Pro Leu Gly
        595                 600                 605

Gly Gln Phe Met Val Phe Asn Asp Thr Ser Phe Ala Gly Asn Thr Tyr
    610                 615                 620

Leu Cys Leu Pro His His Val Ser Cys Pro Thr Arg Pro Gly Gln Thr
625                 630                 635                 640

Ser Asp Arg Asn Pro Thr Ala Leu Phe Ser Pro Ser Arg Ile Val Ile
                645                 650                 655

Thr Val Ile Ala Ala Ile Thr Ala Leu Ile Leu Ile Ser Val Ala Ile
            660                 665                 670

Arg Gln Met Asn Lys Lys Lys Asn Gln Lys Ser Leu Ala Trp Lys Leu
        675                 680                 685

Thr Ala Phe Gln Lys Leu Asp Phe Lys Ser Glu Asp Val Leu Glu Cys
    690                 695                 700

Leu Lys Glu Glu Asn Ile Ile Gly Lys Gly Gly Ala Gly Ile Val Tyr
```

705 710 715 720

Arg Gly Ser Met Pro Asn Asn Val Asp Val Ala Ile Lys Arg Leu Val
725 730 735

Gly Arg Gly Thr Gly Arg Ser Asp His Gly Phe Thr Ala Glu Ile Gln
740 745 750

Thr Leu Gly Arg Ile Arg His Arg His Ile Val Arg Leu Leu Gly Tyr
755 760 765

Val Ala Asn Lys Asp Thr Asn Leu Leu Leu Tyr Glu Tyr Met Pro Asn
770 775 780

Gly Ser Leu Gly Glu Leu Leu His Gly Ser Lys Gly Gly His Leu Gln
785 790 795 800

Trp Glu Thr Arg His Arg Val Ala Val Glu Ala Ala Lys Gly Leu Cys
805 810 815

Tyr Leu His His Asp Cys Ser Pro Leu Ile Leu His Arg Asp Val Lys
820 825 830

Ser Asn Asn Ile Leu Leu Asp Ser Asp Phe Glu Ala His Val Ala Asp
835 840 845

Phe Gly Leu Ala Lys Phe Leu Val Asp Gly Ala Ala Ser Glu Cys Met
850 855 860

Ser Ser Ile Ala Gly Ser Tyr Gly Tyr Ile Ala Pro Glu Tyr Ala Tyr
865 870 875 880

Thr Leu Lys Val Asp Glu Lys Ser Asp Val Tyr Ser Phe Gly Val Val
885 890 895

Leu Leu Glu Leu Ile Ala Gly Lys Lys Pro Val Gly Glu Phe Gly Glu
900 905 910

Gly Val Asp Ile Val Arg Trp Val Arg Asn Thr Glu Glu Glu Ile Ser
915 920 925

Gln Pro Ser Asp Ala Ala Ile Val Val Ala Ile Val Asp Ser Arg Leu
930 935 940

Thr Gly Tyr Thr Leu Thr Ser Val Val His Val Phe Lys Ile Ala Met
945 950 955 960

Met Cys Val Glu Asp Glu Ala Ala Thr Arg Pro Thr Met Arg Glu Val
965 970 975

Val His Met Leu Thr Asn Pro Pro Lys Ser Val Ala Asn Leu Ile Ala
980 985 990

Phe

<210> SEQ ID NO 15
<211> LENGTH: 3783
<212> TYPE: DNA
<213> ORGANISM: Cannabis sativa
<220> FEATURE:
<221> NAME/KEY: CDS
<222> LOCATION: (1)..(3783)
<220> FEATURE:
<221> NAME/KEY: misc_feature
<222> LOCATION: (1663)..(1663)
<223> OTHER INFORMATION: n is a, c, g, or t

<400> SEQUENCE: 15 atg gcg atg aga ctt ttg aag act cat ctt ctg ttt ctg cat ctg tat 48
Met Ala Met Arg Leu Leu Lys Thr His Leu Leu Phe Leu His Leu Tyr
1 5 10 15 act act cag ctt tac gtt atc tct ttc ttc ttt gta ttc ttc tca aca 96
Thr Thr Gln Leu Tyr Val Ile Ser Phe Phe Phe Val Phe Phe Ser Thr
20 25 30 tgc tta gct tac act gat atg gaa gtt ctt ctc aat ctc aaa tcc tcc 144

-continued

```
Cys Leu Ala Tyr Thr Asp Met Glu Val Leu Leu Asn Leu Lys Ser Ser
        35                  40                  45

atg att ggt cat aac ggc gac ggt ctc cat gac tgg att cac tca cct      192
Met Ile Gly His Asn Gly Asp Gly Leu His Asp Trp Ile His Ser Pro
    50                  55                  60

tct ccg gca gct cac tgc tct ttc acc ggc gtt tca tgt gac ggc gaa      240
Ser Pro Ala Ala His Cys Ser Phe Thr Gly Val Ser Cys Asp Gly Glu
65                  70                  75                  80

gct cga gtt atc tct ctc aac gtc tcc ttt act cct ttg ttc gga aaa      288
Ala Arg Val Ile Ser Leu Asn Val Ser Phe Thr Pro Leu Phe Gly Lys
                85                  90                  95

atc tca ccg gag att ggg atg tta aac cgt ctg gtg aat cta aca tta      336
Ile Ser Pro Glu Ile Gly Met Leu Asn Arg Leu Val Asn Leu Thr Leu
            100                 105                 110

gca gcc aac aat ttc acc ggt gaa tta cca ttg gag atg aag agt cta      384
Ala Ala Asn Asn Phe Thr Gly Glu Leu Pro Leu Glu Met Lys Ser Leu
        115                 120                 125

act tca ctc aag gtt ttg aac atc tcc aac aat gta aac ctc agc gga      432
Thr Ser Leu Lys Val Leu Asn Ile Ser Asn Asn Val Asn Leu Ser Gly
    130                 135                 140

agc ttc cct gga gag atg gtt aaa gcc atg gtt gat ctt gaa gtt ctt      480
Ser Phe Pro Gly Glu Met Val Lys Ala Met Val Asp Leu Glu Val Leu
145                 150                 155                 160

gac gct tac aac aac aat ttc acc ggt acg tta cca cta gag att tca      528
Asp Ala Tyr Asn Asn Asn Phe Thr Gly Thr Leu Pro Leu Glu Ile Ser
                165                 170                 175

gag ctc aag aac ctc aaa cat ctc tct ctc ggt gga aac ttc ttc acc      576
Glu Leu Lys Asn Leu Lys His Leu Ser Leu Gly Gly Asn Phe Phe Thr
            180                 185                 190

ggc gag att cct gag agt tac gga gat atc caa agc cta gag tat ctc      624
Gly Glu Ile Pro Glu Ser Tyr Gly Asp Ile Gln Ser Leu Glu Tyr Leu
        195                 200                 205

gga ctc aac gga gct gga ctc tcc ggt aaa tct ccg gcg ttt cta tct      672
Gly Leu Asn Gly Ala Gly Leu Ser Gly Lys Ser Pro Ala Phe Leu Ser
    210                 215                 220

cgc ctc aag aac ttg aga gaa atg tat gtc gga tac ttc aac agc tac      720
Arg Leu Lys Asn Leu Arg Glu Met Tyr Val Gly Tyr Phe Asn Ser Tyr
225                 230                 235                 240

acc ggt ggt gtt ccc ccg gag ttc ggt ggt tta acg aac ctt cag atc      768
Thr Gly Gly Val Pro Pro Glu Phe Gly Gly Leu Thr Asn Leu Gln Ile
                245                 250                 255

ctc gac atg gcg agt tgt aca ctc acc gga gag atc cca acg agt tta      816
Leu Asp Met Ala Ser Cys Thr Leu Thr Gly Glu Ile Pro Thr Ser Leu
            260                 265                 270

agt aac ctg aaa cat tta cac act ctg ttc cta cac atc aac aac tta      864
Ser Asn Leu Lys His Leu His Thr Leu Phe Leu His Ile Asn Asn Leu
        275                 280                 285

acc gga cac ata cca cca gaa ctc tcc ggt tta atc agc ctc aaa tct      912
Thr Gly His Ile Pro Pro Glu Leu Ser Gly Leu Ile Ser Leu Lys Ser
    290                 295                 300

ctc gat tta tca atc aac cag tta acc gga gag ata cct caa agc ttc      960
Leu Asp Leu Ser Ile Asn Gln Leu Thr Gly Glu Ile Pro Gln Ser Phe
305                 310                 315                 320

atc gac ctc gga aac acc act ctc atc aac ctc ttc aga aac aac ctc     1008
Ile Asp Leu Gly Asn Thr Thr Leu Ile Asn Leu Phe Arg Asn Asn Leu
                325                 330                 335

tac ggt cca ata cca gag ttc atc gga gag tta cca aaa ctc caa gtc     1056
Tyr Gly Pro Ile Pro Glu Phe Ile Gly Glu Leu Pro Lys Leu Gln Val
            340                 345                 350
```

-continued

```
ttc gaa gtc tgg gag aac aac ttc acc tta cag tta ccg gcg aat ctt      1104
Phe Glu Val Trp Glu Asn Asn Phe Thr Leu Gln Leu Pro Ala Asn Leu
        355                 360                 365

ggc cgg aac ggg aat ctg aaa aag ctc gac gtc tct tat aac cac ctc      1152
Gly Arg Asn Gly Asn Leu Lys Lys Leu Asp Val Ser Tyr Asn His Leu
    370                 375                 380

acc gga ctt atc ccc atg gat tta tgc aga ggc gag aag cta gag atg      1200
Thr Gly Leu Ile Pro Met Asp Leu Cys Arg Gly Glu Lys Leu Glu Met
385                 390                 395                 400

ttg ata ctc tct aac aac ttc ctc ttc ggt cca atc cca gaa gag ctt      1248
Leu Ile Leu Ser Asn Asn Phe Leu Phe Gly Pro Ile Pro Glu Glu Leu
                405                 410                 415

ggt aaa tgc aaa tcg tta aac aaa atc aga atc gtc aag aat ctt ctc      1296
Gly Lys Cys Lys Ser Leu Asn Lys Ile Arg Ile Val Lys Asn Leu Leu
            420                 425                 430

aac gga act gta ccg gcg ggg ctt ttc aat cta ccg ctc gtt acg att      1344
Asn Gly Thr Val Pro Ala Gly Leu Phe Asn Leu Pro Leu Val Thr Ile
        435                 440                 445

atc gaa ctc acc gat aat ttc ttc tcc ggt gaa ctt ccg acg acg atg      1392
Ile Glu Leu Thr Asp Asn Phe Phe Ser Gly Glu Leu Pro Thr Thr Met
    450                 455                 460

tcc ggc gct gtt gcc gac cag att tac ctc tct aac aac tgg ttc tcc      1440
Ser Gly Ala Val Ala Asp Gln Ile Tyr Leu Ser Asn Asn Trp Phe Ser
465                 470                 475                 480

ggc gag att cct ccg gcg att ggt aat ttc cct aat tta cag act ctg      1488
Gly Glu Ile Pro Pro Ala Ile Gly Asn Phe Pro Asn Leu Gln Thr Leu
                485                 490                 495

ttc cta gat cgg aac cga ttc cgc ggc agt atc ccg aga gag atc ttc      1536
Phe Leu Asp Arg Asn Arg Phe Arg Gly Ser Ile Pro Arg Glu Ile Phe
            500                 505                 510

gaa ttg aag cat cta tcg aag atc aac acg agt gcg aac aac atc acc      1584
Glu Leu Lys His Leu Ser Lys Ile Asn Thr Ser Ala Asn Asn Ile Thr
        515                 520                 525

ggc gtt atc cca gat tca atc tca cgc tgc act act cta atc tcc gtc      1632
Gly Val Ile Pro Asp Ser Ile Ser Arg Cys Thr Thr Leu Ile Ser Val
    530                 535                 540

gat ctc agc cgt aac cga atc aac gga gat nga cat ggc gag ttg tac      1680
Asp Leu Ser Arg Asn Arg Ile Asn Gly Asp Xaa His Gly Glu Leu Tyr
545                 550                 555                 560

act cac cgg aga gat ccc aac gag ttt aac ctc aaa tct ctc gat tta      1728
Thr His Arg Arg Asp Pro Asn Glu Phe Asn Leu Lys Ser Leu Asp Leu
                565                 570                 575

tca atc aac cag tta acc gga gag ata cct caa agc ttc atc gac ctc      1776
Ser Ile Asn Gln Leu Thr Gly Glu Ile Pro Gln Ser Phe Ile Asp Leu
            580                 585                 590

gga aac acc act ctc atc aac ctc ttc aga aac aac ctc tac ggt cca      1824
Gly Asn Thr Thr Leu Ile Asn Leu Phe Arg Asn Asn Leu Tyr Gly Pro
        595                 600                 605

ata cca gag ttc atc gga gag tta cca aaa ctc caa gtc ttc gaa gtc      1872
Ile Pro Glu Phe Ile Gly Glu Leu Pro Lys Leu Gln Val Phe Glu Val
    610                 615                 620

tgg gag aac aac ttc acc tta cag tta ccg gcg aat ctt ggc cgg aac      1920
Trp Glu Asn Asn Phe Thr Leu Gln Leu Pro Ala Asn Leu Gly Arg Asn
625                 630                 635                 640

ggg aat ctg aaa aag ctc gac gtc tct tat aac cac ctc acc gga ctt      1968
Gly Asn Leu Lys Lys Leu Asp Val Ser Tyr Asn His Leu Thr Gly Leu
                645                 650                 655

atc ccc atg gat tta tgc aga ggc gag aag cta gag atg ttg ata ctc      2016
Ile Pro Met Asp Leu Cys Arg Gly Glu Lys Leu Glu Met Leu Ile Leu
            660                 665                 670
```

-continued

```
tct aac aac ttc ctc ttc ggt cca atc cca gaa gag ctt ggt aaa tgc      2064
Ser Asn Asn Phe Leu Phe Gly Pro Ile Pro Glu Glu Leu Gly Lys Cys
        675                 680                 685

aaa tcg tta aac aaa atc aga atc gtc aag aat ctt ctc aac gga act      2112
Lys Ser Leu Asn Lys Ile Arg Ile Val Lys Asn Leu Leu Asn Gly Thr
    690                 695                 700

gta ccg gcg ggg ctt ttc aat cta ccg ctc gtt acg att atc gaa ctc      2160
Val Pro Ala Gly Leu Phe Asn Leu Pro Leu Val Thr Ile Ile Glu Leu
705                 710                 715                 720

acc gat aat ttc ttc tcc ggt gaa ctt ccg acg acg atg tcc ggc gct      2208
Thr Asp Asn Phe Phe Ser Gly Glu Leu Pro Thr Thr Met Ser Gly Ala
                725                 730                 735

gtt gcc gac cag att tac ctc tct aac aac tgg ttc tcc ggc gag att      2256
Val Ala Asp Gln Ile Tyr Leu Ser Asn Asn Trp Phe Ser Gly Glu Ile
            740                 745                 750

cct ccg gcg att ggt aat ttc cct aat tta cag act ctg ttc cta gat      2304
Pro Pro Ala Ile Gly Asn Phe Pro Asn Leu Gln Thr Leu Phe Leu Asp
        755                 760                 765

cgg aac cga ttc cgc ggc agt atc ccg aga gag atc ttc gaa ttg aag      2352
Arg Asn Arg Phe Arg Gly Ser Ile Pro Arg Glu Ile Phe Glu Leu Lys
    770                 775                 780

cat cta tcg aag atc aac acg agt gcg aac aac atc acc ggc gtt atc      2400
His Leu Ser Lys Ile Asn Thr Ser Ala Asn Asn Ile Thr Gly Val Ile
785                 790                 795                 800

cca gat tca atc tca cgc tgc act act cta atc tcc gtc gat ctc agc      2448
Pro Asp Ser Ile Ser Arg Cys Thr Thr Leu Ile Ser Val Asp Leu Ser
                805                 810                 815

cgt aac cga atc aac gga gat ata cct aaa gag atc aac aac gtg att      2496
Arg Asn Arg Ile Asn Gly Asp Ile Pro Lys Glu Ile Asn Asn Val Ile
            820                 825                 830

aac ctc ggt aca ctt aat ctc tcc ggt aat caa cta acc ggt tcg atc      2544
Asn Leu Gly Thr Leu Asn Leu Ser Gly Asn Gln Leu Thr Gly Ser Ile
        835                 840                 845

cca acc gga atc gga aac atg acg agt tta aca acg cta gat ctc tct      2592
Pro Thr Gly Ile Gly Asn Met Thr Ser Leu Thr Thr Leu Asp Leu Ser
    850                 855                 860

ttc aac gat ctc tca ggg aga gta cca cta ggt ggt caa ttt atg gtg      2640
Phe Asn Asp Leu Ser Gly Arg Val Pro Leu Gly Gly Gln Phe Met Val
865                 870                 875                 880

ttc aac gac act tcc ttc gcc gga aac act tac ctc tgt tta cct cac      2688
Phe Asn Asp Thr Ser Phe Ala Gly Asn Thr Tyr Leu Cys Leu Pro His
                885                 890                 895

cac gtc tca tgt cca aca cgg cca gga caa acc tcc gat cgc aac ccc      2736
His Val Ser Cys Pro Thr Arg Pro Gly Gln Thr Ser Asp Arg Asn Pro
            900                 905                 910

ccc gcg ttg ttc tca ccg tcg agg atc gta atc aca gtt atc gca gcg      2784
Pro Ala Leu Phe Ser Pro Ser Arg Ile Val Ile Thr Val Ile Ala Ala
        915                 920                 925

atc acg ggg tta atc cta atc agc gta gcg att cgt cag atg aac aaa      2832
Ile Thr Gly Leu Ile Leu Ile Ser Val Ala Ile Arg Gln Met Asn Lys
    930                 935                 940

aag aag aat caa aaa tct ctc gcc tgg aaa cta acc gcc ttc cag aaa      2880
Lys Lys Asn Gln Lys Ser Leu Ala Trp Lys Leu Thr Ala Phe Gln Lys
945                 950                 955                 960

ctc gat ttc aaa tcc gca gac gtc ctc gag tgt ttg aaa gaa gag aac      2928
Leu Asp Phe Lys Ser Ala Asp Val Leu Glu Cys Leu Lys Glu Glu Asn
                965                 970                 975

ata atc gga aaa ggc gga gct gga atc gta tac cgt gga tct atg cca      2976
Ile Ile Gly Lys Gly Gly Ala Gly Ile Val Tyr Arg Gly Ser Met Pro
```

```
            980                 985                 990

aac aac gtt gac gtc gcg atc aaa  cga ctc gtt ggt cgt  ggc act ggg   3024
Asn Asn Val Asp Val Ala Ile Lys  Arg Leu Val Gly Arg  Gly Thr Gly
        995                 1000                1005

agg agc  gat cat gga ttc acg  gcg gag att caa act  ttg gga agg      3069
Arg Ser  Asp His Gly Phe Thr  Ala Glu Ile Gln Thr  Leu Gly Arg
    1010                 1015                 1020

att cgt  cac cgt cac atc gtg  agg ctt cta ggt tac  gta gcg aac      3114
Ile Arg  His Arg His Ile Val  Arg Leu Leu Gly Tyr  Val Ala Asn
    1025                 1030                 1035

aag gac  acc aac ttg ctt ctc  tat gag tac atg cct  aat gga agc      3159
Lys Asp  Thr Asn Leu Leu Leu  Tyr Glu Tyr Met Pro  Asn Gly Ser
    1040                 1045                 1050

ctt ggt  gag ctt ttg cat gga  tct aaa ggt ggt cac  ctc caa tgg      3204
Leu Gly  Glu Leu Leu His Gly  Ser Lys Gly Gly His  Leu Gln Trp
    1055                 1060                 1065

gag acg  aga cat aga gta gcc  gtg gaa gca gcg aag  ggc ttg tgt      3249
Glu Thr  Arg His Arg Val Ala  Val Glu Ala Ala Lys  Gly Leu Cys
    1070                 1075                 1080

tac ctt  cac cat gac tgt tca  cca ttg atc ttg cac  aga gat gtt      3294
Tyr Leu  His His Asp Cys Ser  Pro Leu Ile Leu His  Arg Asp Val
    1085                 1090                 1095

aag tcc  aat aac att ctt ttg  gac tct gat ttt gaa  gcc cat gtt      3339
Lys Ser  Asn Asn Ile Leu Leu  Asp Ser Asp Phe Glu  Ala His Val
    1100                 1105                 1110

gct gat  ttt ggg ctt gct aag  ttc tta gtg gac ggt  gct gct tct      3384
Ala Asp  Phe Gly Leu Ala Lys  Phe Leu Val Asp Gly  Ala Ala Ser
    1115                 1120                 1125

gag tgt  atg tct tca att gct  ggc tct tat gga tac  atc gcc cca      3429
Glu Cys  Met Ser Ser Ile Ala  Gly Ser Tyr Gly Tyr  Ile Ala Pro
    1130                 1135                 1140

gag tat  gca tat acc ttg aaa  gtg gac gag aag agt  gat gtg tat      3474
Glu Tyr  Ala Tyr Thr Leu Lys  Val Asp Glu Lys Ser  Asp Val Tyr
    1145                 1150                 1155

agt ttc  gga gtg gtt tta ttg  gag cta ata gcc ggt  aag aaa ccg      3519
Ser Phe  Gly Val Val Leu Leu  Glu Leu Ile Ala Gly  Lys Lys Pro
    1160                 1165                 1170

gtt ggt  gaa ttt gga gaa gga  gtc gat ata gtt agg  tgg gtg aga      3564
Val Gly  Glu Phe Gly Glu Gly  Val Asp Ile Val Arg  Trp Val Arg
    1175                 1180                 1185

aac acg  gaa gaa gag atg tct  cag ccg tcg gat gcc  gct att gtt      3609
Asn Thr  Glu Glu Glu Met Ser  Gln Pro Ser Asp Ala  Ala Ile Val
    1190                 1195                 1200

gtt gcg  atc gtt gac tcg agg  ttg act ggt tat ccg  ttg acc agt      3654
Val Ala  Ile Val Asp Ser Arg  Leu Thr Gly Tyr Pro  Leu Thr Ser
    1205                 1210                 1215

gtg gtt  cat gtg ttc aag att  gca atg atg tgt gtg  gag gat gag      3699
Val Val  His Val Phe Lys Ile  Ala Met Met Cys Val  Glu Asp Glu
    1220                 1225                 1230

gcc gca  aca agg cct acg atg  agg gag gtt gtg cac  atg ctc act      3744
Ala Ala  Thr Arg Pro Thr Met  Arg Glu Val Val His  Met Leu Thr
    1235                 1240                 1245

aac cct  ccg aaa tcc gtg gct  aac ttg att gcg ttc  taa              3783
Asn Pro  Pro Lys Ser Val Ala  Asn Leu Ile Ala Phe
    1250                 1255                 1260
```

<210> SEQ ID NO 16
<211> LENGTH: 1260
<212> TYPE: PRT
<213> ORGANISM: Cannabis sativa
<220> FEATURE:
<221> NAME/KEY: misc_feature
<222> LOCATION: (555)..(555)
<223> OTHER INFORMATION: The 'Xaa' at location 555 stands for Arg, or
Gly.

<400> SEQUENCE: 16

```
Met Ala Met Arg Leu Leu Lys Thr His Leu Leu Phe Leu His Leu Tyr
1               5                   10                  15

Thr Thr Gln Leu Tyr Val Ile Ser Phe Phe Phe Val Phe Phe Ser Thr
            20                  25                  30

Cys Leu Ala Tyr Thr Asp Met Glu Val Leu Leu Asn Leu Lys Ser Ser
        35                  40                  45

Met Ile Gly His Asn Gly Asp Gly Leu His Asp Trp Ile His Ser Pro
    50                  55                  60

Ser Pro Ala Ala His Cys Ser Phe Thr Gly Val Ser Cys Asp Gly Glu
65                  70                  75                  80

Ala Arg Val Ile Ser Leu Asn Val Ser Phe Thr Pro Leu Phe Gly Lys
                85                  90                  95

Ile Ser Pro Glu Ile Gly Met Leu Asn Arg Leu Val Asn Leu Thr Leu
            100                 105                 110

Ala Ala Asn Asn Phe Thr Gly Glu Leu Pro Leu Glu Met Lys Ser Leu
        115                 120                 125

Thr Ser Leu Lys Val Leu Asn Ile Ser Asn Asn Val Asn Leu Ser Gly
    130                 135                 140

Ser Phe Pro Gly Glu Met Val Lys Ala Met Val Asp Leu Glu Val Leu
145                 150                 155                 160

Asp Ala Tyr Asn Asn Asn Phe Thr Gly Thr Leu Pro Leu Glu Ile Ser
                165                 170                 175

Glu Leu Lys Asn Leu Lys His Leu Ser Leu Gly Gly Asn Phe Phe Thr
            180                 185                 190

Gly Glu Ile Pro Glu Ser Tyr Gly Asp Ile Gln Ser Leu Glu Tyr Leu
        195                 200                 205

Gly Leu Asn Gly Ala Gly Leu Ser Gly Lys Ser Pro Ala Phe Leu Ser
    210                 215                 220

Arg Leu Lys Asn Leu Arg Glu Met Tyr Val Gly Tyr Phe Asn Ser Tyr
225                 230                 235                 240

Thr Gly Gly Val Pro Pro Glu Phe Gly Gly Leu Thr Asn Leu Gln Ile
                245                 250                 255

Leu Asp Met Ala Ser Cys Thr Leu Thr Gly Glu Ile Pro Thr Ser Leu
            260                 265                 270

Ser Asn Leu Lys His Leu His Thr Leu Phe Leu His Ile Asn Asn Leu
        275                 280                 285

Thr Gly His Ile Pro Pro Glu Leu Ser Gly Leu Ile Ser Leu Lys Ser
    290                 295                 300

Leu Asp Leu Ser Ile Asn Gln Leu Thr Gly Glu Ile Pro Gln Ser Phe
305                 310                 315                 320

Ile Asp Leu Gly Asn Thr Thr Leu Ile Asn Leu Phe Arg Asn Asn Leu
                325                 330                 335

Tyr Gly Pro Ile Pro Glu Phe Ile Gly Glu Leu Pro Lys Leu Gln Val
            340                 345                 350

Phe Glu Val Trp Glu Asn Asn Phe Thr Leu Gln Leu Pro Ala Asn Leu
        355                 360                 365

Gly Arg Asn Gly Asn Leu Lys Lys Leu Asp Val Ser Tyr Asn His Leu
    370                 375                 380
```

```
Thr Gly Leu Ile Pro Met Asp Leu Cys Arg Gly Glu Lys Leu Glu Met
385                 390                 395                 400

Leu Ile Leu Ser Asn Asn Phe Leu Phe Gly Pro Ile Pro Glu Glu Leu
                405                 410                 415

Gly Lys Cys Lys Ser Leu Asn Lys Ile Arg Ile Val Lys Asn Leu Leu
            420                 425                 430

Asn Gly Thr Val Pro Ala Gly Leu Phe Asn Leu Pro Leu Val Thr Ile
        435                 440                 445

Ile Glu Leu Thr Asp Asn Phe Phe Ser Gly Glu Leu Pro Thr Thr Met
    450                 455                 460

Ser Gly Ala Val Ala Asp Gln Ile Tyr Leu Ser Asn Asn Trp Phe Ser
465                 470                 475                 480

Gly Glu Ile Pro Pro Ala Ile Gly Asn Phe Pro Asn Leu Gln Thr Leu
                485                 490                 495

Phe Leu Asp Arg Asn Arg Phe Arg Gly Ser Ile Pro Arg Glu Ile Phe
            500                 505                 510

Glu Leu Lys His Leu Ser Lys Ile Asn Thr Ser Ala Asn Asn Ile Thr
        515                 520                 525

Gly Val Ile Pro Asp Ser Ile Ser Arg Cys Thr Thr Leu Ile Ser Val
    530                 535                 540

Asp Leu Ser Arg Asn Arg Ile Asn Gly Asp Xaa His Gly Glu Leu Tyr
545                 550                 555                 560

Thr His Arg Arg Asp Pro Asn Glu Phe Asn Leu Lys Ser Leu Asp Leu
                565                 570                 575

Ser Ile Asn Gln Leu Thr Gly Glu Ile Pro Gln Ser Phe Ile Asp Leu
            580                 585                 590

Gly Asn Thr Thr Leu Ile Asn Leu Phe Arg Asn Asn Leu Tyr Gly Pro
        595                 600                 605

Ile Pro Glu Phe Ile Gly Glu Leu Pro Lys Leu Gln Val Phe Glu Val
    610                 615                 620

Trp Glu Asn Asn Phe Thr Leu Gln Leu Pro Ala Asn Leu Gly Arg Asn
625                 630                 635                 640

Gly Asn Leu Lys Lys Leu Asp Val Ser Tyr Asn His Leu Thr Gly Leu
                645                 650                 655

Ile Pro Met Asp Leu Cys Arg Gly Glu Lys Leu Glu Met Leu Ile Leu
            660                 665                 670

Ser Asn Asn Phe Leu Phe Gly Pro Ile Pro Glu Glu Leu Gly Lys Cys
        675                 680                 685

Lys Ser Leu Asn Lys Ile Arg Ile Val Lys Asn Leu Leu Asn Gly Thr
    690                 695                 700

Val Pro Ala Gly Leu Phe Asn Leu Pro Leu Val Thr Ile Ile Glu Leu
705                 710                 715                 720

Thr Asp Asn Phe Phe Ser Gly Glu Leu Pro Thr Thr Met Ser Gly Ala
                725                 730                 735

Val Ala Asp Gln Ile Tyr Leu Ser Asn Asn Trp Phe Ser Gly Glu Ile
            740                 745                 750

Pro Pro Ala Ile Gly Asn Phe Pro Asn Leu Gln Thr Leu Phe Leu Asp
        755                 760                 765

Arg Asn Arg Phe Arg Gly Ser Ile Pro Arg Glu Ile Phe Glu Leu Lys
    770                 775                 780

His Leu Ser Lys Ile Asn Thr Ser Ala Asn Asn Ile Thr Gly Val Ile
785                 790                 795                 800
```

-continued

```
Pro Asp Ser Ile Ser Arg Cys Thr Thr Leu Ile Ser Val Asp Leu Ser
                805                 810                 815

Arg Asn Arg Ile Asn Gly Asp Ile Pro Lys Glu Ile Asn Asn Val Ile
            820                 825                 830

Asn Leu Gly Thr Leu Asn Leu Ser Gly Asn Gln Leu Thr Gly Ser Ile
        835                 840                 845

Pro Thr Gly Ile Gly Asn Met Thr Ser Leu Thr Thr Leu Asp Leu Ser
    850                 855                 860

Phe Asn Asp Leu Ser Gly Arg Val Pro Leu Gly Gly Gln Phe Met Val
865                 870                 875                 880

Phe Asn Asp Thr Ser Phe Ala Gly Asn Thr Tyr Leu Cys Leu Pro His
                885                 890                 895

His Val Ser Cys Pro Thr Arg Pro Gly Gln Thr Ser Asp Arg Asn Pro
            900                 905                 910

Pro Ala Leu Phe Ser Pro Ser Arg Ile Val Ile Thr Val Ile Ala Ala
        915                 920                 925

Ile Thr Gly Leu Ile Leu Ile Ser Val Ala Ile Arg Gln Met Asn Lys
    930                 935                 940

Lys Lys Asn Gln Lys Ser Leu Ala Trp Lys Leu Thr Ala Phe Gln Lys
945                 950                 955                 960

Leu Asp Phe Lys Ser Ala Asp Val Leu Glu Cys Leu Lys Glu Glu Asn
                965                 970                 975

Ile Ile Gly Lys Gly Gly Ala Gly Ile Val Tyr Arg Gly Ser Met Pro
            980                 985                 990

Asn Asn Val Asp Val Ala Ile Lys  Arg Leu Val Gly Arg  Gly Thr Gly
        995                 1000                1005

Arg Ser  Asp His Gly Phe Thr  Ala Glu Ile Gln Thr  Leu Gly Arg
    1010                1015                1020

Ile Arg  His Arg His Ile Val  Arg Leu Leu Gly Tyr  Val Ala Asn
    1025                1030                1035

Lys Asp  Thr Asn Leu Leu Leu  Tyr Glu Tyr Met Pro  Asn Gly Ser
    1040                1045                1050

Leu Gly  Glu Leu Leu His Gly  Ser Lys Gly Gly His  Leu Gln Trp
    1055                1060                1065

Glu Thr  Arg His Arg Val Ala  Val Glu Ala Ala Lys  Gly Leu Cys
    1070                1075                1080

Tyr Leu  His His Asp Cys Ser  Pro Leu Ile Leu His  Arg Asp Val
    1085                1090                1095

Lys Ser  Asn Asn Ile Leu Leu  Asp Ser Asp Phe Glu  Ala His Val
    1100                1105                1110

Ala Asp  Phe Gly Leu Ala Lys  Phe Leu Val Asp Gly  Ala Ala Ser
    1115                1120                1125

Glu Cys  Met Ser Ser Ile Ala  Gly Ser Tyr Gly Tyr  Ile Ala Pro
    1130                1135                1140

Glu Tyr  Ala Tyr Thr Leu Lys  Val Asp Glu Lys Ser  Asp Val Tyr
    1145                1150                1155

Ser Phe  Gly Val Val Leu Leu  Glu Leu Ile Ala Gly  Lys Lys Pro
    1160                1165                1170

Val Gly  Glu Phe Gly Glu Gly  Val Asp Ile Val Arg  Trp Val Arg
    1175                1180                1185

Asn Thr  Glu Glu Glu Met Ser  Gln Pro Ser Asp Ala  Ala Ile Val
    1190                1195                1200

Val Ala  Ile Val Asp Ser Arg  Leu Thr Gly Tyr Pro  Leu Thr Ser
```

```
    1205                1210                1215

Val Val  His Val Phe Lys Ile  Ala Met Met Cys Val  Glu Asp Glu
    1220                1225                1230

Ala Ala  Thr Arg Pro Thr Met  Arg Glu Val Val His  Met Leu Thr
    1235                1240                1245

Asn Pro  Pro Lys Ser Val Ala  Asn Leu Ile Ala Phe
    1250                1255                1260


<210> SEQ ID NO 17
<211> LENGTH: 2970
<212> TYPE: DNA
<213> ORGANISM: Thlaspi arvense
<220> FEATURE:
<221> NAME/KEY: CDS
<222> LOCATION: (1)..(2970)

<400> SEQUENCE: 17

atg gcg atg aga ctt ttg aag act cac ctt ctg ttt ctg cat ctt cac       48
Met Ala Met Arg Leu Leu Lys Thr His Leu Leu Phe Leu His Leu His
1               5                   10                  15

cag ctt tac gtt atc tcg att ttg ctt cta ctt ttc tca ccg tgc ttt       96
Gln Leu Tyr Val Ile Ser Ile Leu Leu Leu Leu Phe Ser Pro Cys Phe
            20                  25                  30

gct tac act gac atg gaa gtt ctc ctc aac ctc aaa tcc tcc atg act      144
Ala Tyr Thr Asp Met Glu Val Leu Leu Asn Leu Lys Ser Ser Met Thr
        35                  40                  45

ggt cca aaa ggc aac ggc ctc cac gac tgg gtt cac tcc act tct ccg      192
Gly Pro Lys Gly Asn Gly Leu His Asp Trp Val His Ser Thr Ser Pro
    50                  55                  60

gcg gct cac tgc tct ttc tcc ggc gtt tcc tgc gac ggc gac act cgt      240
Ala Ala His Cys Ser Phe Ser Gly Val Ser Cys Asp Gly Asp Thr Arg
65                  70                  75                  80

gtt gtc tcc ctc aac gtc tct ttt act cct ctg ttt gga acc atc tca      288
Val Val Ser Leu Asn Val Ser Phe Thr Pro Leu Phe Gly Thr Ile Ser
                85                  90                  95

ccg gag att ggg atg ttg act cgt ttg gtg aat ctg act tta gct gcg      336
Pro Glu Ile Gly Met Leu Thr Arg Leu Val Asn Leu Thr Leu Ala Ala
            100                 105                 110

aac aat tta acc ggt agt ttg ccg tcg gag atg aag agt cta act gct      384
Asn Asn Leu Thr Gly Ser Leu Pro Ser Glu Met Lys Ser Leu Thr Ala
        115                 120                 125

ctc aag gtt ttg aat gtc tcc aac aac gga aac ctc agc gga agc ttc      432
Leu Lys Val Leu Asn Val Ser Asn Asn Gly Asn Leu Ser Gly Ser Phe
    130                 135                 140

ccc gga ggg att cta act tcc atg gct gag ctt gaa gtc ctt gac gca      480
Pro Gly Gly Ile Leu Thr Ser Met Ala Glu Leu Glu Val Leu Asp Ala
145                 150                 155                 160

tat aac aac aac ttc acc ggg acg tta ccg ccg gag att ccg ggg ctt      528
Tyr Asn Asn Asn Phe Thr Gly Thr Leu Pro Pro Glu Ile Pro Gly Leu
                165                 170                 175

aag aag ctg aaa cac ctc tcc ctc ggc gga aat ttc ttc acc gga gag      576
Lys Lys Leu Lys His Leu Ser Leu Gly Gly Asn Phe Phe Thr Gly Glu
            180                 185                 190

att cca gag agc tac gga gat atc aag agc ttg gag tat ctt gga ctc      624
Ile Pro Glu Ser Tyr Gly Asp Ile Lys Ser Leu Glu Tyr Leu Gly Leu
        195                 200                 205

aac ggc gct ggt ctc tcc ggc gat tct ccg ggg ttc ttg tca cgc ctt      672
Asn Gly Ala Gly Leu Ser Gly Asp Ser Pro Gly Phe Leu Ser Arg Leu
    210                 215                 220

aag aat ctc aga gaa atg tac gtt ggc tac ttc aac agc tac acc ggc      720
```

-continued

```
Lys Asn Leu Arg Glu Met Tyr Val Gly Tyr Phe Asn Ser Tyr Thr Gly
225                 230                 235                 240

ggt gtt ccg ccg gag ttc ggt gga ttg tcg aag ctt gag gtc ctt gac      768
Gly Val Pro Pro Glu Phe Gly Gly Leu Ser Lys Leu Glu Val Leu Asp
                245                 250                 255

atg gcg agt tgt aca ctc acc gga gag att ccg acg aca ctg agt aac      816
Met Ala Ser Cys Thr Leu Thr Gly Glu Ile Pro Thr Thr Leu Ser Asn
            260                 265                 270

ctg aag cat ttg cat acg ttg ttt ctt cat atc aac aat tta acc gga      864
Leu Lys His Leu His Thr Leu Phe Leu His Ile Asn Asn Leu Thr Gly
        275                 280                 285

cat atc cca cca gag ctc tcc ggt tta atc agc ctt aaa tcg ctc gat      912
His Ile Pro Pro Glu Leu Ser Gly Leu Ile Ser Leu Lys Ser Leu Asp
    290                 295                 300

cta tca atc aac cag cta acc gga gag att cct cag agc ttc atc ggt      960
Leu Ser Ile Asn Gln Leu Thr Gly Glu Ile Pro Gln Ser Phe Ile Gly
305                 310                 315                 320

ctg gga aac atc act ctg atc aat ctg ttc agg aac aat ctc tac ggg     1008
Leu Gly Asn Ile Thr Leu Ile Asn Leu Phe Arg Asn Asn Leu Tyr Gly
                325                 330                 335

caa ata ccg gag ttc atc gga gaa ttg ccg aag ctg gag gtg ttc aaa     1056
Gln Ile Pro Glu Phe Ile Gly Glu Leu Pro Lys Leu Glu Val Phe Lys
            340                 345                 350

gtt tgg gag aac aac ttc acg tta gag ttg ccg gcg aat ctt gga cgg     1104
Val Trp Glu Asn Asn Phe Thr Leu Glu Leu Pro Ala Asn Leu Gly Arg
        355                 360                 365

aac ggg aag ctg aag cag ctc gat gtc tct gac aat cat ctc acg gga     1152
Asn Gly Lys Leu Lys Gln Leu Asp Val Ser Asp Asn His Leu Thr Gly
    370                 375                 380

ctc atc ccc aag gat ttg tgc aga ggc gag aag ctg gag atg ctg ata     1200
Leu Ile Pro Lys Asp Leu Cys Arg Gly Glu Lys Leu Glu Met Leu Ile
385                 390                 395                 400

ctc tcc aac aac ttc ttg ttt ggc cct att ccg gaa gag cta ggt cag     1248
Leu Ser Asn Asn Phe Leu Phe Gly Pro Ile Pro Glu Glu Leu Gly Gln
                405                 410                 415

tgc aag tcg cta aac aaa atc aga atc gtt aag aat ctt ctc aac ggg     1296
Cys Lys Ser Leu Asn Lys Ile Arg Ile Val Lys Asn Leu Leu Asn Gly
            420                 425                 430

act gtt ccg gcg ggt ctc ttc aac ctg ccg ctg gtt acg att atc gaa     1344
Thr Val Pro Ala Gly Leu Phe Asn Leu Pro Leu Val Thr Ile Ile Glu
        435                 440                 445

ctc acg gat aat ttc ttc tcc ggc gaa ctt ccg gca gcg atg tcc ggc     1392
Leu Thr Asp Asn Phe Phe Ser Gly Glu Leu Pro Ala Ala Met Ser Gly
    450                 455                 460

gat gtt ctc gat cag att tac ctc tcg aac aac tgg ttt tcc ggc gaa     1440
Asp Val Leu Asp Gln Ile Tyr Leu Ser Asn Asn Trp Phe Ser Gly Glu
465                 470                 475                 480

atc ccc tct gcg atc ggt aat ttc cct aat tta cag acc ttg ttc ttg     1488
Ile Pro Ser Ala Ile Gly Asn Phe Pro Asn Leu Gln Thr Leu Phe Leu
                485                 490                 495

gac agg aac cga ttt cgc ggg aac att ccg aga gaa atc ttc gag ttg     1536
Asp Arg Asn Arg Phe Arg Gly Asn Ile Pro Arg Glu Ile Phe Glu Leu
            500                 505                 510

aag cat ctc tcg aag atc aac aca agt gcg aac aac atc acc ggc gaa     1584
Lys His Leu Ser Lys Ile Asn Thr Ser Ala Asn Asn Ile Thr Gly Glu
        515                 520                 525

att ccc gat tcc atc tcc agc tgc act tcc tta atc tcc gtc gat ctc     1632
Ile Pro Asp Ser Ile Ser Ser Cys Thr Ser Leu Ile Ser Val Asp Leu
    530                 535                 540
```

-continued

```
agc cgt aac cgt ata gaa gga gaa atc cct aag gag atc cac aac gtg      1680
Ser Arg Asn Arg Ile Glu Gly Glu Ile Pro Lys Glu Ile His Asn Val
545                 550                 555                 560

att aac ctg gga act ctg aat ctc tcc ggc aat cag tta acc ggc ccc      1728
Ile Asn Leu Gly Thr Leu Asn Leu Ser Gly Asn Gln Leu Thr Gly Pro
                565                 570                 575

ata cct acc gga atc gga aac atg acg agt tta acc act ctc gat ctc      1776
Ile Pro Thr Gly Ile Gly Asn Met Thr Ser Leu Thr Thr Leu Asp Leu
            580                 585                 590

tcc ttc aac gac ctc tcc gga cga gta cca ctc ggc ggt caa ttc atg      1824
Ser Phe Asn Asp Leu Ser Gly Arg Val Pro Leu Gly Gly Gln Phe Met
        595                 600                 605

gtg ttc aac gac act tcc ttc gcc gga aat cct tac ctc tgc ttg cct      1872
Val Phe Asn Asp Thr Ser Phe Ala Gly Asn Pro Tyr Leu Cys Leu Pro
    610                 615                 620

cac cac gtc tca tgt cta acg cgg cca ggg caa acc tcc gat cac agc      1920
His His Val Ser Cys Leu Thr Arg Pro Gly Gln Thr Ser Asp His Ser
625                 630                 635                 640

cac acg gcg ttg ttc tca cca tca agg atc gtc atc acg gtt atc gca      1968
His Thr Ala Leu Phe Ser Pro Ser Arg Ile Val Ile Thr Val Ile Ala
                645                 650                 655

gcg atc act gcc ttg atc ctg atc agc gta gcg att cga cag atg aac      2016
Ala Ile Thr Ala Leu Ile Leu Ile Ser Val Ala Ile Arg Gln Met Asn
            660                 665                 670

aag aag aaa cac cag aag tcc ctc gcc tgg aag cta acc gcc ttc cag      2064
Lys Lys Lys His Gln Lys Ser Leu Ala Trp Lys Leu Thr Ala Phe Gln
        675                 680                 685

cga cta gat ttc aaa gcc gac gac gtc ctc gag tgc ctt cag gaa gag      2112
Arg Leu Asp Phe Lys Ala Asp Asp Val Leu Glu Cys Leu Gln Glu Glu
    690                 695                 700

aac ata atc ggc aaa ggc gga gcc ggg atc gtc tac cgc gga tcc atg      2160
Asn Ile Ile Gly Lys Gly Gly Ala Gly Ile Val Tyr Arg Gly Ser Met
705                 710                 715                 720

cca aac aac gta gac gtc gcg atc aaa cgc ctc gta ggc cgt gga acg      2208
Pro Asn Asn Val Asp Val Ala Ile Lys Arg Leu Val Gly Arg Gly Thr
                725                 730                 735

gga aga agc gac cac gga ttc acg gcg gag atc cag acg ctc gga agg      2256
Gly Arg Ser Asp His Gly Phe Thr Ala Glu Ile Gln Thr Leu Gly Arg
            740                 745                 750

atc cgg cac cgc cac atc gtg aga ctc ctc ggc tac gta gcg aac aag      2304
Ile Arg His Arg His Ile Val Arg Leu Leu Gly Tyr Val Ala Asn Lys
        755                 760                 765

gac acg aat ctg ctt ctc tac gag tac atg cct aac ggt agc ctc gga      2352
Asp Thr Asn Leu Leu Leu Tyr Glu Tyr Met Pro Asn Gly Ser Leu Gly
    770                 775                 780

gag ctc ttg cac gga tcc aaa ggc gga cat ctt caa tgg gag acg aga      2400
Glu Leu Leu His Gly Ser Lys Gly Gly His Leu Gln Trp Glu Thr Arg
785                 790                 795                 800

cac aga gta gcc gtg gaa gca gcg aag gga ctg tgt tat ctt cac cat      2448
His Arg Val Ala Val Glu Ala Ala Lys Gly Leu Cys Tyr Leu His His
                805                 810                 815

gac tgt tca cca ctg atc ttg cac aga gac gtg aag tcc aat aac att      2496
Asp Cys Ser Pro Leu Ile Leu His Arg Asp Val Lys Ser Asn Asn Ile
            820                 825                 830

ctt ctg gac tct gat ttt gaa gcc cac gtt gct gat ttt ggg ctt gct      2544
Leu Leu Asp Ser Asp Phe Glu Ala His Val Ala Asp Phe Gly Leu Ala
        835                 840                 845

aag ttc tta gtg gac ggt gct gct tct gag tgt atg tcc tca ata gcc      2592
Lys Phe Leu Val Asp Gly Ala Ala Ser Glu Cys Met Ser Ser Ile Ala
    850                 855                 860
```

```
ggc tct tat gga tac atc gct cca gag tat gct tac act ttg aaa gtg      2640
Gly Ser Tyr Gly Tyr Ile Ala Pro Glu Tyr Ala Tyr Thr Leu Lys Val
865                 870                 875                 880

gac gag aag agt gat gtg tac agt ttt ggt gtg gtt ctg ttg gag cta      2688
Asp Glu Lys Ser Asp Val Tyr Ser Phe Gly Val Val Leu Leu Glu Leu
                885                 890                 895

ata gct ggg aag aaa ccg gtt ggt gaa ttt ggg gaa gga gtg gat ata      2736
Ile Ala Gly Lys Lys Pro Val Gly Glu Phe Gly Glu Gly Val Asp Ile
            900                 905                 910

gtt agg tgg gtg agg aac acg gag ggt gag ata cct caa ccg tcg gat      2784
Val Arg Trp Val Arg Asn Thr Glu Gly Glu Ile Pro Gln Pro Ser Asp
        915                 920                 925

gca gct act gtt gtt gcg atc gtt gac ccg agg ttg act ggt tat ccg      2832
Ala Ala Thr Val Val Ala Ile Val Asp Pro Arg Leu Thr Gly Tyr Pro
    930                 935                 940

ttg acc agt gtg ata cat gtg ttc aag ata gcg atg atg tgt gta gag      2880
Leu Thr Ser Val Ile His Val Phe Lys Ile Ala Met Met Cys Val Glu
945                 950                 955                 960

gat gag gca gcg tca agg ccg aca atg aga gag gtt gtg cac atg ctc      2928
Asp Glu Ala Ala Ser Arg Pro Thr Met Arg Glu Val Val His Met Leu
                965                 970                 975

acg aac cct ccc aag tcc gtg act aac ttg atc gcg ttc tga              2970
Thr Asn Pro Pro Lys Ser Val Thr Asn Leu Ile Ala Phe
            980                 985


<210> SEQ ID NO 18
<211> LENGTH: 989
<212> TYPE: PRT
<213> ORGANISM: Thlaspi arvense

<400> SEQUENCE: 18

Met Ala Met Arg Leu Leu Lys Thr His Leu Leu Phe Leu His Leu His
1               5                   10                  15

Gln Leu Tyr Val Ile Ser Ile Leu Leu Leu Leu Phe Ser Pro Cys Phe
            20                  25                  30

Ala Tyr Thr Asp Met Glu Val Leu Leu Asn Leu Lys Ser Ser Met Thr
        35                  40                  45

Gly Pro Lys Gly Asn Gly Leu His Asp Trp Val His Ser Thr Ser Pro
    50                  55                  60

Ala Ala His Cys Ser Phe Ser Gly Val Ser Cys Asp Gly Asp Thr Arg
65                  70                  75                  80

Val Val Ser Leu Asn Val Ser Phe Thr Pro Leu Phe Gly Thr Ile Ser
                85                  90                  95

Pro Glu Ile Gly Met Leu Thr Arg Leu Val Asn Leu Thr Leu Ala Ala
            100                 105                 110

Asn Asn Leu Thr Gly Ser Leu Pro Ser Glu Met Lys Ser Leu Thr Ala
        115                 120                 125

Leu Lys Val Leu Asn Val Ser Asn Asn Gly Asn Leu Ser Gly Ser Phe
    130                 135                 140

Pro Gly Gly Ile Leu Thr Ser Met Ala Glu Leu Glu Val Leu Asp Ala
145                 150                 155                 160

Tyr Asn Asn Asn Phe Thr Gly Thr Leu Pro Pro Glu Ile Pro Gly Leu
                165                 170                 175

Lys Lys Leu Lys His Leu Ser Leu Gly Gly Asn Phe Phe Thr Gly Glu
            180                 185                 190

Ile Pro Glu Ser Tyr Gly Asp Ile Lys Ser Leu Glu Tyr Leu Gly Leu
        195                 200                 205
```

```
Asn Gly Ala Gly Leu Ser Gly Asp Ser Pro Gly Phe Leu Ser Arg Leu
    210                 215                 220

Lys Asn Leu Arg Glu Met Tyr Val Gly Tyr Phe Asn Ser Tyr Thr Gly
225                 230                 235                 240

Gly Val Pro Pro Glu Phe Gly Gly Leu Ser Lys Leu Glu Val Leu Asp
                245                 250                 255

Met Ala Ser Cys Thr Leu Thr Gly Glu Ile Pro Thr Thr Leu Ser Asn
            260                 265                 270

Leu Lys His Leu His Thr Leu Phe Leu His Ile Asn Asn Leu Thr Gly
        275                 280                 285

His Ile Pro Pro Glu Leu Ser Gly Leu Ile Ser Leu Lys Ser Leu Asp
    290                 295                 300

Leu Ser Ile Asn Gln Leu Thr Gly Glu Ile Pro Gln Ser Phe Ile Gly
305                 310                 315                 320

Leu Gly Asn Ile Thr Leu Ile Asn Leu Phe Arg Asn Asn Leu Tyr Gly
                325                 330                 335

Gln Ile Pro Glu Phe Ile Gly Glu Leu Pro Lys Leu Glu Val Phe Lys
            340                 345                 350

Val Trp Glu Asn Asn Phe Thr Leu Glu Leu Pro Ala Asn Leu Gly Arg
        355                 360                 365

Asn Gly Lys Leu Lys Gln Leu Asp Val Ser Asp Asn His Leu Thr Gly
    370                 375                 380

Leu Ile Pro Lys Asp Leu Cys Arg Gly Glu Lys Leu Glu Met Leu Ile
385                 390                 395                 400

Leu Ser Asn Asn Phe Leu Phe Gly Pro Ile Pro Glu Glu Leu Gly Gln
                405                 410                 415

Cys Lys Ser Leu Asn Lys Ile Arg Ile Val Lys Asn Leu Leu Asn Gly
            420                 425                 430

Thr Val Pro Ala Gly Leu Phe Asn Leu Pro Leu Val Thr Ile Ile Glu
        435                 440                 445

Leu Thr Asp Asn Phe Phe Ser Gly Glu Leu Pro Ala Ala Met Ser Gly
    450                 455                 460

Asp Val Leu Asp Gln Ile Tyr Leu Ser Asn Asn Trp Phe Ser Gly Glu
465                 470                 475                 480

Ile Pro Ser Ala Ile Gly Asn Phe Pro Asn Leu Gln Thr Leu Phe Leu
                485                 490                 495

Asp Arg Asn Arg Phe Arg Gly Asn Ile Pro Arg Glu Ile Phe Glu Leu
            500                 505                 510

Lys His Leu Ser Lys Ile Asn Thr Ser Ala Asn Asn Ile Thr Gly Glu
        515                 520                 525

Ile Pro Asp Ser Ile Ser Ser Cys Thr Ser Leu Ile Ser Val Asp Leu
    530                 535                 540

Ser Arg Asn Arg Ile Glu Gly Glu Ile Pro Lys Glu Ile His Asn Val
545                 550                 555                 560

Ile Asn Leu Gly Thr Leu Asn Leu Ser Gly Asn Gln Leu Thr Gly Pro
                565                 570                 575

Ile Pro Thr Gly Ile Gly Asn Met Thr Ser Leu Thr Thr Leu Asp Leu
            580                 585                 590

Ser Phe Asn Asp Leu Ser Gly Arg Val Pro Leu Gly Gly Gln Phe Met
        595                 600                 605

Val Phe Asn Asp Thr Ser Phe Ala Gly Asn Pro Tyr Leu Cys Leu Pro
    610                 615                 620
```

-continued

```
His His Val Ser Cys Leu Thr Arg Pro Gly Gln Thr Ser Asp His Ser
625                 630                 635                 640

His Thr Ala Leu Phe Ser Pro Ser Arg Ile Val Ile Thr Val Ile Ala
                645                 650                 655

Ala Ile Thr Ala Leu Ile Leu Ile Ser Val Ala Ile Arg Gln Met Asn
            660                 665                 670

Lys Lys Lys His Gln Lys Ser Leu Ala Trp Lys Leu Thr Ala Phe Gln
        675                 680                 685

Arg Leu Asp Phe Lys Ala Asp Asp Val Leu Glu Cys Leu Gln Glu Glu
    690                 695                 700

Asn Ile Ile Gly Lys Gly Gly Ala Gly Ile Val Tyr Arg Gly Ser Met
705                 710                 715                 720

Pro Asn Asn Val Asp Val Ala Ile Lys Arg Leu Val Gly Arg Gly Thr
                725                 730                 735

Gly Arg Ser Asp His Gly Phe Thr Ala Glu Ile Gln Thr Leu Gly Arg
            740                 745                 750

Ile Arg His Arg His Ile Val Arg Leu Leu Gly Tyr Val Ala Asn Lys
        755                 760                 765

Asp Thr Asn Leu Leu Leu Tyr Glu Tyr Met Pro Asn Gly Ser Leu Gly
    770                 775                 780

Glu Leu Leu His Gly Ser Lys Gly Gly His Leu Gln Trp Glu Thr Arg
785                 790                 795                 800

His Arg Val Ala Val Glu Ala Ala Lys Gly Leu Cys Tyr Leu His His
                805                 810                 815

Asp Cys Ser Pro Leu Ile Leu His Arg Asp Val Lys Ser Asn Asn Ile
            820                 825                 830

Leu Leu Asp Ser Asp Phe Glu Ala His Val Ala Asp Phe Gly Leu Ala
        835                 840                 845

Lys Phe Leu Val Asp Gly Ala Ala Ser Glu Cys Met Ser Ser Ile Ala
    850                 855                 860

Gly Ser Tyr Gly Tyr Ile Ala Pro Glu Tyr Ala Tyr Thr Leu Lys Val
865                 870                 875                 880

Asp Glu Lys Ser Asp Val Tyr Ser Phe Gly Val Val Leu Leu Glu Leu
                885                 890                 895

Ile Ala Gly Lys Lys Pro Val Gly Glu Phe Gly Glu Gly Val Asp Ile
            900                 905                 910

Val Arg Trp Val Arg Asn Thr Glu Gly Glu Ile Pro Gln Pro Ser Asp
        915                 920                 925

Ala Ala Thr Val Val Ala Ile Val Asp Pro Arg Leu Thr Gly Tyr Pro
    930                 935                 940

Leu Thr Ser Val Ile His Val Phe Lys Ile Ala Met Met Cys Val Glu
945                 950                 955                 960

Asp Glu Ala Ala Ser Arg Pro Thr Met Arg Glu Val Val His Met Leu
                965                 970                 975

Thr Asn Pro Pro Lys Ser Val Thr Asn Leu Ile Ala Phe
            980                 985
```

```
<210> SEQ ID NO 19
<211> LENGTH: 65
<212> TYPE: PRT
<213> ORGANISM: Brassica napus

<400> SEQUENCE: 19

Ile Pro Lys Asp Ile His Asp Val Met Asn Leu Gly Thr Leu Asn Leu
1               5                   10                  15
```

```
Ser Gly Asn Gln Leu Thr Gly Ser Ile Pro Ile Gly Ile Gly Lys Met
            20                  25                  30

Thr Ser Leu Thr Thr Leu Asp Leu Ser Phe Asn Asp Leu Ser Gly Arg
        35                  40                  45

Val Pro Leu Gly Gly Gln Phe Leu Val Phe Asn Asp Thr Ser Phe Ala
    50                  55                  60

Gly
65


<210> SEQ ID NO 20
<211> LENGTH: 65
<212> TYPE: PRT
<213> ORGANISM: Brassica napus

<400> SEQUENCE: 20

Ile Pro Lys Asp Ile His Asp Val Ile Asn Leu Gly Thr Leu Asn Leu
1               5                   10                  15

Ser Gly Asn Gln Leu Thr Gly Ser Ile Pro Ile Gly Ile Gly Lys Met
            20                  25                  30

Thr Ser Leu Thr Thr Leu Asp Leu Ser Phe Asn Asp Leu Ser Gly Arg
        35                  40                  45

Val Pro Leu Gly Gly Gln Phe Leu Val Phe Asn Asp Thr Ser Phe Ala
    50                  55                  60

Gly
65


<210> SEQ ID NO 21
<211> LENGTH: 65
<212> TYPE: PRT
<213> ORGANISM: Brassica oleracea

<400> SEQUENCE: 21

Ile Pro Lys Asp Ile His Asp Val Ile Asn Leu Gly Thr Leu Asn Leu
1               5                   10                  15

Ser Gly Asn Gln Leu Thr Gly Ser Ile Pro Ile Gly Ile Gly Lys Met
            20                  25                  30

Thr Ser Leu Thr Thr Leu Asp Leu Ser Phe Asn Asp Leu Ser Gly Arg
        35                  40                  45

Val Pro Leu Gly Gly Gln Phe Leu Val Phe Asn Asp Thr Ser Phe Ala
    50                  55                  60

Gly
65


<210> SEQ ID NO 22
<211> LENGTH: 65
<212> TYPE: PRT
<213> ORGANISM: Cannabis sativa

<400> SEQUENCE: 22

Ile Pro Lys Glu Ile Asn Asn Val Ile Asn Leu Gly Thr Leu Asn Leu
1               5                   10                  15

Ser Gly Asn Gln Leu Thr Gly Ser Ile Pro Thr Gly Ile Gly Asn Met
            20                  25                  30

Thr Ser Leu Thr Thr Leu Asp Leu Ser Phe Asn Asp Leu Ser Gly Arg
        35                  40                  45

Val Pro Leu Gly Gly Gln Phe Met Val Phe Asn Asp Thr Ser Phe Ala
    50                  55                  60
```

Gly
65

<210> SEQ ID NO 23
<211> LENGTH: 65
<212> TYPE: PRT
<213> ORGANISM: Thlaspi arvense

<400> SEQUENCE: 23

Ile Pro Lys Glu Ile His Asn Val Ile Asn Leu Gly Thr Leu Asn Leu
1 5 10 15

Ser Gly Asn Gln Leu Thr Gly Pro Ile Pro Thr Gly Ile Gly Asn Met
20 25 30

Thr Ser Leu Thr Thr Leu Asp Leu Ser Phe Asn Asp Leu Ser Gly Arg
35 40 45

Val Pro Leu Gly Gly Gln Phe Met Val Phe Asn Asp Thr Ser Phe Ala
50 55 60

Gly
65

<210> SEQ ID NO 24
<211> LENGTH: 65
<212> TYPE: PRT
<213> ORGANISM: Brassica rapa

<400> SEQUENCE: 24

Ile Pro Lys Asp Ile His Asp Val Ile Asn Leu Gly Thr Leu Asn Leu
1 5 10 15

Ser Gly Asn Gln Leu Thr Gly Ser Ile Pro Ile Gly Ile Gly Lys Met
20 25 30

Thr Ser Leu Thr Thr Leu Asp Leu Ser Phe Asn Asp Leu Ser Gly Arg
35 40 45

Val Pro Leu Gly Gly Gln Phe Leu Val Phe Asn Asp Thr Ser Phe Ala
50 55 60

Gly
65

<210> SEQ ID NO 25
<211> LENGTH: 985
<212> TYPE: PRT
<213> ORGANISM: Malus domestica
<220> FEATURE:
<221> NAME/KEY: misc_feature
<222> LOCATION: (512)..(512)
<223> OTHER INFORMATION: Xaa can be any naturally occurring amino acid

<400> SEQUENCE: 25

Met Ser Asn Tyr Arg Ala Leu Leu Ser Leu Lys Ser Ser Ile Thr Ser
1 5 10 15

Asp Pro Asn Ser Ala Leu Ser Thr Trp Thr Pro Thr Thr Ser His Cys
20 25 30

Thr Trp Ser Gly Val Thr Cys Asp Ser Ser Arg Arg Tyr Val Thr Ser
35 40 45

Leu Asp Leu Ser Gly Leu Asp Leu Thr Gly Thr Leu Ser Pro Asp Leu
50 55 60

Ala His Leu Arg Phe Leu Ala Asn Leu Thr Leu Ala Asp Asn Gln Phe
65 70 75 80

Ser Gly Pro Ile Pro Pro Glu Ile Ser Ala Leu Ser Gly Leu Arg Leu
85 90 95

-continued

```
Leu Asn Leu Ser Asn Asn Leu Ser Asn Leu Thr Arg Leu Thr Val Leu
            100                 105                 110

Asp Leu Tyr Asn Asn Asn Leu Thr Gly Asp Leu Pro Val Ser Val Thr
        115                 120                 125

His Met Thr Ser Leu Arg His Leu His Leu Gly Gly Asn Phe Phe Ser
    130                 135                 140

Gly Gln Ile Pro Pro Glu Phe Gly Arg Phe Pro Phe Leu Glu Tyr Leu
145                 150                 155                 160

Ala Val Ser Gly Asn Glu Leu Gly Gly Pro Ile Pro Pro Glu Ile Gly
                165                 170                 175

Asn Leu Thr Thr Leu Lys Glu Leu Tyr Ile Gly Tyr Phe Asn Ser Tyr
            180                 185                 190

Glu Gly Gly Ile Pro Pro Glu Ile Gly Asn Leu Ser Asn Leu Val Arg
        195                 200                 205

Phe Asp Ala Ala Asn Cys Asn Leu Thr Gly Glu Val Pro Pro Glu Leu
    210                 215                 220

Gly Arg Leu Gln Asn Val Asp Thr Leu Phe Leu Gln Val Asn Ala Leu
225                 230                 235                 240

Ser Gly Ser Leu Thr Pro Glu Leu Gly Tyr Leu Lys Ser Leu Lys Ser
                245                 250                 255

Met Asp Leu Ser Asn Asn Val Phe Thr Gly Glu Ile Pro Gly Ser Phe
            260                 265                 270

Ser Glu Leu Lys Asn Leu Thr Leu Leu Asn Leu Phe Arg Asn Arg Leu
        275                 280                 285

His Gly Ala Ile Pro Asp Phe Ile Gly Asp Leu Pro Glu Leu Gln Val
    290                 295                 300

Leu Gln Leu Trp Glu Asn Asn Phe Thr Gly Ser Ile Pro Gln Gly Leu
305                 310                 315                 320

Gly Lys Asn Gly Lys Leu Gln Ile Leu Asp Leu Ser Ser Asn Lys Leu
                325                 330                 335

Thr Gly Thr Leu Pro Pro Asp Met Cys Phe Gly Asn Asn Leu Gln Thr
            340                 345                 350

Leu Ile Thr Leu Ser Asn Phe Leu Phe Gly Pro Ile Pro Glu Ser Leu
        355                 360                 365

Gly Arg Cys Asp Ser Leu Ser Arg Ile Arg Met Gly Asp Asn Tyr Leu
    370                 375                 380

Asn Gly Ser Ile Pro Lys Gly Leu Leu Ser Leu Pro Lys Leu Thr Gln
385                 390                 395                 400

Val Glu Leu Gln Asp Asn Leu Leu Asp Gly Ser Phe Pro Glu Thr Asp
                405                 410                 415

Ser Ile Ser Gly Asn Leu Gly Gln Ile Ser Leu Ser Asn Asn Arg Leu
            420                 425                 430

Ser Gly Ser Leu Pro Pro Thr Ile Gly Asn Phe Ser Gly Val Gln Lys
        435                 440                 445

Leu Leu Leu Asp Gly Asn Lys Phe Ser Gly Arg Ile Pro Pro Glu Ile
    450                 455                 460

Gly Arg Leu Gln Gln Leu Ser Lys Ile Asp Phe Lys His Asn Lys Phe
465                 470                 475                 480

Met Gly Ser Ile Thr Pro Glu Ile Ser His Cys Lys Leu Leu Thr Phe
                485                 490                 495

Val Asp Leu Ser Arg Asn Glu Leu Ser Gly Glu Ile Pro Lys Glu Xaa
            500                 505                 510

Thr Gly Met Arg Ile Leu Asn Tyr Leu Asn Leu Ser Arg Asn His Leu
```

-continued

```
        515                 520                 525

Val Gly Ser Ile Pro Ser Ser Ile Ser Thr Met Gln Ser Leu Thr Ser
    530                 535                 540

Val Asp Phe Ser Tyr Asn Asn Leu Ser Gly Leu Val Pro Gly Thr Gly
545                 550                 555                 560

Gln Phe Ser Tyr Phe Asn Tyr Thr Ser Phe Leu Gly Asn Pro Asp Leu
                565                 570                 575

Cys Gly Pro Tyr Leu Val Pro Cys Lys Asp Gly Val Ala Asn Gly Thr
            580                 585                 590

His Gln Pro His Val Lys Gly Ala Leu Thr Ala Ser Leu Lys Leu Leu
        595                 600                 605

Leu Val Ile Gly Leu Leu Leu Cys Ser Ile Val Phe Ala Val Ala Ala
    610                 615                 620

Ile Ile Lys Ala Arg Ser Leu Lys Lys Ala Ser Asp Ser Arg Ala Trp
625                 630                 635                 640

Lys Leu Thr Ala Phe Gln Arg Leu Asp Phe Thr Val Asp Asp Val Leu
                645                 650                 655

Asp Ser Leu Lys Glu Asp Asn Ile Ile Gly Lys Gly Gly Ala Gly Ile
            660                 665                 670

Val Tyr Lys Gly Ala Met Pro Ser Gly Asp Asn Val Ala Val Lys Arg
        675                 680                 685

Leu Pro Ala Met Ser Arg Gly Ser Ser His Asp His Gly Phe Asn Ala
    690                 695                 700

Glu Ile Gln Thr Leu Gly Arg Ile Arg His Arg His Ile Val Arg Leu
705                 710                 715                 720

Leu Gly Phe Cys Ser Asn His Glu Thr Asn Leu Leu Val Tyr Glu Tyr
                725                 730                 735

Met Pro Asn Gly Ser Leu Gly Glu Val Leu His Gly Lys Lys Gly Gly
            740                 745                 750

His Leu His Trp Asp Thr Arg Tyr Lys Ile Ala Ile Glu Ala Ala Lys
        755                 760                 765

Gly Leu Cys Tyr Leu His His Asp Cys Ser Pro Leu Ile Val His Arg
    770                 775                 780

Asp Val Lys Ser Asn Asn Ile Leu Leu Asp Ser Asn Phe Glu Ala His
785                 790                 795                 800

Val Ala Asp Phe Gly Leu Ala Lys Phe Leu Gln Asp Ser Gly Thr Ser
                805                 810                 815

Glu Cys Met Ser Ala Ile Ala Gly Ser Tyr Gly Tyr Ile Ala Pro Glu
            820                 825                 830

Tyr Ala Tyr Thr Leu Lys Val Asp Glu Lys Ser Asp Val Tyr Ser Phe
        835                 840                 845

Gly Val Val Leu Leu Glu Leu Val Ser Gly Arg Lys Pro Val Gly Glu
    850                 855                 860

Phe Gly Asp Gly Val Asp Ile Val Gln Trp Val Arg Lys Met Thr Asp
865                 870                 875                 880

Ser Asn Lys Glu Gly Val Leu Lys Ile Leu Asp Pro Arg Leu Pro Ser
                885                 890                 895

Val Pro Leu His Glu Val Met His Val Phe Tyr Val Ala Met Leu Cys
            900                 905                 910

Val Glu Glu Gln Ala Val Glu Arg Pro Thr Met Arg Glu Val Val Gln
        915                 920                 925

Ile Leu Thr Glu Leu Pro Lys Ala Pro Gly Ser Lys Leu Val Glu Asp
    930                 935                 940
```

Ser Ala Ile Thr Glu Ser Ser Pro Pro Pro Ala Thr Thr Ala Ser Glu
945 950 955 960

Ser Pro Gly Thr Thr Ser Lys Asp Thr Lys Asp Gln Pro Pro Leu Gln
965 970 975

Ser Pro Pro Pro Asp Leu Leu Ser Ile
980 985

<210> SEQ ID NO 26
<211> LENGTH: 56
<212> TYPE: PRT
<213> ORGANISM: Malus domestica

<400> SEQUENCE: 26

Met Arg Ile Leu Asn Tyr Leu Asn Leu Ser Arg Asn His Leu Val Gly
1 5 10 15

Ser Ile Pro Ser Ser Ile Ser Thr Met Gln Ser Leu Thr Ser Val Asp
20 25 30

Phe Ser Tyr Asn Asn Leu Ser Gly Leu Val Pro Gly Thr Gly Gln Phe
35 40 45

Ser Tyr Phe Asn Tyr Thr Ser Phe
50 55

<210> SEQ ID NO 27
<211> LENGTH: 1015
<212> TYPE: PRT
<213> ORGANISM: Malus domestica
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid

<400> SEQUENCE: 27

Met Arg Leu Leu Phe Phe Leu Leu Leu Leu Leu Leu His His His Ser
1 5 10 15

Leu Ser Ala Ile Ala Met Ser Asn Tyr Arg Ala Leu Leu Ser Leu Lys
20 25 30

Ser Ser Ile Thr Ser Xaa Pro Asn Ser Ala Leu Ser Thr Trp Thr Pro
35 40 45

Thr Thr Ser His Cys Thr Trp Ser Gly Val Thr Cys Asp Ser Ser Arg
50 55 60

Arg Tyr Val Thr Ser Leu Asp Leu Ser Gly Leu Asp Leu Thr Gly Thr
65 70 75 80

Leu Ser Pro Asp Leu Ala His Leu Arg Phe Leu Ala Asn Leu Thr Leu
85 90 95

Ala Asp Asn Gln Phe Ser Gly Pro Ile Pro Pro Glu Ile Ser Ala Leu
100 105 110

Ser Gly Leu Arg Leu Leu Asn Leu Ser Asn Asn Val Phe Asn Thr Thr
115 120 125

Phe Pro Pro Lys Leu Ser Asn Leu Thr Arg Leu Thr Val Leu Asp Leu
130 135 140

Tyr Asn Asn Asn Leu Thr Gly Asp Leu Pro Val Ser Val Thr His Met
145 150 155 160

Thr Ser Leu Arg His Leu His Leu Gly Gly Asn Phe Phe Ser Gly Gln
165 170 175

-continued

```
Ile Pro Pro Glu Phe Gly Arg Phe Pro Phe Leu Glu Tyr Leu Ala Val
            180                 185                 190

Ser Gly Asn Glu Leu Gly Gly Pro Ile Pro Pro Glu Ile Gly Asn Leu
        195                 200                 205

Thr Thr Leu Lys Glu Leu Tyr Ile Gly Tyr Phe Asn Ser Tyr Glu Gly
    210                 215                 220

Gly Ile Pro Pro Glu Ile Gly Asn Leu Ser Asn Leu Val Arg Phe Asp
225                 230                 235                 240

Ala Ala Asn Cys Asn Leu Thr Gly Glu Val Pro Pro Glu Leu Gly Arg
                245                 250                 255

Leu Gln Asn Val Asp Thr Leu Phe Leu Gln Val Asn Ala Leu Ser Gly
            260                 265                 270

Ser Leu Thr Pro Glu Leu Gly Tyr Leu Lys Ser Leu Lys Ser Met Asp
        275                 280                 285

Leu Ser Asn Asn Val Phe Thr Gly Glu Ile Pro Gly Ser Phe Ser Glu
    290                 295                 300

Leu Lys Asn Leu Thr Leu Leu Asn Leu Phe Arg Asn Arg Leu His Gly
305                 310                 315                 320

Ala Ile Pro Asp Phe Ile Gly Asp Leu Pro Glu Leu Gln Val Leu Gln
                325                 330                 335

Leu Trp Glu Asn Asn Phe Thr Gly Ser Ile Pro Gln Gly Leu Gly Lys
            340                 345                 350

Asn Gly Lys Leu Gln Ile Leu Asp Leu Ser Ser Asn Lys Leu Thr Gly
        355                 360                 365

Thr Leu Pro Pro Asp Met Cys Phe Gly Asn Asn Leu Gln Thr Leu Ile
    370                 375                 380

Thr Leu Ser Asn Phe Leu Phe Gly Pro Ile Pro Glu Ser Leu Gly Arg
385                 390                 395                 400

Cys Asp Ser Leu Ser Arg Ile Arg Met Gly Asp Asn Tyr Leu Asn Gly
                405                 410                 415

Ser Ile Pro Lys Gly Leu Leu Ser Leu Pro Lys Leu Thr Gln Val Glu
            420                 425                 430

Leu Gln Asp Asn Leu Leu Asp Gly Ser Phe Pro Glu Thr Asp Ser Ile
        435                 440                 445

Ser Gly Asn Leu Gly Gln Ile Ser Leu Ser Asn Asn Arg Leu Ser Gly
    450                 455                 460

Ser Leu Pro Pro Thr Ile Gly Asn Phe Ser Gly Val Gln Lys Leu Leu
465                 470                 475                 480

Leu Asp Gly Asn Lys Phe Ser Gly Arg Ile Pro Pro Glu Ile Gly Arg
                485                 490                 495

Leu Gln Gln Leu Ser Lys Ile Asp Phe Lys His Asn Lys Phe Met Gly
            500                 505                 510

Ser Ile Thr Pro Glu Ile Ser His Cys Lys Leu Leu Thr Phe Val Asp
        515                 520                 525

Leu Ser Arg Asn Glu Leu Ser Gly Glu Ile Pro Lys Glu Xaa Thr Gly
    530                 535                 540

Met Arg Ile Leu Asn Tyr Leu Asn Leu Ser Arg Asn His Leu Val Gly
545                 550                 555                 560

Ser Ile Pro Ser Ser Ile Ser Thr Met Gln Ser Leu Thr Ser Val Asp
                565                 570                 575

Phe Ser Tyr Asn Asn Leu Ser Gly Leu Val Pro Gly Thr Gly Gln Phe
            580                 585                 590

Ser Tyr Phe Asn Tyr Thr Ser Phe Leu Gly Asn Pro Asp Leu Cys Gly
```

-continued

```
        595                 600                 605

Pro Tyr Leu Val Pro Cys Lys Asp Gly Val Ala Asn Gly Thr His Gln
    610                 615                 620

Pro His Val Lys Gly Ala Leu Thr Ala Ser Leu Lys Leu Leu Leu Val
625                 630                 635                 640

Ile Gly Leu Leu Leu Cys Ser Ile Val Phe Ala Val Ala Ala Ile Ile
                645                 650                 655

Lys Ala Arg Ser Leu Lys Lys Ala Ser Asp Ser Arg Ala Trp Lys Leu
            660                 665                 670

Thr Ala Phe Gln Arg Leu Asp Phe Thr Val Asp Asp Val Leu Asp Ser
        675                 680                 685

Leu Lys Glu Asp Asn Ile Ile Gly Lys Gly Gly Ala Gly Ile Val Tyr
    690                 695                 700

Lys Gly Ala Met Pro Ser Gly Asp Asn Val Ala Val Lys Arg Leu Pro
705                 710                 715                 720

Ala Met Ser Arg Gly Ser Ser His Asp His Gly Phe Asn Ala Glu Ile
                725                 730                 735

Gln Thr Leu Gly Arg Ile Arg His Arg His Ile Val Arg Leu Leu Gly
            740                 745                 750

Phe Cys Ser Asn His Glu Thr Asn Leu Leu Val Tyr Glu Tyr Met Pro
        755                 760                 765

Asn Gly Ser Leu Gly Glu Val Leu His Gly Lys Lys Gly Gly His Leu
    770                 775                 780

His Trp Asp Thr Arg Tyr Lys Ile Ala Ile Glu Ala Ala Lys Gly Leu
785                 790                 795                 800

Cys Tyr Leu His His Asp Cys Ser Pro Leu Ile Val His Arg Asp Val
                805                 810                 815

Lys Ser Asn Asn Ile Leu Leu Asp Ser Asn Phe Glu Ala His Val Ala
            820                 825                 830

Asp Phe Gly Leu Ala Lys Phe Leu Gln Asp Ser Gly Thr Ser Glu Cys
        835                 840                 845

Met Ser Ala Ile Ala Gly Ser Tyr Gly Tyr Ile Ala Pro Glu Tyr Ala
    850                 855                 860

Tyr Thr Leu Lys Val Asp Glu Lys Ser Asp Val Tyr Ser Phe Gly Val
865                 870                 875                 880

Val Leu Leu Glu Leu Val Ser Gly Arg Lys Pro Val Gly Glu Phe Gly
                885                 890                 895

Asp Gly Val Asp Ile Val Gln Trp Val Arg Lys Met Thr Asp Ser Asn
            900                 905                 910

Lys Glu Gly Val Leu Lys Ile Leu Asp Pro Arg Leu Pro Ser Val Pro
        915                 920                 925

Leu His Glu Val Met His Val Phe Tyr Val Ala Met Leu Cys Val Glu
    930                 935                 940

Glu Gln Ala Val Glu Arg Pro Thr Met Arg Glu Val Val Gln Ile Leu
945                 950                 955                 960

Thr Glu Leu Pro Lys Ala Pro Gly Ser Lys Leu Val Glu Asp Ser Ala
                965                 970                 975

Ile Thr Glu Ser Ser Pro Pro Pro Ala Thr Thr Ala Ser Glu Ser Pro
            980                 985                 990

Gly Thr Thr Ser Lys Asp Thr Lys  Asp Gln Pro Pro Leu  Gln Ser Pro
        995                 1000                1005

Pro Pro  Asp Leu Leu Ser Ile
    1010                1015
```

<210> SEQ ID NO 28
<211> LENGTH: 56
<212> TYPE: PRT
<213> ORGANISM: Malus domestica

<400> SEQUENCE: 28

Met Arg Ile Leu Asn Tyr Leu Asn Leu Ser Arg Asn His Leu Val Gly
1 5 10 15

Ser Ile Pro Ser Ser Ile Ser Thr Met Gln Ser Leu Thr Ser Val Asp
20 25 30

Phe Ser Tyr Asn Asn Leu Ser Gly Leu Val Pro Gly Thr Gly Gln Phe
35 40 45

Ser Tyr Phe Asn Tyr Thr Ser Phe
50 55

<210> SEQ ID NO 29
<211> LENGTH: 1014
<212> TYPE: PRT
<213> ORGANISM: Malus domestica
<220> FEATURE:
<221> NAME/KEY: misc_feature
<222> LOCATION: (423)..(423)
<223> OTHER INFORMATION: Xaa can be any naturally occurring amino acid
<220> FEATURE:
<221> NAME/KEY: misc_feature
<222> LOCATION: (558)..(558)
<223> OTHER INFORMATION: Xaa can be any naturally occurring amino acid
<220> FEATURE:
<221> NAME/KEY: misc_feature
<222> LOCATION: (789)..(789)
<223> OTHER INFORMATION: Xaa can be any naturally occurring amino acid
<220> FEATURE:
<221> NAME/KEY: misc_feature
<222> LOCATION: (924)..(924)
<223> OTHER INFORMATION: Xaa can be any naturally occurring amino acid
<220> FEATURE:
<221> NAME/KEY: misc_feature
<222> LOCATION: (986)..(986)
<223> OTHER INFORMATION: Xaa can be any naturally occurring amino acid

<400> SEQUENCE: 29

Met Arg Leu Leu Phe Leu Leu Phe Leu Leu His Leu His Arg Ser Leu
1 5 10 15

Ser Ala Gly Ala Met Ser Asp Tyr Arg Ala Leu Leu Ser Leu Lys Ser
20 25 30

Ser Ile Thr Ser Asp Pro Asn Ser Ala Leu Ser Thr Trp Thr Pro Thr
35 40 45

Thr Ser His Cys Thr Trp Ser Gly Val Thr Cys Asp Ser Ser Arg Arg
50 55 60

Tyr Val Thr Ser Leu Asp Leu Ser Gly Leu Asp Leu Thr Gly Thr Leu
65 70 75 80

Ser Pro Asp Leu Ala His Leu Arg Phe Leu Ser Asn Leu Thr Leu Ala
85 90 95

Glu Asn Gln Phe Ser Gly Pro Ile Pro Pro Asp Ile Ser Ala Leu Ser
100 105 110

Gly Leu Arg Leu Leu Asn Leu Ser Asn Asn Val Phe Asn Thr Thr Phe
115 120 125

Pro Arg Gln Leu Ser Asn Leu Thr Arg Leu Thr Val Leu Asp Leu Tyr
130 135 140

Asn Asn Asn Leu Thr Gly Lys Leu Pro Val Ser Val Thr His Met Thr
145 150 155 160

-continued

```
Ser Leu Arg His Leu His Leu Gly Gly Asn Phe Phe Ser Gly Gln Ile
                165                 170                 175

Pro Pro Glu Phe Gly Arg Phe Pro Phe Leu Glu Tyr Leu Ala Val Ser
            180                 185                 190

Gly Asn Glu Leu Gly Gly Ser Ile Pro Pro Glu Ile Gly Asn Leu Thr
        195                 200                 205

Thr Leu Lys Glu Leu Tyr Ile Gly Tyr Phe Asn Ser Tyr Glu Gly Gly
    210                 215                 220

Ile Pro Pro Glu Ile Gly Asn Leu Ser Asn Leu Val Arg Phe Asp Ala
225                 230                 235                 240

Ala Asn Cys Asn Leu Thr Gly Glu Val Pro Pro Glu Leu Gly Arg Leu
                245                 250                 255

Gln Asn Val Asp Thr Leu Phe Leu Gln Val Asn Ala Leu Ser Gly Trp
            260                 265                 270

Leu Thr Pro Glu Leu Gly Tyr Leu Lys Ser Leu Lys Ser Met Asp Leu
        275                 280                 285

Ser Asn Asn Met Tyr Thr Gly Glu Ile Pro Gly Ser Phe Ser Glu Leu
    290                 295                 300

Lys Asn Leu Thr Leu Leu Asn Leu Phe Arg Asn Arg Leu His Gly Ala
305                 310                 315                 320

Ile Pro Glu Phe Ile Gly Asp Leu Pro Glu Leu Gln Val Leu Gln Leu
                325                 330                 335

Trp Glu Asn Asn Phe Thr Gly Ser Ile Pro Gln Gly Leu Gly Lys Asn
            340                 345                 350

Gly Lys Leu Gln Ile Leu Asp Leu Ser Ser Asn Lys Leu Thr Gly Thr
        355                 360                 365

Leu Pro Pro Asp Met Cys Phe Gly Asn Ser Leu Gln Thr Leu Ile Thr
    370                 375                 380

Leu Ser Asn Phe Leu Phe Gly Pro Ile Pro Glu Ser Leu Gly Arg Cys
385                 390                 395                 400

Asp Ser Leu Ser Arg Ile Arg Met Gly Asp Asn Phe Leu Asn Gly Ser
                405                 410                 415

Ile Pro Lys Gly Leu Phe Xaa Leu Pro Lys Leu Thr Gln Val Glu Leu
            420                 425                 430

Gln Asp Asn Leu Leu Asp Gly Ser Phe Pro Glu Thr Asp Thr Ile Ser
        435                 440                 445

Gly Asn Leu Gly Gln Ile Ser Leu Ser Asn Asn Arg Leu Ser Gly Ser
    450                 455                 460

Leu Pro Pro Thr Ile Gly Asn Phe Ser Gly Val Gln Lys Leu Leu Leu
465                 470                 475                 480

Asp Gly Asn Lys Phe Ser Gly Arg Ile Pro Pro Glu Ile Gly Arg Leu
                485                 490                 495

Gln Gln Leu Ser Lys Met Asp Phe Lys His Asn Lys Phe Met Gly Ser
            500                 505                 510

Ile Thr Pro Glu Ile Ser Leu Cys Lys Leu Leu Thr Phe Val Asp Leu
        515                 520                 525

Ser Arg Asn Glu Leu Ser Gly Glu Ile Pro Lys Glu Ile Thr Gly Met
    530                 535                 540

Arg Ile Leu Asn Tyr Leu Asn Leu Ser Arg Asn His Leu Xaa Gly Ser
545                 550                 555                 560

Ile Pro Ser Ser Ile Ser Thr Met Gln Ser Leu Thr Ser Val Asp Phe
                565                 570                 575

Ser Tyr Asn Asn Leu Ser Gly Leu Val Pro Gly Thr Gly Gln Phe Ser
```

```
            580                 585                 590

Tyr Phe Asn Tyr Thr Ser Phe Leu Gly Asn Pro Asp Leu Cys Gly Pro
        595                 600                 605

Tyr Leu Val Pro Cys Lys Asp Gly Val Ala Asn Gly Thr His Gln Pro
    610                 615                 620

His Val Lys Gly Ala Leu Thr Ala Ser Leu Lys Leu Leu Leu Val Ile
625                 630                 635                 640

Gly Leu Leu Leu Cys Ser Ile Ile Phe Ala Val Ala Ala Ile Ile Lys
                645                 650                 655

Ala Arg Ser Leu Lys Arg Ala Ser Asp Ser Arg Ala Trp Lys Leu Thr
            660                 665                 670

Ala Phe Gln Arg Leu Asp Phe Ser Val Asp Asp Val Leu Asp Ser Leu
        675                 680                 685

Lys Glu Asp Asn Ile Ile Gly Lys Gly Gly Ala Gly Ile Val Tyr Lys
    690                 695                 700

Gly Ala Met Pro Thr Gly Asp Ser Val Ala Val Lys Arg Leu Pro Ala
705                 710                 715                 720

Met Ser Arg Gly Ser Ser His Asp His Gly Phe Asn Ala Glu Ile Gln
                725                 730                 735

Thr Leu Gly Arg Ile Arg His Arg His Ile Val Arg Leu Leu Gly Phe
            740                 745                 750

Cys Ser Asn His Glu Thr Asn Leu Leu Val Tyr Glu Tyr Met Pro Asn
        755                 760                 765

Gly Ser Leu Gly Glu Val Leu His Gly Lys Lys Gly Gly His Leu His
    770                 775                 780

Trp Asp Thr Arg Xaa Lys Ile Ala Ile Glu Ala Ala Lys Gly Leu Cys
785                 790                 795                 800

Tyr Leu His His Asp Cys Ser Pro Leu Ile Val His Arg Asp Val Lys
                805                 810                 815

Ser Asn Asn Ile Leu Leu Asp Ser Asn Phe Glu Ala His Val Ala Asp
            820                 825                 830

Phe Gly Leu Ala Lys Phe Leu Gln Asp Ser Gly Thr Ser Glu Cys Met
        835                 840                 845

Ser Ala Ile Ala Gly Ser Tyr Gly Tyr Ile Ala Pro Glu Tyr Ala Tyr
    850                 855                 860

Thr Leu Lys Val Asp Glu Lys Ser Asp Val Tyr Ser Phe Gly Val Val
865                 870                 875                 880

Leu Leu Glu Leu Val Ser Gly Arg Lys Pro Val Gly Glu Phe Gly Asp
                885                 890                 895

Gly Val Asp Ile Val Gln Trp Val Arg Lys Met Thr Asp Ser Asn Lys
            900                 905                 910

Glu Gly Val Leu Lys Ile Leu Asp Pro Arg Leu Xaa Ser Val Pro Leu
        915                 920                 925

His Glu Val Met His Val Phe Tyr Val Ala Met Leu Cys Val Glu Glu
    930                 935                 940

Gln Ala Val Glu Arg Pro Thr Met Arg Glu Val Val Gln Ile Leu Thr
945                 950                 955                 960

Glu Leu Pro Lys Gly Pro Gly Ser Lys Leu Val Glu Glu Ser Ala Ile
                965                 970                 975

Thr Glu Ser Ser Pro Pro Pro Ala Thr Xaa Ala Ser Glu Ser Pro Gly
            980                 985                 990

Thr Thr Ser Lys Asp Thr Lys Asp  Gln Pro Pro Pro Gln  Ser Leu Pro
        995                 1000                 1005
```

```
Pro Asp  Leu Leu Ser Ile
    1010


<210> SEQ ID NO 30
<211> LENGTH: 56
<212> TYPE: PRT
<213> ORGANISM: Malus domestica
<220> FEATURE:
<221> NAME/KEY: misc_feature
<222> LOCATION: (15)..(15)
<223> OTHER INFORMATION: Xaa can be any naturally occurring amino acid

<400> SEQUENCE: 30

Met Arg Ile Leu Asn Tyr Leu Asn Leu Ser Arg Asn His Leu Xaa Gly
1               5                   10                  15

Ser Ile Pro Ser Ser Ile Ser Thr Met Gln Ser Leu Thr Ser Val Asp
            20                  25                  30

Phe Ser Tyr Asn Asn Leu Ser Gly Leu Val Pro Gly Thr Gly Gln Phe
        35                  40                  45

Ser Tyr Phe Asn Tyr Thr Ser Phe
    50                  55


<210> SEQ ID NO 31
<211> LENGTH: 973
<212> TYPE: PRT
<213> ORGANISM: Malus domestica
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (621)..(621)
<223> OTHER INFORMATION: Xaa can be any naturally occurring amino acid
<220> FEATURE:
<221> NAME/KEY: misc_feature
<222> LOCATION: (654)..(654)
<223> OTHER INFORMATION: Xaa can be any naturally occurring amino acid

<400> SEQUENCE: 31

Met Val Thr Ser Gly Phe Arg Arg Ile Leu Pro Val Cys Phe Val Val
1               5                   10                  15

Leu Leu Leu Cys Ser Ala Thr Cys Gly Gly His Gly Asp Leu Asp Xaa
            20                  25                  30

Leu Leu Lys Leu Lys Ala Ala Met Ile Gly Xaa Lys Arg Ser Gly Leu
        35                  40                  45

Glu Asp Trp Asn Pro Ser Ser Ser His Cys Ser Phe Ser Gly Val Leu
    50                  55                  60

Cys Asp Arg Asp Ser Arg Val Val Ser Leu Asn Val Ser Asn Leu Pro
65                  70                  75                  80
```

-continued

```
Leu Tyr Gly Thr Ile Ala Ala Glu Ile Gly Leu Leu Asp Lys Leu Val
                85                  90                  95

Asn Leu Thr Ile Ala Gly Asn Asn Phe Thr Gly Arg Leu Pro Ala Glu
            100                 105                 110

Met Ala Asn Leu Thr Ala Leu Lys His Leu Asn Ile Ser Gly Asn Leu
        115                 120                 125

Phe His Gly Ser Phe Pro Ile Glu Ile Val Val Gly Met Thr Glu Leu
    130                 135                 140

Glu Val Leu Asp Ala Tyr Asn Asn Asn Phe Thr Gly Thr Leu Pro Val
145                 150                 155                 160

Glu Leu Val Ser Leu Lys Asn Leu Lys His Leu Gln Leu Gly Gly Asn
                165                 170                 175

Phe Ile Thr Gly Glu Ile Pro Glu Asn Tyr Ser Glu Ile Gln Ser Leu
            180                 185                 190

Glu Tyr Leu Gly Val Asn Gly Asn Met Leu Ser Gly Arg Val Pro Ala
        195                 200                 205

Ser Leu Ser Arg Leu Lys Asn Leu Arg Glu Leu Tyr Val Gly Tyr Tyr
    210                 215                 220

Asn Ser Tyr Ser Gly Gly Ile Pro Pro Glu Leu Gly Ser Leu Ser Ser
225                 230                 235                 240

Leu Gln Ile Leu Asp Met Gly Ser Cys Asn Leu Val Gly Pro Ile Pro
                245                 250                 255

Thr Thr Leu Ser Leu Leu Lys His Leu His Thr Leu Phe Leu Gln Val
            260                 265                 270

Asn Arg Leu Ser Gly Ser Ile Pro Pro Glu Leu Ser Ala Leu Asn Arg
        275                 280                 285

Leu Met Ser Leu Asp Leu Ser Ile Asn Glu Leu Ser Gly Glu Ile Pro
    290                 295                 300

Glu Ser Phe Ser Glu Leu Lys Asn Ile Thr Leu Ile Asn Leu Tyr Arg
305                 310                 315                 320

Asn Asn Leu Tyr Gly Pro Ile Pro Lys Phe Ile Gly Asp Phe Pro His
                325                 330                 335

Leu Glu Val Leu Gln Ile Trp Glu Asn Asn Phe Thr Phe Glu Leu Pro
            340                 345                 350

Glu Asn Leu Gly Arg Asn Gly Arg Leu Lys Glu Leu Asp Val Thr Gly
        355                 360                 365

Asn His Leu Thr Gly Leu Ile Pro Arg Asp Leu Cys Thr Gly Gly Asn
    370                 375                 380

Leu Lys Thr Ala Ile Leu Met Glu Asn His Phe Phe Gly Pro Ile Pro
385                 390                 395                 400

Glu Glu Leu Gly Arg Cys Asn Ser Leu Thr Lys Ile Arg Met Met Lys
                405                 410                 415

Asn Ser Leu Ser Gly Thr Ile Pro Ala Gly Ile Phe Ser Leu Pro Asn
            420                 425                 430

Leu Ile Met Ile Glu Leu Asn Asp Asn Phe Leu Ser Gly Glu Leu Pro
        435                 440                 445

Glu Gln Met Ser Gly Gly Asn Ile Gly Ile Leu Thr Leu Ser Gly Asn
    450                 455                 460

His Leu Ser Gly Lys Ile Pro Pro Ala Xaa Gly Asn Leu Lys Ser Leu
465                 470                 475                 480

Gln Thr Leu Xaa Leu Glu Met Asn Gly Phe Ser Gly Glu Ile Pro Ser
                485                 490                 495

Glu Ile Phe Asp Leu Lys Leu Leu Ser Arg Ile Asn Ile Ser Ala Asn
```

```
            500                 505                 510

Asn Xaa Gly Arg Lys Ile Pro Asp Ser Ile Ser Arg Cys Ser Ser Leu
        515                 520                 525

Thr Ser Ala Asp Leu Ser Gln Asn Asn Leu Val Gly Glu Ile Pro Lys
    530                 535                 540

Gly Ile Ala Lys Leu Lys Val Leu Ser Ile Leu Asn Phe Ser Arg Asn
545                 550                 555                 560

Gln Leu Thr Gly Glu Ile Pro Ala Glu Ile Arg Tyr Met Thr Ser Leu
                565                 570                 575

Thr Thr Leu Asp Leu Ser Asp Asn Asn Phe Val Gly Arg Ile Pro Thr
            580                 585                 590

Gly Gly Gln Phe Leu Val Phe Asn Asp Thr Ser Phe Ser Gly Asn Pro
        595                 600                 605

His Leu Cys Ser Pro Arg Ser Val Gln Cys Pro Leu Xaa His Arg Pro
    610                 615                 620

Lys Pro Phe Ala Thr Ser Lys Ile Val Leu Ile Val Ile Gly Leu Cys
625                 630                 635                 640

Thr Ile Leu Leu Phe Leu Phe Ile Thr Ala Tyr Arg Met Xaa Arg Ser
                645                 650                 655

Lys Ile Gln Asn Ser Arg Ala Trp Arg Leu Thr Ala Phe Lys Pro Leu
            660                 665                 670

Gly Phe Arg Ala Glu Asp Val Leu Glu Cys Leu Lys Glu Glu Asn Ile
        675                 680                 685

Ile Gly Lys Gly Gly Ala Gly Ile Val Tyr Arg Gly Ser Met Pro Asp
    690                 695                 700

Gly Val Asp Val Ala Ile Lys Arg Leu Val Gly Arg Gly Thr Gly Arg
705                 710                 715                 720

Asn Asp His Gly Phe Ser Ala Glu Ile Lys Thr Leu Gly Arg Ile Arg
                725                 730                 735

His Arg Asn Ile Val Arg Leu Leu Gly Tyr Val Ser Asn Lys Asp Thr
            740                 745                 750

Asn Leu Leu Leu Tyr Glu Tyr Met Pro Asn Gly Ser Leu Gly Glu Leu
        755                 760                 765

Leu His Gly Thr Lys Gly Gly His Leu Gln Trp Glu Arg Arg Tyr Arg
    770                 775                 780

Ile Ala Val Glu Ala Ala Lys Gly Leu Cys Tyr Leu His His Asp Cys
785                 790                 795                 800

Ser Pro Leu Ile Ile His Arg Asp Val Lys Ser Asn Asn Ile Leu Leu
                805                 810                 815

Asp Ser Asp Leu Glu Ala His Val Ala Asp Phe Gly Leu Ala Lys Phe
            820                 825                 830

Leu Gln Asp Ala Gly Ala Ser Glu Cys Met Ser Ser Ile Ala Gly Ser
        835                 840                 845

Tyr Gly Tyr Ile Ala Pro Glu Tyr Ala Tyr Thr Leu Lys Val Asp Glu
    850                 855                 860

Lys Ser Asp Val Tyr Ser Phe Gly Val Val Leu Leu Glu Leu Ile Ala
865                 870                 875                 880

Gly Arg Lys Pro Val Gly Glu Phe Gly Asp Gly Val Asp Ile Val Arg
                885                 890                 895

Trp Val Arg Glu Thr Thr Ser Glu Leu Pro Gln Pro Ser Asp Thr Ala
            900                 905                 910

Ser Val Leu Ala Val Val Asp Ser Arg Leu Ser Gly Tyr Pro Leu Ala
        915                 920                 925
```

Gly Val Val His Leu Phe Lys Ile Ala Met Met Cys Val Glu Asp Glu
930 935 940

Ser Thr Ala Arg Pro Thr Met Arg Glu Val Val His Met Leu Thr Asn
945 950 955 960

Pro Pro Pro Ala Ala Pro Thr Pro Ser Leu Leu Asn Leu
965 970

<210> SEQ ID NO 32
<211> LENGTH: 56
<212> TYPE: PRT
<213> ORGANISM: Malus domestica

<400> SEQUENCE: 32

Leu Lys Val Leu Ser Ile Leu Asn Phe Ser Arg Asn Gln Leu Thr Gly
1 5 10 15

Glu Ile Pro Ala Glu Ile Arg Tyr Met Thr Ser Leu Thr Thr Leu Asp
20 25 30

Leu Ser Asp Asn Asn Phe Val Gly Arg Ile Pro Thr Gly Gly Gln Phe
35 40 45

Leu Val Phe Asn Asp Thr Ser Phe
50 55

<210> SEQ ID NO 33
<211> LENGTH: 778
<212> TYPE: PRT
<213> ORGANISM: Malus domestica
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (621)..(621)
<223> OTHER INFORMATION: Xaa can be any naturally occurring amino acid
<220> FEATURE:
<221> NAME/KEY: misc_feature
<222> LOCATION: (654)..(654)
<223> OTHER INFORMATION: Xaa can be any naturally occurring amino acid

<400> SEQUENCE: 33

Met Val Thr Ser Gly Phe Arg Arg Ile Leu Pro Val Cys Phe Val Val
1 5 10 15

Leu Leu Leu Cys Ser Ala Thr Cys Gly Gly His Gly Asp Leu Asp Ala
20 25 30

Leu Leu Lys Leu Lys Ala Ala Met Ile Gly Arg Lys Arg Ser Gly Leu
35 40 45

Glu Asp Trp Asn Pro Ser Ser Ser His Cys Ser Phe Ser Gly Val Leu
50 55 60

Cys Asp Arg Asp Ser Arg Val Val Ser Leu Asn Val Ser Asn Leu Pro
65 70 75 80

Leu Tyr Gly Thr Ile Ala Ala Glu Ile Gly Leu Leu Asp Lys Leu Val
85 90 95

Asn Leu Thr Ile Ala Gly Asn Asn Phe Thr Gly Arg Leu Pro Ala Glu
100 105 110

-continued

```
Met Ala Asn Leu Thr Ala Leu Lys His Leu Asn Ile Ser Gly Asn Leu
        115                 120                 125

Phe His Gly Ser Phe Pro Ile Glu Ile Val Val Gly Met Thr Glu Leu
    130                 135                 140

Glu Val Leu Asp Ala Tyr Asn Asn Asn Phe Thr Gly Thr Leu Pro Val
145                 150                 155                 160

Glu Leu Val Ser Leu Lys Asn Leu Lys His Leu Gln Leu Gly Gly Asn
                165                 170                 175

Phe Ile Thr Gly Glu Ile Pro Glu Asn Tyr Ser Glu Ile Gln Ser Leu
            180                 185                 190

Glu Tyr Leu Gly Val Asn Gly Asn Met Leu Ser Gly Arg Val Pro Ala
        195                 200                 205

Ser Leu Ser Arg Leu Lys Asn Leu Arg Glu Leu Tyr Val Gly Tyr Tyr
    210                 215                 220

Asn Ser Tyr Ser Gly Gly Ile Pro Pro Glu Leu Gly Ser Leu Ser Ser
225                 230                 235                 240

Leu Gln Ile Leu Asp Met Gly Ser Cys Asn Leu Val Gly Pro Ile Pro
                245                 250                 255

Thr Thr Leu Ser Leu Leu Lys His Leu His Thr Leu Phe Leu Gln Val
            260                 265                 270

Asn Arg Leu Ser Gly Ser Ile Pro Pro Glu Leu Ser Ala Leu Asn Arg
        275                 280                 285

Leu Met Ser Leu Asp Leu Ser Ile Asn Glu Leu Ser Gly Glu Ile Pro
    290                 295                 300

Glu Ser Phe Ser Glu Leu Lys Asn Ile Thr Leu Ile Asn Leu Tyr Arg
305                 310                 315                 320

Asn Asn Leu Tyr Gly Pro Ile Pro Lys Phe Ile Gly Asp Phe Pro His
                325                 330                 335

Leu Glu Val Leu Gln Ile Trp Glu Asn Asn Phe Thr Phe Glu Leu Pro
            340                 345                 350

Glu Asn Leu Gly Arg Asn Gly Arg Leu Lys Glu Leu Asp Val Thr Gly
        355                 360                 365

Asn His Leu Thr Gly Leu Ile Pro Arg Asp Leu Cys Thr Gly Gly Asn
    370                 375                 380

Leu Lys Thr Ala Ile Leu Met Glu Asn His Phe Phe Gly Pro Ile Pro
385                 390                 395                 400

Glu Glu Leu Gly Arg Cys Asn Ser Leu Thr Lys Ile Arg Met Met Lys
                405                 410                 415

Asn Ser Leu Ser Gly Thr Ile Pro Ala Gly Ile Phe Ser Leu Pro Asn
            420                 425                 430

Leu Ile Met Ile Glu Leu Asn Asp Asn Phe Leu Ser Gly Glu Leu Pro
        435                 440                 445

Glu Gln Met Ser Gly Gly Asn Ile Gly Ile Leu Thr Leu Ser Gly Asn
    450                 455                 460

His Leu Ser Gly Lys Ile Pro Pro Ala Xaa Gly Asn Leu Lys Ser Leu
465                 470                 475                 480

Gln Thr Leu Xaa Leu Glu Met Asn Gly Phe Ser Gly Glu Ile Pro Ser
                485                 490                 495

Glu Ile Phe Asp Leu Lys Leu Leu Ser Arg Ile Asn Ile Ser Ala Asn
            500                 505                 510

Asn Xaa Gly Arg Lys Ile Pro Asp Ser Ile Ser Arg Cys Ser Ser Leu
        515                 520                 525

Thr Ser Ala Asp Leu Ser Gln Asn Asn Leu Val Gly Glu Ile Pro Lys
```

```
    530                 535                 540

Gly Ile Ala Lys Leu Lys Val Leu Ser Ile Leu Asn Phe Ser Arg Asn
545                 550                 555                 560

Gln Leu Thr Gly Glu Ile Pro Ala Glu Ile Arg Tyr Met Thr Ser Leu
                565                 570                 575

Thr Thr Leu Asp Leu Ser Asp Asn Asn Phe Val Gly Arg Ile Pro Thr
            580                 585                 590

Gly Gly Gln Phe Leu Val Phe Asn Asp Thr Ser Phe Ser Gly Asn Pro
        595                 600                 605

His Leu Cys Ser Pro Arg Ser Val Gln Cys Pro Leu Xaa His Arg Pro
    610                 615                 620

Lys Pro Phe Ala Thr Ser Lys Ile Val Leu Ile Val Ile Gly Leu Cys
625                 630                 635                 640

Thr Ile Leu Leu Phe Leu Phe Ile Thr Ala Tyr Arg Met Xaa Arg Ser
                645                 650                 655

Lys Ile Gln Asn Ser Arg Ala Trp Arg Leu Thr Ala Phe Lys Pro Leu
            660                 665                 670

Gly Phe Arg Ala Glu Asp Val Leu Glu Cys Leu Lys Glu Glu Asn Ile
        675                 680                 685

Ile Gly Lys Gly Gly Ala Gly Ile Val Tyr Arg Gly Ser Met Pro Asp
    690                 695                 700

Gly Val Asp Val Ala Ile Lys Arg Leu Val Gly Arg Gly Thr Gly Arg
705                 710                 715                 720

Asn Asp His Gly Phe Ser Ala Glu Ile Lys Thr Leu Gly Arg Ile Arg
                725                 730                 735

His Arg Asn Ile Val Arg Leu Leu Gly Tyr Val Ser Asn Lys Asp Thr
            740                 745                 750

Asn Leu Leu Leu Tyr Glu Tyr Met Pro Asn Gly Ser Leu Gly Glu Leu
        755                 760                 765

Leu His Gly Thr Lys Gly Gly His Leu Gln
    770                 775


<210> SEQ ID NO 34
<211> LENGTH: 55
<212> TYPE: PRT
<213> ORGANISM: Malus domestica

<400> SEQUENCE: 34

Leu Lys Val Leu Ser Ile Leu Asn Phe Ser Arg Asn Gln Leu Thr Gly
1               5                   10                  15

Glu Ile Pro Ala Glu Ile Arg Tyr Met Thr Ser Leu Thr Thr Leu Asp
            20                  25                  30

Leu Ser Asp Asn Asn Phe Val Gly Arg Ile Pro Thr Gly Gly Gln Phe
        35                  40                  45

Leu Val Phe Asn Asp Thr Ser
    50                  55


<210> SEQ ID NO 35
<211> LENGTH: 973
<212> TYPE: PRT
<213> ORGANISM: Malus domestica

<400> SEQUENCE: 35

Met Val Thr Ser Ser Pro Arg Arg Ile Leu Pro Leu Cys Phe Val Val
1               5                   10                  15

Leu Leu Leu Cys Ser Ala Pro Cys Gly Gly His Arg Asp Leu Asp Ala
```

```
            20                  25                  30

Leu Leu Lys Leu Lys Ala Ala Met Val Gly Pro Lys Gly Ser Gly Leu
        35                  40                  45

Glu Asp Trp Asn Ser Ser Ser Ser His Cys Phe Phe Ser Gly Val Leu
    50                  55                  60

Cys Asp Arg Asp Ser Arg Val Val Ala Leu Asn Val Ser Asn Ile Pro
65                  70                  75                  80

Leu Phe Gly Thr Ile Pro Ala Ala Ile Gly Leu Leu Asp Lys Leu Val
                85                  90                  95

Asn Leu Glu Ile Thr Asp Asp Asn Leu Thr Gly Arg Leu Pro Ala Glu
            100                 105                 110

Met Ala Asn Leu Thr Ser Leu Lys His Leu Asn Ile Ser Asn Asn Ala
        115                 120                 125

Phe Ser Gly Ser Phe Pro Gly Glu Ile Val Leu Gly Met Thr Asp Leu
    130                 135                 140

Glu Val Leu Asp Ala Tyr Asn Asn Asn Phe Asn Gly Thr Leu Pro Ile
145                 150                 155                 160

Gln Leu Val Ser Leu Lys Asn Ile Lys His Leu His Leu Gly Gly Asn
                165                 170                 175

Tyr Ile Thr Gly Glu Ile Pro Glu Asp Tyr Ser Glu Ile Gln Ser Leu
            180                 185                 190

Glu Tyr Leu Gly Leu Asn Gly Asn Leu Leu Thr Gly Lys Leu Pro Ala
        195                 200                 205

Ser Leu Ser Arg Leu Lys Asn Leu Arg Glu Met Tyr Val Gly Tyr Tyr
    210                 215                 220

Asn Ser Tyr Asp Gly Gly Ile Pro Pro Glu Leu Gly Ser Val Ser Ser
225                 230                 235                 240

Leu Gln Val Leu Asp Met Ser Ser Cys Asn Leu Val Gly Pro Ile Pro
                245                 250                 255

Thr Thr Leu Ser Leu Leu Lys His Leu His Ser Leu Phe Leu Gln Val
            260                 265                 270

Asn Arg Leu Ser Gly Ser Ile Pro Pro Gln Leu Ser Ala Leu Asn Met
        275                 280                 285

Leu Met Ser Leu Asp Leu Ser Ile Asn Glu Leu Thr Gly Glu Ile Pro
    290                 295                 300

Glu Ser Phe Ser Glu Leu Lys Asn Leu Thr Leu Val Asn Leu Tyr Lys
305                 310                 315                 320

Asn Asn Leu Tyr Gly Pro Ile Pro Lys Phe Val Gly Asp Phe Pro His
                325                 330                 335

Leu Glu Val Leu Gln Ile Trp Glu Asn Asn Phe Thr Phe Glu Leu Pro
            340                 345                 350

Glu Asn Leu Gly Arg Asn Gly Arg Leu Lys Asp Leu Asp Val Thr Gly
        355                 360                 365

Asn His Leu Thr Gly Leu Ile Pro Arg Asp Leu Cys Lys Gly Gly Asn
    370                 375                 380

Leu Lys Thr Ala Ile Leu Met Glu Asn His Phe Phe Gly Pro Ile Pro
385                 390                 395                 400

Glu Glu Leu Gly Leu Cys Asn Ser Leu Val Lys Ile Arg Met Met Lys
                405                 410                 415

Asn Thr Leu Thr Gly Thr Ile Pro Ala Gly Ile Phe Ser Leu Pro Asn
            420                 425                 430

Leu Ile Met Ile Glu Leu Asn Asp Asn Phe Leu Ser Gly Glu Leu Pro
        435                 440                 445
```

```
Gln Gln Ile Ser Gly Gly Asn Ile Gly Ile Leu Thr Leu Ser Gly Asn
    450                 455                 460

His Ile Ser Gly Lys Ile Pro Pro Ala Ile Gly Asn Leu Lys Ser Leu
465                 470                 475                 480

Gln Thr Leu Ser Leu Glu Met Asn Arg Phe Ser Gly Glu Ile Pro Thr
                485                 490                 495

Glu Ile Phe Tyr Leu Lys Leu Leu Ser Lys Ile Asn Ile Ser Ala Asn
            500                 505                 510

Asn Leu Ser Ser Asp Ile Ser Glu Ser Ile Ser Arg Cys Ser Ser Leu
        515                 520                 525

Thr Ser Val Asp Leu Ser Gly Asn Asn Leu Val Gly Glu Ile Pro Arg
    530                 535                 540

Gly Ile Ala Lys Leu Lys Val Leu Ser Ile Leu Asn Phe Ser Arg Asn
545                 550                 555                 560

Gln Leu Thr Gly Glu Ile Pro Ala Glu Met Arg Ser Met Thr Ser Leu
                565                 570                 575

Thr Thr Leu Asp Leu Ser Asn Asn Asn Phe Val Gly Arg Leu Pro Thr
            580                 585                 590

Gly Gly Gln Phe Leu Val Phe Asn Asp Thr Ser Phe Ala Gly Asn Pro
        595                 600                 605

Tyr Leu Cys Ser Pro Arg Arg Val Gln Cys Pro Ser Phe His Ser Arg
    610                 615                 620

Lys Pro Phe Ala Thr Ser Lys Ile Ala Leu Ile Val Ile Gly Leu Cys
625                 630                 635                 640

Thr Ile Leu Leu Phe Leu Phe Ile Thr Ala Tyr Arg Met Ser Lys Ser
                645                 650                 655

Glu Ile Gln Lys Ser Leu Val Trp Arg Leu Thr Ala Phe Gln Arg Leu
            660                 665                 670

Asp Phe Gly Ala Glu Asp Val Leu Glu Cys Leu Lys Glu Glu Asn Ile
        675                 680                 685

Ile Gly Lys Gly Gly Ala Gly Ile Val Tyr Arg Gly Ser Met Pro Asp
    690                 695                 700

Gly Val Asp Val Ala Ile Lys Arg Leu Val Gly Arg Gly Thr Gly Arg
705                 710                 715                 720

Asn Asp His Gly Phe Ser Ala Glu Ile Lys Thr Leu Gly Arg Ile Arg
                725                 730                 735

His Arg Asn Ile Val Arg Leu Leu Gly Tyr Val Ser Asn Lys Asp Thr
            740                 745                 750

Asn Leu Leu Leu Tyr Glu Tyr Met Pro Asn Gly Ser Leu Gly Glu Leu
        755                 760                 765

Leu His Gly Pro Lys Gly Gly His Leu Gln Trp Glu Arg Arg Tyr Arg
    770                 775                 780

Ile Ala Val Glu Ala Ala Lys Gly Leu Cys Tyr Leu His His Asp Cys
785                 790                 795                 800

Ser Pro Leu Ile Ile His Arg Asp Val Lys Ser Asn Asn Ile Leu Leu
                805                 810                 815

Asp Ser Asp Leu Glu Ala His Val Ala Asp Phe Gly Leu Ala Lys Phe
            820                 825                 830

Leu Gln Asp Ala Gly Ala Ser Glu Cys Met Ser Ser Val Ala Gly Ser
        835                 840                 845

Tyr Gly Tyr Ile Ala Pro Glu Tyr Ala Tyr Thr Leu Lys Val Asp Glu
    850                 855                 860
```

```
Lys Ser Asp Val Tyr Ser Phe Gly Val Val Leu Leu Glu Leu Ile Ala
865                 870                 875                 880

Gly Arg Lys Pro Val Gly Glu Phe Gly Asp Gly Val Asp Ile Val Arg
                885                 890                 895

Trp Val Arg Lys Thr Thr Ser Glu Leu Ser Gln Pro Ser Asp Ala Ala
            900                 905                 910

Ser Val Leu Ala Val Val Asp His Arg Leu Ser Gly Tyr Pro Leu Ala
        915                 920                 925

Gly Val Val His Leu Phe Lys Ile Ala Met Met Ser Val Glu Asp Glu
    930                 935                 940

Ser Ser Ala Arg Pro Thr Met Arg Glu Val Val His Met Leu Thr Asn
945                 950                 955                 960

Pro Pro Pro Ala Ala Pro Thr Pro Ser Leu Leu Asn Leu
                965                 970


<210> SEQ ID NO 36
<211> LENGTH: 56
<212> TYPE: PRT
<213> ORGANISM: Malus domestica

<400> SEQUENCE: 36

Leu Lys Val Leu Ser Ile Leu Asn Phe Ser Arg Asn Gln Leu Thr Gly
1               5                   10                  15

Glu Ile Pro Ala Glu Met Arg Ser Met Thr Ser Leu Thr Thr Leu Asp
            20                  25                  30

Leu Ser Asn Asn Asn Phe Val Gly Arg Leu Pro Thr Gly Gly Gln Phe
        35                  40                  45

Leu Val Phe Asn Asp Thr Ser Phe
    50                  55


<210> SEQ ID NO 37
<211> LENGTH: 977
<212> TYPE: PRT
<213> ORGANISM: Prunus persica

<400> SEQUENCE: 37

Met Val Ser Ser Ser Cys Cys Gln Ile Leu Thr Ile Cys Phe Met Ile
1               5                   10                  15

Phe Leu Leu Cys Ser Ala Cys Gly Gly Tyr Ser Asp Leu His Ala Leu
            20                  25                  30

Leu Lys Leu Lys Ser Ala Met Ile Gly Pro Lys Gly Ser Gly Leu Glu
        35                  40                  45

Asp Trp Asn Thr Ser Ser Leu Ser Pro Ser Ser His Cys Ser Phe Ser
    50                  55                  60

Gly Val Ser Cys Asp Arg Asp Phe Arg Val Val Ala Leu Asn Val Ser
65                  70                  75                  80

Asn Gln Pro Leu Leu Gly Thr Leu Pro Pro Glu Ile Gly Leu Leu Asn
                85                  90                  95

Lys Leu Val Asn Leu Thr Ile Ala Gly Asp Asn Ile Thr Gly Arg Leu
            100                 105                 110

Pro Met Gln Met Ala Asn Leu Thr Ala Leu Arg His Leu Asn Ile Ser
        115                 120                 125

Asn Asn Val Phe Arg Gly Arg Phe Pro Gly Asn Ile Thr Leu Gln Met
    130                 135                 140

Thr Glu Leu Gln Val Leu Asp Ala Tyr Asn Asn Asn Phe Thr Gly Thr
145                 150                 155                 160
```

-continued

```
Leu Pro Leu Glu Ile Val Asn Leu Lys Asn Leu Lys His Leu Gln Leu
                165                 170                 175

Gly Gly Asn Tyr Phe Thr Gly Asn Ile Pro Glu Thr Tyr Ser Glu Met
            180                 185                 190

Gln Ser Leu Glu His Phe Gly Leu Asn Gly Asn Trp Leu Thr Gly Lys
        195                 200                 205

Phe Pro Ala Ser Leu Ala Arg Leu Lys Asn Leu Lys Glu Met Tyr Val
    210                 215                 220

Gly Tyr Phe Asn Ser Tyr Asp Gly Gly Ile Pro Pro Glu Leu Gly Ser
225                 230                 235                 240

Leu Ser Ser Leu Gln Val Leu Asp Met Ala Ser Cys Asn Leu Ser Gly
                245                 250                 255

Thr Ile Pro Thr Asn Leu Ser Leu Leu Lys Asn Leu Asn Ser Leu Phe
            260                 265                 270

Leu Gln Val Asn Arg Leu Ser Gly Gly Ile Pro Pro Glu Leu Ser Gly
        275                 280                 285

Leu Val Ser Leu Met Ser Leu Asp Leu Ser Ile Asn Asp Leu Thr Gly
    290                 295                 300

Glu Ile Pro Gln Ser Phe Ser Glu Leu Lys Asn Ile Thr Leu Ile Asn
305                 310                 315                 320

Leu Tyr Lys Asn Asn Leu Tyr Gly Pro Ile Pro Arg Phe Val Gly Asp
                325                 330                 335

Phe Pro His Leu Glu Val Leu Gln Val Trp Glu Asn Asn Phe Thr Phe
            340                 345                 350

Glu Leu Pro Glu Asn Leu Gly Arg Asn Gly Arg Leu Lys Asp Leu Asp
        355                 360                 365

Ile Thr Gly Asn His Ile Thr Gly Leu Ile Pro Arg Asp Leu Cys Lys
    370                 375                 380

Gly Gly Gln Leu Lys Thr Ala Ile Leu Met Asp Asn His Phe Phe Gly
385                 390                 395                 400

Pro Ile Pro Glu Glu Leu Gly Arg Cys Lys Ser Leu Val Lys Ile Arg
                405                 410                 415

Met Met Lys Asn Thr Leu Thr Gly Thr Ile Pro Ala Gly Ile Phe Ser
            420                 425                 430

Leu Pro Asn Val Ser Met Ile Glu Leu Asn Asp Asn Tyr Leu Ser Gly
        435                 440                 445

Gln Leu Pro Glu Gln Met Ser Gly Gly Leu Leu Gly Ile Leu Thr Leu
    450                 455                 460

Ser Arg Asn Arg Ile Ser Gly Lys Ile Pro Pro Ala Ile Gly Asn Leu
465                 470                 475                 480

Lys Ser Leu Gln Thr Leu Ser Leu Glu Met Asn Arg Phe Ser Gly Glu
                485                 490                 495

Ile Pro Thr Glu Ile Phe Asp Leu Lys Ser Leu Ser Lys Ile Asn Ile
            500                 505                 510

Ser Ala Asn Asn Leu Ser Ser Glu Ile Pro Ala Ser Ile Ser Gln Cys
        515                 520                 525

Ser Ser Leu Ala Leu Ala Asp Leu Ser Arg Asn Asn Leu Ile Gly Glu
    530                 535                 540

Ile Pro Arg Asp Ile Tyr Lys Leu Arg Val Leu Ser Ile Leu Asn Leu
545                 550                 555                 560

Ser Ser Asn Gln Leu Thr Gly Glu Ile Pro Asn Glu Ile Arg Asn Met
                565                 570                 575

Thr Ser Leu Thr Thr Leu Asp Leu Ser Asp Asn Asn Phe Ile Gly Lys
```

```
            580                 585                 590

Ile Pro Thr Gly Gly Gln Phe Met Val Phe Asn Asp Thr Ser Phe Ala
        595                 600                 605

Gly Asn Pro Tyr Leu Cys Ser Pro Gln Arg His Val Gln Cys Pro Ser
    610                 615                 620

Phe Pro His His Lys Ala Phe Gly Ser Ser Arg Ile Ala Leu Val Val
625                 630                 635                 640

Ile Gly Leu Ala Thr Val Leu Leu Phe Leu Phe Ile Thr Val Tyr Arg
                645                 650                 655

Met Arg Arg Arg Glu Met His Lys Ser Arg Ala Trp Arg Leu Thr Ala
            660                 665                 670

Phe Gln Arg Leu Asp Phe Lys Ala Glu Asp Val Leu Glu Cys Leu Lys
        675                 680                 685

Glu Glu Asn Ile Ile Gly Lys Gly Gly Ala Gly Ile Val Tyr Arg Gly
    690                 695                 700

Ser Met Pro Asp Gly Val Asp Val Ala Ile Lys Arg Leu Val Gly Arg
705                 710                 715                 720

Gly Thr Gly Arg Asn Cys Asn Asp His Gly Phe Ser Ala Glu Ile Lys
                725                 730                 735

Thr Leu Gly Arg Ile Arg His Arg Asn Ile Val Arg Leu Leu Gly Tyr
            740                 745                 750

Val Ser Asn Lys Asp Thr Asn Leu Leu Leu Tyr Glu Tyr Met Pro Asn
        755                 760                 765

Gly Ser Leu Gly Glu Leu Leu His Gly Ser Lys Gly Gly His Leu Gln
    770                 775                 780

Trp Glu Arg Arg Tyr Arg Ile Ala Val Glu Ala Ala Lys Gly Leu Cys
785                 790                 795                 800

Tyr Leu His His Asp Cys Ser Pro Leu Ile Ile His Arg Asp Val Lys
                805                 810                 815

Ser Asn Asn Ile Leu Leu Asp Ser Asp Leu Glu Ala His Val Ala Asp
            820                 825                 830

Phe Gly Leu Ala Lys Phe Leu Gln Asp Ala Gly Ala Ser Glu Cys Met
        835                 840                 845

Ser Ser Ile Ala Gly Ser Tyr Gly Tyr Ile Ala Pro Glu Tyr Ala Tyr
    850                 855                 860

Thr Leu Lys Val Asp Glu Lys Ser Asp Val Tyr Ser Phe Gly Val Val
865                 870                 875                 880

Leu Leu Glu Leu Ile Ala Gly Arg Lys Pro Val Gly Glu Phe Gly Asp
                885                 890                 895

Gly Val Asp Ile Val Arg Trp Val Arg Lys Thr Thr Ser Glu Leu Ser
            900                 905                 910

Gln Pro Ser Asp Ala Ala Ser Val Leu Ala Val Val Asp Ala Arg Leu
        915                 920                 925

Cys Gly Tyr Pro Leu Ala Gly Val Ile His Leu Phe Lys Ile Ala Met
    930                 935                 940

Met Cys Val Glu Asp Glu Ser Ser Ala Arg Pro Thr Met Arg Glu Val
945                 950                 955                 960

Val His Met Leu Thr Asn Pro Pro Arg Ser Ala Pro Ser Leu Leu Asn
                965                 970                 975

Leu

<210> SEQ ID NO 38
<211> LENGTH: 56
```

<212> TYPE: PRT
<213> ORGANISM: Prunus persica

<400> SEQUENCE: 38

Leu Arg Val Leu Ser Ile Leu Asn Leu Ser Ser Asn Gln Leu Thr Gly
1               5                   10                  15

Glu Ile Pro Asn Glu Ile Arg Asn Met Thr Ser Leu Thr Thr Leu Asp
            20                  25                  30

Leu Ser Asp Asn Asn Phe Ile Gly Lys Ile Pro Thr Gly Gly Gln Phe
        35                  40                  45

Met Val Phe Asn Asp Thr Ser Phe
    50                  55

<210> SEQ ID NO 39
<211> LENGTH: 988
<212> TYPE: PRT
<213> ORGANISM: Prunus persica

<400> SEQUENCE: 39

Met Val Arg Ser Ala Ser Ser His Ile Leu Leu Leu Pro Ile Cys Phe
1               5                   10                  15

Ile Phe Leu Ser Phe Ser Ser Pro Cys Cys Ala Asn Ser Gly Asp Leu
            20                  25                  30

Asp Ala Leu Leu Lys Leu Lys Asn Ala Met Asn Thr Gly His Lys Thr
        35                  40                  45

Ser Gly Val Leu Glu Asp Trp Lys Pro Ser Val His Tyr Cys Ser Phe
    50                  55                  60

Ser Gly Val Ser Cys Asp Gln Gln Gln Ser Arg Val Val Ser Leu Asn
65                  70                  75                  80

Val Ser Asn Val Pro Leu Ile Gly Ser Ile Pro Ala Glu Ile Gly Leu
                85                  90                  95

Leu Asn Lys Leu Val Asn Leu Thr Ile Ala Gly Asn Asn Leu Thr Gly
            100                 105                 110

Arg Leu Pro Ala Ala Met Ala Asn Leu Thr Cys Leu Lys His Leu Asn
        115                 120                 125

Ile Ser Asn Asn Ile Phe Ile Gly Arg Phe Pro Gly Glu Ile Phe Leu
    130                 135                 140

Gly Met Pro Glu Leu Glu Val Leu Asp Ala Tyr Asn Asn Gln Phe Ser
145                 150                 155                 160

Gly Gln Leu Pro Pro Glu Leu Ala Ser Cys Lys Arg Leu Lys His Leu
                165                 170                 175

Gln Met Gly Gly Asn Tyr Phe Thr Gly Glu Ile Pro Glu Asn Tyr Ser
            180                 185                 190

Asn Ile Gln Ser Leu Glu Tyr Leu Gly Leu Asn Gly Asn Trp Leu Thr
        195                 200                 205

Gly Lys Leu Pro Ala Ser Leu Ala Leu Leu Lys Asn Leu Lys Glu Leu
    210                 215                 220

Tyr Val Gly Tyr Phe Asn Ser Phe Asp Gly Gly Ile Pro Pro Glu Leu
225                 230                 235                 240

Gly Ser Leu Thr Trp Leu Gln Val Leu Asp Leu Ala Ser Cys Asn Leu
                245                 250                 255

Ser Gly Ser Ile Pro Arg Ser Leu Gly Leu Leu Lys His Leu Arg Ser
            260                 265                 270

Leu Phe Leu Gln Val Asn Cys Leu Asn Gly Phe Ile Pro Pro Glu Leu
        275                 280                 285

-continued

```
Ser Gly Met Ala Ser Leu Val Leu Leu Asp Leu Ser Ile Asn Lys Leu
    290                 295                 300

Thr Gly Glu Ile Pro Glu Ser Phe Ser Glu Leu Lys Thr Ile Ser Leu
305                 310                 315                 320

Leu Asn Leu Tyr Lys Asn Asn Leu Tyr Gly Phe Val Pro Asp Phe Ile
                325                 330                 335

Gly His Leu Pro His Leu Glu Val Leu Asn Leu Trp Glu Asn Asn Phe
            340                 345                 350

Thr Phe Glu Leu Pro Glu Ser Leu Gly Arg Asn Gly Arg Leu Val Asp
        355                 360                 365

Leu Asp Val Thr Gly Asn His Leu Thr Gly Leu Ile Pro Gln Asp Leu
    370                 375                 380

Cys Arg Gly Gly Arg Leu Lys Thr Leu Ile Leu Met Glu Asn His Phe
385                 390                 395                 400

Phe Gly Pro Ile Pro Glu Glu Leu Gly Gln Cys Lys Ser Leu Val Lys
                405                 410                 415

Ile Arg Met Met Lys Asn Thr Ile Thr Gly Thr Val Pro Val Gly Ile
            420                 425                 430

Phe Asn Leu Pro Asn Val Val Met Ile Glu Leu Asn Glu Asn Tyr Leu
        435                 440                 445

Ser Gly Gln Leu Pro Thr Gln Met Tyr Ala Asp Ser Leu Ala Ile Leu
    450                 455                 460

Thr Leu Ser Gly Asn Gln Ile Ser Gly Val Ile Pro Arg Ala Ile Gly
465                 470                 475                 480

Asn Leu Asn Asn Leu Gln Ile Leu Ser Leu Glu Met Asn Lys Phe Tyr
                485                 490                 495

Gly Lys Ile Pro Lys Glu Ile Phe Tyr Leu Lys Trp Leu Ser Lys Ile
            500                 505                 510

Asn Ile Ser Ile Asn Asn Leu Asp Gly Glu Ile Pro Ala Ser Ile Ser
        515                 520                 525

Asn Cys Ser Ser Leu Ala Ile Leu Asp Phe Ser Arg Asn Asn Leu Val
    530                 535                 540

Gly Glu Ile Pro Arg Gly Thr Thr Lys Leu Glu Ala Ile Asp Leu Val
545                 550                 555                 560

Asn Phe Ser Arg Asn Gln Leu Thr Gly Gln Ile Pro Asp Glu Ile Pro
                565                 570                 575

Tyr Ile Thr Ser Leu Thr Thr Leu Asp Leu Ser Tyr Asn Asn Phe Thr
            580                 585                 590

Gly Thr Ile Pro Gln Ser Ser Gln Phe Leu Ala Ile Val Ser Phe Glu
        595                 600                 605

Gly Asn Pro Tyr Leu Cys Arg Asn Val Ser Cys Pro Ser Leu Ile Asn
    610                 615                 620

Gln Arg Ala Arg Glu His Asn Ala Phe Gly Ser Pro Ser Lys Leu Ala
625                 630                 635                 640

Leu Ile Ile Ile Gly Pro Leu Leu Val Leu Leu Leu Ile Ile Leu Leu
                645                 650                 655

Ile Phe Leu Leu Leu Lys Val Tyr Arg Ile Thr Lys Met Arg Lys Ile
            660                 665                 670

Gln Lys Ser Lys Gly Trp Arg Leu Ile Val Phe Gln Gln Leu His Leu
        675                 680                 685

Asn Val Glu Asp Leu Leu Gln Cys Leu Lys Leu Glu Asn Ile Ile Gly
    690                 695                 700

Lys Gly Ser Ala Gly Val Val Tyr Arg Gly Thr Met Pro Ser Gly Leu
```

-continued

```
705                 710                 715                 720

Glu Val Ala Ile Lys Gln Leu Val Gly Ser Ser Arg Gly Gly Gln Arg
                725                 730                 735

Asp His Gly Phe Ser Ala Glu Ile Lys Thr Leu Gly Gln Ile Lys His
            740                 745                 750

Arg Asn Ile Val Arg Leu Leu Gly Tyr Met Ser Asn Asn Glu Ser Asn
        755                 760                 765

Leu Leu Leu Tyr Glu Tyr Met Pro Asn Gly Ser Leu Gly Lys Leu Leu
    770                 775                 780

His Gly Pro Asn Ala Ala Glu Leu Gln Trp Glu Arg Arg Tyr Lys Ile
785                 790                 795                 800

Ser Val Glu Ala Ala Lys Gly Leu Cys Tyr Leu His His Asp Cys Ser
                805                 810                 815

Pro Leu Ile Ile His Arg Asp Val Lys Ser His Asn Ile Leu Leu Asp
            820                 825                 830

Ser Asn Leu Glu Ala His Val Ala Asp Phe Gly Leu Ala Lys Tyr Phe
        835                 840                 845

Gln Gly Pro Ala Asp Cys Met Ser Ser Ile Ala Gly Ser Phe Gly Tyr
    850                 855                 860

Ile Ala Pro Glu Tyr Gly Tyr Thr Leu Lys Val Asp Glu Lys Ile Asp
865                 870                 875                 880

Val Tyr Ser Phe Gly Val Val Leu Leu Glu Leu Ile Thr Gly Arg Lys
                885                 890                 895

Pro Val Met Asn Leu Glu Asp Glu Asp Met Asn Ile Val Ser Trp Val
            900                 905                 910

Arg Lys Thr Thr Ser Lys Ile Pro Tyr Lys Pro Ser Pro Ala Ser Pro
        915                 920                 925

Ala Val Leu Leu Ala Leu Val Asp Pro Lys Leu Ser Gly Tyr Pro Leu
    930                 935                 940

Gln Gly Val Leu Tyr Val Phe Asn Ile Ala Met Met Cys Val Glu Asn
945                 950                 955                 960

Asp Ser Cys Ala Arg Pro Thr Met Arg Ala Val Val Asn Met Leu Thr
                965                 970                 975

Asn Pro Pro Pro Ser Ser Pro Thr Glu Val Tyr Leu
            980                 985


<210> SEQ ID NO 40
<211> LENGTH: 54
<212> TYPE: PRT
<213> ORGANISM: Prunus persica

<400> SEQUENCE: 40

Leu Glu Ala Ile Asp Leu Val Asn Phe Ser Arg Asn Gln Leu Thr Gly
1               5                   10                  15

Gln Ile Pro Asp Glu Ile Pro Tyr Ile Thr Ser Leu Thr Thr Leu Asp
            20                  25                  30

Leu Ser Tyr Asn Asn Phe Thr Gly Thr Ile Pro Gln Ser Ser Gln Phe
        35                  40                  45

Leu Ala Ile Val Ser Phe
    50


<210> SEQ ID NO 41
<211> LENGTH: 1017
<212> TYPE: PRT
<213> ORGANISM: Prunus persica
```

-continued

<400> SEQUENCE: 41

```
Met Arg Leu Leu Leu Leu Leu Leu Leu Leu Leu His Leu His His Ser
1               5                   10                  15

Leu Ala Ala Arg Glu Met Ser Asp Tyr Arg Ala Leu Leu Ser Phe Lys
            20                  25                  30

Ser Ser Ile Ser Ser Asp Pro Asn Ser Val Leu Ser Ser Trp Thr Pro
        35                  40                  45

Thr Thr Ser His Cys Thr Trp Thr Gly Val Thr Cys Asp Ser Arg Arg
    50                  55                  60

His Val Thr Ser Leu Asp Leu Ser Ser Ser Asp Leu Val Gly Thr Leu
65                  70                  75                  80

Ser Ser Asp Ile Ala His Leu Arg Phe Leu Ser Asn Leu Thr Leu Ala
                85                  90                  95

Asp Asn Gln Phe Ser Gly Pro Ile Pro Ser Glu Ile Ser Ala Leu Ser
            100                 105                 110

Gly Leu Arg Leu Leu Asn Leu Ser Asn Asn Ile Phe Asn Thr Thr Phe
        115                 120                 125

Pro Pro Gln Leu Ser Asn Leu Thr Arg Leu Ala Val Leu Asp Leu Tyr
    130                 135                 140

Asn Asn Asn Leu Thr Gly Asp Leu Pro Val Ser Val Thr His Met Thr
145                 150                 155                 160

Ser Leu Arg His Leu His Leu Gly Gly Asn Phe Phe Ser Gly Arg Ile
                165                 170                 175

Pro Pro Glu Phe Gly Arg Phe Pro Leu Leu Glu Tyr Leu Ala Ile Ser
            180                 185                 190

Gly Asn Glu Leu Gly Gly Ser Ile Pro Pro Glu Ile Gly Asn Leu Thr
        195                 200                 205

Ser Leu Lys Glu Leu Tyr Ile Gly Tyr Tyr Asn Ile Tyr Glu Gly Gly
    210                 215                 220

Ile Pro Pro Glu Ile Gly Asn Leu Ser Gln Leu Val Arg Leu Asp Ala
225                 230                 235                 240

Ala Asn Cys Asn Leu Thr Gly Glu Val Pro Arg Glu Leu Gly Arg Leu
                245                 250                 255

Gln Asn Val Asp Thr Leu Phe Leu Gln Val Asn Ala Leu Ser Gly Ser
            260                 265                 270

Leu Thr Ala Glu Leu Gly Ser Leu Lys Ser Leu Lys Ser Met Asp Leu
        275                 280                 285

Ser Asn Asn Met Phe Ser Gly Glu Ile Pro Gly Ser Phe Ser Glu Leu
    290                 295                 300

Lys Asn Leu Thr Leu Leu Asn Leu Phe Arg Asn Lys Leu His Gly Ala
305                 310                 315                 320

Ile Pro Glu Phe Ile Gly Asp Leu Pro Glu Leu Gln Val Leu Gln Leu
                325                 330                 335

Trp Glu Asn Asn Phe Thr Gly Ser Ile Pro Gln Gly Leu Gly Lys Asn
            340                 345                 350

Gly Lys Leu Ile Thr Leu Asp Leu Ser Ser Asn Lys Leu Thr Gly Thr
        355                 360                 365

Leu Pro Pro Asp Met Cys Phe Gly Asn Asn Leu Gln Thr Leu Ile Thr
    370                 375                 380

Leu Gly Asn Phe Leu Phe Gly Pro Ile Pro Glu Ser Leu Gly Arg Cys
385                 390                 395                 400

Gly Ser Leu Ser Arg Ile Arg Met Gly Glu Asn Phe Leu Asn Gly Ser
                405                 410                 415
```

-continued

```
Ile Pro Lys Gly Leu Phe Gly Leu Pro Lys Leu Ser Gln Val Glu Leu
            420                 425                 430

Gln Asp Asn Leu Leu Ala Gly Ser Phe Pro Glu Thr Asp Thr Ile Ser
        435                 440                 445

Val Asn Leu Gly Gln Ile Ser Leu Ser Asn Asn Arg Leu Ser Gly Ser
    450                 455                 460

Leu Pro Pro Thr Ile Gly Asn Phe Ser Gly Val Gln Lys Leu Leu Leu
465                 470                 475                 480

Asp Gly Asn Lys Phe Ser Gly Arg Ile Pro Pro Glu Ile Gly Arg Leu
                485                 490                 495

Gln Gln Leu Ser Lys Ile Asp Phe Ser His Asn Lys Phe Leu Gly Pro
            500                 505                 510

Ile Ala Pro Glu Ile Ser Gln Cys Lys Leu Leu Thr Phe Val Asp Leu
        515                 520                 525

Ser Arg Asn Glu Leu Ala Gly Glu Ile Pro Lys Glu Ile Thr Gly Met
    530                 535                 540

Arg Ile Leu Asn Tyr Leu Asn Leu Ser Arg Asn His Leu Val Gly Ser
545                 550                 555                 560

Ile Pro Ser Ser Ile Ser Thr Met Gln Ser Leu Thr Ser Val Asp Phe
                565                 570                 575

Ser Tyr Asn Asn Leu Ser Gly Leu Val Pro Gly Thr Gly Gln Phe Ser
            580                 585                 590

Tyr Phe Asn Tyr Thr Ser Phe Leu Gly Asn Pro Asp Leu Cys Gly Pro
        595                 600                 605

Tyr Leu Val Pro Cys Lys Asp Gly Val Ala Asn Gly Thr His Gln Pro
    610                 615                 620

His Val Lys Gly Ser Leu Thr Ala Ser Leu Lys Leu Leu Leu Val Ile
625                 630                 635                 640

Gly Leu Leu Leu Cys Ser Ile Ile Phe Ala Val Ala Ala Ile Ile Lys
                645                 650                 655

Ala Arg Ser Leu Lys Lys Ala Ser Glu Ser Arg Ala Trp Lys Leu Thr
            660                 665                 670

Ala Phe Gln Arg Leu Asp Phe Thr Val Asp Asp Val Leu Asp Ser Leu
        675                 680                 685

Lys Glu Asp Asn Ile Ile Gly Lys Gly Gly Ala Gly Ile Val Tyr Lys
    690                 695                 700

Gly Ala Met Pro Asn Gly Asp Asn Val Ala Val Lys Arg Leu Pro Ala
705                 710                 715                 720

Met Ser Arg Gly Ser Ser His Asp His Gly Phe Asn Ala Glu Ile Gln
                725                 730                 735

Thr Leu Gly Arg Ile Arg His Arg His Ile Val Arg Leu Leu Gly Phe
            740                 745                 750

Cys Ser Asn His Glu Thr Asn Leu Leu Val Tyr Glu Tyr Met Pro Asn
        755                 760                 765

Gly Ser Leu Gly Glu Val Leu His Gly Lys Lys Gly Gly His Leu His
    770                 775                 780

Trp Asp Thr Arg Tyr Lys Ile Ala Ile Glu Ala Ala Lys Gly Leu Cys
785                 790                 795                 800

Tyr Leu His His Asp Cys Ser Pro Leu Ile Val His Arg Asp Val Lys
                805                 810                 815

Ser Asn Asn Ile Leu Leu Asp Ser Asn Phe Glu Ala His Val Ala Asp
            820                 825                 830
```

-continued

Phe Gly Leu Ala Lys Phe Leu Gln Asp Ser Gly Thr Ser Glu Cys Met
        835                 840                 845

Ser Ala Ile Ala Gly Ser Tyr Gly Tyr Ile Ala Pro Glu Tyr Ala Tyr
    850                 855                 860

Thr Leu Lys Val Asp Glu Lys Ser Asp Val Tyr Ser Phe Gly Val Val
865                 870                 875                 880

Leu Leu Glu Leu Val Ser Gly Arg Lys Pro Val Gly Glu Phe Gly Asp
                885                 890                 895

Gly Val Asp Ile Val Gln Trp Val Arg Lys Met Thr Asp Ser Asn Lys
            900                 905                 910

Glu Gly Val Leu Lys Ile Leu Asp Pro Arg Leu Pro Ser Val Pro Leu
        915                 920                 925

His Glu Val Met His Val Phe Tyr Val Ala Met Leu Cys Val Glu Glu
    930                 935                 940

Gln Ala Val Glu Arg Pro Thr Met Arg Glu Val Val Gln Ile Leu Thr
945                 950                 955                 960

Glu Leu Pro Lys Ala Pro Gly Ser Lys Gln Gly Gly Gly Asp Ser Ala
                965                 970                 975

Ile Thr Glu Ser Phe Pro Pro Ser Gly Thr Ser Ala Ser Glu Ser Pro
            980                 985                 990

Thr Thr Thr Ser Asn Thr Lys Asp  His Gln Gln Gln Ala  Pro Pro Gln
        995                 1000                1005

Ser Pro  Pro Pro Asp Leu Leu  Ser Ile
    1010                1015

<210> SEQ ID NO 42
<211> LENGTH: 56
<212> TYPE: PRT
<213> ORGANISM: Prunus persica

<400> SEQUENCE: 42

Met Arg Ile Leu Asn Tyr Leu Asn Leu Ser Arg Asn His Leu Val Gly
1               5                   10                  15

Ser Ile Pro Ser Ser Ile Ser Thr Met Gln Ser Leu Thr Ser Val Asp
            20                  25                  30

Phe Ser Tyr Asn Asn Leu Ser Gly Leu Val Pro Gly Thr Gly Gln Phe
        35                  40                  45

Ser Tyr Phe Asn Tyr Thr Ser Phe
    50                  55

<210> SEQ ID NO 43
<211> LENGTH: 1010
<212> TYPE: PRT
<213> ORGANISM: Citrus sinensis

<400> SEQUENCE: 43

Met Arg Leu Leu Leu Leu Leu Leu Leu Leu Leu Leu His Ile Ser Gln
1               5                   10                  15

Ser Arg Thr Val Pro Glu Tyr Lys Ala Leu Leu Ser Ile Lys Ser Ser
            20                  25                  30

Ile Thr Asp Asp Pro Gln Ser Ser Leu Ala Ala Trp Asn Ala Thr Thr
        35                  40                  45

Ser His Cys Thr Trp Pro Gly Val Thr Cys Asp Ser Arg Arg His Val
    50                  55                  60

Thr Ser Leu Asp Leu Ser Gly Leu Asn Leu Ser Gly Ala Leu Ser Pro
65                  70                  75                  80

-continued

```
Asp Val Ala His Leu Arg Phe Leu Gln Asn Leu Ser Val Ala Ala Asn
                85                  90                  95

Gln Leu Ser Gly Pro Ile Pro Pro Glu Ile Ser Ala Leu Ser Ser Leu
            100                 105                 110

Arg Leu Leu Asn Leu Ser Asn Asn Val Phe Asn Gly Ser Phe Pro Pro
        115                 120                 125

Gln Leu Ser Gln Leu Ala Ser Leu Gln Val Leu Asp Leu Tyr Asn Asn
    130                 135                 140

Asn Met Thr Gly Asp Leu Pro Leu Ala Val Thr Gln Leu Arg Asn Leu
145                 150                 155                 160

Arg His Leu His Leu Gly Gly Asn Phe Phe Ser Gly Gln Ile Pro Pro
                165                 170                 175

Glu Tyr Gly Ile Trp Glu Phe Leu Glu Tyr Leu Ala Val Ser Gly Asn
            180                 185                 190

Glu Leu Gly Gly Lys Ile Pro Gly Glu Ile Gly Asn Leu Thr Lys Leu
        195                 200                 205

Gln Gln Leu Tyr Ile Gly Tyr Tyr Asn Ser Tyr Thr Gly Gly Leu Pro
    210                 215                 220

Pro Glu Ile Gly Asn Leu Ser Ser Leu Val Arg Phe Asp Ala Ala Asn
225                 230                 235                 240

Cys Gly Leu Ser Gly Glu Ile Pro Thr Asp Ile Gly Arg Leu Gln Asn
                245                 250                 255

Leu Asp Thr Leu Phe Leu Gln Val Asn Ala Leu Ser Gly Pro Leu Thr
            260                 265                 270

Thr Glu Leu Gly Tyr Leu Lys Ser Leu Lys Ser Met Asp Leu Ser Asn
        275                 280                 285

Asn Ile Phe Thr Gly Glu Ile Pro Ala Ser Phe Ala Glu Leu Lys Asn
    290                 295                 300

Leu Thr Leu Leu Asn Leu Phe Arg Asn Lys Leu His Gly Ala Ile Pro
305                 310                 315                 320

Glu Phe Ile Gly Val Met Pro Arg Leu Glu Val Leu Gln Leu Trp Glu
                325                 330                 335

Asn Asn Phe Thr Gly Ser Ile Pro Gln Arg Leu Gly Ser Asn Gly Lys
            340                 345                 350

Leu Arg Ile Leu Asp Leu Ser Ser Asn Lys Leu Thr Gly Thr Leu Pro
        355                 360                 365

Pro Asp Met Cys Ala Gly Asn Cys Leu Gln Thr Leu Ile Thr Leu Gly
    370                 375                 380

Asn Phe Leu Phe Gly Pro Ile Pro Glu Ser Leu Gly Lys Cys Asp Ser
385                 390                 395                 400

Leu Ser Arg Met Arg Met Gly Glu Asn Phe Leu Asn Gly Ser Ile Pro
                405                 410                 415

Lys Gly Leu Phe Gly Leu Pro Ser Leu Ser Gln Val Glu Leu Gln Asp
            420                 425                 430

Asn Tyr Leu Thr Gly Gln Phe Pro Val Ser Asp Ser Ile Ser Val Asn
        435                 440                 445

Leu Gly Gln Ile Cys Leu Ser Asn Asn Gln Leu Ser Gly Ser Leu Pro
    450                 455                 460

Ala Ser Ile Gly Lys Phe Ser Gly Val Gln Lys Leu Leu Leu Asp Gly
465                 470                 475                 480

Asn Lys Phe Ser Gly Gln Ile Pro Ala Glu Ile Gly Lys Leu Gln Gln
                485                 490                 495

Leu Ser Lys Met Asp Phe Ser His Asn Lys Phe Ser Gly Arg Ile Ala
```

-continued

```
            500                 505                 510

Pro Glu Ile Ser Gln Cys Lys Leu Leu Thr Phe Val Asp Leu Ser Arg
        515                 520                 525

Asn Glu Leu Ser Gly Glu Ile Pro Asn Gln Leu Thr Gly Met Arg Ile
    530                 535                 540

Leu Asn Tyr Leu Asn Leu Ser Arg Asn His Leu Val Gly Ser Ile Pro
545                 550                 555                 560

Ala Ser Ile Ala Ser Met Gln Ser Leu Thr Ser Val Asp Phe Ser Tyr
                565                 570                 575

Asn Asn Leu Ser Gly Leu Val Pro Gly Thr Gly Gln Phe Ser Tyr Phe
            580                 585                 590

Asn Tyr Thr Ser Phe Leu Gly Asn Ser Glu Leu Cys Gly Pro Tyr Leu
        595                 600                 605

Gly Pro Cys Lys Asp Gly Val Ala Asn Gly Thr His Gln Pro His Val
    610                 615                 620

Lys Gly Pro Leu Ser Ala Ser Val Lys Leu Leu Leu Val Val Gly Leu
625                 630                 635                 640

Leu Val Cys Ser Ile Ala Phe Ala Val Ala Ala Ile Ile Lys Ala Arg
                645                 650                 655

Ser Leu Lys Lys Ala Ser Glu Ser Arg Ala Trp Lys Leu Thr Ala Phe
            660                 665                 670

Gln Arg Leu Asp Phe Thr Cys Asp Asp Val Leu Asp Cys Leu Lys Glu
        675                 680                 685

Asp Asn Ile Ile Gly Lys Gly Gly Ala Gly Ile Val Tyr Lys Gly Leu
    690                 695                 700

Met Pro Asn Gly Asp Gln Val Ala Val Lys Arg Leu Pro Ala Met Ser
705                 710                 715                 720

Arg Gly Ser Ser His Asp His Gly Phe Asn Ala Glu Ile Gln Thr Leu
                725                 730                 735

Gly Arg Ile Arg His Arg His Ile Val Arg Leu Leu Gly Phe Cys Ser
            740                 745                 750

Asn His Glu Thr Asn Leu Leu Val Tyr Glu Tyr Met Pro Asn Gly Ser
        755                 760                 765

Leu Gly Glu Val Leu His Gly Lys Lys Gly Gly His Leu His Trp Asp
    770                 775                 780

Thr Arg Tyr Lys Ile Ala Val Glu Ala Ala Lys Gly Leu Cys Tyr Leu
785                 790                 795                 800

His His Asp Cys Ser Pro Leu Ile Val His Arg Asp Val Lys Ser Asn
                805                 810                 815

Asn Ile Leu Leu Asp Ser Gly Phe Glu Ala His Val Ala Asp Phe Gly
            820                 825                 830

Leu Ala Lys Phe Leu Gln Asp Ser Gly Thr Ser Glu Cys Met Ser Ala
        835                 840                 845

Ile Ala Gly Ser Tyr Gly Tyr Ile Ala Pro Glu Tyr Ala Tyr Thr Leu
    850                 855                 860

Lys Val Asp Glu Lys Ser Asp Val Tyr Ser Phe Gly Val Val Leu Leu
865                 870                 875                 880

Glu Leu Ile Thr Gly Arg Lys Pro Val Gly Glu Phe Gly Asp Gly Val
                885                 890                 895

Asp Ile Val Gln Trp Val Arg Lys Met Thr Asp Ser Lys Lys Glu Gly
            900                 905                 910

Val Leu Lys Ile Leu Asp Pro Arg Leu Pro Ser Val Pro Leu His Glu
        915                 920                 925
```

```
Val Met His Val Phe Tyr Val Ala Met Leu Cys Val Glu Glu Gln Ala
    930                 935                 940

Val Glu Arg Pro Thr Met Arg Glu Val Val Gln Ile Leu Thr Glu Leu
945                 950                 955                 960

Pro Lys Pro Pro Thr Ser Lys Gln Gly Glu Glu Ser Leu Pro Pro Ser
                965                 970                 975

Gly Thr Thr Ser Leu Asp Ser Pro Asn Ala Ser Asn Lys Asp Gln Lys
            980                 985                 990

Asp His Gln Arg Pro Ala Pro Pro  Gln Ser Pro Pro Pro  Asp Leu Leu
        995                 1000                1005

Ser Ile
    1010


<210> SEQ ID NO 44
<211> LENGTH: 56
<212> TYPE: PRT
<213> ORGANISM: Citrus sinensis

<400> SEQUENCE: 44

Met Arg Ile Leu Asn Tyr Leu Asn Leu Ser Arg Asn His Leu Val Gly
1               5                   10                  15

Ser Ile Pro Ala Ser Ile Ala Ser Met Gln Ser Leu Thr Ser Val Asp
            20                  25                  30

Phe Ser Tyr Asn Asn Leu Ser Gly Leu Val Pro Gly Thr Gly Gln Phe
        35                  40                  45

Ser Tyr Phe Asn Tyr Thr Ser Phe
    50                  55


<210> SEQ ID NO 45
<211> LENGTH: 995
<212> TYPE: PRT
<213> ORGANISM: Citrus sinensis

<400> SEQUENCE: 45

Met Ala Phe Phe Ile Val Val Thr Leu Leu Phe Ser Leu Leu Asn Ile
1               5                   10                  15

Pro Asn Leu Ser Ser Ala Ala Ser Leu Val Asn Asp Phe His Val Leu
            20                  25                  30

Val Ala Leu Lys Gln Gly Phe Glu Asn Pro Glu Pro Ala Leu Ile Ser
        35                  40                  45

Trp Asn Ser Ser Asn Pro Ser Ser Val Cys Ser Trp Ala Gly Ile Cys
    50                  55                  60

Cys Ser Arg Asp Arg Val Ala Ser Leu Asp Leu Thr Asp Leu Asn Leu
65                  70                  75                  80

Cys Gly Ser Val Pro Ala Gln Ile Leu Arg Leu Asp Lys Leu Thr Asn
                85                  90                  95

Leu Ser Leu Ala Gly Asn Asn Phe Thr Gly Ser Ile Glu Ile Gly Asn
            100                 105                 110

Leu Ser Ser Leu Gln Phe Leu Asn Ile Ser Asn Asn Gln Phe Ser Gly
        115                 120                 125

Gly Leu Asp Trp Asn Tyr Ser Ser Leu Val Asn Leu Glu Val Phe Asp
    130                 135                 140

Ala Tyr Asn Asn Asn Phe Thr Ala Leu Leu Pro Val Gly Ile Leu Lys
145                 150                 155                 160

Leu Glu Lys Leu Lys Tyr Leu Asp Leu Gly Gly Asn Tyr Phe Phe Gly
                165                 170                 175
```

```
Lys Ile Pro Asn Ser Tyr Gly Glu Leu Gln Gly Leu Glu Tyr Leu Ser
            180                 185                 190

Leu Ala Gly Asn Asp Leu Thr Gly Lys Ile Pro Gly Glu Leu Gly Asn
        195                 200                 205

Leu Thr Asn Leu Arg Glu Ile Tyr Leu Gly Tyr Tyr Asn Val Phe Glu
    210                 215                 220

Gly Gly Ile Pro Arg Glu Val Gly Lys Leu Val Asn Leu Val His Leu
225                 230                 235                 240

Asp Leu Ser Ser Cys Glu Leu Asp Gly Gln Ile Pro His Glu Ile Gly
                245                 250                 255

Asn Leu Lys Leu Leu Asp Thr Val Phe Leu His Ile Asn Leu Leu Ser
            260                 265                 270

Gly Ser Ile Pro Lys Gln Leu Gly Asn Leu Thr Asn Leu Val Asn Leu
        275                 280                 285

Asp Leu Ser Asn Asn Ala Leu Thr Gly Glu Ile Pro Tyr Ser Phe Ile
    290                 295                 300

Asn Leu Arg Gln Leu Lys Leu Phe Asn Leu Phe Met Asn Arg Leu His
305                 310                 315                 320

Gly Ser Ile Pro Asp Tyr Leu Ala Asp Leu Pro Asn Leu Glu Thr Leu
                325                 330                 335

Gly Leu Trp Gln Asn Asn Phe Thr Gly Val Ile Pro Glu Asn Leu Gly
            340                 345                 350

Gln Asn Gly Lys Leu Gln Val Leu Asp Leu Ser Ser Asn Lys Leu Thr
        355                 360                 365

Gly Thr Ile Pro Thr Asp Leu Cys Ser Ser Asn Gln Leu Arg Ile Leu
    370                 375                 380

Ile Leu Leu Lys Asn Phe Leu Phe Gly Pro Ile Pro Glu Arg Leu Gly
385                 390                 395                 400

Ala Cys Tyr Ser Leu Thr Arg Val Arg Leu Gly Gln Asn Tyr Leu Asn
                405                 410                 415

Gly Ser Ile Pro Asp Gly Phe Ile Tyr Leu Pro Gly Leu Asn Leu Ala
            420                 425                 430

Glu Leu Gln Ser Asn Tyr Leu Ser Gly Ser Leu Pro Glu Asn Gly Asn
        435                 440                 445

Ser Ser Ser Asn Pro Asp Arg Leu Gly Gln Leu Asn Leu Ser Asn Asn
    450                 455                 460

Leu Leu Ser Gly Pro Leu Pro Phe Ser Leu Ser Asn Phe Ser Ser Leu
465                 470                 475                 480

Gln Ile Leu Leu Leu Ser Gly Asn Gln Phe Ser Gly Pro Ile Pro Pro
                485                 490                 495

Ser Ile Gly Glu Leu Arg Gln Val Leu Lys Leu Asp Leu Ser Arg Asn
            500                 505                 510

Ser Leu Ser Gly Glu Ile Pro Pro Ala Ile Gly Tyr Cys Asn His Leu
        515                 520                 525

Thr Tyr Leu Asp Met Ser Gln Asn Asn Leu Ser Gly Ser Ile Pro Pro
    530                 535                 540

Glu Ile Ser Asn Val Arg Ile Leu Asn Tyr Leu Asn Leu Ser Arg Asn
545                 550                 555                 560

His Leu Asn Gln Asn Ile Pro Lys Ser Ile Gly Ser Met Lys Ser Leu
                565                 570                 575

Thr Ile Ala Asp Phe Ser Phe Asn Asp Phe Ser Gly Lys Leu Pro Glu
            580                 585                 590
```

-continued

```
Ser Gly Gln Phe Thr Val Phe Asn Ala Ser Ser Phe Ala Gly Asn Pro
        595                 600                 605

Gln Leu Cys Gly Thr Leu Leu Asn Asn Pro Cys Asn Val Ala Pro Ile
    610                 615                 620

Thr His Gln Pro Gly Lys Ala Pro Gly Asp Phe Lys Leu Ile Phe Ala
625                 630                 635                 640

Leu Gly Leu Leu Ile Cys Ser Leu Ile Phe Ala Thr Ala Ala Ile Ile
                645                 650                 655

Lys Ala Lys Ser Phe Lys Lys Thr Gly Ser Asp Ser Trp Lys Met Thr
            660                 665                 670

Ala Phe Gln Lys Leu Glu Phe Ser Val Ser Asp Ile Leu Glu Cys Val
        675                 680                 685

Lys Asp Gly Asn Val Ile Gly Arg Gly Gly Ala Gly Ile Val Tyr His
    690                 695                 700

Gly Lys Met Pro Asn Gly Val Glu Ile Ala Val Lys Lys Leu Leu Gly
705                 710                 715                 720

Phe Gly Thr His Ser His Asp His Gly Phe Arg Ala Glu Ile Gln Thr
                725                 730                 735

Leu Gly Asn Ile Arg His Arg Asn Ile Val Arg Leu Leu Ala Phe Cys
            740                 745                 750

Ser Asn Lys Glu Thr Asn Leu Leu Val Tyr Glu Tyr Met Arg Asn Gly
        755                 760                 765

Ser Leu Gly Glu Ala Leu His Gly Lys Lys Gly Ala Phe Leu Gly Trp
    770                 775                 780

Asn Leu Arg Tyr Lys Ile Ala Ile Glu Ala Ala Lys Gly Leu Cys Tyr
785                 790                 795                 800

Leu His His Asp Cys Ser Pro Leu Ile Val His Arg Asp Val Lys Ser
                805                 810                 815

Asn Asn Ile Leu Leu Asn Ser Ala Phe Glu Ala His Val Ala Asp Phe
            820                 825                 830

Gly Leu Ala Lys Phe Leu Ile Asp Gly Gly Ala Ser Glu Cys Met Ser
        835                 840                 845

Ala Ile Ala Gly Ser Tyr Gly Tyr Ile Ala Pro Glu Tyr Ala Tyr Thr
    850                 855                 860

Leu Arg Val Asp Glu Lys Ser Asp Val Tyr Ser Phe Gly Val Val Leu
865                 870                 875                 880

Leu Glu Leu Leu Thr Gly Arg Arg Pro Val Gly Asp Phe Gly Asp Gly
                885                 890                 895

Val Asp Ile Val Gln Trp Ser Lys Arg Ala Thr Asn Gly Arg Lys Glu
            900                 905                 910

Glu Phe Leu Ser Ile Leu Asp Pro Arg Leu Ser Met Val Pro Lys Glu
        915                 920                 925

Glu Ala Met His Leu Leu Phe Val Ala Met Leu Cys Ile Gln Glu Asn
    930                 935                 940

Ser Ile Glu Arg Pro Arg Met Arg Glu Val Val Gln Met Leu Ser Glu
945                 950                 955                 960

Phe Pro Arg His Ser Ser Asp Phe Asn Gln Ser Ser Ser Ser Ser Leu
                965                 970                 975

Lys Asn Leu Glu Lys Asp Pro Lys Gly Cys Pro Asn Asn Lys Leu Lys
            980                 985                 990

Gln Asp Leu
        995
```

<210> SEQ ID NO 46
<211> LENGTH: 55
<212> TYPE: PRT
<213> ORGANISM: Citrus sinensis

<400> SEQUENCE: 46

```
Arg Ile Leu Asn Tyr Leu Asn Leu Ser Arg Asn His Leu Asn Gln Asn
1               5                   10                  15

Ile Pro Lys Ser Ile Gly Ser Met Lys Ser Leu Thr Ile Ala Asp Phe
            20                  25                  30

Ser Phe Asn Asp Phe Ser Gly Lys Leu Pro Glu Ser Gly Gln Phe Thr
        35                  40                  45

Val Phe Asn Ala Ser Ser Phe
    50                  55
```

<210> SEQ ID NO 47
<211> LENGTH: 982
<212> TYPE: PRT
<213> ORGANISM: Citrus sinensis

<400> SEQUENCE: 47

```
Met Arg Ala Thr Ala Ser Phe Asn Pro His Leu Tyr Ile Ser Leu Phe
1               5                   10                  15

Leu Leu Leu Phe Ser Leu Ser Cys Ala Tyr Ser Asp Met Asp Val Leu
            20                  25                  30

Leu Lys Leu Lys Ser Ser Met Ile Gly Pro Lys Gly Ser Gly Leu Lys
        35                  40                  45

Asn Trp Glu Pro Ser Ser Ser Pro Ser Ala His Cys Ser Phe Ser Gly
    50                  55                  60

Val Thr Cys Asp Gln Asp Ser Arg Val Val Ser Leu Asn Val Ser Phe
65                  70                  75                  80

Met Pro Leu Phe Gly Ser Ile Pro Pro Glu Ile Gly Leu Leu Thr Lys
                85                  90                  95

Leu Val Asn Leu Thr Ile Ser Asn Val Asn Leu Thr Gly Arg Leu Pro
            100                 105                 110

Ser Glu Met Ala Leu Leu Thr Ser Leu Lys Val Phe Asn Ile Ser Gly
        115                 120                 125

Asn Val Phe Gln Gly Asn Phe Ala Gly Gln Ile Val Arg Gly Met Thr
    130                 135                 140

Glu Leu Gln Val Leu Asp Ala Tyr Asn Asn Asn Phe Thr Gly Pro Leu
145                 150                 155                 160

Pro Val Glu Ile Ala Ser Leu Lys Ser Leu Arg His Leu Ser Phe Gly
                165                 170                 175

Gly Asn Tyr Phe Thr Gly Lys Ile Pro Gln Ser Tyr Ser Glu Ile Gln
            180                 185                 190

Ser Leu Glu Tyr Ile Gly Leu Asn Gly Ile Gly Leu Asn Gly Thr Val
        195                 200                 205

Pro Ala Phe Leu Ser Arg Leu Lys Asn Leu Arg Glu Met Tyr Ile Gly
    210                 215                 220

Tyr Phe Asn Thr Tyr Thr Gly Gly Ile Pro Pro Gly Phe Gly Ala Leu
225                 230                 235                 240

Thr Gln Leu Gln Val Leu Asp Met Ala Ser Cys Asn Ile Ser Gly Glu
                245                 250                 255

Ile Pro Thr Ser Leu Ser Arg Leu Lys Leu Leu His Ser Leu Phe Leu
            260                 265                 270

Gln Met Asn Lys Leu Thr Gly His Ile Pro Pro Gln Leu Ser Gly Leu
```

-continued

```
        275                 280                 285

Ile Ser Leu Lys Ser Leu Asp Leu Ser Leu Asn Tyr Leu Thr Gly Glu
    290                 295                 300

Ile Pro Glu Ser Phe Ala Ala Leu Lys Asn Leu Thr Leu Leu Gln Leu
305                 310                 315                 320

Phe Lys Asn Asn Leu Arg Gly Pro Ile Pro Ser Phe Leu Gly Asp Phe
                325                 330                 335

Pro Asn Leu Glu Val Leu Gln Val Trp Gly Asn Asn Phe Thr Phe Glu
            340                 345                 350

Leu Pro Glu Asn Leu Gly Arg Asn Gly Lys Leu Leu Ile Leu Asp Val
        355                 360                 365

Thr Ser Asn His Leu Thr Gly Thr Ile Pro Arg Asp Leu Cys Lys Gly
    370                 375                 380

Gly Lys Leu Lys Ser Leu Ile Leu Met Gln Asn Phe Phe Ile Gly Pro
385                 390                 395                 400

Ile Pro Glu Glu Leu Gly Gln Cys Lys Ser Leu Thr Lys Ile Arg Phe
                405                 410                 415

Ser Lys Asn Tyr Leu Asn Gly Thr Ile Pro Ala Gly Leu Phe Asn Leu
            420                 425                 430

Pro Leu Leu Asn Met Met Glu Leu Asp Asp Asn Leu Leu Ser Gly Glu
        435                 440                 445

Leu Pro Glu Lys Met Ser Gly Ala Ser Leu Asn Gln Leu Lys Val Ala
    450                 455                 460

Asn Asn Asn Ile Thr Gly Lys Ile Pro Ala Ala Ile Gly Asn Leu Pro
465                 470                 475                 480

Ser Leu Asn Ile Leu Ser Leu Gln Asn Asn Arg Leu Glu Gly Glu Ile
                485                 490                 495

Pro Val Glu Ser Phe Asn Leu Lys Met Ile Thr Ser Ile Asn Ile Ser
            500                 505                 510

Asp Asn Asn Ile Ser Gly Glu Ile Pro Tyr Ser Ile Ser Gln Cys His
        515                 520                 525

Ser Leu Thr Ser Val Asp Leu Ser Arg Asn Ser Leu Tyr Gly Lys Ile
    530                 535                 540

Pro Pro Gly Ile Ser Lys Leu Ile Asp Leu Ser Ile Leu Asn Leu Ser
545                 550                 555                 560

Arg Asn Gly Ile Thr Gly Ser Ile Pro Asn Glu Met Arg Asn Met Met
                565                 570                 575

Ser Leu Thr Thr Leu Asp Leu Ser Tyr Asn Asn Leu Ile Gly Asn Ile
            580                 585                 590

Pro Ser Gly Gly Gln Phe Leu Ala Phe Asn Glu Thr Ser Phe Ile Gly
        595                 600                 605

Asn Pro Asn Leu Cys Leu Leu Arg Asn Gly Thr Cys Gln Ser Leu Ile
    610                 615                 620

Asn Ser Ala Lys His Ser Gly Asp Gly Tyr Gly Ser Ser Phe Gly Ala
625                 630                 635                 640

Ser Lys Ile Val Ile Thr Val Ile Ala Leu Leu Thr Phe Met Leu Leu
                645                 650                 655

Val Ile Leu Thr Ile Tyr Gln Leu Arg Lys Arg Arg Leu Gln Lys Ser
            660                 665                 670

Lys Ala Trp Lys Leu Thr Ala Phe Gln Arg Leu Asp Phe Lys Ala Glu
        675                 680                 685

Asp Val Leu Glu Ser Leu Lys Asp Glu Asn Ile Ile Gly Lys Gly Gly
    690                 695                 700
```

Ala Gly Ile Val Tyr Arg Gly Ser Met Pro Asp Gly Ile Asp Val Ala
705 710 715 720

Ile Lys Arg Leu Val Gly Arg Gly Thr Gly Gly Asn Asp His Gly Phe
725 730 735

Leu Ala Glu Ile Gln Thr Leu Gly Arg Ile Arg His Arg Asn Ile Val
740 745 750

Arg Leu Leu Gly Tyr Val Ser Asn Arg Asp Thr Asn Leu Leu Leu Tyr
755 760 765

Glu Tyr Met Pro Asn Gly Ser Leu Gly Glu Met Leu His Gly Ala Lys
770 775 780

Gly Gly His Leu Lys Trp Glu Thr Arg Tyr Arg Ile Ala Leu Glu Ala
785 790 795 800

Ala Lys Gly Leu Cys Tyr Leu His His Asp Cys Ser Pro Leu Ile Ile
805 810 815

His Arg Asp Val Lys Ser Asn Asn Ile Leu Leu Asp Ser Asp Phe Glu
820 825 830

Ala His Val Ala Asp Phe Gly Leu Ala Lys Phe Leu Gln Asp Ala Gly
835 840 845

Ala Ser Glu Cys Met Ser Ser Val Ala Gly Ser Tyr Gly Tyr Ile Ala
850 855 860

Pro Glu Tyr Ala Tyr Thr Leu Lys Val Asp Glu Lys Ser Asp Val Tyr
865 870 875 880

Ser Phe Gly Val Val Leu Leu Glu Leu Ile Ala Gly Lys Lys Pro Val
885 890 895

Gly Glu Phe Gly Asp Gly Val Asp Ile Val Arg Trp Val Arg Lys Thr
900 905 910

Thr Ser Glu Val Ser Gln Pro Ser Asp Ala Ala Ser Val Leu Ala Val
915 920 925

Val Asp Pro Arg Leu Ser Gly Tyr Pro Leu Thr Gly Val Ile His Leu
930 935 940

Phe Lys Val Ala Met Met Cys Val Glu Asp Glu Ser Ser Ala Arg Pro
945 950 955 960

Thr Met Arg Glu Val Val His Met Leu Ala Asn Pro Pro Gln Ser Ala
965 970 975

Pro Ser Leu Ile Thr Leu
980

<210> SEQ ID NO 48
<211> LENGTH: 56
<212> TYPE: PRT
<213> ORGANISM: Citrus sinensis

<400> SEQUENCE: 48

Leu Ile Asp Leu Ser Ile Leu Asn Leu Ser Arg Asn Gly Ile Thr Gly
1 5 10 15

Ser Ile Pro Asn Glu Met Arg Asn Met Met Ser Leu Thr Thr Leu Asp
20 25 30

Leu Ser Tyr Asn Asn Leu Ile Gly Asn Ile Pro Ser Gly Gly Gln Phe
35 40 45

Leu Ala Phe Asn Glu Thr Ser Phe
50 55

<210> SEQ ID NO 49
<211> LENGTH: 997
<212> TYPE: PRT

<213> ORGANISM: Ananas comosus

<400> SEQUENCE: 49

Met Ala Pro Pro Pro Pro Asn Val Val Ala Thr Phe Leu Met Trp Leu
1 5 10 15

Phe Ile Phe Leu Leu Ser Ser Phe Leu Ser Cys Ser His Ser Thr Asn
20 25 30

Pro Pro Gln Leu Ser Leu Arg Lys Gln Ala Ser Ile Leu Val Ser Val
35 40 45

Lys Gln Ser Leu Tyr Ser Ser Ser Ser Ile Leu Gln Thr Trp Asn Val
50 55 60

Ser Asn His Ala Ser Leu Cys Ser Ser Trp Phe Gly Val Arg Cys Asp
65 70 75 80

Asp Asp Gly Lys Phe Val Ile Gly Leu Asp Ile Ala Asn Ser Asn Ile
85 90 95

Ser Gly Ser Leu Ser Ala Ser Val Ser Glu Leu Lys Thr Leu Thr Ser
100 105 110

Leu Ser Val Ala Gly Asn Gly Leu Ser Gly Glu Leu Pro Arg Ala Val
115 120 125

Gly Ala Leu Arg Arg Leu Arg His Leu Asn Ile Ser Asn Asn Gln Phe
130 135 140

Asn Gly Ser Met Asn Glu Trp Asn Leu Thr Gly Leu Ser Ala Ile Glu
145 150 155 160

Val Phe Asp Ala Tyr Asn Asn Asp Phe Ser Gly Pro Leu Pro Val Gly
165 170 175

Phe Ala Asp Val Pro Ser Leu Arg His Leu Asp Leu Gly Gly Asn Tyr
180 185 190

Phe Ser Gly Ala Ile Pro Ala Glu Phe Gly Asn Phe Lys Thr Leu Gln
195 200 205

Tyr Leu Ser Leu Ala Gly Asn Asp Leu Ser Gly Arg Ile Pro Ala Glu
210 215 220

Ile Gly Asn Val Thr Thr Leu Glu Gln Leu Tyr Leu Gly Tyr Tyr Asn
225 230 235 240

Lys Phe Ser Gly Gly Val Pro Lys Glu Ile Gly Lys Leu Ile Asn Leu
245 250 255

Val His Leu Asp Leu Ser Ser Cys Gly Met Asp Gly Glu Ile Pro Arg
260 265 270

Glu Leu Gly Asn Leu Lys Lys Leu Asp Thr Leu Tyr Leu Gln Thr Asn
275 280 285

Gln Leu Ser Gly Ala Ile Pro Arg Ser Leu Gly Asn Leu Ser Ser Leu
290 295 300

Gln Phe Leu Asp Met Ser Asn Asn Ala Leu Ser Gly Glu Ile Pro Arg
305 310 315 320

Glu Leu Ser Gln Leu Arg Glu Leu Val Leu Leu His Met Phe Ile Asn
325 330 335

Gln Leu Arg Gly Glu Ile Pro Glu Phe Val Ala Glu Leu Pro Asn Leu
340 345 350

Gln Val Leu Lys Leu Trp Gln Asn Asn Phe Thr Ser Glu Ile Pro Pro
355 360 365

Ala Leu Gly Gly Asn Gly Lys Leu Arg Glu Val Asp Leu Ser Thr Asn
370 375 380

Lys Leu Thr Gly Tyr Ile Pro Lys Thr Ile Cys Gln Gly Arg Arg Leu
385 390 395 400

-continued

```
Glu Lys Leu Ile Leu Leu Asn Asn Phe Leu Phe Gly Pro Leu Pro Glu
                405                 410                 415

Asp Leu Gly Asp Cys Pro Thr Leu Ser Arg Val Arg Leu Gly Gln Asn
            420                 425                 430

Tyr Leu Thr Gly Pro Ile Pro Arg Gly Phe Leu Tyr Leu Pro Glu Met
        435                 440                 445

Cys Leu Leu Glu Leu Gln Asn Asn Tyr Leu Thr Gly Ser Ile Glu Asn
    450                 455                 460

Glu Pro Ala Lys Arg Pro Ser Lys Leu Ala Gln Leu Asn Leu Ser Asn
465                 470                 475                 480

Asn Arg Leu Ser Gly Pro Leu Pro Pro Ser Val Gly Asn Phe Ser Ala
                485                 490                 495

Leu Gln Ile Leu Leu Leu Ser Gly Asn Gln Phe Thr Gly Lys Ile Pro
            500                 505                 510

Ser Gln Leu Gly Arg Leu Lys Ser Leu Leu Lys Ile Asp Met Ser Arg
        515                 520                 525

Asn Asn Phe Ser Gly Val Ile Pro Gln Glu Ile Gly Asp Cys Ser Leu
    530                 535                 540

Leu Thr Tyr Leu Asp Leu Ser Arg Asn Gln Leu Gly Gly Leu Val Pro
545                 550                 555                 560

Pro Arg Val Ser His Ile Arg Val Leu Asn Tyr Leu Asn Ile Ser Trp
                565                 570                 575

Asn Asn Leu Asn Gly Ser Ile Pro Lys Glu Val Gly Ser Met Arg Ser
            580                 585                 590

Leu Thr Cys Ala Asp Phe Ser His Asn Asp Phe Ser Gly Arg Val Pro
        595                 600                 605

Gln Asn Gly Gln Phe Thr Phe Phe Asn Ser Ser Ser Phe Leu Ala Asn
    610                 615                 620

Pro Leu Leu Cys Gly Phe Ala Ser Asn Pro Cys Asn Phe Ser Ser Thr
625                 630                 635                 640

Asp Ser Pro Ser Arg Ser Asp Glu His Arg Arg Val Lys Ser Gln Val
                645                 650                 655

Pro Ala Lys Phe Lys Leu Leu Phe Ala Leu Gly Leu Leu Leu Cys Ser
            660                 665                 670

Met Ile Phe Ala Ala Thr Val Val Val Lys Thr Arg Leu Met Met Arg
        675                 680                 685

Arg Asn Ser Lys Ser Trp Lys Ile Thr Ala Phe Gln Lys Ile Glu Phe
    690                 695                 700

Arg Cys Glu Asp Ile Leu Ser Cys Leu Arg Glu Asp Gln Val Ile Gly
705                 710                 715                 720

Arg Gly Gly Ala Gly Ile Val Tyr Arg Gly Ile Leu Pro Asn Gly Asp
                725                 730                 735

Gln Val Ala Val Lys Arg Leu Leu Gly Ile Gly Lys Gly Ser Ser His
            740                 745                 750

Asp Asn Gly Phe Ser Ala Glu Ile Gln Thr Leu Gly Arg Ile Arg His
        755                 760                 765

Arg Asn Ile Val Arg Leu Leu Ala Met Cys Ser Asn Lys Glu Thr Asn
    770                 775                 780

Leu Leu Val Tyr Glu Tyr Met Met Asn Gly Ser Leu Gly Glu Val Leu
785                 790                 795                 800

His Gly Lys Arg Gly Gly Tyr Leu Asn Trp Gly Ile Arg Leu Arg Ile
                805                 810                 815

Ala Thr Glu Ala Ala Lys Gly Leu Ser Tyr Leu His His Asp Cys Ser
```

820 825 830

Pro Pro Ile Leu His Arg Asp Val Lys Ser Asn Asn Ile Leu Leu Asp
835 840 845

Ala Asp Phe Glu Ala His Val Ala Asp Phe Gly Leu Ala Lys Tyr Leu
850 855 860

Arg Asp Thr Gly Ala Ser Glu Cys Met Ser Ala Ile Ala Gly Ser Tyr
865 870 875 880

Gly Tyr Ile Ala Pro Glu Tyr Ala Tyr Thr Leu Lys Val Asp Glu Lys
885 890 895

Ser Asp Val Tyr Ser Phe Gly Val Val Leu Leu Glu Leu Ile Thr Gly
900 905 910

Arg Arg Pro Val Gly Asp Phe Gly Glu Glu Gly Leu Asp Ile Val Gln
915 920 925

Trp Ala Lys Thr Asn Thr Asn Trp Ser Lys Glu Gly Val Val Asn Ile
930 935 940

Leu Asp Pro Arg Leu Ile Asn Val Pro Leu Glu Glu Ala Met Gln Val
945 950 955 960

Phe Phe Val Gly Met Leu Cys Val Gln Glu His Ser Val Glu Arg Pro
965 970 975

Ala Met Arg Glu Val Val Gln Met Leu Glu Gln Ala Lys Gln Pro Tyr
980 985 990

Gly Val Arg Ala Arg
995

<210> SEQ ID NO 50
<211> LENGTH: 56
<212> TYPE: PRT
<213> ORGANISM: Ananas comosus

<400> SEQUENCE: 50

Ile Arg Val Leu Asn Tyr Leu Asn Ile Ser Trp Asn Asn Leu Asn Gly
1 5 10 15

Ser Ile Pro Lys Glu Val Gly Ser Met Arg Ser Leu Thr Cys Ala Asp
20 25 30

Phe Ser His Asn Asp Phe Ser Gly Arg Val Pro Gln Asn Gly Gln Phe
35 40 45

Thr Phe Phe Asn Ser Ser Ser Phe
50 55

<210> SEQ ID NO 51
<211> LENGTH: 995
<212> TYPE: PRT
<213> ORGANISM: Solanum lycopersicum

<400> SEQUENCE: 51

Met Leu Pro Leu Ile Leu Val Thr Leu Phe Thr Leu Val Gly Thr Ser
1 5 10 15

Leu Ser Ser Ile Ser Thr Asp Val His Ala Leu Leu Ser Leu Lys Gln
20 25 30

Gly Phe Asp Phe Ser Asn Ser Val Leu Ser Ser Trp Asp Val Ser Asn
35 40 45

Pro Ser Ser Val Cys Ser Trp Val Gly Ile Lys Cys Leu Gln Asp Arg
50 55 60

Val Val Ser Ile Asn Leu Ser Asn Met Glu Leu Tyr Gly Ser Val Ser
65 70 75 80

Pro Val Ile Ser Arg Leu Asp Lys Leu Val Glu Leu Ser Ile Asp Gly

```
                85                  90                  95

Asn Asn Phe Thr Gly Glu Ile Lys Ile Glu Asn Met Arg Ser Leu Lys
            100                 105                 110

Ser Leu Asn Ile Ser Asn Asn Met Phe Ser Gly Ser Leu Asp Trp Asn
        115                 120                 125

Tyr Thr Ser Leu Ala Asn Leu Glu Val Leu Asp Ala Tyr Asn Asn Asn
    130                 135                 140

Phe Ser Ser Phe Leu Pro Val Gly Val Val Ser Leu Glu Lys Leu Lys
145                 150                 155                 160

Tyr Leu Asp Leu Gly Gly Asn Tyr Phe Tyr Gly Arg Ile Pro Glu Ser
                165                 170                 175

Tyr Gly Asp Leu Ile Gly Leu Glu Tyr Leu Gln Leu Ala Gly Asn Asp
            180                 185                 190

Leu His Gly Arg Ile Pro Arg Ala Leu Gly Asn Leu Thr Asn Leu Lys
        195                 200                 205

Glu Ile Tyr Leu Gly Tyr Phe Asn Val Phe Val Gly Gly Ile Pro Lys
    210                 215                 220

Glu Phe Gly Lys Leu Glu Asn Leu Val His Met Asp Ile Ser Asn Cys
225                 230                 235                 240

Glu Leu Asp Gly Pro Ile Pro Pro Glu Leu Gly Asn Leu Lys Leu Leu
                245                 250                 255

Asn Thr Leu Phe Leu His Ile Asn Leu Leu Ser Gly Gln Ile Pro Lys
            260                 265                 270

Glu Leu Gly Asn Leu Thr Gly Leu Val Asn Leu Asp Leu Ser Ala Asn
        275                 280                 285

Ala Leu Thr Gly Glu Ile Pro Phe Glu Leu Ile Asn Leu Gln Gln Leu
    290                 295                 300

Ser Leu Phe Asn Leu Phe Met Asn Lys Leu His Gly Ser Ile Pro Asp
305                 310                 315                 320

Phe Ile Ala Asp Tyr Pro Asp Leu Lys Val Leu Gly Leu Trp Met Asn
                325                 330                 335

Asn Phe Thr Gly Ile Ile Pro Gln Lys Leu Gly Gln Asn Glu Lys Leu
            340                 345                 350

Gln Glu Leu Asp Leu Ser Ser Asn Lys Leu Thr Gly Thr Ile Pro Lys
        355                 360                 365

His Leu Cys Ala Ser Lys Gln Leu Arg Ile Leu Ile Leu Leu Lys Asn
    370                 375                 380

Phe Leu Phe Gly Ser Ile Pro Glu Asp Leu Gly Thr Cys Leu Ser Leu
385                 390                 395                 400

Val Arg Leu Arg Leu Gly Gln Asn Tyr Leu Asn Gly Ser Ile Pro Asn
                405                 410                 415

Gly Phe Ile Tyr Met Pro Glu Leu Asn Leu Val Glu Leu His Asn Asn
            420                 425                 430

Tyr Leu Ser Gly Asn Leu Ser Glu Asn Ser Ile Thr Ser Ser Lys Pro
        435                 440                 445

Ala Lys Leu Gly Gln Leu Asn Leu Ser Asn Asn Gln Leu Ser Gly Ser
    450                 455                 460

Leu Pro Phe Ser Leu Ser Asn Phe Ser Ser Leu Gln Ile Leu Ser Leu
465                 470                 475                 480

Gly Gly Asn Gln Phe Ser Gly Pro Ile Pro Thr Ser Ile Gly Gln Leu
                485                 490                 495

Thr Gln Ala Leu Lys Ile Asp Leu Ser His Asn Phe Leu Ser Gly Glu
            500                 505                 510
```

-continued

```
Ile Pro Pro Glu Ile Gly Asn Cys Val His Leu Thr Tyr Leu Asp Leu
        515                 520                 525

Ser Gln Asn Asn Phe Ser Gly Ser Ile Pro Pro Arg Val Ser Glu Ile
    530                 535                 540

Arg Ile Leu Asn Tyr Leu Asn Leu Ser Arg Asn His Leu Asn Glu Thr
545                 550                 555                 560

Ile Pro Lys Ser Ile Gly Thr Met Arg Ser Leu Thr Thr Ala Asp Phe
                565                 570                 575

Ser Phe Asn Asp Leu Ser Gly Lys Leu Pro Glu Ser Gly Gln Phe Ala
            580                 585                 590

Tyr Phe Asn Ala Thr Ser Phe Ala Gly Asn Pro Gln Leu Cys Gly Ser
        595                 600                 605

Leu Leu Asn Asn Pro Cys Asn Phe Thr Leu Ile Thr Asp Pro Pro Gly
    610                 615                 620

Lys Ser His Gly Asp Phe Lys Leu Ile Phe Ala Leu Gly Leu Leu Ile
625                 630                 635                 640

Cys Ser Leu Val Phe Ala Ala Ala Ala Ile Ile Lys Ala Lys Ser Phe
                645                 650                 655

Lys Lys Thr Gly Ala Asp Ser Trp Lys Met Thr Ala Phe Gln Lys Val
            660                 665                 670

Glu Phe Ser Val Ala Asn Val Leu Glu Cys Val Lys Asp Gly Asn Val
        675                 680                 685

Ile Gly Arg Gly Gly Ala Gly Ile Val Tyr His Gly Lys Met Pro Asn
    690                 695                 700

Gly Val Glu Ile Ala Val Lys Lys Leu Leu Gly Phe Gly Asn Asn Ser
705                 710                 715                 720

His Asp His Gly Phe Arg Ala Glu Ile Arg Thr Leu Gly Asn Ile Arg
                725                 730                 735

His Arg Asn Ile Val Arg Leu Val Ala Phe Cys Ser Asn Lys Glu Thr
            740                 745                 750

Asn Leu Leu Val Tyr Glu Tyr Met Arg Asn Gly Ser Leu Gly Glu Ala
        755                 760                 765

Leu His Gly Lys Lys Gly Gly Phe Leu Ser Trp Asn Leu Arg Tyr Lys
    770                 775                 780

Ile Ala Ile Glu Ala Ala Lys Gly Leu Cys Tyr Leu His His Asp Cys
785                 790                 795                 800

Ser Pro Leu Ile Val His Arg Asp Val Lys Ser Asn Asn Ile Leu Leu
                805                 810                 815

Asn Ser Asn Phe Glu Ala His Val Ala Asp Phe Gly Leu Ala Lys Phe
            820                 825                 830

Leu Val Asp Gly Gly Ala Ser Glu Cys Met Ser Ala Val Ala Gly Ser
        835                 840                 845

Tyr Gly Tyr Ile Ala Pro Glu Tyr Ala Tyr Thr Leu Arg Val Asp Glu
    850                 855                 860

Lys Ser Asp Val Tyr Ser Phe Gly Val Val Leu Leu Glu Leu Ile Thr
865                 870                 875                 880

Gly Arg Arg Pro Val Gly Glu Phe Gly Asp Gly Val Asp Ile Val Gln
                885                 890                 895

Trp Ser Lys Lys Val Thr Asn Cys Lys Arg Glu Gln Val Thr His Ile
            900                 905                 910

Val Asp Pro Arg Leu Thr Ser Val Pro Gln Asp Glu Ala Met His Leu
        915                 920                 925
```

```
Phe Phe Ile Ser Met Leu Cys Ile Gln Glu Asn Ser Val Glu Arg Pro
    930                 935                 940

Thr Met Arg Glu Val Ile Gln Met Leu Ser Glu Phe Pro Arg Gln Ser
945                 950                 955                 960

Pro Glu Tyr His Arg Pro Ser Ser Ser Lys Val Val Leu Gln Lys Leu
                965                 970                 975

Lys Ser Leu Glu Asn Asp Gln Ile Thr Cys Pro Lys Ile Arg Lys Glu
            980                 985                 990

Asn Leu Val
        995
```

<210> SEQ ID NO 52
<211> LENGTH: 56
<212> TYPE: PRT
<213> ORGANISM: Solanum lycopersicum

<400> SEQUENCE: 52

```
Ile Arg Ile Leu Asn Tyr Leu Asn Leu Ser Arg Asn His Leu Asn Glu
1               5                   10                  15

Thr Ile Pro Lys Ser Ile Gly Thr Met Arg Ser Leu Thr Thr Ala Asp
            20                  25                  30

Phe Ser Phe Asn Asp Leu Ser Gly Lys Leu Pro Glu Ser Gly Gln Phe
        35                  40                  45

Ala Tyr Phe Asn Ala Thr Ser Phe
    50                  55
```

<210> SEQ ID NO 53
<211> LENGTH: 1016
<212> TYPE: PRT
<213> ORGANISM: Solanum lycopersicum

<400> SEQUENCE: 53

```
Met Arg Leu Leu Phe Phe Leu Leu Leu Leu Met His Phe Thr Asp Phe
1               5                   10                  15

Ser Ala Gly Lys Gln Pro Arg Leu Pro Glu Tyr Gln Ala Leu Leu Ala
            20                  25                  30

Leu Lys Thr Ala Ile Thr Asp Asp Pro Gln Leu Thr Leu Ala Ser Trp
        35                  40                  45

Asn Ile Ser Thr Ser His Cys Thr Trp Asn Gly Val Thr Cys Asp Thr
    50                  55                  60

His Arg His Val Thr Ser Leu Asp Ile Ser Gly Phe Asn Leu Thr Gly
65                  70                  75                  80

Thr Leu Pro Pro Glu Val Gly Asn Leu Arg Phe Leu Gln Asn Leu Ser
                85                  90                  95

Val Ala Val Asn Gln Phe Thr Gly Pro Val Pro Val Glu Ile Ser Phe
            100                 105                 110

Ile Pro Asn Leu Ser Tyr Leu Asn Leu Ser Asn Asn Ile Phe Gly Met
        115                 120                 125

Glu Phe Pro Ser Gln Leu Thr Arg Leu Arg Asn Leu Gln Val Leu Asp
    130                 135                 140

Leu Tyr Asn Asn Asn Met Thr Gly Glu Leu Pro Val Glu Val Tyr Gln
145                 150                 155                 160

Met Thr Lys Leu Arg His Leu His Leu Gly Gly Asn Phe Phe Ser Gly
                165                 170                 175

Arg Ile Pro Pro Glu Tyr Gly Arg Phe Pro Ser Leu Glu Tyr Leu Ala
            180                 185                 190
```

-continued

```
Val Ser Gly Asn Ala Leu Val Gly Glu Ile Pro Pro Glu Ile Gly Asn
        195                 200                 205

Ile Ala Thr Leu Gln Gln Leu Tyr Val Gly Tyr Tyr Asn Thr Phe Thr
    210                 215                 220

Gly Gly Ile Pro Pro Ala Ile Gly Asn Leu Ser Gln Leu Leu Arg Phe
225                 230                 235                 240

Asp Ala Ala Asn Cys Gly Leu Ser Gly Lys Ile Pro Pro Glu Ile Gly
                245                 250                 255

Lys Leu Gln Asn Leu Asp Thr Leu Phe Leu Gln Val Asn Ser Leu Ser
            260                 265                 270

Gly Ser Leu Thr Pro Glu Ile Gly Tyr Leu Lys Ser Leu Lys Ser Leu
        275                 280                 285

Asp Leu Ser Asn Asn Met Phe Ser Gly Glu Ile Pro Pro Thr Phe Ala
    290                 295                 300

Glu Leu Lys Asn Ile Thr Leu Val Asn Leu Phe Arg Asn Lys Leu Tyr
305                 310                 315                 320

Gly Ser Ile Pro Glu Phe Ile Glu Asp Leu Pro Glu Leu Glu Val Leu
                325                 330                 335

Gln Leu Trp Glu Asn Asn Phe Thr Gly Ser Ile Pro Gln Gly Leu Gly
            340                 345                 350

Thr Lys Ser Lys Leu Lys Thr Leu Asp Leu Ser Ser Asn Lys Leu Thr
        355                 360                 365

Gly Asn Leu Pro Pro Asn Met Cys Ser Gly Asn Asn Leu Gln Thr Ile
    370                 375                 380

Ile Thr Leu Gly Asn Phe Leu Phe Gly Pro Ile Pro Glu Ser Leu Gly
385                 390                 395                 400

Arg Cys Glu Ser Leu Asn Arg Ile Arg Met Gly Glu Asn Tyr Leu Asn
                405                 410                 415

Gly Ser Ile Pro Lys Gly Leu Leu Ser Leu Pro His Leu Ser Gln Val
            420                 425                 430

Glu Leu Gln Asn Asn Ile Leu Thr Gly Thr Phe Pro Asp Ile Ser Ser
        435                 440                 445

Lys Ser Asn Ser Leu Gly Gln Ile Ile Leu Ser Asn Asn Arg Leu Thr
    450                 455                 460

Gly Pro Leu Pro Pro Ser Ile Gly Asn Phe Ala Val Ala Gln Lys Leu
465                 470                 475                 480

Leu Leu Asp Gly Asn Lys Phe Ser Gly Arg Ile Pro Ala Glu Ile Gly
                485                 490                 495

Lys Leu Gln Gln Leu Ser Lys Ile Asp Phe Ser His Asn Asn Leu Ser
            500                 505                 510

Gly Pro Ile Ala Pro Glu Ile Ser Gln Cys Lys Leu Leu Thr Tyr Val
        515                 520                 525

Asp Leu Ser Arg Asn Gln Leu Ser Gly Glu Ile Pro Thr Glu Ile Thr
    530                 535                 540

Gly Met Arg Ile Leu Asn Tyr Leu Asn Leu Ser Arg Asn His Leu Val
545                 550                 555                 560

Gly Ser Ile Pro Ala Pro Ile Ser Ser Met Gln Ser Leu Thr Ser Val
                565                 570                 575

Asp Phe Ser Tyr Asn Asn Phe Ser Gly Leu Val Pro Gly Thr Gly Gln
            580                 585                 590

Phe Ser Tyr Phe Asn Tyr Thr Ser Phe Leu Gly Asn Pro Asp Leu Cys
        595                 600                 605

Gly Pro Tyr Leu Gly Pro Cys Lys Glu Gly Val Val Asp Gly Val Ser
```

```
    610                 615                 620

Gln Pro His Gln Arg Gly Ala Leu Thr Pro Ser Met Lys Leu Leu Leu
625                 630                 635                 640

Val Ile Gly Leu Leu Val Cys Ser Ile Val Phe Ala Val Ala Ala Ile
                645                 650                 655

Ile Lys Ala Arg Ser Leu Lys Lys Ala Ser Glu Ala Arg Ala Trp Lys
            660                 665                 670

Leu Thr Ala Phe Gln Arg Leu Asp Phe Thr Cys Asp Asp Ile Leu Asp
        675                 680                 685

Ser Leu Lys Glu Asp Asn Val Ile Gly Lys Gly Gly Ala Gly Ile Val
    690                 695                 700

Tyr Lys Gly Val Met Pro Ser Gly Glu His Val Ala Val Lys Arg Leu
705                 710                 715                 720

Pro Ala Met Ser Arg Gly Ser Ser His Asp His Gly Phe Asn Ala Glu
                725                 730                 735

Ile Gln Thr Leu Gly Arg Ile Arg His Arg His Ile Val Arg Leu Leu
            740                 745                 750

Gly Phe Cys Ser Asn His Glu Thr Asn Leu Leu Val Tyr Glu Tyr Met
        755                 760                 765

Pro Asn Gly Ser Leu Gly Glu Met Leu His Gly Lys Lys Gly Gly His
    770                 775                 780

Leu His Trp Asp Thr Arg Tyr Lys Ile Ala Leu Glu Ser Ala Lys Gly
785                 790                 795                 800

Leu Cys Tyr Leu His His Asp Cys Ser Pro Leu Ile Leu His Arg Asp
                805                 810                 815

Val Lys Ser Asn Asn Ile Leu Leu Asp Ser Ser Phe Glu Ala His Val
            820                 825                 830

Ala Asp Phe Gly Leu Ala Lys Phe Leu Gln Asp Ser Gly Thr Ser Glu
        835                 840                 845

Cys Met Ser Ala Ile Ala Gly Ser Tyr Gly Tyr Ile Ala Pro Glu Tyr
    850                 855                 860

Ala Tyr Thr Leu Lys Val Asp Glu Lys Ser Asp Val Tyr Ser Phe Gly
865                 870                 875                 880

Val Val Leu Leu Glu Leu Val Ser Gly Lys Lys Pro Val Gly Glu Phe
                885                 890                 895

Gly Asp Gly Val Asp Ile Val Gln Trp Val Arg Lys Met Thr Asp Gly
            900                 905                 910

Lys Lys Asp Gly Val Leu Lys Ile Leu Asp Pro Arg Leu Ser Thr Val
        915                 920                 925

Pro Leu Asn Glu Val Met His Val Phe Tyr Val Ala Leu Leu Cys Val
    930                 935                 940

Glu Glu Gln Ala Val Glu Arg Pro Thr Met Arg Glu Val Val Gln Ile
945                 950                 955                 960

Leu Thr Glu Leu Pro Lys Pro Pro Gly Ala Lys Ser Asp Asp Ser Thr
                965                 970                 975

Val Thr Asp Gln Ser Pro Pro Ser Ala Ser Ala Leu Glu Ser Pro Thr
            980                 985                 990

Ser Ile Pro Gly Asp Thr Lys Asp  His His Gln Pro Thr  Pro Gln Ser
        995                 1000                1005

Pro Pro  Pro Asp Leu Leu Ser  Ile
    1010                1015
```

<210> SEQ ID NO 54

<211> LENGTH: 56
<212> TYPE: PRT
<213> ORGANISM: Solanum lycopersicum

<400> SEQUENCE: 54

Met Arg Ile Leu Asn Tyr Leu Asn Leu Ser Arg Asn His Leu Val Gly
1 5 10 15

Ser Ile Pro Ala Pro Ile Ser Ser Met Gln Ser Leu Thr Ser Val Asp
20 25 30

Phe Ser Tyr Asn Asn Phe Ser Gly Leu Val Pro Gly Thr Gly Gln Phe
35 40 45

Ser Tyr Phe Asn Tyr Thr Ser Phe
50 55

<210> SEQ ID NO 55
<211> LENGTH: 1012
<212> TYPE: PRT
<213> ORGANISM: Glycine max

<400> SEQUENCE: 55

Met Arg Val Leu Phe Leu Phe Leu Phe Phe Gln Phe Leu His Phe His
1 5 10 15

Phe Pro Lys Thr Leu Ser Ala Pro Ile Ser Glu Tyr Arg Ala Leu Leu
20 25 30

Ser Leu Arg Ser Ala Ile Thr Asp Ala Thr Pro Pro Leu Leu Thr Ser
35 40 45

Trp Asn Ser Ser Thr Pro Tyr Cys Ser Trp Leu Gly Val Thr Cys Asp
50 55 60

Asn Arg Arg His Val Thr Ser Leu Asp Leu Thr Gly Leu Asp Leu Ser
65 70 75 80

Gly Pro Leu Ser Ala Asp Val Ala His Leu Pro Phe Leu Ser Asn Leu
85 90 95

Ser Leu Ala Ser Asn Lys Phe Ser Gly Pro Ile Pro Pro Ser Leu Ser
100 105 110

Ala Leu Ser Gly Leu Arg Phe Leu Asn Leu Ser Asn Asn Val Phe Asn
115 120 125

Glu Thr Phe Pro Ser Glu Leu Ser Arg Leu Gln Asn Leu Glu Val Leu
130 135 140

Asp Leu Tyr Asn Asn Asn Met Thr Gly Val Leu Pro Leu Ala Val Ala
145 150 155 160

Gln Met Gln Asn Leu Arg His Leu His Leu Gly Gly Asn Phe Phe Ser
165 170 175

Gly Gln Ile Pro Pro Glu Tyr Gly Arg Trp Gln Arg Leu Gln Tyr Leu
180 185 190

Ala Val Ser Gly Asn Glu Leu Glu Gly Thr Ile Pro Pro Glu Ile Gly
195 200 205

Asn Leu Ser Ser Leu Arg Glu Leu Tyr Ile Gly Tyr Tyr Asn Thr Tyr
210 215 220

Thr Gly Gly Ile Pro Pro Glu Ile Gly Asn Leu Ser Glu Leu Val Arg
225 230 235 240

Leu Asp Ala Ala Tyr Cys Gly Leu Ser Gly Glu Ile Pro Ala Ala Leu
245 250 255

Gly Lys Leu Gln Lys Leu Asp Thr Leu Phe Leu Gln Val Asn Ala Leu
260 265 270

Ser Gly Ser Leu Thr Pro Glu Leu Gly Asn Leu Lys Ser Leu Lys Ser
275 280 285

-continued

```
Met Asp Leu Ser Asn Asn Met Leu Ser Gly Glu Ile Pro Ala Arg Phe
    290                 295                 300

Gly Glu Leu Lys Asn Ile Thr Leu Leu Asn Leu Phe Arg Asn Lys Leu
305                 310                 315                 320

His Gly Ala Ile Pro Glu Phe Ile Gly Glu Leu Pro Ala Leu Glu Val
                325                 330                 335

Val Gln Leu Trp Glu Asn Asn Phe Thr Gly Ser Ile Pro Glu Gly Leu
            340                 345                 350

Gly Lys Asn Gly Arg Leu Asn Leu Val Asp Leu Ser Ser Asn Lys Leu
        355                 360                 365

Thr Gly Thr Leu Pro Thr Tyr Leu Cys Ser Gly Asn Thr Leu Gln Thr
    370                 375                 380

Leu Ile Thr Leu Gly Asn Phe Leu Phe Gly Pro Ile Pro Glu Ser Leu
385                 390                 395                 400

Gly Ser Cys Glu Ser Leu Thr Arg Ile Arg Met Gly Glu Asn Phe Leu
                405                 410                 415

Asn Gly Ser Ile Pro Arg Gly Leu Phe Gly Leu Pro Lys Leu Thr Gln
            420                 425                 430

Val Glu Leu Gln Asp Asn Tyr Leu Ser Gly Glu Phe Pro Glu Val Gly
        435                 440                 445

Ser Val Ala Val Asn Leu Gly Gln Ile Thr Leu Ser Asn Asn Gln Leu
    450                 455                 460

Ser Gly Val Leu Pro Pro Ser Ile Gly Asn Phe Ser Ser Val Gln Lys
465                 470                 475                 480

Leu Leu Leu Asp Gly Asn Met Phe Thr Gly Arg Ile Pro Pro Gln Ile
                485                 490                 495

Gly Arg Leu Gln Gln Leu Ser Lys Ile Asp Phe Ser Gly Asn Lys Phe
            500                 505                 510

Ser Gly Pro Ile Val Pro Glu Ile Ser Gln Cys Lys Leu Leu Thr Phe
        515                 520                 525

Leu Asp Leu Ser Arg Asn Glu Leu Ser Gly Asp Ile Pro Asn Glu Ile
    530                 535                 540

Thr Gly Met Arg Ile Leu Asn Tyr Leu Asn Leu Ser Arg Asn His Leu
545                 550                 555                 560

Val Gly Gly Ile Pro Ser Ser Ile Ser Ser Met Gln Ser Leu Thr Ser
                565                 570                 575

Val Asp Phe Ser Tyr Asn Asn Leu Ser Gly Leu Val Pro Gly Thr Gly
            580                 585                 590

Gln Phe Ser Tyr Phe Asn Tyr Thr Ser Phe Leu Gly Asn Pro Asp Leu
        595                 600                 605

Cys Gly Pro Tyr Leu Gly Ala Cys Lys Asp Gly Val Ala Asn Gly Ala
    610                 615                 620

His Gln Pro His Val Lys Gly Leu Ser Ser Ser Phe Lys Leu Leu Leu
625                 630                 635                 640

Val Val Gly Leu Leu Leu Cys Ser Ile Ala Phe Ala Val Ala Ala Ile
                645                 650                 655

Phe Lys Ala Arg Ser Leu Lys Lys Ala Ser Gly Ala Arg Ala Trp Lys
            660                 665                 670

Leu Thr Ala Phe Gln Arg Leu Asp Phe Thr Val Asp Asp Val Leu His
        675                 680                 685

Cys Leu Lys Glu Asp Asn Ile Ile Gly Lys Gly Gly Ala Gly Ile Val
    690                 695                 700
```

-continued

```
Tyr Lys Gly Ala Met Pro Asn Gly Asp His Val Ala Val Lys Arg Leu
705                 710                 715                 720

Pro Ala Met Ser Arg Gly Ser Ser His Asp His Gly Phe Asn Ala Glu
                725                 730                 735

Ile Gln Thr Leu Gly Arg Ile Arg His Arg His Ile Val Arg Leu Leu
            740                 745                 750

Gly Phe Cys Ser Asn His Glu Thr Asn Leu Leu Val Tyr Glu Tyr Met
        755                 760                 765

Pro Asn Gly Ser Leu Gly Glu Val Leu His Gly Lys Lys Gly Gly His
    770                 775                 780

Leu His Trp Asp Thr Arg Tyr Lys Ile Ala Val Glu Ala Ala Lys Gly
785                 790                 795                 800

Leu Cys Tyr Leu His His Asp Cys Ser Pro Leu Ile Val His Arg Asp
                805                 810                 815

Val Lys Ser Asn Asn Ile Leu Leu Asp Ser Asn His Glu Ala His Val
            820                 825                 830

Ala Asp Phe Gly Leu Ala Lys Phe Leu Gln Asp Ser Gly Thr Ser Glu
        835                 840                 845

Cys Met Ser Ala Ile Ala Gly Ser Tyr Gly Tyr Ile Ala Pro Glu Tyr
    850                 855                 860

Ala Tyr Thr Leu Lys Val Asp Glu Lys Ser Asp Val Tyr Ser Phe Gly
865                 870                 875                 880

Val Val Leu Leu Glu Leu Ile Thr Gly Arg Lys Pro Val Gly Glu Phe
                885                 890                 895

Gly Asp Gly Val Asp Ile Val Gln Trp Val Arg Lys Met Thr Asp Ser
            900                 905                 910

Asn Lys Glu Gly Val Leu Lys Val Leu Asp Pro Arg Leu Pro Ser Val
        915                 920                 925

Pro Leu His Glu Val Met His Val Phe Tyr Val Ala Met Leu Cys Val
    930                 935                 940

Glu Glu Gln Ala Val Glu Arg Pro Thr Met Arg Glu Val Val Gln Ile
945                 950                 955                 960

Leu Thr Glu Leu Pro Lys Pro Pro Asp Ser Lys Glu Gly Asn Leu Thr
                965                 970                 975

Ile Thr Glu Ser Ser Leu Ser Ser Ser Asn Ala Leu Glu Ser Pro Ser
            980                 985                 990

Ser Ala Ser Lys Glu Asp Gln Asn  Pro Pro Gln Ser Pro  Pro Pro Asp
        995                 1000                1005

Leu Leu  Ser Ile
    1010
```

```
<210> SEQ ID NO 56
<211> LENGTH: 56
<212> TYPE: PRT
<213> ORGANISM: Glycine max

<400> SEQUENCE: 56

Met Arg Ile Leu Asn Tyr Leu Asn Leu Ser Arg Asn His Leu Val Gly
1               5                   10                  15

Gly Ile Pro Ser Ser Ile Ser Ser Met Gln Ser Leu Thr Ser Val Asp
            20                  25                  30

Phe Ser Tyr Asn Asn Leu Ser Gly Leu Val Pro Gly Thr Gly Gln Phe
        35                  40                  45

Ser Tyr Phe Asn Tyr Thr Ser Phe
    50                  55
```

<210> SEQ ID NO 57
<211> LENGTH: 1008
<212> TYPE: PRT
<213> ORGANISM: Glycine max

<400> SEQUENCE: 57

Met Arg Val Leu Val Leu Phe Phe Leu Phe Leu His Ser Leu Gln Ala
1               5                   10                  15

Ala Arg Ile Ser Glu Tyr Arg Ala Leu Leu Ser Phe Lys Ala Ser Ser
            20                  25                  30

Leu Thr Asp Asp Pro Thr His Ala Leu Ser Ser Trp Asn Ser Ser Thr
        35                  40                  45

Pro Phe Cys Ser Trp Phe Gly Leu Thr Cys Asp Ser Arg Arg His Val
    50                  55                  60

Thr Ser Leu Asn Leu Thr Ser Leu Ser Leu Ser Gly Thr Leu Ser Asp
65                  70                  75                  80

Asp Leu Ser His Leu Pro Phe Leu Ser His Leu Ser Leu Ala Asp Asn
                85                  90                  95

Lys Phe Ser Gly Pro Ile Pro Ala Ser Phe Ser Ala Leu Ser Ala Leu
            100                 105                 110

Arg Phe Leu Asn Leu Ser Asn Asn Val Phe Asn Ala Thr Phe Pro Ser
        115                 120                 125

Gln Leu Asn Arg Leu Ala Asn Leu Glu Val Leu Asp Leu Tyr Asn Asn
    130                 135                 140

Asn Met Thr Gly Glu Leu Pro Leu Ser Val Ala Ala Met Pro Leu Leu
145                 150                 155                 160

Arg His Leu His Leu Gly Gly Asn Phe Phe Ser Gly Gln Ile Pro Pro
                165                 170                 175

Glu Tyr Gly Thr Trp Gln His Leu Gln Tyr Leu Ala Leu Ser Gly Asn
            180                 185                 190

Glu Leu Ala Gly Thr Ile Ala Pro Glu Leu Gly Asn Leu Ser Ser Leu
        195                 200                 205

Arg Glu Leu Tyr Ile Gly Tyr Tyr Asn Thr Tyr Ser Gly Gly Ile Pro
    210                 215                 220

Pro Glu Ile Gly Asn Leu Ser Asn Leu Val Arg Leu Asp Ala Ala Tyr
225                 230                 235                 240

Cys Gly Leu Ser Gly Glu Ile Pro Ala Glu Leu Gly Lys Leu Gln Asn
                245                 250                 255

Leu Asp Thr Leu Phe Leu Gln Val Asn Ala Leu Ser Gly Ser Leu Thr
            260                 265                 270

Pro Glu Leu Gly Ser Leu Lys Ser Leu Lys Ser Met Asp Leu Ser Asn
        275                 280                 285

Asn Met Leu Ser Gly Glu Val Pro Ala Ser Phe Ala Glu Leu Lys Asn
    290                 295                 300

Leu Thr Leu Leu Asn Leu Phe Arg Asn Lys Leu His Gly Ala Ile Pro
305                 310                 315                 320

Glu Phe Val Gly Glu Leu Pro Ala Leu Glu Val Leu Gln Leu Trp Glu
                325                 330                 335

Asn Asn Phe Thr Gly Ser Ile Pro Gln Asn Leu Gly Asn Asn Gly Arg
            340                 345                 350

Leu Thr Leu Val Asp Leu Ser Ser Asn Lys Ile Thr Gly Thr Leu Pro
        355                 360                 365

Pro Asn Met Cys Tyr Gly Asn Arg Leu Gln Thr Leu Ile Thr Leu Gly

```
    370                 375                 380

Asn Tyr Leu Phe Gly Pro Ile Pro Asp Ser Leu Gly Lys Cys Lys Ser
385                 390                 395                 400

Leu Asn Arg Ile Arg Met Gly Glu Asn Phe Leu Asn Gly Ser Ile Pro
                405                 410                 415

Lys Gly Leu Phe Gly Leu Pro Lys Leu Thr Gln Val Glu Leu Gln Asp
            420                 425                 430

Asn Leu Leu Thr Gly Gln Phe Pro Glu Asp Gly Ser Ile Ala Thr Asp
        435                 440                 445

Leu Gly Gln Ile Ser Leu Ser Asn Asn Gln Leu Ser Gly Ser Leu Pro
    450                 455                 460

Ser Thr Ile Gly Asn Phe Thr Ser Met Gln Lys Leu Leu Leu Asn Gly
465                 470                 475                 480

Asn Glu Phe Thr Gly Arg Ile Pro Pro Gln Ile Gly Met Leu Gln Gln
                485                 490                 495

Leu Ser Lys Ile Asp Phe Ser His Asn Lys Phe Ser Gly Pro Ile Ala
            500                 505                 510

Pro Glu Ile Ser Lys Cys Lys Leu Leu Thr Phe Ile Asp Leu Ser Gly
        515                 520                 525

Asn Glu Leu Ser Gly Glu Ile Pro Asn Lys Ile Thr Ser Met Arg Ile
    530                 535                 540

Leu Asn Tyr Leu Asn Leu Ser Arg Asn His Leu Asp Gly Ser Ile Pro
545                 550                 555                 560

Gly Asn Ile Ala Ser Met Gln Ser Leu Thr Ser Val Asp Phe Ser Tyr
                565                 570                 575

Asn Asn Phe Ser Gly Leu Val Pro Gly Thr Gly Gln Phe Gly Tyr Phe
            580                 585                 590

Asn Tyr Thr Ser Phe Leu Gly Asn Pro Glu Leu Cys Gly Pro Tyr Leu
        595                 600                 605

Gly Pro Cys Lys Asp Gly Val Ala Asn Gly Pro Arg Gln Pro His Val
    610                 615                 620

Lys Gly Pro Phe Ser Ser Ser Leu Lys Leu Leu Leu Val Ile Gly Leu
625                 630                 635                 640

Leu Val Cys Ser Ile Leu Phe Ala Val Ala Ala Ile Phe Lys Ala Arg
                645                 650                 655

Ala Leu Lys Lys Ala Ser Glu Ala Arg Ala Trp Lys Leu Thr Ala Phe
            660                 665                 670

Gln Arg Leu Asp Phe Thr Val Asp Asp Val Leu Asp Cys Leu Lys Glu
        675                 680                 685

Asp Asn Ile Ile Gly Lys Gly Gly Ala Gly Ile Val Tyr Lys Gly Ala
    690                 695                 700

Met Pro Asn Gly Gly Asn Val Ala Val Lys Arg Leu Pro Ala Met Ser
705                 710                 715                 720

Arg Gly Ser Ser His Asp His Gly Phe Asn Ala Glu Ile Gln Thr Leu
                725                 730                 735

Gly Arg Ile Arg His Arg His Ile Val Arg Leu Leu Gly Phe Cys Ser
            740                 745                 750

Asn His Glu Thr Asn Leu Leu Val Tyr Glu Tyr Met Pro Asn Gly Ser
        755                 760                 765

Leu Gly Glu Val Leu His Gly Lys Lys Gly Gly His Leu His Trp Asp
    770                 775                 780

Thr Arg Tyr Lys Ile Ala Val Glu Ala Ala Lys Gly Leu Cys Tyr Leu
785                 790                 795                 800
```

```
His His Asp Cys Ser Pro Leu Ile Val His Arg Asp Val Lys Ser Asn
                805                 810                 815

Asn Ile Leu Leu Asp Ser Asn Phe Glu Ala His Val Ala Asp Phe Gly
            820                 825                 830

Leu Ala Lys Phe Leu Gln Asp Ser Gly Ala Ser Glu Cys Met Ser Ala
        835                 840                 845

Ile Ala Gly Ser Tyr Gly Tyr Ile Ala Pro Glu Tyr Ala Tyr Thr Leu
    850                 855                 860

Lys Val Asp Glu Lys Ser Asp Val Tyr Ser Phe Gly Val Val Leu Leu
865                 870                 875                 880

Glu Leu Val Thr Gly Arg Lys Pro Val Gly Glu Phe Gly Asp Gly Val
                885                 890                 895

Asp Ile Val Gln Trp Val Arg Lys Met Thr Asp Ser Asn Lys Glu Gly
            900                 905                 910

Val Leu Lys Val Leu Asp Ser Arg Leu Pro Ser Val Pro Leu His Glu
        915                 920                 925

Val Met His Val Phe Tyr Val Ala Met Leu Cys Val Glu Glu Gln Ala
    930                 935                 940

Val Glu Arg Pro Thr Met Arg Glu Val Val Gln Ile Leu Thr Glu Leu
945                 950                 955                 960

Pro Lys Pro Pro Ser Ser Lys His Ala Ile Thr Glu Ser Ser Leu Ser
                965                 970                 975

Ser Ser Asn Ser Leu Gly Ser Pro Thr Thr Ala Ser Lys Glu Pro Lys
            980                 985                 990

Asp Asn Gln His Pro Pro Gln Ser  Pro Pro Pro Asp Leu  Leu Ser Ile
        995                 1000                1005


<210> SEQ ID NO 58
<211> LENGTH: 56
<212> TYPE: PRT
<213> ORGANISM: Glycine max

<400> SEQUENCE: 58

Met Arg Ile Leu Asn Tyr Leu Asn Leu Ser Arg Asn His Leu Asp Gly
1               5                   10                  15

Ser Ile Pro Gly Asn Ile Ala Ser Met Gln Ser Leu Thr Ser Val Asp
            20                  25                  30

Phe Ser Tyr Asn Asn Phe Ser Gly Leu Val Pro Gly Thr Gly Gln Phe
        35                  40                  45

Gly Tyr Phe Asn Tyr Thr Ser Phe
    50                  55


<210> SEQ ID NO 59
<211> LENGTH: 1012
<212> TYPE: PRT
<213> ORGANISM: Glycine max

<400> SEQUENCE: 59

Met Pro Lys Met Arg Val Leu Phe Val Phe Leu Phe Phe His Phe His
1               5                   10                  15

Phe Pro Glu Thr Leu Ser Ala Pro Ile Ser Glu Tyr Arg Ala Leu Leu
            20                  25                  30

Ser Leu Arg Ser Val Ile Thr Asp Ala Thr Pro Pro Val Leu Ser Ser
        35                  40                  45

Trp Asn Ala Ser Ile Pro Tyr Cys Ser Trp Leu Gly Val Thr Cys Asp
    50                  55                  60
```

```
Asn Arg Arg His Val Thr Ala Leu Asn Leu Thr Gly Leu Asp Leu Ser
65                  70                  75                  80

Gly Thr Leu Ser Ala Asp Val Ala His Leu Pro Phe Leu Ser Asn Leu
                85                  90                  95

Ser Leu Ala Ala Asn Lys Phe Ser Gly Pro Ile Pro Pro Ser Leu Ser
            100                 105                 110

Ala Leu Ser Gly Leu Arg Tyr Leu Asn Leu Ser Asn Asn Val Phe Asn
        115                 120                 125

Glu Thr Phe Pro Ser Glu Leu Trp Arg Leu Gln Ser Leu Glu Val Leu
    130                 135                 140

Asp Leu Tyr Asn Asn Asn Met Thr Gly Val Leu Pro Leu Ala Val Ala
145                 150                 155                 160

Gln Met Gln Asn Leu Arg His Leu His Leu Gly Gly Asn Phe Phe Ser
                165                 170                 175

Gly Gln Ile Pro Pro Glu Tyr Gly Arg Trp Gln Arg Leu Gln Tyr Leu
            180                 185                 190

Ala Val Ser Gly Asn Glu Leu Asp Gly Thr Ile Pro Pro Glu Ile Gly
        195                 200                 205

Asn Leu Thr Ser Leu Arg Glu Leu Tyr Ile Gly Tyr Tyr Asn Thr Tyr
    210                 215                 220

Thr Gly Gly Ile Pro Pro Glu Ile Gly Asn Leu Ser Glu Leu Val Arg
225                 230                 235                 240

Leu Asp Val Ala Tyr Cys Ala Leu Ser Gly Glu Ile Pro Ala Ala Leu
                245                 250                 255

Gly Lys Leu Gln Lys Leu Asp Thr Leu Phe Leu Gln Val Asn Ala Leu
            260                 265                 270

Ser Gly Ser Leu Thr Pro Glu Leu Gly Asn Leu Lys Ser Leu Lys Ser
        275                 280                 285

Met Asp Leu Ser Asn Asn Met Leu Ser Gly Glu Ile Pro Ala Ser Phe
    290                 295                 300

Gly Glu Leu Lys Asn Ile Thr Leu Leu Asn Leu Phe Arg Asn Lys Leu
305                 310                 315                 320

His Gly Ala Ile Pro Glu Phe Ile Gly Glu Leu Pro Ala Leu Glu Val
                325                 330                 335

Val Gln Leu Trp Glu Asn Asn Leu Thr Gly Ser Ile Pro Glu Gly Leu
            340                 345                 350

Gly Lys Asn Gly Arg Leu Asn Leu Val Asp Leu Ser Ser Asn Lys Leu
        355                 360                 365

Thr Gly Thr Leu Pro Pro Tyr Leu Cys Ser Gly Asn Thr Leu Gln Thr
    370                 375                 380

Leu Ile Thr Leu Gly Asn Phe Leu Phe Gly Pro Ile Pro Glu Ser Leu
385                 390                 395                 400

Gly Thr Cys Glu Ser Leu Thr Arg Ile Arg Met Gly Glu Asn Phe Leu
                405                 410                 415

Asn Gly Ser Ile Pro Lys Gly Leu Phe Gly Leu Pro Lys Leu Thr Gln
            420                 425                 430

Val Glu Leu Gln Asp Asn Tyr Leu Ser Gly Glu Phe Pro Glu Val Gly
        435                 440                 445

Ser Val Ala Val Asn Leu Gly Gln Ile Thr Leu Ser Asn Asn Gln Leu
    450                 455                 460

Ser Gly Ala Leu Ser Pro Ser Ile Gly Asn Phe Ser Ser Val Gln Lys
465                 470                 475                 480
```

-continued

```
Leu Leu Leu Asp Gly Asn Met Phe Thr Gly Arg Ile Pro Thr Gln Ile
                485                 490                 495

Gly Arg Leu Gln Gln Leu Ser Lys Ile Asp Phe Ser Gly Asn Lys Phe
            500                 505                 510

Ser Gly Pro Ile Ala Pro Glu Ile Ser Gln Cys Lys Leu Leu Thr Phe
        515                 520                 525

Leu Asp Leu Ser Arg Asn Glu Leu Ser Gly Asp Ile Pro Asn Glu Ile
    530                 535                 540

Thr Gly Met Arg Ile Leu Asn Tyr Leu Asn Leu Ser Lys Asn His Leu
545                 550                 555                 560

Val Gly Ser Ile Pro Ser Ser Ile Ser Ser Met Gln Ser Leu Thr Ser
                565                 570                 575

Val Asp Phe Ser Tyr Asn Asn Leu Ser Gly Leu Val Pro Gly Thr Gly
            580                 585                 590

Gln Phe Ser Tyr Phe Asn Tyr Thr Ser Phe Leu Gly Asn Pro Asp Leu
        595                 600                 605

Cys Gly Pro Tyr Leu Gly Ala Cys Lys Gly Gly Val Ala Asn Gly Ala
    610                 615                 620

His Gln Pro His Val Lys Gly Leu Ser Ser Ser Leu Lys Leu Leu Leu
625                 630                 635                 640

Val Val Gly Leu Leu Leu Cys Ser Ile Ala Phe Ala Val Ala Ala Ile
                645                 650                 655

Phe Lys Ala Arg Ser Leu Lys Lys Ala Ser Glu Ala Arg Ala Trp Lys
            660                 665                 670

Leu Thr Ala Phe Gln Arg Leu Asp Phe Thr Val Asp Asp Val Leu His
        675                 680                 685

Cys Leu Lys Glu Asp Asn Ile Ile Gly Lys Gly Gly Ala Gly Ile Val
    690                 695                 700

Tyr Lys Gly Ala Met Pro Asn Gly Asp His Val Ala Val Lys Arg Leu
705                 710                 715                 720

Pro Ala Met Ser Arg Gly Ser Ser His Asp His Gly Phe Asn Ala Glu
                725                 730                 735

Ile Gln Thr Leu Gly Arg Ile Arg His Arg His Ile Val Arg Leu Leu
            740                 745                 750

Gly Phe Cys Ser Asn His Glu Thr Asn Leu Leu Val Tyr Glu Tyr Met
        755                 760                 765

Pro Asn Gly Ser Leu Gly Glu Val Leu His Gly Lys Lys Gly Gly His
    770                 775                 780

Leu His Trp Asp Thr Arg Tyr Lys Ile Ala Val Glu Ala Ala Lys Gly
785                 790                 795                 800

Leu Cys Tyr Leu His His Asp Cys Ser Pro Leu Ile Val His Arg Asp
                805                 810                 815

Val Lys Ser Asn Asn Ile Leu Leu Asp Ser Asn His Glu Ala His Val
            820                 825                 830

Ala Asp Phe Gly Leu Ala Lys Phe Leu Gln Asp Ser Gly Thr Ser Glu
        835                 840                 845

Cys Met Ser Ala Ile Ala Gly Ser Tyr Gly Tyr Ile Ala Pro Glu Tyr
    850                 855                 860

Ala Tyr Thr Leu Lys Val Asp Glu Lys Ser Asp Val Tyr Ser Phe Gly
865                 870                 875                 880

Val Val Leu Leu Glu Leu Ile Thr Gly Arg Lys Pro Val Gly Glu Phe
                885                 890                 895

Gly Asp Gly Val Asp Ile Val Gln Trp Val Arg Lys Met Thr Asp Ser
```

```
            900                 905                 910

Asn Lys Glu Gly Val Leu Lys Val Leu Asp Pro Arg Leu Pro Ser Val
        915                 920                 925

Pro Leu His Glu Val Met His Val Phe Tyr Val Ala Met Leu Cys Val
    930                 935                 940

Glu Glu Gln Ala Val Glu Arg Pro Thr Met Arg Glu Val Val Gln Ile
945                 950                 955                 960

Leu Thr Glu Leu Pro Lys Pro Pro Gly Ser Lys Glu Gly Asp Leu Thr
                965                 970                 975

Ile Thr Glu Ser Ser Leu Ser Ser Ser Asn Ala Leu Glu Ser Pro Ser
            980                 985                 990

Ser Ala Ser Lys Glu Asp Gln Asn  Pro Pro Gln Ser Pro  Pro Pro Asp
        995                 1000                1005

Leu Leu  Ser Ile
    1010


<210> SEQ ID NO 60
<211> LENGTH: 56
<212> TYPE: PRT
<213> ORGANISM: Glycine max

<400> SEQUENCE: 60

Met Arg Ile Leu Asn Tyr Leu Asn Leu Ser Lys Asn His Leu Val Gly
1               5                   10                  15

Ser Ile Pro Ser Ser Ile Ser Ser Met Gln Ser Leu Thr Ser Val Asp
            20                  25                  30

Phe Ser Tyr Asn Asn Leu Ser Gly Leu Val Pro Gly Thr Gly Gln Phe
        35                  40                  45

Ser Tyr Phe Asn Tyr Thr Ser Phe
    50                  55


<210> SEQ ID NO 61
<211> LENGTH: 981
<212> TYPE: PRT
<213> ORGANISM: Glycine max

<400> SEQUENCE: 61

Met Arg Ser Cys Val Cys Tyr Thr Leu Leu Leu Phe Val Phe Phe Ile
1               5                   10                  15

Trp Leu His Val Ala Thr Cys Ser Ser Phe Ser Asp Met Asp Ala Leu
            20                  25                  30

Leu Lys Leu Lys Glu Ser Met Lys Gly Asp Arg Ala Lys Asp Asp Ala
        35                  40                  45

Leu His Asp Trp Lys Phe Ser Thr Ser Leu Ser Ala His Cys Phe Phe
    50                  55                  60

Ser Gly Val Ser Cys Asp Gln Glu Leu Arg Val Val Ala Ile Asn Val
65                  70                  75                  80

Ser Phe Val Pro Leu Phe Gly His Val Pro Pro Glu Ile Gly Glu Leu
                85                  90                  95

Asp Lys Leu Glu Asn Leu Thr Ile Ser Gln Asn Asn Leu Thr Gly Glu
            100                 105                 110

Leu Pro Lys Glu Leu Ala Ala Leu Thr Ser Leu Lys His Leu Asn Ile
        115                 120                 125

Ser His Asn Val Phe Ser Gly Tyr Phe Pro Gly Lys Ile Ile Leu Pro
    130                 135                 140

Met Thr Glu Leu Glu Val Leu Asp Val Tyr Asp Asn Asn Phe Thr Gly
```

-continued

```
145                 150                 155                 160

Ser Leu Pro Glu Glu Phe Val Lys Leu Glu Lys Leu Lys Tyr Leu Lys
                165                 170                 175

Leu Asp Gly Asn Tyr Phe Ser Gly Ser Ile Pro Glu Ser Tyr Ser Glu
            180                 185                 190

Phe Lys Ser Leu Glu Phe Leu Ser Leu Ser Thr Asn Ser Leu Ser Gly
        195                 200                 205

Asn Ile Pro Lys Ser Leu Ser Lys Leu Lys Thr Leu Arg Ile Leu Lys
    210                 215                 220

Leu Gly Tyr Asn Asn Ala Tyr Glu Gly Gly Ile Pro Pro Glu Phe Gly
225                 230                 235                 240

Thr Met Glu Ser Leu Lys Tyr Leu Asp Leu Ser Ser Cys Asn Leu Ser
                245                 250                 255

Gly Glu Ile Pro Pro Ser Leu Ala Asn Met Arg Asn Leu Asp Thr Leu
            260                 265                 270

Phe Leu Gln Met Asn Asn Leu Thr Gly Thr Ile Pro Ser Glu Leu Ser
        275                 280                 285

Asp Met Val Ser Leu Met Ser Leu Asp Leu Ser Phe Asn Gly Leu Thr
    290                 295                 300

Gly Glu Ile Pro Thr Arg Phe Ser Gln Leu Lys Asn Leu Thr Leu Met
305                 310                 315                 320

Asn Phe Phe His Asn Asn Leu Arg Gly Ser Val Pro Ser Phe Val Gly
                325                 330                 335

Glu Leu Pro Asn Leu Glu Thr Leu Gln Leu Trp Glu Asn Asn Phe Ser
            340                 345                 350

Ser Glu Leu Pro Gln Asn Leu Gly Gln Asn Gly Lys Phe Lys Phe Phe
        355                 360                 365

Asp Val Thr Lys Asn His Phe Ser Gly Leu Ile Pro Arg Asp Leu Cys
    370                 375                 380

Lys Ser Gly Arg Leu Gln Thr Phe Leu Ile Thr Asp Asn Phe Phe His
385                 390                 395                 400

Gly Pro Ile Pro Asn Glu Ile Ala Asn Cys Lys Ser Leu Thr Lys Ile
                405                 410                 415

Arg Ala Ser Asn Asn Tyr Leu Asn Gly Ala Val Pro Ser Gly Ile Phe
            420                 425                 430

Lys Leu Pro Ser Val Thr Ile Ile Glu Leu Ala Asn Asn Arg Phe Asn
        435                 440                 445

Gly Glu Leu Pro Pro Glu Ile Ser Gly Asp Ser Leu Gly Ile Leu Thr
    450                 455                 460

Leu Ser Asn Asn Leu Phe Thr Gly Lys Ile Pro Pro Ala Leu Lys Asn
465                 470                 475                 480

Leu Arg Ala Leu Gln Thr Leu Ser Leu Asp Thr Asn Glu Phe Leu Gly
                485                 490                 495

Glu Ile Pro Gly Glu Val Phe Asp Leu Pro Met Leu Thr Val Val Asn
            500                 505                 510

Ile Ser Gly Asn Asn Leu Thr Gly Pro Ile Pro Thr Thr Phe Thr Arg
        515                 520                 525

Cys Val Ser Leu Ala Ala Val Asp Leu Ser Arg Asn Met Leu Asp Gly
    530                 535                 540

Glu Ile Pro Lys Gly Met Lys Asn Leu Thr Asp Leu Ser Ile Phe Asn
545                 550                 555                 560

Val Ser Ile Asn Gln Ile Ser Gly Ser Val Pro Asp Glu Ile Arg Phe
                565                 570                 575
```

-continued

```
Met Leu Ser Leu Thr Thr Leu Asp Leu Ser Tyr Asn Asn Phe Ile Gly
            580                 585                 590

Lys Val Pro Thr Gly Gly Gln Phe Leu Val Phe Ser Asp Lys Ser Phe
        595                 600                 605

Ala Gly Asn Pro Asn Leu Cys Ser Ser His Ser Cys Pro Asn Ser Ser
    610                 615                 620

Leu Lys Lys Arg Arg Gly Pro Trp Ser Leu Lys Ser Thr Arg Val Ile
625                 630                 635                 640

Val Met Val Ile Ala Leu Ala Thr Ala Ala Ile Leu Val Ala Gly Thr
                645                 650                 655

Glu Tyr Met Arg Arg Arg Arg Lys Leu Lys Leu Ala Met Thr Trp Lys
            660                 665                 670

Leu Thr Gly Phe Gln Arg Leu Asn Leu Lys Ala Glu Glu Val Val Glu
        675                 680                 685

Cys Leu Lys Glu Glu Asn Ile Ile Gly Lys Gly Gly Ala Gly Ile Val
    690                 695                 700

Tyr Arg Gly Ser Met Arg Asn Gly Ser Asp Val Ala Ile Lys Arg Leu
705                 710                 715                 720

Val Gly Ala Gly Ser Gly Arg Asn Asp Tyr Gly Phe Lys Ala Glu Ile
                725                 730                 735

Glu Thr Val Gly Lys Ile Arg His Arg Asn Ile Met Arg Leu Leu Gly
            740                 745                 750

Tyr Val Ser Asn Lys Glu Thr Asn Leu Leu Leu Tyr Glu Tyr Met Pro
        755                 760                 765

Asn Gly Ser Leu Gly Glu Trp Leu His Gly Ala Lys Gly Gly His Leu
    770                 775                 780

Lys Trp Glu Met Arg Tyr Lys Ile Ala Val Glu Ala Ala Lys Gly Leu
785                 790                 795                 800

Cys Tyr Leu His His Asp Cys Ser Pro Leu Ile Ile His Arg Asp Val
                805                 810                 815

Lys Ser Asn Asn Ile Leu Leu Asp Ala His Phe Glu Ala His Val Ala
            820                 825                 830

Asp Phe Gly Leu Ala Lys Phe Leu Tyr Asp Leu Gly Ser Ser Gln Ser
        835                 840                 845

Met Ser Ser Ile Ala Gly Ser Tyr Gly Tyr Ile Ala Pro Glu Tyr Ala
    850                 855                 860

Tyr Thr Leu Lys Val Asp Glu Lys Ser Asp Val Tyr Ser Phe Gly Val
865                 870                 875                 880

Val Leu Leu Glu Leu Ile Ile Gly Arg Lys Pro Val Gly Glu Phe Gly
                885                 890                 895

Asp Gly Val Asp Ile Val Gly Trp Val Asn Lys Thr Arg Leu Glu Leu
            900                 905                 910

Ser Gln Pro Ser Asp Ala Ala Val Val Leu Ala Val Val Asp Pro Arg
        915                 920                 925

Leu Ser Gly Tyr Pro Leu Ile Ser Val Ile Tyr Met Phe Asn Ile Ala
    930                 935                 940

Met Met Cys Val Lys Glu Val Gly Pro Thr Arg Pro Thr Met Arg Glu
945                 950                 955                 960

Val Val His Met Leu Ser Asn Pro Pro His Ser Thr Thr His Thr His
                965                 970                 975

Asn Leu Ile Asn Leu
            980
```

<210> SEQ ID NO 62
<211> LENGTH: 56
<212> TYPE: PRT
<213> ORGANISM: Glycine max

<400> SEQUENCE: 62

Leu Thr Asp Leu Ser Ile Phe Asn Val Ser Ile Asn Gln Ile Ser Gly
1 5 10 15

Ser Val Pro Asp Glu Ile Arg Phe Met Leu Ser Leu Thr Thr Leu Asp
20 25 30

Leu Ser Tyr Asn Asn Phe Ile Gly Lys Val Pro Thr Gly Gly Gln Phe
35 40 45

Leu Val Phe Ser Asp Lys Ser Phe
50 55

<210> SEQ ID NO 63
<211> LENGTH: 987
<212> TYPE: PRT
<213> ORGANISM: Glycine max

<400> SEQUENCE: 63

Met Arg Ser Cys Val Cys Tyr Thr Leu Leu Leu Phe Ile Phe Phe Ile
1 5 10 15

Trp Leu Arg Val Ala Thr Cys Ser Ser Phe Thr Asp Met Glu Ser Leu
20 25 30

Leu Lys Leu Lys Asp Ser Met Lys Gly Asp Lys Ala Lys Asp Asp Ala
35 40 45

Leu His Asp Trp Lys Phe Phe Pro Ser Leu Ser Ala His Cys Phe Phe
50 55 60

Ser Gly Val Lys Cys Asp Arg Glu Leu Arg Val Val Ala Ile Asn Val
65 70 75 80

Ser Phe Val Pro Leu Phe Gly His Leu Pro Pro Glu Ile Gly Gln Leu
85 90 95

Asp Lys Leu Glu Asn Leu Thr Val Ser Gln Asn Asn Leu Thr Gly Val
100 105 110

Leu Pro Lys Glu Leu Ala Ala Leu Thr Ser Leu Lys His Leu Asn Ile
115 120 125

Ser His Asn Val Phe Ser Gly His Phe Pro Gly Gln Ile Ile Leu Pro
130 135 140

Met Thr Lys Leu Glu Val Leu Asp Val Tyr Asp Asn Asn Phe Thr Gly
145 150 155 160

Pro Leu Pro Val Glu Leu Val Lys Leu Glu Lys Leu Lys Tyr Leu Lys
165 170 175

Leu Asp Gly Asn Tyr Phe Ser Gly Ser Ile Pro Glu Ser Tyr Ser Glu
180 185 190

Phe Lys Ser Leu Glu Phe Leu Ser Leu Ser Thr Asn Ser Leu Ser Gly
195 200 205

Lys Ile Pro Lys Ser Leu Ser Lys Leu Lys Thr Leu Arg Tyr Leu Lys
210 215 220

Leu Gly Tyr Asn Asn Ala Tyr Glu Gly Gly Ile Pro Pro Glu Phe Gly
225 230 235 240

Ser Met Lys Ser Leu Arg Tyr Leu Asp Leu Ser Ser Cys Asn Leu Ser
245 250 255

Gly Glu Ile Pro Pro Ser Leu Ala Asn Leu Thr Asn Leu Asp Thr Leu
260 265 270

-continued

```
Phe Leu Gln Ile Asn Asn Leu Thr Gly Thr Ile Pro Ser Glu Leu Ser
        275                 280                 285

Ala Met Val Ser Leu Met Ser Leu Asp Leu Ser Ile Asn Asp Leu Thr
    290                 295                 300

Gly Glu Ile Pro Met Ser Phe Ser Gln Leu Arg Asn Leu Thr Leu Met
305                 310                 315                 320

Asn Phe Phe Gln Asn Asn Leu Arg Gly Ser Val Pro Ser Phe Val Gly
                325                 330                 335

Glu Leu Pro Asn Leu Glu Thr Leu Gln Leu Trp Asp Asn Asn Phe Ser
            340                 345                 350

Phe Val Leu Pro Pro Asn Leu Gly Gln Asn Gly Lys Leu Lys Phe Phe
        355                 360                 365

Asp Val Ile Lys Asn His Phe Thr Gly Leu Ile Pro Arg Asp Leu Cys
    370                 375                 380

Lys Ser Gly Arg Leu Gln Thr Ile Met Ile Thr Asp Asn Phe Phe Arg
385                 390                 395                 400

Gly Pro Ile Pro Asn Glu Ile Gly Asn Cys Lys Ser Leu Thr Lys Ile
                405                 410                 415

Arg Ala Ser Asn Asn Tyr Leu Asn Gly Val Val Pro Ser Gly Ile Phe
            420                 425                 430

Lys Leu Pro Ser Val Thr Ile Ile Glu Leu Ala Asn Asn Arg Phe Asn
        435                 440                 445

Gly Glu Leu Pro Pro Glu Ile Ser Gly Glu Ser Leu Gly Ile Leu Thr
    450                 455                 460

Leu Ser Asn Asn Leu Phe Ser Gly Lys Ile Pro Pro Ala Leu Lys Asn
465                 470                 475                 480

Leu Arg Ala Leu Gln Thr Leu Ser Leu Asp Ala Asn Glu Phe Val Gly
                485                 490                 495

Glu Ile Pro Gly Glu Val Phe Asp Leu Pro Met Leu Thr Val Val Asn
            500                 505                 510

Ile Ser Gly Asn Asn Leu Thr Gly Pro Ile Pro Thr Thr Leu Thr Arg
        515                 520                 525

Cys Val Ser Leu Thr Ala Val Asp Leu Ser Arg Asn Met Leu Glu Gly
    530                 535                 540

Lys Ile Pro Lys Gly Ile Lys Asn Leu Thr Asp Leu Ser Ile Phe Asn
545                 550                 555                 560

Val Ser Ile Asn Gln Ile Ser Gly Pro Val Pro Glu Glu Ile Arg Phe
                565                 570                 575

Met Leu Ser Leu Thr Thr Leu Asp Leu Ser Asn Asn Asn Phe Ile Gly
            580                 585                 590

Lys Val Pro Thr Gly Gly Gln Phe Ala Val Phe Ser Glu Lys Ser Phe
        595                 600                 605

Ala Gly Asn Pro Asn Leu Cys Thr Ser His Ser Cys Pro Asn Ser Ser
    610                 615                 620

Leu Tyr Pro Asp Asp Ala Leu Lys Lys Arg Arg Gly Pro Trp Ser Leu
625                 630                 635                 640

Lys Ser Thr Arg Val Ile Val Ile Val Ile Ala Leu Gly Thr Ala Ala
                645                 650                 655

Leu Leu Val Ala Val Thr Val Tyr Met Met Arg Arg Arg Lys Met Asn
            660                 665                 670

Leu Ala Lys Thr Trp Lys Leu Thr Ala Phe Gln Arg Leu Asn Phe Lys
        675                 680                 685

Ala Glu Asp Val Val Glu Cys Leu Lys Glu Glu Asn Ile Ile Gly Lys
```

-continued

```
    690                 695                 700

Gly Gly Ala Gly Ile Val Tyr Arg Gly Ser Met Pro Asn Gly Thr Asp
705                 710                 715                 720

Val Ala Ile Lys Arg Leu Val Gly Ala Gly Ser Gly Arg Asn Asp Tyr
                725                 730                 735

Gly Phe Lys Ala Glu Ile Glu Thr Leu Gly Lys Ile Arg His Arg Asn
            740                 745                 750

Ile Met Arg Leu Leu Gly Tyr Val Ser Asn Lys Glu Thr Asn Leu Leu
        755                 760                 765

Leu Tyr Glu Tyr Met Pro Asn Gly Ser Leu Gly Glu Trp Leu His Gly
    770                 775                 780

Ala Lys Gly Gly His Leu Lys Trp Glu Met Arg Tyr Lys Ile Ala Val
785                 790                 795                 800

Glu Ala Ala Lys Gly Leu Cys Tyr Leu His His Asp Cys Ser Pro Leu
                805                 810                 815

Ile Ile His Arg Asp Val Lys Ser Asn Asn Ile Leu Leu Asp Gly Asp
            820                 825                 830

Leu Glu Ala His Val Ala Asp Phe Gly Leu Ala Lys Phe Leu Tyr Asp
        835                 840                 845

Pro Gly Ala Ser Gln Ser Met Ser Ser Ile Ala Gly Ser Tyr Gly Tyr
    850                 855                 860

Ile Ala Pro Glu Tyr Ala Tyr Thr Leu Lys Val Asp Glu Lys Ser Asp
865                 870                 875                 880

Val Tyr Ser Phe Gly Val Val Leu Leu Glu Leu Ile Ile Gly Arg Lys
                885                 890                 895

Pro Val Gly Glu Phe Gly Asp Gly Val Asp Ile Val Gly Trp Val Asn
            900                 905                 910

Lys Thr Arg Leu Glu Leu Ala Gln Pro Ser Asp Ala Ala Leu Val Leu
        915                 920                 925

Ala Val Val Asp Pro Arg Leu Ser Gly Tyr Pro Leu Thr Ser Val Ile
    930                 935                 940

Tyr Met Phe Asn Ile Ala Met Met Cys Val Lys Glu Met Gly Pro Ala
945                 950                 955                 960

Arg Pro Thr Met Arg Glu Val Val His Met Leu Ser Glu Pro Pro His
                965                 970                 975

Ser Ala Thr His Thr His Asn Leu Ile Asn Leu
            980                 985


<210> SEQ ID NO 64
<211> LENGTH: 56
<212> TYPE: PRT
<213> ORGANISM: Glycine max

<400> SEQUENCE: 64

Leu Thr Asp Leu Ser Ile Phe Asn Val Ser Ile Asn Gln Ile Ser Gly
1               5                   10                  15

Pro Val Pro Glu Glu Ile Arg Phe Met Leu Ser Leu Thr Thr Leu Asp
            20                  25                  30

Leu Ser Asn Asn Asn Phe Ile Gly Lys Val Pro Thr Gly Gly Gln Phe
        35                  40                  45

Ala Val Phe Ser Glu Lys Ser Phe
    50                  55


<210> SEQ ID NO 65
<211> LENGTH: 1010
```

<212> TYPE: PRT
<213> ORGANISM: Glycine max

<400> SEQUENCE: 65

```
Met Arg Val Leu Val Leu Leu Met Leu Phe Leu His Ser Leu His Ala
1               5                   10                  15

Ala Arg Ile Ser Glu Tyr Arg Ala Leu Leu Ser Phe Lys Ala Ser Ser
            20                  25                  30

Ile Thr Asn Asp Pro Thr His Ala Leu Ser Ser Trp Asn Ser Ser Thr
        35                  40                  45

Pro Phe Cys Ser Trp Phe Gly Val Thr Cys Asp Ser Arg Arg His Val
    50                  55                  60

Thr Gly Leu Asn Leu Thr Ser Leu Ser Leu Ser Ala Thr Leu Tyr Asp
65                  70                  75                  80

His Leu Ser His Leu Pro Phe Leu Ser His Leu Ser Leu Ala Asp Asn
                85                  90                  95

Gln Phe Ser Gly Pro Ile Pro Val Ser Phe Ser Ala Leu Ser Ala Leu
            100                 105                 110

Arg Phe Leu Asn Leu Ser Asn Asn Val Phe Asn Gln Thr Phe Pro Ser
        115                 120                 125

Gln Leu Ala Arg Leu Ser Asn Leu Glu Val Leu Asp Leu Tyr Asn Asn
    130                 135                 140

Asn Met Thr Gly Pro Leu Pro Leu Ala Val Ala Ser Met Pro Leu Leu
145                 150                 155                 160

Arg His Leu His Leu Gly Gly Asn Phe Phe Ser Gly Gln Ile Pro Pro
                165                 170                 175

Glu Tyr Gly Thr Trp Gln His Leu Arg Tyr Leu Ala Leu Ser Gly Asn
            180                 185                 190

Glu Leu Ala Gly Tyr Ile Ala Pro Glu Leu Gly Asn Leu Ser Ala Leu
        195                 200                 205

Arg Glu Leu Tyr Ile Gly Tyr Tyr Asn Thr Tyr Ser Gly Gly Ile Pro
    210                 215                 220

Pro Glu Ile Gly Asn Leu Ser Asn Leu Val Arg Leu Asp Ala Ala Tyr
225                 230                 235                 240

Cys Gly Leu Ser Gly Glu Ile Pro Ala Glu Leu Gly Lys Leu Gln Asn
                245                 250                 255

Leu Asp Thr Leu Phe Leu Gln Val Asn Ser Leu Ser Gly Ser Leu Thr
            260                 265                 270

Ser Glu Leu Gly Asn Leu Lys Ser Leu Lys Ser Met Asp Leu Ser Asn
        275                 280                 285

Asn Met Leu Ser Gly Glu Val Pro Ala Ser Phe Ala Glu Leu Lys Asn
    290                 295                 300

Leu Thr Leu Leu Asn Leu Phe Arg Asn Lys Leu His Gly Ala Ile Pro
305                 310                 315                 320

Glu Phe Val Gly Glu Leu Pro Ala Leu Glu Val Leu Gln Leu Trp Glu
                325                 330                 335

Asn Asn Phe Thr Gly Ser Ile Pro Gln Ser Leu Gly Lys Asn Gly Arg
            340                 345                 350

Leu Thr Leu Val Asp Leu Ser Ser Asn Lys Ile Thr Gly Thr Leu Pro
        355                 360                 365

Pro Tyr Met Cys Tyr Gly Asn Arg Leu Gln Thr Leu Ile Thr Leu Gly
    370                 375                 380

Asn Tyr Leu Phe Gly Pro Ile Pro Asp Ser Leu Gly Lys Cys Glu Ser
385                 390                 395                 400
```

Leu Asn Arg Ile Arg Met Gly Glu Asn Phe Leu Asn Gly Ser Ile Pro
405 410 415

Lys Gly Leu Phe Gly Leu Pro Lys Leu Thr Gln Val Glu Leu Gln Asp
420 425 430

Asn Leu Leu Thr Gly Gln Phe Pro Glu Tyr Gly Ser Ile Ala Thr Asp
435 440 445

Leu Gly Gln Ile Ser Leu Ser Asn Asn Lys Leu Ser Gly Pro Leu Pro
450 455 460

Ser Thr Ile Gly Asn Phe Thr Ser Met Gln Lys Leu Leu Leu Asp Gly
465 470 475 480

Asn Glu Phe Ser Gly Arg Ile Pro Pro Gln Ile Gly Arg Leu Gln Gln
485 490 495

Leu Ser Lys Ile Asp Phe Ser His Asn Lys Phe Ser Gly Pro Ile Ala
500 505 510

Pro Glu Ile Ser Arg Cys Lys Leu Leu Thr Phe Ile Asp Leu Ser Gly
515 520 525

Asn Glu Leu Ser Gly Glu Ile Pro Asn Gln Ile Thr Ser Met Arg Ile
530 535 540

Leu Asn Tyr Leu Asn Leu Ser Arg Asn His Leu Asp Gly Ser Ile Pro
545 550 555 560

Gly Ser Ile Ala Ser Met Gln Ser Leu Thr Ser Val Asp Phe Ser Tyr
565 570 575

Asn Asn Phe Ser Gly Leu Val Pro Gly Thr Gly Gln Phe Gly Tyr Phe
580 585 590

Asn Tyr Thr Ser Phe Leu Gly Asn Pro Glu Leu Cys Gly Pro Tyr Leu
595 600 605

Gly Pro Cys Lys Asp Gly Val Ala Asn Gly Pro Arg Gln Pro His Val
610 615 620

Lys Gly Pro Leu Ser Ser Ser Leu Lys Leu Leu Leu Val Ile Gly Leu
625 630 635 640

Leu Val Cys Ser Ile Leu Phe Ala Val Ala Ala Ile Ile Lys Ala Arg
645 650 655

Ala Leu Lys Lys Ala Ser Glu Ala Arg Ala Trp Lys Leu Thr Ala Phe
660 665 670

Gln Arg Leu Asp Phe Thr Val Asp Asp Val Leu Asp Cys Leu Lys Glu
675 680 685

Asp Asn Ile Ile Gly Lys Gly Gly Ala Gly Ile Val Tyr Lys Gly Ala
690 695 700

Met Pro Asn Gly Asp Asn Val Ala Val Lys Arg Leu Pro Ala Met Ser
705 710 715 720

Arg Gly Ser Ser His Asp His Gly Phe Asn Ala Glu Ile Gln Thr Leu
725 730 735

Gly Arg Ile Arg His Arg His Ile Val Arg Leu Leu Gly Phe Cys Ser
740 745 750

Asn His Glu Thr Asn Leu Leu Val Tyr Glu Tyr Met Pro Asn Gly Ser
755 760 765

Leu Gly Glu Val Leu His Gly Lys Lys Gly Gly His Leu His Trp Tyr
770 775 780

Thr Arg Tyr Lys Ile Ala Val Glu Ala Ser Lys Gly Leu Cys Tyr Leu
785 790 795 800

His His Asp Cys Ser Pro Leu Ile Val His Arg Asp Val Lys Ser Asn
805 810 815

Asn Ile Leu Leu Asp Ser Asn Phe Glu Ala His Val Ala Asp Phe Gly
820 825 830

Leu Ala Lys Phe Leu Gln Asp Ser Gly Ala Ser Glu Cys Met Ser Ala
835 840 845

Ile Ala Gly Ser Tyr Gly Tyr Ile Ala Pro Glu Tyr Ala Tyr Thr Leu
850 855 860

Lys Val Asp Glu Lys Ser Asp Val Tyr Ser Phe Gly Val Val Leu Leu
865 870 875 880

Glu Leu Val Thr Gly Arg Lys Pro Val Gly Glu Phe Gly Asp Gly Val
885 890 895

Asp Ile Val Gln Trp Val Arg Lys Met Thr Asp Ser Asn Lys Glu Gly
900 905 910

Val Leu Lys Val Leu Asp Pro Arg Leu Pro Ser Val Pro Leu His Glu
915 920 925

Val Met His Val Phe Tyr Val Ala Met Leu Cys Val Glu Glu Gln Ala
930 935 940

Val Glu Arg Pro Thr Met Arg Glu Val Val Gln Ile Leu Thr Glu Leu
945 950 955 960

Pro Lys Pro Pro Ser Ser Lys Gln Gly Asp Leu Thr Ile Thr Glu Ser
965 970 975

Ser Leu Ser Ser Ser Asn Ser Leu Glu Ser Pro Thr Thr Ala Ser Lys
980 985 990

Glu Pro Lys Asp Gln His Pro Pro Gln Ser Pro Pro Thr Asp Leu Leu
995 1000 1005

Ser Ile
1010

<210> SEQ ID NO 66
<211> LENGTH: 56
<212> TYPE: PRT
<213> ORGANISM: Glycine max

<400> SEQUENCE: 66

Met Arg Ile Leu Asn Tyr Leu Asn Leu Ser Arg Asn His Leu Asp Gly
1 5 10 15

Ser Ile Pro Gly Ser Ile Ala Ser Met Gln Ser Leu Thr Ser Val Asp
20 25 30

Phe Ser Tyr Asn Asn Phe Ser Gly Leu Val Pro Gly Thr Gly Gln Phe
35 40 45

Gly Tyr Phe Asn Tyr Thr Ser Phe
50 55

<210> SEQ ID NO 67
<211> LENGTH: 1018
<212> TYPE: PRT
<213> ORGANISM: Phaseolus vulgaris

<400> SEQUENCE: 67

Met Arg Leu Leu Leu Cys Pro Leu Phe Phe Ile Val Phe Phe Ile Phe
1 5 10 15

His Ser His Lys Leu Thr Ala Ala Arg Ile Ser Glu Tyr Arg Ala Leu
20 25 30

Leu Ser Phe Lys Ala Ser Ser Ile Thr Asp Asp Pro Thr Asn Ala Leu
35 40 45

Ser Ser Trp Asn Ser Ser Thr Thr Tyr Cys Ser Trp Leu Gly Ile Thr
50 55 60

-continued

```
Cys Asp Ser Arg Leu His Val Thr Thr Leu Asn Leu Thr Ser Ser Ser
65                  70                  75                  80

Leu Ser Gly Thr Leu Tyr Asp His Leu Ser His Leu Pro Phe Leu Ser
                85                  90                  95

Tyr Leu Ser Leu Ala Asp Asn Gln Phe Ser Gly Pro Ile Pro Ala Ser
            100                 105                 110

Phe Ser Ser Leu Ser Ala Leu Arg His Leu Asn Leu Ser Asn Asn Ala
        115                 120                 125

Phe Asn Ala Thr Phe Pro Ser Asn Leu Ser Arg Leu Ala Asn Leu Gln
    130                 135                 140

Val Leu Asp Leu Tyr Asn Asn Asn Met Thr Gly Pro Leu Pro Leu Ala
145                 150                 155                 160

Val Ala Ser Met Pro Leu Leu Arg His Leu His Leu Gly Gly Asn Phe
                165                 170                 175

Phe Ser Gly Gln Ile Pro Pro Glu Tyr Gly Thr Trp Gln His Leu Gln
            180                 185                 190

Tyr Leu Ala Val Ser Gly Asn Glu Leu Ser Gly Asn Ile Pro Pro Glu
        195                 200                 205

Leu Gly Asn Leu Thr Ala Leu Arg Glu Leu Tyr Ile Gly Tyr Tyr Asn
    210                 215                 220

Ala Tyr Ser Gly Gly Ile Pro Pro Glu Ile Gly Asn Leu Ser Gln Leu
225                 230                 235                 240

Val Arg Phe Asp Ala Ala Tyr Cys Gly Leu Ser Gly Glu Ile Pro Ala
                245                 250                 255

Asp Leu Gly Arg Leu Gln Asn Met Asp Thr Leu Phe Leu Gln Val Asn
            260                 265                 270

Ala Leu Ser Gly Ser Leu Thr Pro Glu Leu Gly Asn Leu Lys Ser Leu
        275                 280                 285

Lys Ser Met Asp Leu Ser Asn Asn Ile Leu Ser Gly Glu Val Pro Ala
    290                 295                 300

Ser Phe Thr Glu Leu Lys Asn Leu Thr Leu Leu Asn Leu Phe Arg Asn
305                 310                 315                 320

Lys Leu His Gly Ala Ile Pro Glu Phe Val Gly Glu Leu Pro Ala Leu
                325                 330                 335

Glu Val Leu Gln Leu Trp Glu Asn Asn Phe Thr Gly Ser Ile Pro Gln
            340                 345                 350

Ser Leu Gly Arg Asn Gly Lys Leu Thr Val Val Asp Leu Ser Ser Asn
        355                 360                 365

Lys Leu Thr Gly Met Leu Pro Pro Asp Met Cys Tyr Gly Asn Arg Leu
    370                 375                 380

Gln Thr Leu Ile Thr Leu Gly Asn Tyr Leu Phe Gly Pro Ile Pro Asp
385                 390                 395                 400

Ser Ile Gly Lys Cys Glu Ser Leu Asn Arg Ile Arg Met Gly Glu Asn
                405                 410                 415

Phe Leu Asn Gly Ser Ile Pro Ile Gly Leu Phe Gly Leu Pro Lys Leu
            420                 425                 430

Thr Gln Val Glu Leu Gln Asn Asn Leu Leu Thr Gly Gln Phe Pro Glu
        435                 440                 445

Gly Gly Ser Ile Ala Val Asn Leu Gly Gln Ile Ser Leu Ser Asn Asn
    450                 455                 460

Lys Leu Ser Gly Ser Leu Pro Pro Thr Ile Gly Asn Phe Thr Ser Met
465                 470                 475                 480

Gln Lys Leu Leu Leu Asp Gly Asn Lys Phe Ser Gly Gln Ile Pro Ser
```

-continued

```
                485                 490                 495

Gln Ile Gly Arg Leu Gln Gln Leu Ser Lys Ile Asp Phe Ser Arg Asn
            500                 505                 510

Glu Phe Ser Gly Pro Ile Ala Pro Glu Ile Ser Arg Cys Lys Leu Leu
        515                 520                 525

Thr Phe Ile Asp Leu Ser Arg Asn Glu Leu Ser Gly Glu Ile Pro Asn
    530                 535                 540

Gln Ile Thr Ala Met Arg Ile Leu Asn Tyr Leu Asn Leu Ser Arg Asn
545                 550                 555                 560

His Leu Val Gly Ser Ile Pro Gly Ser Ile Ala Ser Met Gln Ser Leu
                565                 570                 575

Thr Ser Val Asp Phe Ser Tyr Asn Asn Leu Ser Gly Leu Val Pro Gly
            580                 585                 590

Thr Gly Gln Phe Gly Tyr Phe Asn Tyr Thr Ser Phe Leu Gly Asn Pro
        595                 600                 605

Glu Leu Cys Gly Pro Tyr Leu Gly Pro Cys Lys Asp Gly Val Ser Asn
    610                 615                 620

Gly Pro Arg Gln Pro His Leu Lys Gly Pro Leu Ser Ser Ser Leu Lys
625                 630                 635                 640

Leu Leu Leu Val Val Gly Leu Leu Val Cys Ser Ile Ala Phe Ala Val
                645                 650                 655

Ala Ala Ile Ile Lys Ala Arg Ala Leu Lys Lys Ala Ser Glu Ala Arg
            660                 665                 670

Ala Trp Lys Leu Thr Ala Phe Gln Arg Leu Asp Phe Thr Ala Asp Asp
        675                 680                 685

Val Leu Asp Ser Leu Lys Glu Asp Asn Ile Ile Gly Lys Gly Gly Ala
    690                 695                 700

Gly Ile Val Tyr Lys Gly Ala Met Pro Asn Gly Asp Gln Val Ala Val
705                 710                 715                 720

Lys Arg Leu Pro Ala Met Ser Arg Gly Ser Ser His Asp His Gly Phe
                725                 730                 735

Asn Ala Glu Ile Gln Thr Leu Gly Arg Ile Arg His Arg His Ile Val
            740                 745                 750

Arg Leu Leu Gly Phe Cys Ser Asn His Glu Thr Asn Leu Leu Val Tyr
        755                 760                 765

Glu Tyr Met Pro Asn Gly Ser Leu Gly Glu Val Leu His Gly Lys Lys
    770                 775                 780

Gly Gly His Leu His Trp Asp Thr Arg Tyr Lys Ile Ala Val Glu Ala
785                 790                 795                 800

Ser Lys Gly Leu Cys Tyr Leu His His Asp Cys Ser Pro Leu Ile Val
                805                 810                 815

His Arg Asp Val Lys Ser Asn Asn Ile Leu Leu Asp Ser Asn Phe Glu
            820                 825                 830

Ala His Val Ala Asp Phe Gly Leu Ala Lys Phe Leu Gln Asp Ser Gly
        835                 840                 845

Thr Ser Glu Cys Met Ser Ala Ile Ala Gly Ser Tyr Gly Tyr Ile Ala
    850                 855                 860

Pro Glu Tyr Ala Tyr Thr Leu Lys Val Asp Glu Lys Ser Asp Val Tyr
865                 870                 875                 880

Ser Phe Gly Val Val Leu Leu Glu Leu Val Thr Gly Arg Lys Pro Val
                885                 890                 895

Gly Glu Phe Gly Asp Gly Val Asp Ile Val Gln Trp Val Arg Lys Met
            900                 905                 910
```

Thr Asp Ser Asn Lys Glu Gly Val Leu Lys Val Leu Asp Pro Arg Leu
915 920 925

Pro Ser Val Pro Leu His Glu Val Met His Val Phe Tyr Val Ala Met
930 935 940

Leu Cys Val Glu Glu Gln Ala Val Glu Arg Pro Thr Met Arg Glu Val
945 950 955 960

Val Gln Ile Leu Thr Glu Leu Pro Lys Ser Ala Ser Ser Lys Gln Gly
965 970 975

Asp Leu Thr Ile Thr Glu Ser Ser Leu Pro Ser Ser Asn Ser Leu Glu
980 985 990

Ser Pro Thr Thr Ala Ser Met Glu Pro Lys Asp Asn Gln His Leu Pro
995 1000 1005

Gln Ser Ser Pro Pro Asp Leu Leu Ser Ile
1010 1015

<210> SEQ ID NO 68
<211> LENGTH: 56
<212> TYPE: PRT
<213> ORGANISM: Phaseolus vulgaris

<400> SEQUENCE: 68

Met Arg Ile Leu Asn Tyr Leu Asn Leu Ser Arg Asn His Leu Val Gly
1 5 10 15

Ser Ile Pro Gly Ser Ile Ala Ser Met Gln Ser Leu Thr Ser Val Asp
20 25 30

Phe Ser Tyr Asn Asn Leu Ser Gly Leu Val Pro Gly Thr Gly Gln Phe
35 40 45

Gly Tyr Phe Asn Tyr Thr Ser Phe
50 55

<210> SEQ ID NO 69
<211> LENGTH: 1008
<212> TYPE: PRT
<213> ORGANISM: Phaseolus vulgaris

<400> SEQUENCE: 69

Met Ser Lys Glu Gly Ala Ala Lys Cys Met Ser Arg Arg Lys Glu Glu
1 5 10 15

Arg Glu Met Arg Asn Gly Val Cys Tyr Arg Leu Leu Phe Leu Val Leu
20 25 30

Val Trp Phe Ser Val Ala Lys Cys Ser Ser Phe Ser Asp Met Asp Ala
35 40 45

Leu Arg Lys Leu Lys Asp Ser Met Lys Gly Ala Lys Ala Lys Asp Asp
50 55 60

Ala Leu His Asp Trp Lys Phe Ser Thr Ser Leu Ser Ala His Cys Leu
65 70 75 80

Phe Pro Gly Val Thr Cys Asp Gln Asp Leu Arg Val Val Ala Ile Asn
85 90 95

Val Ser Phe Val Pro Leu Phe Gly Asn Leu Pro Pro Glu Ile Gly His
100 105 110

Phe Asp Lys Leu Gln Asn Leu Thr Ile Thr Gln Asn Asn Leu Thr Gly
115 120 125

Gln Leu Pro Lys Glu Leu Ala Ala Leu Thr Ser Leu Lys Leu Leu Asn
130 135 140

Ile Ser His Asn Ser Phe Ser His Tyr Phe Pro Gly Gln Ser Phe Leu
145 150 155 160

-continued

```
Pro Ile Thr Gln Leu Glu Val Phe Asp Ala Tyr Asp Asn Asn Phe Ile
                165                 170                 175

Gly Gln Leu Pro Glu Glu Phe Val Lys Leu Glu Lys Leu Arg Tyr Leu
            180                 185                 190

Lys Leu Asp Gly Asn Tyr Phe Ser Gly Ser Ile Pro Glu Ser Tyr Ser
        195                 200                 205

Glu Phe Lys Ser Leu Glu Phe Leu Ser Leu Ser Thr Asn Ser Leu Ser
    210                 215                 220

Gly Lys Ile Pro Glu Ser Leu Ser Arg Leu Lys Thr Leu Lys Tyr Leu
225                 230                 235                 240

Lys Leu Gly Tyr Asn Asn Ala Tyr Glu Gly Gly Ile Pro Pro Glu Phe
                245                 250                 255

Gly Ala Met Lys Ser Leu Ile Tyr Leu Asp Leu Ser Ser Cys Asn Leu
            260                 265                 270

Ser Gly Glu Ile Pro Pro Ser Leu Ser Ser Leu Lys Lys Leu Asp Thr
        275                 280                 285

Leu Phe Leu Gln Met Asn Asn Leu Thr Gly Thr Ile Pro Ser Glu Phe
    290                 295                 300

Ser Ala Met Glu Ser Leu Met Ser Leu Asp Leu Ser Phe Asn Gly Leu
305                 310                 315                 320

Thr Gly Glu Ile Pro Gln Ser Phe Ser Gln Leu Arg Asn Leu Thr Leu
                325                 330                 335

Met Asn Phe Phe His Asn Lys Leu Ser Gly Ser Val Pro Ala Phe Val
            340                 345                 350

Gly Glu Leu Pro Asn Leu Glu Thr Leu Gln Leu Trp Glu Asn Asn Phe
        355                 360                 365

Ser Phe Val Leu Pro Pro Asn Leu Gly Gln Asn Gly Arg Leu Lys Phe
    370                 375                 380

Phe Asp Val Thr Thr Asn His Phe Thr Gly Leu Ile Pro Pro Gly Leu
385                 390                 395                 400

Cys Lys Ser Gly Arg Leu Gln Thr Phe Leu Ile Thr Asp Asn Phe Phe
                405                 410                 415

His Gly Gln Ile Pro Asp Asp Ile Gly Asn Cys Lys Ser Leu Val Lys
            420                 425                 430

Ile Arg Ala Ser Asn Asn Tyr Leu Ser Gly Ala Ile Pro Ser Gly Ile
        435                 440                 445

Phe Lys Leu Pro Ser Val Lys Ile Ile Glu Leu Ala Asn Asn Arg Phe
    450                 455                 460

Asp Gly Glu Leu Pro Pro Glu Ile Ser Gly Asp Ser Leu Gly Ile Leu
465                 470                 475                 480

Thr Leu Ser Asn Asn Leu Leu Thr Gly Arg Ile Pro Pro Ala Leu Lys
                485                 490                 495

Asn Leu Arg Ala Leu Gln Thr Leu Ser Leu Asp Ala Asn Glu Leu Val
            500                 505                 510

Gly Glu Ile Pro Gly Glu Val Phe Val Leu Pro Met Leu Thr Thr Val
        515                 520                 525

Asn Ile Ser Gly Asn Asn Leu Thr Gly Ala Ile Pro Thr Thr Leu Ile
    530                 535                 540

His Cys Val Ser Leu Ser Ser Val Asp Leu Ser Arg Asn Met Leu Val
545                 550                 555                 560

Gly Glu Ile Pro Lys Gly Ile Lys Asn Leu Thr Asp Leu Ser Ile Leu
                565                 570                 575
```

-continued

```
Asn Val Ser Arg Asn Leu Ile Thr Gly Pro Ile Pro Asp Glu Ile Arg
            580                 585                 590

Phe Met Ala Ser Leu Thr Thr Leu Asp Leu Ser Tyr Asn Asn Phe Lys
        595                 600                 605

Gly Lys Leu Pro Thr Gly Gly Gln Phe Phe Val Phe Ser Asp Lys Ser
    610                 615                 620

Phe Glu Gly Asn Pro Asn Leu Cys Ser Ser Arg Ser Cys Pro Asn Ser
625                 630                 635                 640

Ser Met Tyr Pro Asp Asp Ala Phe Arg Arg Arg Arg Gly Pro Trp Ser
                645                 650                 655

Ser Lys Gln Thr Arg Ala Ile Ile Thr Val Ile Ala Ile Ala Thr Ala
            660                 665                 670

Ala Leu Leu Val Ala Val Thr Val Tyr Met Met Arg Arg Arg Met Leu
        675                 680                 685

His Arg Ala Met Thr Trp Lys Leu Thr Ala Phe Gln Arg Leu Asn Trp
    690                 695                 700

Lys Ala Glu Asp Val Val Glu Cys Leu Lys Glu Glu Asn Ile Ile Gly
705                 710                 715                 720

Lys Gly Gly Ala Gly Ile Val Tyr Arg Gly Ser Met Pro Asn Gly Thr
                725                 730                 735

Asp Val Ala Ile Lys Arg Leu Val Gly Ala Gly Ser Gly Arg Asn Asp
            740                 745                 750

Tyr Gly Phe Arg Ala Glu Ile Glu Thr Leu Gly Lys Ile Arg His Arg
        755                 760                 765

Asn Ile Met Arg Leu Leu Gly Tyr Val Ser Asn Lys Glu Thr Asn Leu
    770                 775                 780

Leu Leu Tyr Glu Tyr Met Pro Asn Gly Ser Leu Gly Glu Trp Leu His
785                 790                 795                 800

Gly Ala Lys Gly Gly His Leu Arg Trp Glu Met Arg Phe Lys Ile Ala
                805                 810                 815

Val Glu Ala Ala Arg Gly Leu Cys Tyr Leu His His Asp Cys Ser Pro
            820                 825                 830

Leu Ile Ile His Arg Asp Val Lys Ser Asn Asn Ile Leu Leu Asp Glu
        835                 840                 845

Asn Phe Glu Ala His Val Ala Asp Phe Gly Leu Ala Lys Phe Leu His
    850                 855                 860

Asp Pro Gly Ala Ser Gln Ser Met Ser Ser Ile Ala Gly Ser Tyr Gly
865                 870                 875                 880

Tyr Ile Ala Pro Glu Tyr Ala Tyr Thr Leu Lys Val Asp Glu Lys Ser
                885                 890                 895

Asp Val Tyr Ser Phe Gly Val Val Leu Leu Glu Leu Ile Ile Gly Arg
            900                 905                 910

Lys Pro Val Gly Glu Phe Gly Asp Gly Val Asp Ile Val Gly Trp Ile
        915                 920                 925

Asn Lys Thr Arg Leu Glu Ile Ser Pro Pro Ser Asp Ala Ala Leu Val
    930                 935                 940

Leu Ala Val Val Asp Pro Arg Leu Ser Gly Tyr Pro Leu Thr Ser Val
945                 950                 955                 960

Ile Tyr Met Phe Asn Ile Gly Met Met Cys Val Arg Glu Met Gly Pro
                965                 970                 975

Ala Arg Pro Thr Met Arg Glu Val Val His Met Leu Thr Asn Pro Pro
            980                 985                 990

His Ser Thr Thr His Thr His Thr  His Asn His Asn Leu  Ile Asn Leu
```

995 1000 1005

<210> SEQ ID NO 70
<211> LENGTH: 55
<212> TYPE: PRT
<213> ORGANISM: Solanum lycopersicum

<400> SEQUENCE: 70

Leu Thr Asp Leu Ser Ile Leu Asn Val Ser Arg Asn Leu Ile Thr Gly
1 5 10 15

Pro Ile Pro Asp Glu Ile Arg Phe Met Ala Ser Leu Thr Thr Leu Asp
20 25 30

Leu Ser Tyr Asn Asn Phe Lys Gly Lys Leu Pro Thr Gly Gly Gln Phe
35 40 45

Phe Val Phe Ser Asp Lys Ser
50 55

<210> SEQ ID NO 71
<211> LENGTH: 1019
<212> TYPE: PRT
<213> ORGANISM: Cucumis sativus

<400> SEQUENCE: 71

Met Arg Leu Leu Leu Leu Leu Leu Leu Cys Leu Leu His Leu Gln Leu
1 5 10 15

His Ile His His Ser Leu Ser Ala Arg Val Ser Glu Tyr Arg Ala Leu
20 25 30

Leu Ser Leu Lys Thr Ser Ile Thr Gly Asp Pro Lys Ser Ser Leu Ala
35 40 45

Ser Trp Asn Ala Ser Thr Ser His Cys Thr Trp Phe Gly Val Thr Cys
50 55 60

Asp Leu Arg Arg His Val Thr Ala Leu Asp Leu Thr Ala Leu Gly Leu
65 70 75 80

Ser Gly Ser Leu Ser Pro Asp Val Ala Phe Leu Arg Phe Leu Thr Asn
85 90 95

Leu Ser Leu Ala Ala Asn Glu Phe Ser Gly Pro Ile Pro Pro Glu Leu
100 105 110

Ser Ser Ile Ser Ser Leu Arg Leu Leu Asn Leu Ser Asn Asn Val Phe
115 120 125

Asp Gly Ser Phe Pro Ser Arg Phe Ser Gln Leu Gln Asn Leu His Val
130 135 140

Leu Asp Leu Tyr Asn Asn Asn Met Thr Gly Asp Phe Pro Ile Val Val
145 150 155 160

Thr Gln Met Ser Gly Leu Arg His Leu His Leu Gly Gly Asn Phe Phe
165 170 175

Ala Gly Arg Ile Pro Pro Glu Val Gly Arg Met Gln Ser Leu Glu Tyr
180 185 190

Leu Ala Val Ser Gly Asn Glu Leu Ser Gly Ser Ile Pro Pro Glu Leu
195 200 205

Gly Asn Leu Thr Asn Leu Arg Glu Leu Tyr Ile Gly Tyr Phe Asn Ala
210 215 220

Tyr Asp Gly Gly Leu Pro Ala Glu Ile Gly Asn Leu Ser Gln Leu Val
225 230 235 240

Arg Leu Asp Ala Ala Asn Cys Gly Leu Ser Gly Arg Ile Pro Pro Glu
245 250 255

Leu Gly Lys Leu Gln Asn Leu Asp Thr Leu Phe Leu Gln Val Asn Ala

```
            260                 265                 270

Leu Ser Gly Pro Leu Thr Pro Glu Ile Gly Gln Leu Asn Ser Leu Lys
        275                 280                 285

Ser Leu Asp Leu Ser Asn Asn Met Leu Val Gly Glu Ile Pro Val Ser
    290                 295                 300

Phe Ala Gln Leu Lys Asn Leu Thr Leu Leu Asn Leu Phe Arg Asn Lys
305                 310                 315                 320

Leu His Gly Ala Ile Pro Ser Phe Ile Gly Asp Leu Pro Lys Leu Glu
                325                 330                 335

Val Leu Gln Leu Trp Glu Asn Asn Phe Thr Glu Ala Ile Pro Gln Asn
            340                 345                 350

Leu Gly Lys Asn Gly Met Leu Gln Ile Leu Asp Leu Ser Ser Asn Lys
        355                 360                 365

Leu Thr Gly Thr Leu Pro Pro Asp Met Cys Phe Gly Asn Arg Leu Gln
    370                 375                 380

Ile Leu Ile Ala Leu Ser Asn Phe Leu Phe Gly Pro Ile Pro Glu Ser
385                 390                 395                 400

Leu Gly Lys Cys Val Ser Leu Asn Arg Ile Arg Met Gly Glu Asn Phe
                405                 410                 415

Leu Asn Gly Ser Ile Pro Lys Gly Leu Leu Ser Leu Pro Lys Leu Ser
            420                 425                 430

Gln Val Glu Leu Gln Asp Asn Phe Leu Ser Gly Glu Phe Pro Ile Thr
        435                 440                 445

Asp Ser Ile Ser Leu Asn Leu Gly Gln Ile Ser Leu Ser Asn Asn Arg
    450                 455                 460

Leu Thr Gly Ser Ile Pro Pro Thr Ile Gly Asn Phe Ser Gly Val Gln
465                 470                 475                 480

Lys Leu Leu Leu Asp Gly Asn Lys Phe Ser Gly Gln Ile Pro Pro Glu
                485                 490                 495

Ile Gly Arg Leu Gln Gln Leu Ser Lys Ile Asp Phe Ser Ser Asn Met
            500                 505                 510

Leu Ser Gly Pro Ile Ala Pro Glu Ile Ser Gln Cys Lys Leu Leu Thr
        515                 520                 525

Phe Val Asp Leu Ser Arg Asn Gln Leu Ser Gly Glu Ile Pro Asn Glu
    530                 535                 540

Ile Thr Ser Met Arg Ile Leu Asn Tyr Leu Asn Leu Ser Lys Asn His
545                 550                 555                 560

Leu Val Gly Gly Ile Pro Ala Thr Ile Ala Ser Met Gln Ser Leu Thr
                565                 570                 575

Ser Val Asp Phe Ser Tyr Asn Asn Leu Ser Gly Leu Val Pro Gly Thr
            580                 585                 590

Gly Gln Phe Ser Tyr Phe Asn Tyr Thr Ser Phe Leu Gly Asn Pro Asp
        595                 600                 605

Leu Cys Gly Pro Tyr Leu Gly Pro Cys Lys Asp Gly Val Ala Asn Ser
    610                 615                 620

Asn Tyr Gln Gln His Val Lys Gly Pro Leu Ser Ala Ser Leu Lys Leu
625                 630                 635                 640

Leu Leu Val Ile Gly Leu Leu Leu Cys Ser Ile Ala Phe Ala Val Ala
                645                 650                 655

Ala Ile Ile Lys Ala Arg Ser Leu Lys Arg Ala Ser Glu Ser Arg Ala
            660                 665                 670

Trp Lys Leu Thr Ser Phe Gln Arg Leu Asp Phe Thr Val Asp Asp Val
        675                 680                 685
```

Leu Asp Cys Leu Lys Glu Asp Asn Ile Ile Gly Lys Gly Gly Ala Gly
    690                 695                 700

Ile Val Tyr Lys Gly Ala Met Ser Ser Gly Asp Gln Val Ala Val Lys
705                 710                 715                 720

Arg Leu Pro Ala Met Ser Arg Gly Ser Ser His Asp His Gly Phe Asn
                725                 730                 735

Ala Glu Ile Gln Thr Leu Gly Arg Ile Arg His Arg His Ile Val Arg
            740                 745                 750

Leu Leu Gly Phe Cys Ser Asn His Glu Thr Asn Leu Leu Ile Tyr Glu
        755                 760                 765

Phe Met Pro Asn Gly Ser Leu Gly Glu Val Leu His Gly Lys Lys Gly
    770                 775                 780

Gly His Leu Gln Trp Asp Thr Arg Tyr Lys Ile Ala Ile Glu Ala Ala
785                 790                 795                 800

Lys Gly Leu Cys Tyr Leu His His Asp Cys Ser Pro Leu Ile Val His
                805                 810                 815

Arg Asp Val Lys Ser Asn Asn Ile Leu Leu Asp Thr Asn Phe Glu Ala
            820                 825                 830

His Val Ala Asp Phe Gly Leu Ala Lys Phe Leu Gln Asp Ser Gly Thr
        835                 840                 845

Ser Glu Cys Met Ser Ala Ile Ala Gly Ser Tyr Gly Tyr Ile Ala Pro
    850                 855                 860

Glu Tyr Ala Tyr Thr Leu Lys Val Asp Glu Lys Ser Asp Val Tyr Ser
865                 870                 875                 880

Phe Gly Val Val Leu Leu Glu Leu Val Ser Gly Arg Lys Pro Val Gly
                885                 890                 895

Glu Phe Gly Asp Gly Val Asp Ile Val Gln Trp Val Arg Lys Met Thr
            900                 905                 910

Asp Ser Asn Lys Glu Glu Val Val Lys Ile Leu Asp Pro Arg Leu Ser
        915                 920                 925

Ser Val Pro Leu His Glu Val Met His Val Phe Tyr Val Ala Met Leu
    930                 935                 940

Cys Val Glu Glu Gln Ala Val Glu Arg Pro Thr Met Arg Glu Val Ile
945                 950                 955                 960

Gln Ile Leu Ser Glu Ile Pro Gln Pro Pro Ser Ser Lys Gln Gly Gly
                965                 970                 975

Asp Ser Thr Leu Pro Asn Ser Ser Pro Pro Pro Pro Pro Thr Ala Ala
            980                 985                 990

Asp Leu Asp Leu Pro Thr Thr Gly  Thr Lys Asn Lys Lys  Glu His Gln
        995                 1000                1005

Gln Gln  Gln Pro Pro Pro Asp  Leu Leu Ser Ile
    1010                1015

<210> SEQ ID NO 72
<211> LENGTH: 56
<212> TYPE: PRT
<213> ORGANISM: Cucumis sativus

<400> SEQUENCE: 72

Met Arg Ile Leu Asn Tyr Leu Asn Leu Ser Lys Asn His Leu Val Gly
1               5                   10                  15

Gly Ile Pro Ala Thr Ile Ala Ser Met Gln Ser Leu Thr Ser Val Asp
            20                  25                  30

Phe Ser Tyr Asn Asn Leu Ser Gly Leu Val Pro Gly Thr Gly Gln Phe

```
        35                  40                  45

Ser Tyr Phe Asn Tyr Thr Ser Phe
    50                  55


<210> SEQ ID NO 73
<211> LENGTH: 973
<212> TYPE: PRT
<213> ORGANISM: Cucumis sativus

<400> SEQUENCE: 73

Met Lys Arg Arg Pro Ile Asp Pro Phe Val Gly Arg Leu Ser Ser Phe
1               5                   10                  15

Phe Ile Phe Leu Phe Tyr Ala Ser Leu Cys Phe Ala Asn Arg Asp Met
            20                  25                  30

Glu Ala Leu Leu Lys Ile Lys Ser Ser Met Ile Gly Pro Gly Arg Ser
        35                  40                  45

Glu Leu Gly Asp Trp Glu Pro Ser Pro Thr Ser Ser Pro Ser Ala His
    50                  55                  60

Cys Asp Phe Ser Gly Val Thr Cys Asp Gly Asp Asn Arg Val Val Ala
65                  70                  75                  80

Leu Asn Val Ser Asn Leu Arg Leu Phe Ser Ser Ile Pro Pro Glu Ile
                85                  90                  95

Gly Met Leu Glu Lys Ile Glu Asn Leu Thr Leu Val Ser Asn Asn Leu
            100                 105                 110

Thr Gly Lys Leu Pro Leu Glu Met Ala Lys Leu Thr Ser Leu Lys Phe
        115                 120                 125

Leu Asn Leu Ser Asn Asn Ala Phe Arg Asp Asn Leu Thr Ala Glu Ile
    130                 135                 140

Thr Val Glu Met Thr Glu Leu Glu Val Phe Asp Ile Tyr Asn Asn Asn
145                 150                 155                 160

Phe Phe Gly Leu Leu Pro Val Glu Phe Val Lys Leu Lys Lys Leu Lys
                165                 170                 175

His Leu Asp Leu Gly Gly Cys Phe Phe Thr Gly Gln Ile Pro Ala Val
            180                 185                 190

Tyr Ser Glu Met Gln Ser Leu Glu Phe Leu Ser Val Arg Gly Asn Met
        195                 200                 205

Leu Thr Gly Arg Ile Pro Ala Ser Leu Gly Arg Leu Lys Asn Leu Arg
    210                 215                 220

Tyr Leu Tyr Ala Gly Tyr Phe Asn His Tyr Asp Gly Gly Ile Pro Ala
225                 230                 235                 240

Glu Phe Gly Ser Leu Ser Ser Leu Glu Leu Ile Asp Leu Ala Asn Cys
                245                 250                 255

Asn Leu Thr Gly Glu Ile Pro Pro Ser Leu Gly Asn Leu Lys His Leu
            260                 265                 270

His Ser Leu Phe Leu Gln Val Asn Asn Leu Thr Gly Arg Ile Pro Ser
        275                 280                 285

Glu Leu Ser Gly Leu Ile Ser Leu Lys Ser Leu Asp Leu Ser Leu Asn
    290                 295                 300

Glu Leu Thr Gly Glu Ile Pro Ser Ser Phe Val Ala Leu Gln Asn Leu
305                 310                 315                 320

Thr Leu Ile Asn Leu Phe Asn Asn Lys Leu His Gly Pro Ile Pro Gly
                325                 330                 335

Phe Val Gly Asp Phe Pro His Leu Glu Val Leu Gln Leu Trp Asn Asn
            340                 345                 350
```

```
Asn Phe Thr Leu Glu Leu Pro Glu Asn Leu Gly Arg Asn Ser Lys Leu
        355                 360                 365

Phe Leu Leu Asp Val Ala Thr Asn His Leu Thr Gly Leu Ile Pro Pro
    370                 375                 380

Asp Leu Cys Asn Gly Arg Leu Lys Thr Leu Ile Leu Leu Asp Asn Tyr
385                 390                 395                 400

Phe Phe Gly Pro Ile Pro Glu Lys Leu Gly Arg Cys Asp Ser Leu Thr
                405                 410                 415

Lys Ile Arg Ile Ala Gly Asn Phe Phe Asn Gly Thr Val Pro Ala Gly
            420                 425                 430

Phe Phe Asn Phe Pro Ala Leu Glu Gln Leu Asp Ile Ser Asn Asn Tyr
        435                 440                 445

Phe Ser Gly Ala Leu Pro Ala Gln Met Ser Gly Glu Phe Leu Gly Ser
    450                 455                 460

Leu Leu Leu Ser Asn Asn His Ile Thr Gly Asp Ile Pro Ala Ala Ile
465                 470                 475                 480

Lys Asn Leu Glu Asn Leu Gln Val Val Ser Leu Glu His Asn Gln Phe
                485                 490                 495

Thr Gly Asn Leu Pro Lys Glu Ile Phe Gln Leu Asn Lys Leu Leu Arg
            500                 505                 510

Ile Asn Ile Ser Phe Asn Asn Ile Ser Gly Glu Ile Pro Tyr Ser Val
        515                 520                 525

Val Gln Cys Thr Ser Leu Thr Leu Val Asp Leu Ser Glu Asn Tyr Leu
    530                 535                 540

Val Gly Val Ile Pro Arg Gly Ile Ser Lys Leu Lys Ile Leu Ser Val
545                 550                 555                 560

Leu Asn Leu Ser Arg Asn His Leu Thr Gly Gln Ile Pro Asn Glu Ile
                565                 570                 575

Arg Ser Met Met Ser Leu Thr Thr Leu Asp Leu Ser Tyr Asn Asn Phe
            580                 585                 590

Phe Gly Lys Ile Pro Ser Gly Gly Gln Phe Ser Val Phe Asn Val Ser
        595                 600                 605

Ala Phe Ile Gly Asn Pro Asn Leu Cys Phe Pro Asn His Gly Pro Cys
    610                 615                 620

Ala Ser Leu Arg Lys Asn Ser Lys Tyr Val Lys Leu Ile Ile Pro Ile
625                 630                 635                 640

Val Ala Ile Phe Ile Val Leu Leu Cys Val Leu Thr Ala Leu Tyr Leu
                645                 650                 655

Arg Lys Arg Lys Lys Ile Gln Lys Ser Lys Ala Trp Lys Leu Thr Ala
            660                 665                 670

Phe Gln Arg Leu Asn Phe Lys Ala Glu Asp Val Leu Glu Cys Leu Lys
        675                 680                 685

Asp Glu Asn Ile Ile Gly Lys Gly Gly Ala Gly Val Val Tyr Arg Gly
    690                 695                 700

Ser Met Pro Asp Gly Ser Val Val Ala Ile Lys Leu Leu Leu Gly Ser
705                 710                 715                 720

Gly Arg Asn Asp His Gly Phe Ser Ala Glu Ile Gln Thr Leu Gly Arg
                725                 730                 735

Ile Lys His Arg Asn Ile Val Arg Leu Leu Gly Tyr Val Ser Asn Arg
            740                 745                 750

Asp Thr Asn Leu Leu Leu Tyr Glu Tyr Met Pro Asn Gly Ser Leu Asp
        755                 760                 765

Gln Ser Leu His Gly Val Lys Gly Gly His Leu His Trp Asp Leu Arg
```

```
    770                 775                 780

Tyr Lys Ile Ala Ile Glu Ala Ala Lys Gly Leu Cys Tyr Leu His His
785                 790                 795                 800

Asp Cys Thr Pro Leu Ile Ile His Arg Asp Val Lys Ser Asn Asn Ile
                805                 810                 815

Leu Leu Asp Lys Leu Phe Glu Ala His Val Ser Asp Phe Gly Leu Ala
            820                 825                 830

Lys Phe Leu Gln Asn Gly Gly Ala Ser Glu Cys Met Ser Ser Ile Ala
        835                 840                 845

Gly Ser Tyr Gly Tyr Ile Ala Pro Glu Tyr Ala Tyr Thr Leu Lys Val
    850                 855                 860

Asp Glu Lys Ser Asp Val Tyr Ser Phe Gly Val Val Leu Leu Glu Leu
865                 870                 875                 880

Ile Ala Gly Arg Lys Pro Val Gly Asp Phe Gly Glu Gly Val Asp Ile
                885                 890                 895

Val Arg Trp Val Leu Lys Thr Thr Ser Glu Leu Ser Gln Pro Ser Asp
            900                 905                 910

Ala Ala Ser Val Leu Ala Val Val Asp Ser Arg Leu Thr Glu Tyr Pro
        915                 920                 925

Leu Gln Ala Val Ile His Leu Phe Lys Ile Ala Met Met Cys Val Glu
    930                 935                 940

Glu Asp Ser Ser Ala Arg Pro Thr Met Arg Glu Val Val His Met Leu
945                 950                 955                 960

Ser Asn Pro Pro Arg Ser Ala Pro Thr Leu Ile Asn Leu
                965                 970


<210> SEQ ID NO 74
<211> LENGTH: 56
<212> TYPE: PRT
<213> ORGANISM: Cucumis sativus

<400> SEQUENCE: 74

Leu Lys Ile Leu Ser Val Leu Asn Leu Ser Arg Asn His Leu Thr Gly
1               5                   10                  15

Gln Ile Pro Asn Glu Ile Arg Ser Met Met Ser Leu Thr Thr Leu Asp
            20                  25                  30

Leu Ser Tyr Asn Asn Phe Phe Gly Lys Ile Pro Ser Gly Gly Gln Phe
        35                  40                  45

Ser Val Phe Asn Val Ser Ala Phe
    50                  55


<210> SEQ ID NO 75
<211> LENGTH: 1018
<212> TYPE: PRT
<213> ORGANISM: Theobroma cacao

<400> SEQUENCE: 75

Met Arg Leu Leu Leu Leu Leu Leu Phe Leu Leu Leu Pro Ile Ser His
1               5                   10                  15

Ser Ser Ala Ala Arg Pro Val Ser Glu Phe Arg Ala Leu Leu Ala Val
            20                  25                  30

Lys Ser Ser Phe Thr Asp Asp Pro Glu Ser Tyr Leu Ser Asn Trp Asn
        35                  40                  45

Ala Thr Thr Arg Phe Cys Ser Phe Thr Gly Val Ala Cys Asp Tyr Thr
    50                  55                  60

Gly Arg His Val Thr Ser Ile Asp Leu Ser Asn Phe Asn Leu Ser Gly
```

-continued

```
65                  70                  75                  80

Thr Leu Ser Pro Ser Phe Ser His Leu Arg Phe Leu Gln Ser Leu Ser
                85                  90                  95

Leu Ala Ala Asn Gln Ile Ser Gly Pro Ile Pro Thr Glu Leu Ala Ala
            100                 105                 110

Leu Ser Ser Leu Arg Tyr Phe Asn Leu Ser Asn Asn Val Phe Asn Gly
        115                 120                 125

Ser Phe Pro Ser Gln Leu Ser Gln Leu Lys Asn Leu Gln Val Leu Asp
    130                 135                 140

Leu Tyr Asn Asn Asn Met Thr Gly Glu Leu Pro Ile Ser Val Thr Glu
145                 150                 155                 160

Leu Pro Asn Leu Leu His Leu His Leu Gly Gly Asn Phe Phe Ser Gly
                165                 170                 175

Gln Ile Pro Ser Ser Tyr Gly Arg Trp Glu Phe Leu Glu Tyr Leu Ala
            180                 185                 190

Val Ser Gly Asn Glu Leu Asp Gly Lys Ile Pro Pro Glu Ile Gly Asn
        195                 200                 205

Leu Thr Lys Leu Gln Gln Leu Tyr Ile Gly Tyr Tyr Asn Ser Phe Glu
    210                 215                 220

Gly Gly Leu Pro Pro Glu Ile Gly Asn Leu Ser Glu Leu Val Arg Phe
225                 230                 235                 240

Asp Ala Ala Asn Cys Met Leu Ser Gly Glu Ile Pro Pro Glu Ile Gly
                245                 250                 255

Lys Leu Gln Lys Leu Asp Thr Leu Phe Leu Gln Val Asn Ala Leu Ser
            260                 265                 270

Gly Ser Leu Thr Pro Glu Leu Gly Thr Leu Lys Ser Leu Lys Ser Met
        275                 280                 285

Asp Leu Ser Asn Asn Met Leu Ala Gly Glu Ile Pro Glu Ser Phe Ala
    290                 295                 300

Asn Leu Lys Asn Leu Thr Leu Leu Asn Leu Phe Arg Asn Lys Leu His
305                 310                 315                 320

Gly Gln Ile Pro Glu Phe Ile Gly Glu Leu Pro Glu Leu Glu Val Leu
                325                 330                 335

Gln Leu Trp Glu Asn Asn Phe Thr Gly Ser Ile Pro Gln Gln Leu Gly
            340                 345                 350

Ser Asn Lys Lys Leu Gln Leu Leu Asp Leu Ser Ser Asn Lys Leu Thr
        355                 360                 365

Gly Thr Leu Pro Leu Asp Met Cys Ser Gly Asn Thr Leu His Thr Leu
    370                 375                 380

Ile Thr Leu Gly Asn Phe Leu Phe Gly Pro Ile Pro Glu Ser Leu Gly
385                 390                 395                 400

Lys Cys Glu Ser Leu Ser Arg Ile Arg Met Gly Glu Asn Phe Leu Asn
                405                 410                 415

Gly Ser Ile Pro Lys Gly Leu Phe Gly Leu Pro Lys Leu Thr Gln Val
            420                 425                 430

Glu Leu Gln Asp Asn Tyr Leu Thr Gly Glu Phe Pro Val Thr Glu Ser
        435                 440                 445

Ser Ile Ser Ala Asn Leu Gly Gln Ile Ser Leu Ser Asn Asn Lys Leu
    450                 455                 460

Ser Gly Thr Leu Pro Ala Ser Val Gly Asn Phe Ser Gly Val Gln Lys
465                 470                 475                 480

Leu Leu Leu Asp Gly Asn Lys Phe Ser Gly Arg Ile Pro Ala Glu Ile
                485                 490                 495
```

```
Gly Lys Leu Gln Gln Leu Ser Lys Met Asp Phe Ser His Asn Lys Phe
            500                 505                 510

Ser Gly Thr Ile Ala Pro Glu Ile Ser Lys Cys Lys Leu Leu Thr Phe
        515                 520                 525

Val Asp Leu Ser Arg Asn Glu Leu Ser Gly Glu Ile Pro Thr Glu Ile
    530                 535                 540

Thr Gly Met Arg Ile Leu Asn Tyr Leu Asn Leu Ser Arg Asn His Leu
545                 550                 555                 560

Ile Gly Ser Ile Pro Ser Ser Ile Ala Thr Met Gln Ser Leu Thr Ser
                565                 570                 575

Val Asp Phe Ser Tyr Asn Asn Leu Ser Gly Leu Val Pro Gly Thr Gly
            580                 585                 590

Gln Phe Ser Tyr Phe Asn Tyr Thr Ser Phe Leu Gly Asn Pro Glu Leu
        595                 600                 605

Cys Gly Pro Tyr Leu Gly Pro Cys Lys Asp Gly Val Ala Asn Gly Thr
    610                 615                 620

His Gln Thr His Val Lys Gly Gly Leu Ser Ala Ser Leu Lys Leu Leu
625                 630                 635                 640

Leu Val Ile Gly Leu Leu Val Cys Ser Ile Leu Phe Ala Val Ala Ala
                645                 650                 655

Ile Ile Lys Ala Arg Ser Leu Lys Lys Ala Ser Glu Ser Arg Ser Trp
            660                 665                 670

Lys Leu Thr Ala Phe Gln Arg Leu Asp Phe Thr Cys Asp Asp Val Leu
        675                 680                 685

Asp Cys Leu Lys Glu Asp Asn Ile Ile Gly Lys Gly Gly Ala Gly Ile
    690                 695                 700

Val Tyr Lys Gly Ala Met Pro Asn Gly Asp Gln Val Ala Val Lys Arg
705                 710                 715                 720

Leu Pro Ala Met Ser Arg Gly Ser Ser His Asp His Gly Phe Asn Ala
                725                 730                 735

Glu Ile Gln Thr Leu Gly Arg Ile Arg His Arg His Ile Val Arg Leu
            740                 745                 750

Leu Gly Phe Cys Ser Asn His Glu Thr Asn Leu Leu Val Tyr Glu Tyr
        755                 760                 765

Met Pro Asn Gly Ser Leu Gly Glu Val Leu His Gly Lys Lys Gly Gly
    770                 775                 780

His Leu His Trp Asp Thr Arg Tyr Lys Ile Ala Val Glu Ala Ala Lys
785                 790                 795                 800

Gly Leu Cys Tyr Leu His His Asp Cys Ser Pro Leu Ile Val His Arg
                805                 810                 815

Asp Val Lys Ser Asn Asn Ile Leu Leu Asp Cys Asp Phe Glu Ala His
            820                 825                 830

Val Ala Asp Phe Gly Leu Ala Lys Phe Leu Gln Asp Ser Gly Thr Ser
        835                 840                 845

Glu Cys Met Ser Ala Ile Ala Gly Ser Tyr Gly Tyr Ile Ala Pro Glu
    850                 855                 860

Tyr Ala Tyr Thr Leu Lys Val Asp Glu Lys Ser Asp Val Tyr Ser Phe
865                 870                 875                 880

Gly Val Val Leu Leu Glu Leu Val Ser Gly Arg Lys Pro Val Gly Glu
                885                 890                 895

Phe Gly Asp Gly Val Asp Ile Val Gln Trp Val Arg Lys Met Thr Asp
            900                 905                 910
```

```
Ser Asn Lys Glu Gly Val Leu Lys Ile Leu Asp Pro Arg Leu Pro Ser
        915                 920                 925

Val Pro Leu His Glu Val Met His Val Phe Tyr Val Ala Met Leu Cys
    930                 935                 940

Val Glu Glu Gln Ala Val Glu Arg Pro Thr Met Arg Glu Val Val Gln
945                 950                 955                 960

Ile Leu Thr Glu Leu Pro Lys Pro Pro Asn Ser Lys Gln Gly Asp Ser
                965                 970                 975

Thr Val Thr Glu Ser Leu Pro Ser Pro Gly Thr Ser Leu Asp Ser Pro
            980                 985                 990

Asn Ala Thr Thr Lys Asp Gln Lys  Asp Gln Gln Gln Pro  Pro Ala Pro
        995                 1000                 1005

Lys Ser  Pro Pro Pro Asp Leu  Leu Ser Ile
    1010                 1015


<210> SEQ ID NO 76
<211> LENGTH: 56
<212> TYPE: PRT
<213> ORGANISM: Theobroma cacao

<400> SEQUENCE: 76

Met Arg Ile Leu Asn Tyr Leu Asn Leu Ser Arg Asn His Leu Ile Gly
1               5                   10                  15

Ser Ile Pro Ser Ser Ile Ala Thr Met Gln Ser Leu Thr Ser Val Asp
            20                  25                  30

Phe Ser Tyr Asn Asn Leu Ser Gly Leu Val Pro Gly Thr Gly Gln Phe
        35                  40                  45

Ser Tyr Phe Asn Tyr Thr Ser Phe
    50                  55


<210> SEQ ID NO 77
<211> LENGTH: 982
<212> TYPE: PRT
<213> ORGANISM: Theobroma cacao

<400> SEQUENCE: 77

Met Arg Ser Val Cys Ser His Leu Leu Leu Asp Ile Ser Leu Ile Leu
1               5                   10                  15

Leu Leu Phe Ser Ala Ser Ser Asn Gly Tyr Ser Asp Leu Glu Val Leu
            20                  25                  30

Leu Lys Leu Lys Ser Ser Met Ile Gly Pro Lys Gly Ser Gly Leu Glu
        35                  40                  45

Asp Trp Glu Phe Ser Ser Ser Pro Ser Ala His Cys His Phe Ser Gly
    50                  55                  60

Val Gln Cys Asp Glu Glu Phe His Val Val Ser Leu Asn Ala Ser Phe
65                  70                  75                  80

Ala Pro Leu Ser Gly Thr Ile Pro Pro Glu Ile Gly Leu Leu Asn Lys
                85                  90                  95

Leu Val Asn Leu Thr Ile Ala Ala Ala Asn Leu Thr Gly Lys Ile Pro
            100                 105                 110

Val Glu Met Gly Asn Leu Thr Ser Leu Lys Leu Phe Asn Ile Ser Asn
        115                 120                 125

Asn Val Phe Lys Gly Ser Phe Pro Gly Glu Ile Leu Thr Gly Met Thr
    130                 135                 140

Glu Leu Glu Ile Leu Asp Ala Tyr Asn Asn Asn Phe Thr Gly Leu Leu
145                 150                 155                 160
```

-continued

```
Pro Ile Glu Val Ala Asn Leu Thr Asn Ile Lys His Leu Cys Leu Gly
                165                 170                 175

Gly Asn Phe Phe Thr Gly Glu Ile Pro Glu Lys Tyr Ser Asp Ile Gln
            180                 185                 190

Ser Leu Glu Tyr Leu Gly Leu Asn Gly Ile Gly Leu Thr Gly Lys Ser
        195                 200                 205

Pro Ala Phe Leu Ala Arg Leu Lys Asn Leu Lys Glu Met Tyr Ile Gly
    210                 215                 220

Tyr Phe Asn Ala Tyr Val Gly Glu Ile Pro Pro Glu Phe Gly Thr Leu
225                 230                 235                 240

Ser Gln Leu Gln Val Leu Asp Met Ala Ser Cys Asn Leu Thr Gly Glu
                245                 250                 255

Ile Pro Val Ser Leu Ser Asn Leu Lys His Leu His Thr Leu Phe Leu
            260                 265                 270

Gln Leu Asn Arg Leu Thr Gly Arg Ile Pro Ser Glu Leu Ser Gly Leu
        275                 280                 285

Ile Ser Leu Lys Ser Leu Asp Leu Ser Ile Asn Glu Leu Thr Gly Glu
    290                 295                 300

Ile Pro Glu Ser Phe Ser Ala Leu Gln Asn Ile Thr Leu Ile His Leu
305                 310                 315                 320

Phe Lys Asn Asn Leu Tyr Gly Pro Ile Pro Ser Phe Val Gly Asp Phe
                325                 330                 335

Pro His Leu Glu Val Leu Gln Val Trp Gly Asn Asn Phe Thr Arg Glu
            340                 345                 350

Leu Pro Glu Asn Leu Gly Arg Asn Gly Lys Leu Phe Lys Leu Asp Val
        355                 360                 365

Thr Ser Asn His Leu Thr Gly Leu Ile Pro Arg His Leu Cys Glu Gly
    370                 375                 380

Gly Arg Leu Glu Thr Leu Ile Leu Met Asp Asn Phe Phe Phe Gly Pro
385                 390                 395                 400

Leu Pro Arg Glu Leu Gly Asn Cys Thr Ser Leu Thr Lys Ile Arg Ile
                405                 410                 415

Met Lys Asn Leu Leu Asn Gly Thr Ile Pro Ala Gly Ile Phe Asn Leu
            420                 425                 430

Pro Leu Leu Ser Ile Val Glu Leu Asn Asp Asn Phe Phe Ser Gly Glu
        435                 440                 445

Leu Pro Thr Gln Met Ser Gly Ala Ser Leu Gly Gln Leu Lys Val Ser
    450                 455                 460

Asn Asn Trp Ile Thr Gly Lys Ile Pro Pro Ala Ile Ser Asn Leu Arg
465                 470                 475                 480

Asn Leu Gln Val Leu Ser Leu Glu Met Asn Lys Phe Ser Gly Glu Ile
                485                 490                 495

Pro Glu Glu Ile Phe Asn Ile Lys Leu Leu Ser Lys Ile Asn Ile Ser
            500                 505                 510

Asp Asn Ser Ile Thr Gly Glu Ile Pro Pro Ser Ile Ser Arg Cys Thr
        515                 520                 525

Ser Leu Thr Ser Ile Asp Phe Ser Gln Asn Ser Leu Thr Gly Glu Ile
    530                 535                 540

Pro Lys Gly Ile Glu Lys Leu Lys Asp Leu Ser Ile Leu Asn Phe Ser
545                 550                 555                 560

Arg Asn Gln Leu Thr Gly Glu Ile Pro Gly Glu Ile Arg Tyr Met Ile
                565                 570                 575

Ser Leu Thr Thr Leu Asp Leu Ser Tyr Asn Asn Phe Val Gly Arg Ile
```

-continued

```
            580                 585                 590

Pro Ser Gly Gly Gln Phe Ser Val Phe Asn Asp Thr Ser Phe Thr Gly
        595                 600                 605

Asn Pro Asn Leu Cys Pro Pro Arg His Val Thr Cys Pro Ala Leu Met
    610                 615                 620

Asn Gln Ala Lys Gly Ser Gly His Gly Gln Ala Ala Ser Phe Thr Ala
625                 630                 635                 640

Ser Lys Leu Ile Ile Thr Ile Ile Thr Ser Ile Thr Ala Leu Ser Leu
                645                 650                 655

Ile Val Val Thr Val Tyr Arg Met Arg Lys Arg Arg Leu Gln Lys Ser
            660                 665                 670

Arg Ala Trp Lys Leu Thr Ala Phe Gln Arg Leu Asp Phe Lys Ala Glu
        675                 680                 685

Asp Val Leu Glu Cys Leu Lys Glu Glu Asn Ile Ile Gly Lys Gly Gly
    690                 695                 700

Ala Gly Ile Val Tyr Arg Gly Ser Met Pro Asp Gly Leu Asp Val Ala
705                 710                 715                 720

Ile Lys Arg Leu Val Gly Arg Gly Thr Gly Arg Ser Asp His Gly Phe
                725                 730                 735

Ser Ala Glu Ile Gln Thr Leu Gly Arg Ile Arg His Arg Asn Ile Val
            740                 745                 750

Arg Leu Leu Gly Tyr Val Ser Asn Lys Asp Thr Asn Leu Leu Leu Tyr
        755                 760                 765

Glu Tyr Met Pro Asn Gly Ser Leu Gly Glu Met Leu His Gly Ser Lys
    770                 775                 780

Gly Ala His Leu Gln Trp Glu Arg Arg Tyr Arg Ile Ala Val Glu Ala
785                 790                 795                 800

Ala Lys Gly Leu Cys Tyr Leu His His Asp Cys Ser Pro Leu Ile Ile
                805                 810                 815

His Arg Asp Val Lys Ser Asn Asn Ile Leu Leu Asp Glu Asp Tyr Glu
            820                 825                 830

Ser His Val Ala Asp Phe Gly Leu Ala Lys Phe Leu Gln Asp Ala Gly
        835                 840                 845

Ala Ser Glu Cys Met Ser Ser Ile Ala Gly Ser Tyr Gly Tyr Ile Ala
    850                 855                 860

Pro Glu Tyr Ala Tyr Thr Leu Lys Val Asp Glu Lys Ser Asp Val Tyr
865                 870                 875                 880

Ser Phe Gly Val Val Leu Leu Glu Leu Ile Ala Gly Arg Lys Pro Val
                885                 890                 895

Gly Glu Phe Gly Asp Gly Val Asp Ile Val Arg Trp Val Arg Lys Thr
            900                 905                 910

Thr Ser Glu Leu Pro Gln Pro Ser Asp Pro Ala Ser Val Leu Ala Val
        915                 920                 925

Val Asp Pro Arg Leu Ser Glu Tyr Pro Leu Thr Gly Val Ile Tyr Leu
    930                 935                 940

Phe Lys Val Ala Met Met Cys Val Glu Asp Glu Ser Ser Ala Arg Pro
945                 950                 955                 960

Thr Met Arg Glu Val Val His Met Leu Thr Asn Pro Pro Gln Ser Ala
                965                 970                 975

Pro Ser Leu Leu Asn Phe
            980
```

<210> SEQ ID NO 78

<211> LENGTH: 56
<212> TYPE: PRT
<213> ORGANISM: Theobroma cacao

<400> SEQUENCE: 78

Leu Lys Asp Leu Ser Ile Leu Asn Phe Ser Arg Asn Gln Leu Thr Gly
1 5 10 15

Glu Ile Pro Gly Glu Ile Arg Tyr Met Ile Ser Leu Thr Thr Leu Asp
20 25 30

Leu Ser Tyr Asn Asn Phe Val Gly Arg Ile Pro Ser Gly Gly Gln Phe
35 40 45

Ser Val Phe Asn Asp Thr Ser Phe
50 55

<210> SEQ ID NO 79
<211> LENGTH: 1034
<212> TYPE: PRT
<213> ORGANISM: Zea mays

<400> SEQUENCE: 79

Met Arg Leu Leu Pro Leu Leu Leu Leu Leu Ser Leu Ala Ala Val Ala
1 5 10 15

Ala Gly Thr Asp Ala Asp Ala Asp Ala Leu Leu Ala Ala Lys Ala Ala
20 25 30

Leu Ser Asp Pro Thr Gly Ala Leu Ala Ser Trp Asp Ala Ala Ser Ser
35 40 45

Asp His Cys Ala Trp Val Gly Val Thr Cys Ala Pro Arg Gly Ser Gly
50 55 60

Gly Gly Val Val Val Gly Leu Asp Val Ser Gly Leu Asn Leu Ser Gly
65 70 75 80

Ala Leu Pro Pro Ala Leu Ser Arg Leu Arg Gly Leu Gln Arg Leu Ser
85 90 95

Val Ala Ala Asn Gly Phe Tyr Gly Pro Ile Pro Pro Ser Leu Ala Arg
100 105 110

Leu Gln Leu Leu Val His Leu Asn Leu Ser Asn Asn Ala Phe Asn Gly
115 120 125

Ser Phe Pro Pro Ala Leu Ala Arg Leu Arg Ala Leu Arg Val Leu Asp
130 135 140

Leu Tyr Asn Asn Asn Leu Thr Ser Ala Thr Leu Pro Leu Glu Val Thr
145 150 155 160

His Met Pro Met Leu Arg His Leu His Leu Gly Gly Asn Phe Phe Ser
165 170 175

Gly Glu Ile Pro Pro Glu Tyr Gly Arg Trp Pro Arg Leu Gln Tyr Leu
180 185 190

Ala Val Ser Gly Asn Glu Leu Ser Gly Lys Ile Pro Pro Glu Leu Gly
195 200 205

Asn Leu Thr Ser Leu Arg Glu Leu Tyr Ile Gly Tyr Tyr Asn Ser Tyr
210 215 220

Thr Gly Gly Leu Pro Pro Glu Leu Gly Asn Leu Thr Glu Leu Val Arg
225 230 235 240

Leu Asp Ala Ala Asn Cys Gly Leu Ser Gly Glu Ile Pro Pro Glu Leu
245 250 255

Gly Arg Leu Gln Asn Leu Asp Thr Leu Phe Leu Gln Val Asn Gly Leu
260 265 270

Thr Gly Ser Ile Pro Ser Glu Leu Gly Tyr Leu Arg Ser Leu Ser Ser
275 280 285

-continued

```
Leu Asp Leu Ser Asn Asn Ala Leu Thr Gly Glu Ile Pro Ala Ser Phe
    290                 295                 300

Ser Glu Leu Lys Asn Leu Thr Leu Leu Asn Leu Phe Arg Asn Lys Leu
305                 310                 315                 320

Arg Gly Asp Ile Pro Gly Phe Val Gly Asp Leu Pro Ser Leu Glu Val
                325                 330                 335

Leu Gln Leu Trp Glu Asn Asn Phe Thr Gly Gly Val Pro Arg Arg Leu
            340                 345                 350

Gly Arg Asn Gly Arg Leu Gln Leu Leu Asp Leu Ser Ser Asn Lys Leu
        355                 360                 365

Thr Gly Thr Leu Pro Pro Glu Leu Cys Ala Gly Gly Lys Leu Gln Thr
    370                 375                 380

Leu Ile Ala Leu Gly Asn Phe Leu Phe Gly Ala Ile Pro Asp Ser Leu
385                 390                 395                 400

Gly Gln Cys Lys Ser Leu Ser Arg Val Arg Leu Gly Glu Asn Tyr Leu
                405                 410                 415

Asn Gly Ser Ile Pro Lys Gly Leu Phe Glu Leu Pro Lys Leu Thr Gln
            420                 425                 430

Val Glu Leu Gln Asp Asn Leu Leu Thr Gly Asn Phe Pro Ala Val Ile
        435                 440                 445

Gly Ala Ala Ala Pro Asn Leu Gly Glu Ile Ser Leu Ser Asn Asn Gln
    450                 455                 460

Leu Thr Gly Ala Leu Pro Ala Ser Leu Gly Asn Phe Ser Gly Val Gln
465                 470                 475                 480

Lys Leu Leu Leu Asp Gln Asn Ala Phe Ser Gly Ala Ile Pro Pro Glu
                485                 490                 495

Ile Gly Arg Leu Gln Gln Leu Ser Lys Ala Asp Leu Ser Ser Asn Lys
            500                 505                 510

Phe Glu Gly Gly Val Pro Pro Glu Val Gly Lys Cys Arg Leu Leu Thr
        515                 520                 525

Tyr Leu Asp Met Ser Gln Asn Asn Leu Ser Gly Lys Ile Pro Pro Ala
    530                 535                 540

Ile Ser Gly Met Arg Ile Leu Asn Tyr Leu Asn Leu Ser Arg Asn His
545                 550                 555                 560

Leu Asp Gly Glu Ile Pro Pro Ser Ile Ala Thr Met Gln Ser Leu Thr
                565                 570                 575

Ala Val Asp Phe Ser Tyr Asn Asn Leu Ser Gly Leu Val Pro Gly Thr
            580                 585                 590

Gly Gln Phe Ser Tyr Phe Asn Ala Thr Ser Phe Val Gly Asn Pro Gly
        595                 600                 605

Leu Cys Gly Pro Tyr Leu Gly Pro Cys Gly Ala Gly Ile Gly Gly Ala
    610                 615                 620

Asp His Ser Val His Gly His Gly Trp Leu Thr Asn Thr Val Lys Leu
625                 630                 635                 640

Leu Ile Val Leu Gly Leu Leu Ile Cys Ser Ile Ala Phe Ala Val Ala
                645                 650                 655

Ala Ile Leu Lys Ala Arg Ser Leu Lys Lys Ala Ser Glu Ala Arg Val
            660                 665                 670

Trp Lys Leu Thr Ala Phe Gln Arg Leu Asp Phe Thr Ser Asp Asp Val
        675                 680                 685

Leu Asp Cys Leu Lys Glu Glu His Ile Ile Gly Lys Gly Gly Ala Gly
    690                 695                 700
```

Ile Val Tyr Lys Gly Ala Met Pro Asn Gly Glu Leu Val Ala Val Lys
705 710 715 720

Arg Leu Pro Ala Met Gly Arg Gly Ser Ser His Asp His Gly Phe Ser
725 730 735

Ala Glu Ile Gln Thr Leu Gly Arg Ile Arg His Arg His Ile Val Arg
740 745 750

Leu Leu Gly Phe Cys Ser Asn Asn Glu Thr Asn Leu Leu Val Tyr Glu
755 760 765

Tyr Met Pro Asn Gly Ser Leu Gly Glu Met Leu His Gly Lys Lys Gly
770 775 780

Gly His Leu His Trp Asp Thr Arg Tyr Ser Ile Ala Ile Glu Ala Ala
785 790 795 800

Lys Gly Leu Cys Tyr Leu His His Asp Cys Ser Pro Leu Ile Leu His
805 810 815

Arg Asp Val Lys Ser Asn Asn Ile Leu Leu Asp Ser Asn Phe Glu Ala
820 825 830

His Val Ala Asp Phe Gly Leu Ala Lys Phe Leu Gln Asp Ser Gly Ala
835 840 845

Ser Glu Cys Met Ser Ala Ile Ala Gly Ser Tyr Gly Tyr Ile Ala Pro
850 855 860

Glu Tyr Ala Tyr Thr Leu Lys Val Asp Glu Lys Ser Asp Val Tyr Ser
865 870 875 880

Phe Gly Val Val Leu Leu Glu Leu Val Thr Gly Arg Lys Pro Val Gly
885 890 895

Glu Phe Gly Asp Gly Val Asp Ile Val Gln Trp Ala Lys Met Thr Thr
900 905 910

Asn Ser Asn Lys Glu Gln Val Met Lys Val Leu Asp Pro Arg Leu Ser
915 920 925

Thr Val Pro Leu His Glu Val Thr His Val Phe Tyr Val Ala Leu Leu
930 935 940

Cys Thr Glu Glu Gln Ser Val Gln Arg Pro Thr Met Arg Glu Val Val
945 950 955 960

Gln Ile Leu Ser Glu Leu Pro Lys Pro Pro Ser Thr Lys Gln Gly Glu
965 970 975

Glu Asn Ser Thr Lys Gln Gly Glu Glu Val Pro Asn Ser Gly Asp Gly
980 985 990

Ser Ala Pro Ser Pro Leu His Ser Ala Pro Val Gly Thr Asn Glu Ala
995 1000 1005

Pro Ala Val Glu Ala Arg Asp His Gln Gln Gln Thr Ser Ser Pro
1010 1015 1020

Ser Ser Pro Pro Pro Pro Asp Leu Ile Ser Ile
1025 1030

<210> SEQ ID NO 80
<211> LENGTH: 56
<212> TYPE: PRT
<213> ORGANISM: Zea mays

<400> SEQUENCE: 80

Met Arg Ile Leu Asn Tyr Leu Asn Leu Ser Arg Asn His Leu Asp Gly
1 5 10 15

Glu Ile Pro Pro Ser Ile Ala Thr Met Gln Ser Leu Thr Ala Val Asp
20 25 30

Phe Ser Tyr Asn Asn Leu Ser Gly Leu Val Pro Gly Thr Gly Gln Phe
35 40 45

```
Ser Tyr Phe Asn Ala Thr Ser Phe
    50                  55


<210> SEQ ID NO 81
<211> LENGTH: 1037
<212> TYPE: PRT
<213> ORGANISM: Zea mays

<400> SEQUENCE: 81

Met Pro Met Arg Leu Leu Leu Leu Leu Leu Leu Thr Phe Leu Ala Thr
1               5                   10                  15

Ala Ala Ala Val Ala Gly Ala Ala Gly Gly Ala Ala Ala Ala Gly Ser
            20                  25                  30

Asp Ala Asp Ala Leu Leu Ala Ala Lys Ala Val Leu Ser Asp Pro Ala
        35                  40                  45

Gly Ala Leu Ala Ser Trp Thr Asn Ala Thr Ser Thr Gly Ala Cys Ala
    50                  55                  60

Trp Ser Gly Val Thr Cys Asn Ala Arg Ala Ala Val Ile Gly Leu Asp
65                  70                  75                  80

Leu Ser Gly Arg Asn Leu Ser Gly Pro Val Pro Thr Ala Leu Ser Arg
                85                  90                  95

Leu Ala His Leu Ala Arg Leu Asp Leu Ala Ala Asn Ala Leu Cys Gly
            100                 105                 110

Pro Ile Pro Ala Pro Leu Ser Arg Leu Gln Ser Leu Thr His Leu Asn
        115                 120                 125

Leu Ser Asn Asn Val Leu Asn Gly Thr Phe Pro Pro Pro Leu Ala Arg
    130                 135                 140

Leu Arg Ala Leu Arg Val Leu Asp Leu Tyr Asn Asn Asn Leu Thr Gly
145                 150                 155                 160

Pro Leu Pro Leu Ala Val Val Gly Leu Pro Val Leu Arg His Leu His
                165                 170                 175

Leu Gly Gly Asn Phe Phe Ser Gly Glu Ile Pro Pro Glu Tyr Gly Arg
            180                 185                 190

Trp Arg Arg Leu Gln Tyr Leu Ala Val Ser Gly Asn Glu Leu Ser Gly
        195                 200                 205

Arg Ile Pro Pro Glu Leu Gly Gly Leu Thr Thr Leu Arg Glu Leu Tyr
    210                 215                 220

Ile Gly Tyr Tyr Asn Ser Tyr Ser Ser Gly Leu Pro Pro Glu Leu Gly
225                 230                 235                 240

Asn Met Thr Asp Leu Val Arg Leu Asp Ala Ala Asn Cys Gly Leu Ser
                245                 250                 255

Gly Glu Ile Pro Pro Glu Leu Gly Asn Leu Ala Asn Leu Asp Thr Leu
            260                 265                 270

Phe Leu Gln Val Asn Gly Leu Ala Gly Ala Ile Pro Pro Glu Leu Gly
        275                 280                 285

Arg Leu Lys Ser Leu Ser Ser Leu Asp Leu Ser Asn Asn Ala Leu Thr
    290                 295                 300

Gly Glu Ile Pro Ala Ser Phe Ala Ala Leu Arg Asn Leu Thr Leu Leu
305                 310                 315                 320

Asn Leu Phe Arg Asn Lys Leu Arg Gly Ser Ile Pro Glu Leu Val Gly
                325                 330                 335

Asp Leu Pro Ser Leu Glu Val Leu Gln Leu Trp Glu Asn Asn Phe Thr
            340                 345                 350

Gly Gly Ile Pro Arg Arg Leu Gly Arg Asn Gly Arg Leu Gln Leu Val
```

```
        355                 360                 365

Asp Leu Ser Ser Asn Arg Leu Thr Gly Thr Leu Pro Pro Glu Leu Cys
    370                 375                 380

Ala Gly Gly Lys Leu Glu Thr Leu Ile Ala Leu Gly Asn Phe Leu Phe
385                 390                 395                 400

Gly Ser Ile Pro Glu Pro Leu Gly Lys Cys Glu Ala Leu Ser Arg Ile
                405                 410                 415

Arg Leu Gly Glu Asn Tyr Leu Asn Gly Ser Ile Pro Asp Gly Leu Phe
            420                 425                 430

Glu Leu Pro Asn Leu Thr Gln Val Glu Leu Gln Asp Asn Leu Leu Ser
        435                 440                 445

Gly Gly Phe Pro Ala Val Ser Gly Thr Gly Ala Pro Asn Leu Gly Ala
    450                 455                 460

Ile Thr Leu Ser Asn Asn Gln Leu Thr Gly Ala Leu Pro Ala Ser Ile
465                 470                 475                 480

Gly Lys Phe Ser Gly Leu Gln Lys Leu Leu Leu Asp Gln Asn Ala Phe
                485                 490                 495

Thr Gly Ala Val Pro Pro Glu Ile Gly Arg Leu Gln Gln Leu Ser Lys
            500                 505                 510

Ala Asp Leu Ser Gly Asn Thr Leu Asp Gly Gly Val Pro Pro Glu Ile
        515                 520                 525

Gly Lys Cys Arg Leu Leu Thr Tyr Leu Asp Leu Ser Arg Asn Asn Leu
    530                 535                 540

Ser Gly Glu Ile Pro Pro Ala Ile Ser Gly Met Arg Ile Leu Asn Tyr
545                 550                 555                 560

Leu Asn Leu Ser Arg Asn His Leu Gly Gly Glu Ile Pro Ala Thr Ile
                565                 570                 575

Ala Ala Met Gln Ser Leu Thr Ala Val Asp Phe Ser Tyr Asn Asn Leu
            580                 585                 590

Ser Gly Leu Val Pro Ala Thr Gly Gln Phe Ser Tyr Phe Asn Ala Thr
        595                 600                 605

Ser Phe Val Gly Asn Pro Gly Leu Cys Gly Pro Tyr Leu Gly Pro Cys
    610                 615                 620

His Ser Gly Gly Ala Gly Thr Gly His Asp Ala His Thr Tyr Gly Gly
625                 630                 635                 640

Met Ser Asn Thr Phe Lys Leu Leu Ile Val Leu Gly Leu Leu Val Cys
                645                 650                 655

Ser Ile Ala Phe Ala Ala Met Ala Ile Leu Lys Ala Arg Ser Leu Lys
            660                 665                 670

Lys Ala Ser Glu Ala Arg Ala Trp Arg Leu Thr Ala Phe Gln Arg Leu
        675                 680                 685

Glu Phe Thr Cys Asp Asp Val Leu Asp Ser Leu Lys Glu Glu Asn Ile
    690                 695                 700

Ile Gly Lys Gly Gly Ala Gly Ile Val Tyr Lys Gly Thr Met Pro Asp
705                 710                 715                 720

Gly Glu His Val Ala Val Lys Arg Leu Ser Ser Met Ser Arg Gly Ser
                725                 730                 735

Ser His Asp His Gly Phe Ser Ala Glu Ile Gln Thr Leu Gly Arg Ile
            740                 745                 750

Arg His Arg Tyr Ile Val Arg Leu Leu Gly Phe Cys Ser Asn Asn Glu
        755                 760                 765

Thr Asn Leu Leu Val Tyr Glu Phe Met Pro Asn Gly Ser Leu Gly Glu
    770                 775                 780
```

Leu Leu His Gly Lys Lys Gly Gly His Leu His Trp Asp Thr Arg Tyr
785 790 795 800

Lys Ile Ala Val Glu Ala Ala Lys Gly Leu Ser Tyr Leu His His Asp
805 810 815

Cys Ser Pro Pro Ile Leu His Arg Asp Val Lys Ser Asn Asn Ile Leu
820 825 830

Leu Asp Ser Asp Phe Glu Ala His Val Ala Asp Phe Gly Leu Ala Lys
835 840 845

Phe Leu Gln Asp Ser Gly Ala Ser Gln Cys Met Ser Ala Ile Ala Gly
850 855 860

Ser Tyr Gly Tyr Ile Ala Pro Glu Tyr Ala Tyr Thr Leu Lys Val Asp
865 870 875 880

Glu Lys Ser Asp Val Tyr Ser Phe Gly Val Val Leu Leu Glu Leu Val
885 890 895

Thr Gly Lys Lys Pro Val Gly Glu Phe Gly Asp Gly Val Asp Ile Val
900 905 910

His Trp Val Arg Ser Thr Thr Ala Gly Ala Ser Lys Glu Gln Val Val
915 920 925

Lys Val Met Asp Pro Arg Leu Ser Ser Val Pro Val His Glu Val Ala
930 935 940

His Val Phe Cys Val Ala Leu Leu Cys Val Glu Glu Gln Ser Val Gln
945 950 955 960

Arg Pro Thr Met Arg Glu Val Val Gln Met Leu Gly Glu Leu Pro Lys
965 970 975

Pro Ala Ala Ala Ala Ala Ala Ala Gly Gln Gly Asp Glu Val Pro Gly
980 985 990

Ser Gly Asp Gly Asp Glu Cys Ser Ala Ala Pro Ser Gly Ala Pro Ala
995 1000 1005

Ala Asp Glu Ser Val Glu Ala Pro His Gly Glu Ala Thr Lys Glu
1010 1015 1020

Pro Ser Ser Gln Ser Ser Pro Thr Thr Asp Leu Ile Ser Ile
1025 1030 1035

<210> SEQ ID NO 82
<211> LENGTH: 56
<212> TYPE: PRT
<213> ORGANISM: Zea mays

<400> SEQUENCE: 82

Met Arg Ile Leu Asn Tyr Leu Asn Leu Ser Arg Asn His Leu Gly Gly
1 5 10 15

Glu Ile Pro Ala Thr Ile Ala Ala Met Gln Ser Leu Thr Ala Val Asp
20 25 30

Phe Ser Tyr Asn Asn Leu Ser Gly Leu Val Pro Ala Thr Gly Gln Phe
35 40 45

Ser Tyr Phe Asn Ala Thr Ser Phe
50 55

<210> SEQ ID NO 83
<211> LENGTH: 996
<212> TYPE: PRT
<213> ORGANISM: Zea mays

<400> SEQUENCE: 83

Met Pro Pro Pro Thr Phe Leu Leu Gly Leu Leu Leu Leu Leu Leu Leu
1 5 10 15

-continued

```
Ala Ala Ala Ala Pro Ala Pro Ala Ser Ala Thr Pro Glu Arg Asp Ala
            20                  25                  30

Tyr Ala Leu Ser Arg Leu Lys Ala Ser Leu Val Pro Ser Ala Thr Asn
        35                  40                  45

Ser Thr Ser Ala Pro Leu Ser Asp Trp Asp Pro Ala Ala Thr Pro Pro
    50                  55                  60

Ala His Cys Ala Phe Thr Gly Val Thr Cys Asp Ala Ala Thr Ser Arg
65                  70                  75                  80

Val Val Ala Ile Asn Leu Thr Ala Val Pro Leu His Gly Gly Ala Leu
                85                  90                  95

Pro Pro Glu Val Ala Leu Leu Asp Ala Leu Ala Ser Leu Thr Val Ala
            100                 105                 110

Asn Cys Tyr Leu Arg Gly Arg Leu Pro Pro Ala Leu Ala Ser Met Pro
        115                 120                 125

Ala Leu Arg His Leu Asn Leu Ser Asn Asn Asn Leu Ser Gly Pro Phe
    130                 135                 140

Pro Pro Pro Pro Pro Ala Ala Tyr Phe Pro Ala Leu Glu Ile Val Asp
145                 150                 155                 160

Val Tyr Asn Asn Asn Leu Ser Gly Pro Leu Pro Pro Leu Gly Ala Pro
                165                 170                 175

His Ala Arg Ser Leu Arg Tyr Leu His Leu Gly Gly Asn Tyr Phe Asn
            180                 185                 190

Gly Ser Ile Pro Asp Thr Phe Gly Asp Leu Ala Ala Leu Glu Tyr Leu
        195                 200                 205

Gly Leu Asn Gly Asn Ala Leu Ser Gly Arg Val Pro Pro Ser Leu Ser
    210                 215                 220

Arg Leu Ser Arg Leu Arg Glu Met Tyr Val Gly Tyr Tyr Asn Gln Tyr
225                 230                 235                 240

Ser Gly Gly Val Pro Arg Glu Phe Gly Ala Leu Gln Ser Leu Val Arg
                245                 250                 255

Leu Asp Met Ser Ser Cys Thr Leu Thr Gly Pro Ile Pro Pro Glu Leu
            260                 265                 270

Ala Arg Leu Ser Arg Leu Asp Thr Leu Phe Leu Ala Leu Asn Gln Leu
        275                 280                 285

Thr Gly Glu Ile Pro Pro Glu Leu Gly Ala Leu Thr Ser Leu Arg Ser
    290                 295                 300

Leu Asp Leu Ser Ile Asn Asp Leu Ala Gly Glu Ile Pro Ala Ser Phe
305                 310                 315                 320

Ala Ala Leu Thr Asn Leu Lys Leu Leu Asn Leu Phe Arg Asn His Leu
                325                 330                 335

Arg Gly Glu Ile Pro Ala Phe Leu Gly Asp Phe Pro Phe Leu Glu Val
            340                 345                 350

Leu Gln Val Trp Asp Asn Asn Leu Thr Gly Pro Leu Pro Pro Ala Leu
        355                 360                 365

Gly Arg Asn Gly Arg Leu Lys Thr Leu Asp Val Thr Ser Asn His Leu
    370                 375                 380

Thr Gly Thr Ile Pro Pro Asp Leu Cys Ala Gly Arg Asn Leu Gln Leu
385                 390                 395                 400

Leu Val Leu Met Asp Asn Gly Phe Phe Gly Ser Ile Pro Glu Ser Leu
                405                 410                 415

Gly Asp Cys Lys Thr Leu Thr Arg Val Arg Leu Gly Lys Asn Phe Leu
            420                 425                 430
```

-continued

```
Thr Gly Pro Val Pro Ala Gly Leu Phe Asp Leu Pro Gln Ala Asn Met
        435                 440                 445

Leu Glu Leu Thr Asp Asn Met Leu Thr Gly Glu Leu Pro Asp Val Ile
    450                 455                 460

Ala Gly Asp Lys Ile Gly Met Leu Met Leu Gly Asn Asn Arg Ile Gly
465                 470                 475                 480

Gly Arg Ile Pro Ala Ala Ile Gly Asn Leu Pro Ala Leu Gln Thr Leu
                485                 490                 495

Ser Leu Glu Ser Asn Asn Phe Ser Gly Pro Leu Pro Pro Glu Ile Gly
            500                 505                 510

Arg Leu Arg Asn Leu Thr Arg Leu Asn Ala Ser Gly Asn Ala Leu Thr
        515                 520                 525

Gly Gly Ile Pro Arg Glu Leu Met Gly Cys Ala Ser Leu Gly Ala Val
    530                 535                 540

Asp Leu Ser Arg Asn Gly Leu Thr Gly Glu Ile Pro Asp Thr Val Thr
545                 550                 555                 560

Ser Leu Lys Ile Leu Cys Thr Leu Asn Val Ser Arg Asn Arg Leu Ser
                565                 570                 575

Gly Glu Leu Pro Ala Ala Met Ala Asn Met Thr Ser Leu Thr Thr Leu
            580                 585                 590

Asp Val Ser Tyr Asn Gln Leu Ser Gly Pro Val Pro Met Gln Gly Gln
        595                 600                 605

Phe Leu Val Phe Asn Glu Ser Ser Phe Val Gly Asn Pro Gly Leu Cys
    610                 615                 620

Ser Ala Cys Pro Pro Ser Ser Gly Gly Ala Arg Ser Pro Phe Ser Leu
625                 630                 635                 640

Arg Arg Trp Asp Ser Lys Lys Leu Leu Val Trp Leu Val Val Leu Leu
                645                 650                 655

Thr Leu Leu Val Leu Ala Val Leu Gly Ala Arg Lys Ala His Glu Ala
            660                 665                 670

Trp Arg Glu Ala Ala Arg Arg Arg Ser Gly Ala Trp Lys Met Thr Ala
        675                 680                 685

Phe Gln Lys Leu Asp Phe Ser Ala Asp Asp Val Val Glu Cys Leu Lys
    690                 695                 700

Glu Asp Asn Ile Ile Gly Lys Gly Gly Ala Gly Ile Val Tyr His Gly
705                 710                 715                 720

Val Thr Arg Gly Gly Ala Glu Leu Ala Ile Lys Arg Leu Val Gly Arg
                725                 730                 735

Gly Cys Gly Asp His Asp Arg Gly Phe Thr Ala Glu Val Thr Thr Leu
            740                 745                 750

Gly Arg Ile Arg His Arg Asn Ile Val Arg Leu Leu Gly Phe Val Ser
        755                 760                 765

Asn Arg Glu Ala Asn Leu Leu Leu Tyr Glu Tyr Met Pro Asn Gly Ser
    770                 775                 780

Leu Gly Glu Met Leu His Gly Gly Lys Gly Gly His Leu Gly Trp Glu
785                 790                 795                 800

Ala Arg Ala Arg Val Ala Ala Glu Ala Ala Arg Gly Leu Cys Tyr Leu
                805                 810                 815

His His Asp Cys Ala Pro Arg Ile Ile His Arg Asp Val Lys Ser Asn
            820                 825                 830

Asn Ile Leu Leu Asp Ser Ala Phe Glu Ala His Val Ala Asp Phe Gly
        835                 840                 845

Leu Ala Lys Phe Leu Gly Gly Gly Gly Ala Thr Ser Glu Cys Met Ser
```

```
    850                 855                 860

Ala Ile Ala Gly Ser Tyr Gly Tyr Ile Ala Pro Glu Tyr Ala Tyr Thr
865                 870                 875                 880

Leu Arg Val Asp Glu Lys Ser Asp Val Tyr Ser Phe Gly Val Val Leu
                885                 890                 895

Leu Glu Leu Ile Thr Gly Arg Arg Pro Val Gly Ser Phe Gly Asp Gly
            900                 905                 910

Val Asp Ile Val His Trp Val Arg Lys Val Thr Ala Asp Ala Ala Ala
        915                 920                 925

Ala Glu Glu Pro Val Leu Leu Val Ala Asp Arg Arg Leu Ala Pro Glu
    930                 935                 940

Pro Val Pro Leu Leu Ala Asp Leu Tyr Arg Val Ala Met Ala Cys Val
945                 950                 955                 960

Glu Glu Ala Ser Thr Ala Arg Pro Thr Met Arg Glu Val Val His Met
                965                 970                 975

Leu Ser Thr Ser Ala Ala Ala Gln Pro Asp Val Pro His Ala Leu Cys
            980                 985                 990

Lys Val Val Asp
        995


<210> SEQ ID NO 84
<211> LENGTH: 56
<212> TYPE: PRT
<213> ORGANISM: Zea mays

<400> SEQUENCE: 84

Leu Lys Ile Leu Cys Thr Leu Asn Val Ser Arg Asn Arg Leu Ser Gly
1               5                   10                  15

Glu Leu Pro Ala Ala Met Ala Asn Met Thr Ser Leu Thr Thr Leu Asp
            20                  25                  30

Val Ser Tyr Asn Gln Leu Ser Gly Pro Val Pro Met Gln Gly Gln Phe
        35                  40                  45

Leu Val Phe Asn Glu Ser Ser Phe
    50                  55


<210> SEQ ID NO 85
<211> LENGTH: 1007
<212> TYPE: PRT
<213> ORGANISM: Oryza sativa

<400> SEQUENCE: 85

Met Ala Leu Ala Gly Ser Met Ala Ala Ala Ala Ala Thr Ser Thr Leu
1               5                   10                  15

Leu Leu Leu Leu Leu Leu Leu Leu Leu Ala Thr Ala Thr His Gly Ala
            20                  25                  30

Ala Ala Asp Thr Val Ser Ser Pro Ala Ser Pro Glu Ala Ala Ala Leu
        35                  40                  45

Leu Asn Leu Ser Ala Ala Leu Gly Asp Pro Ser Gly Tyr Leu Ser Thr
    50                  55                  60

His Trp Thr His Asp Thr Ala Phe Cys Ser Trp Pro Arg Leu Ser Cys
65                  70                  75                  80

Asp Ala Asp Gly Ser Arg Val Leu Ser Leu Asp Leu Ser Gly Leu Asn
                85                  90                  95

Leu Ser Gly Pro Ile Pro Ala Ala Ala Leu Ser Ser Leu Ser His Leu
            100                 105                 110

Gln Ser Leu Asn Leu Ser Asn Asn Ile Leu Asn Ser Thr Phe Pro Glu
```

-continued

```
        115                 120                 125

Gly Leu Ile Ala Ser Leu Lys Asn Leu Arg Val Leu Asp Phe Tyr Asn
    130                 135                 140

Asn Asn Leu Thr Gly Ala Leu Pro Ala Ala Leu Pro Asn Leu Thr Asn
145                 150                 155                 160

Leu Val His Leu His Leu Gly Gly Asn Phe Phe Phe Gly Ser Ile Pro
                165                 170                 175

Arg Ser Tyr Gly Gln Trp Ser Arg Ile Lys Tyr Leu Ala Leu Ser Gly
            180                 185                 190

Asn Glu Leu Thr Gly Glu Ile Pro Pro Glu Leu Gly Asn Leu Thr Thr
        195                 200                 205

Leu Arg Glu Leu Tyr Leu Gly Tyr Phe Asn Ser Phe Thr Gly Gly Ile
    210                 215                 220

Pro Pro Glu Leu Gly Arg Leu Lys Glu Leu Val Arg Leu Asp Met Ala
225                 230                 235                 240

Asn Cys Gly Ile Ser Gly Val Val Pro Pro Glu Val Ala Asn Leu Thr
                245                 250                 255

Ser Leu Asp Thr Leu Phe Leu Gln Ile Asn Ala Leu Ser Gly Arg Leu
            260                 265                 270

Pro Pro Glu Ile Gly Ala Met Gly Ala Leu Lys Ser Leu Asp Leu Ser
        275                 280                 285

Asn Asn Leu Phe Val Gly Glu Ile Pro Ala Ser Phe Ala Ser Leu Lys
    290                 295                 300

Asn Leu Thr Leu Leu Asn Leu Phe Arg Asn Arg Leu Ala Gly Glu Ile
305                 310                 315                 320

Pro Glu Phe Val Gly Asp Leu Pro Asn Leu Glu Val Leu Gln Leu Trp
                325                 330                 335

Glu Asn Asn Phe Thr Gly Gly Val Pro Ala Gln Leu Gly Val Ala Ala
            340                 345                 350

Thr Arg Leu Arg Ile Val Asp Val Ser Thr Asn Arg Leu Thr Gly Val
        355                 360                 365

Leu Pro Thr Glu Leu Cys Ala Gly Lys Arg Leu Glu Thr Phe Ile Ala
    370                 375                 380

Leu Gly Asn Ser Leu Phe Gly Ser Ile Pro Asp Gly Leu Ala Gly Cys
385                 390                 395                 400

Pro Ser Leu Thr Arg Leu Arg Leu Gly Glu Asn Tyr Leu Asn Gly Thr
                405                 410                 415

Ile Pro Ala Lys Met Phe Thr Leu Gln Asn Leu Thr Gln Ile Glu Leu
            420                 425                 430

His Asp Asn Leu Leu Ser Gly Glu Leu Arg Leu Asp Ala Gly Val Val
        435                 440                 445

Ser Pro Ser Ile Gly Glu Leu Ser Leu Tyr Asn Asn Arg Leu Ser Gly
    450                 455                 460

Pro Val Pro Val Gly Ile Gly Gly Leu Val Gly Leu Gln Lys Leu Leu
465                 470                 475                 480

Val Ala Gly Asn Arg Leu Ser Gly Glu Leu Pro Arg Glu Ile Gly Lys
                485                 490                 495

Leu Gln Gln Leu Ser Lys Ala Asp Leu Ser Gly Asn Leu Ile Ser Gly
            500                 505                 510

Glu Ile Pro Pro Ala Ile Ala Gly Cys Arg Leu Leu Thr Phe Leu Asp
        515                 520                 525

Leu Ser Gly Asn Arg Leu Ser Gly Arg Ile Pro Pro Ala Leu Ala Gly
    530                 535                 540
```

-continued

```
Leu Arg Ile Leu Asn Tyr Leu Asn Leu Ser His Asn Ala Leu Asp Gly
545                 550                 555                 560

Glu Ile Pro Pro Ala Ile Ala Gly Met Gln Ser Leu Thr Ala Val Asp
                565                 570                 575

Phe Ser Asp Asn Asn Leu Ser Gly Glu Val Pro Ala Thr Gly Gln Phe
            580                 585                 590

Ala Tyr Phe Asn Ala Thr Ser Phe Ala Gly Asn Pro Gly Leu Cys Gly
        595                 600                 605

Ala Phe Leu Ser Pro Cys Arg Ser His Gly Val Ala Thr Thr Ser Thr
    610                 615                 620

Phe Gly Ser Leu Ser Ser Ala Ser Lys Leu Leu Leu Val Leu Gly Leu
625                 630                 635                 640

Leu Ala Leu Ser Ile Val Phe Ala Gly Ala Ala Val Leu Lys Ala Arg
                645                 650                 655

Ser Leu Lys Arg Ser Ala Glu Ala Arg Ala Trp Arg Leu Thr Ala Phe
            660                 665                 670

Gln Arg Leu Asp Phe Ala Val Asp Asp Val Leu Asp Cys Leu Lys Glu
        675                 680                 685

Glu Asn Val Ile Gly Lys Gly Gly Ser Gly Ile Val Tyr Lys Gly Ala
    690                 695                 700

Met Pro Gly Gly Ala Val Val Ala Val Lys Arg Leu Pro Ala Met Gly
705                 710                 715                 720

Arg Ser Gly Ala Ala His Asp Asp Tyr Gly Phe Ser Ala Glu Ile Gln
                725                 730                 735

Thr Leu Gly Arg Ile Arg His Arg His Ile Val Arg Leu Leu Gly Phe
            740                 745                 750

Ala Ala Asn Arg Glu Thr Asn Leu Leu Val Tyr Glu Tyr Met Pro Asn
        755                 760                 765

Gly Ser Leu Gly Glu Val Leu His Gly Lys Lys Gly Gly His Leu Gln
    770                 775                 780

Trp Ala Thr Arg Tyr Lys Ile Ala Val Glu Ala Ala Lys Gly Leu Cys
785                 790                 795                 800

Tyr Leu His His Asp Cys Ser Pro Pro Ile Leu His Arg Asp Val Lys
                805                 810                 815

Ser Asn Asn Ile Leu Leu Asp Ala Glu Phe Glu Ala His Val Ala Asp
            820                 825                 830

Phe Gly Leu Ala Lys Phe Leu Arg Gly Asn Ala Gly Gly Ser Glu Cys
        835                 840                 845

Met Ser Ala Ile Ala Gly Ser Tyr Gly Tyr Ile Ala Pro Glu Tyr Ala
    850                 855                 860

Tyr Thr Leu Lys Val Asp Glu Lys Ser Asp Val Tyr Ser Phe Gly Val
865                 870                 875                 880

Val Leu Leu Glu Leu Ile Ala Gly Arg Lys Pro Val Gly Glu Phe Gly
                885                 890                 895

Asp Gly Val Asp Ile Val His Trp Val Arg Met Val Thr Gly Ser Ser
            900                 905                 910

Lys Glu Gly Val Thr Lys Ile Ala Asp Pro Arg Leu Ser Thr Val Pro
        915                 920                 925

Leu His Glu Leu Thr His Val Phe Tyr Val Ala Met Leu Cys Val Ala
    930                 935                 940

Glu Gln Ser Val Glu Arg Pro Thr Met Arg Glu Val Val Gln Ile Leu
945                 950                 955                 960
```

Thr Asp Leu Pro Gly Thr Ala Ala Ala Thr Ala Met Asp Ala Pro Ser
965 970 975

His Gly Ser Gly Lys Glu Gln Asp Arg Ser Ala Glu Met Gln Gln Gln
980 985 990

Asp Gly Ser Arg Glu Ser Pro Pro Gln Gln Asp Leu Leu Ser Ile
995 1000 1005

<210> SEQ ID NO 86
<211> LENGTH: 56
<212> TYPE: PRT
<213> ORGANISM: Oryza sativa

<400> SEQUENCE: 86

Leu Arg Ile Leu Asn Tyr Leu Asn Leu Ser His Asn Ala Leu Asp Gly
1 5 10 15

Glu Ile Pro Pro Ala Ile Ala Gly Met Gln Ser Leu Thr Ala Val Asp
20 25 30

Phe Ser Asp Asn Asn Leu Ser Gly Glu Val Pro Ala Thr Gly Gln Phe
35 40 45

Ala Tyr Phe Asn Ala Thr Ser Phe
50 55

<210> SEQ ID NO 87
<211> LENGTH: 1029
<212> TYPE: PRT
<213> ORGANISM: Oryza sativa

<400> SEQUENCE: 87

Met His Leu Arg Leu Leu Leu Leu Leu Val Gly Val Ala Ala Ala Ala
1 5 10 15

Ala Asp Ala Asp Ala Asp Ala Asp Ala Leu Leu Ala Ala Lys Ala Ala
20 25 30

Met Ser Asp Pro Thr Gly Ala Leu Ala Ser Trp Gly Gly Asn Gly Thr
35 40 45

Arg Thr Asn Thr Thr Ala Ala Ala Ala Ala His Cys Ala Trp Ala Gly
50 55 60

Val Thr Cys Ser Ser Arg Gly Ala Val Val Gly Leu Asp Val Ser Gly
65 70 75 80

Leu Asn Leu Ser Gly Ala Leu Pro Ala Glu Leu Thr Gly Leu Arg Gly
85 90 95

Leu Met Arg Leu Ser Val Gly Ala Asn Ala Phe Ser Gly Pro Ile Pro
100 105 110

Ala Ser Leu Gly Arg Leu Gln Phe Leu Thr Tyr Leu Asn Leu Ser Asn
115 120 125

Asn Ala Phe Asn Gly Ser Phe Pro Ala Ala Leu Ala Arg Leu Arg Gly
130 135 140

Leu Arg Val Leu Asp Leu Tyr Asn Asn Asn Leu Thr Ser Pro Leu Pro
145 150 155 160

Met Glu Val Val Gln Met Pro Leu Leu Arg His Leu His Leu Gly Gly
165 170 175

Asn Phe Phe Ser Gly Glu Ile Pro Pro Glu Tyr Gly Arg Trp Gly Arg
180 185 190

Met Gln Tyr Leu Ala Val Ser Gly Asn Glu Leu Ser Gly Lys Ile Pro
195 200 205

Pro Glu Leu Gly Asn Leu Thr Ser Leu Arg Glu Leu Tyr Ile Gly Tyr
210 215 220

Tyr Asn Ser Tyr Ser Gly Gly Leu Pro Pro Glu Leu Gly Asn Leu Thr
225 230 235 240

Glu Leu Val Arg Leu Asp Ala Ala Asn Cys Gly Leu Ser Gly Glu Ile
245 250 255

Pro Pro Glu Leu Gly Lys Leu Gln Asn Leu Asp Thr Leu Phe Leu Gln
260 265 270

Val Asn Ser Leu Ala Gly Gly Ile Pro Ser Glu Leu Gly Tyr Leu Lys
275 280 285

Ser Leu Ser Ser Leu Asp Leu Ser Asn Asn Val Leu Thr Gly Glu Ile
290 295 300

Pro Ala Ser Phe Ser Glu Leu Lys Asn Leu Thr Leu Leu Asn Leu Phe
305 310 315 320

Arg Asn Lys Leu Arg Gly Asp Ile Pro Asp Phe Val Gly Asp Leu Pro
325 330 335

Ser Leu Glu Val Leu Gln Leu Trp Glu Asn Asn Phe Thr Gly Gly Val
340 345 350

Pro Arg Arg Leu Gly Arg Asn Gly Arg Leu Gln Leu Leu Asp Leu Ser
355 360 365

Ser Asn Arg Leu Thr Gly Thr Leu Pro Pro Glu Leu Cys Ala Gly Gly
370 375 380

Lys Met His Thr Leu Ile Ala Leu Gly Asn Phe Leu Phe Gly Ala Ile
385 390 395 400

Pro Asp Ser Leu Gly Glu Cys Lys Ser Leu Ser Arg Val Arg Leu Gly
405 410 415

Glu Asn Tyr Leu Asn Gly Ser Ile Pro Lys Gly Leu Phe Glu Leu Pro
420 425 430

Lys Leu Thr Gln Val Glu Leu Gln Asp Asn Leu Leu Thr Gly Asn Phe
435 440 445

Pro Ala Val Ser Gly Ala Ala Ala Pro Asn Leu Gly Glu Ile Ser Leu
450 455 460

Ser Asn Asn Gln Leu Thr Gly Ala Leu Pro Ala Ser Ile Gly Asn Phe
465 470 475 480

Ser Gly Val Gln Lys Leu Leu Leu Asp Arg Asn Ser Phe Ser Gly Val
485 490 495

Val Pro Pro Glu Ile Gly Arg Leu Gln Lys Leu Ser Lys Ala Asp Leu
500 505 510

Ser Ser Asn Ala Leu Glu Gly Gly Val Pro Pro Glu Ile Gly Lys Cys
515 520 525

Arg Leu Leu Thr Tyr Leu Asp Leu Ser Arg Asn Asn Ile Ser Gly Lys
530 535 540

Ile Pro Pro Ala Ile Ser Gly Met Arg Ile Leu Asn Tyr Leu Asn Leu
545 550 555 560

Ser Arg Asn His Leu Asp Gly Glu Ile Pro Pro Ser Ile Ala Thr Met
565 570 575

Gln Ser Leu Thr Ala Val Asp Phe Ser Tyr Asn Asn Leu Ser Gly Leu
580 585 590

Val Pro Gly Thr Gly Gln Phe Ser Tyr Phe Asn Ala Thr Ser Phe Val
595 600 605

Gly Asn Pro Gly Leu Cys Gly Pro Tyr Leu Gly Pro Cys Arg Pro Gly
610 615 620

Val Ala Gly Thr Asp His Gly Gly His Gly His Gly Gly Leu Ser Asn
625 630 635 640

Gly Val Lys Leu Leu Ile Val Leu Gly Leu Leu Ala Cys Ser Ile Ala

-continued

```
                645                 650                 655

Phe Ala Val Gly Ala Ile Leu Lys Ala Arg Ser Leu Lys Lys Ala Ser
            660                 665                 670

Glu Ala Arg Val Trp Lys Leu Thr Ala Phe Gln Arg Leu Asp Phe Thr
        675                 680                 685

Cys Asp Asp Val Leu Asp Cys Leu Lys Glu Glu Asn Val Ile Gly Lys
    690                 695                 700

Gly Gly Ala Gly Ile Val Tyr Lys Gly Ala Met Pro Asn Gly Asp His
705                 710                 715                 720

Val Ala Val Lys Arg Leu Pro Ala Met Gly Arg Gly Ser Ser His Asp
                725                 730                 735

His Gly Phe Ser Ala Glu Ile Gln Thr Leu Gly Arg Ile Arg His Arg
            740                 745                 750

His Ile Val Arg Leu Leu Gly Phe Cys Ser Asn Asn Glu Thr Asn Leu
        755                 760                 765

Leu Val Tyr Glu Tyr Met Pro Asn Gly Ser Leu Gly Glu Leu Leu His
    770                 775                 780

Gly Lys Lys Gly Gly His Leu His Trp Asp Thr Arg Tyr Lys Ile Ala
785                 790                 795                 800

Ile Glu Ala Ala Lys Gly Leu Cys Tyr Leu His His Asp Cys Ser Pro
                805                 810                 815

Leu Ile Leu His Arg Asp Val Lys Ser Asn Asn Ile Leu Leu Asp Ser
            820                 825                 830

Asp Phe Glu Ala His Val Ala Asp Phe Gly Leu Ala Lys Phe Leu Gln
        835                 840                 845

Asp Thr Gly Ala Ser Glu Cys Met Ser Ala Ile Ala Gly Ser Tyr Gly
    850                 855                 860

Tyr Ile Ala Pro Glu Tyr Ala Tyr Thr Leu Lys Val Asp Glu Lys Ser
865                 870                 875                 880

Asp Val Tyr Ser Phe Gly Val Val Leu Leu Glu Leu Val Thr Gly Arg
                885                 890                 895

Lys Pro Val Gly Glu Phe Gly Asp Gly Val Asp Ile Val Gln Trp Val
            900                 905                 910

Arg Met Met Thr Asp Ser Asn Lys Glu Gln Val Met Lys Val Leu Asp
        915                 920                 925

Pro Arg Leu Ser Thr Val Pro Leu His Glu Val Met His Val Phe Tyr
    930                 935                 940

Val Ala Leu Leu Cys Ile Glu Glu Gln Ser Val Gln Arg Pro Thr Met
945                 950                 955                 960

Arg Glu Val Val Gln Ile Leu Ser Glu Leu Pro Lys Leu Ala Pro Arg
                965                 970                 975

Gln Gly Glu Val Leu Ser His Ala Val Asp Gly Phe Ala Ser Asn Pro
            980                 985                 990

Pro Ala Pro Val Pro Ser Gly Ser  Ala Glu Ala Leu Thr  Gly Asp Ala
        995                 1000                1005

Lys Asp  Gln Gln Gln Gln Gln  Thr Asn Ser Glu Ser  Thr Thr Pro
    1010                 1015                1020

Pro Asp  Leu Ile Ser Ile
    1025
```

<210> SEQ ID NO 88
<211> LENGTH: 56
<212> TYPE: PRT
<213> ORGANISM: Oryza sativa

<400> SEQUENCE: 88

Met Arg Ile Leu Asn Tyr Leu Asn Leu Ser Arg Asn His Leu Asp Gly
1               5                   10                  15

Glu Ile Pro Pro Ser Ile Ala Thr Met Gln Ser Leu Thr Ala Val Asp
            20                  25                  30

Phe Ser Tyr Asn Asn Leu Ser Gly Leu Val Pro Gly Thr Gly Gln Phe
        35                  40                  45

Ser Tyr Phe Asn Ala Thr Ser Phe
    50                  55

<210> SEQ ID NO 89
<211> LENGTH: 994
<212> TYPE: PRT
<213> ORGANISM: Oryza sativa

<400> SEQUENCE: 89

Met Pro Pro Thr Leu Leu Leu Leu Leu Leu Leu Leu Pro Pro Ser Leu
1               5                   10                  15

Ala Ser Pro Asp Arg Asp Ile Tyr Ala Leu Ala Lys Leu Lys Ala Ala
            20                  25                  30

Leu Val Pro Ser Pro Ser Ala Thr Ala Pro Pro Pro Leu Ala Asp Trp
        35                  40                  45

Asp Pro Ala Ala Thr Ser Pro Ala His Cys Thr Phe Ser Gly Val Thr
    50                  55                  60

Cys Asp Gly Arg Ser Arg Val Val Ala Ile Asn Leu Thr Ala Leu Pro
65                  70                  75                  80

Leu His Ser Gly Tyr Leu Pro Pro Glu Ile Ala Leu Leu Asp Ser Leu
                85                  90                  95

Ala Asn Leu Thr Ile Ala Ala Cys Cys Leu Pro Gly His Val Pro Leu
            100                 105                 110

Glu Leu Pro Thr Leu Pro Ser Leu Arg His Leu Asn Leu Ser Asn Asn
        115                 120                 125

Asn Leu Ser Gly His Phe Pro Val Pro Asp Ser Gly Gly Gly Ala Ser
    130                 135                 140

Pro Tyr Phe Pro Ser Leu Glu Leu Ile Asp Ala Tyr Asn Asn Asn Leu
145                 150                 155                 160

Ser Gly Leu Leu Pro Pro Phe Ser Ala Ser His Ala Arg Leu Arg Tyr
                165                 170                 175

Leu His Leu Gly Gly Asn Tyr Phe Thr Gly Ala Ile Pro Asp Ser Tyr
            180                 185                 190

Gly Asp Leu Ala Ala Leu Glu Tyr Leu Gly Leu Asn Gly Asn Thr Leu
        195                 200                 205

Ser Gly His Val Pro Val Ser Leu Ser Arg Leu Thr Arg Leu Arg Glu
    210                 215                 220

Met Tyr Ile Gly Tyr Tyr Asn Gln Tyr Asp Gly Gly Val Pro Pro Glu
225                 230                 235                 240

Phe Gly Asp Leu Gly Ala Leu Leu Arg Leu Asp Met Ser Ser Cys Asn
                245                 250                 255

Leu Thr Gly Pro Val Pro Pro Glu Leu Gly Arg Leu Gln Arg Leu Asp
            260                 265                 270

Thr Leu Phe Leu Gln Trp Asn Arg Leu Ser Gly Glu Ile Pro Pro Gln
        275                 280                 285

Leu Gly Asp Leu Ser Ser Leu Ala Ser Leu Asp Leu Ser Val Asn Asp
    290                 295                 300

```
Leu Ala Gly Glu Ile Pro Pro Ser Leu Ala Asn Leu Ser Asn Leu Lys
305                 310                 315                 320

Leu Leu Asn Leu Phe Arg Asn His Leu Arg Gly Ser Ile Pro Asp Phe
                325                 330                 335

Val Ala Gly Phe Ala Gln Leu Glu Val Leu Gln Leu Trp Asp Asn Asn
            340                 345                 350

Leu Thr Gly Asn Ile Pro Ala Gly Leu Gly Lys Asn Gly Arg Leu Lys
        355                 360                 365

Thr Leu Asp Leu Ala Thr Asn His Leu Thr Gly Pro Ile Pro Ala Asp
    370                 375                 380

Leu Cys Ala Gly Arg Arg Leu Glu Met Leu Val Leu Met Glu Asn Gly
385                 390                 395                 400

Leu Phe Gly Pro Ile Pro Asp Ser Leu Gly Asp Cys Lys Thr Leu Thr
                405                 410                 415

Arg Val Arg Leu Ala Lys Asn Phe Leu Thr Gly Pro Val Pro Ala Gly
            420                 425                 430

Leu Phe Asn Leu Pro Gln Ala Asn Met Val Glu Leu Thr Asp Asn Leu
        435                 440                 445

Leu Thr Gly Glu Leu Pro Asp Val Ile Gly Gly Asp Lys Ile Gly Met
    450                 455                 460

Leu Leu Leu Gly Asn Asn Gly Ile Gly Gly Arg Ile Pro Pro Ala Ile
465                 470                 475                 480

Gly Asn Leu Pro Ala Leu Gln Thr Leu Ser Leu Glu Ser Asn Asn Phe
                485                 490                 495

Ser Gly Ala Leu Pro Pro Glu Ile Gly Asn Leu Lys Asn Leu Ser Arg
            500                 505                 510

Leu Asn Val Ser Gly Asn Ala Leu Thr Gly Ala Ile Pro Asp Glu Leu
        515                 520                 525

Ile Arg Cys Ala Ser Leu Ala Ala Val Asp Leu Ser Arg Asn Gly Phe
    530                 535                 540

Ser Gly Glu Ile Pro Glu Ser Ile Thr Ser Leu Lys Ile Leu Cys Thr
545                 550                 555                 560

Leu Asn Val Ser Arg Asn Arg Leu Thr Gly Glu Leu Pro Pro Glu Met
                565                 570                 575

Ser Asn Met Thr Ser Leu Thr Thr Leu Asp Val Ser Tyr Asn Ser Leu
            580                 585                 590

Ser Gly Pro Val Pro Met Gln Gly Gln Phe Leu Val Phe Asn Glu Ser
        595                 600                 605

Ser Phe Val Gly Asn Pro Gly Leu Cys Gly Gly Pro Val Ala Asp Ala
    610                 615                 620

Cys Pro Pro Ser Met Ala Gly Gly Gly Gly Gly Ala Gly Ser Gln Leu
625                 630                 635                 640

Arg Leu Arg Trp Asp Ser Lys Lys Met Leu Val Ala Leu Val Ala Ala
                645                 650                 655

Phe Ala Ala Val Ala Val Ala Phe Leu Gly Ala Arg Lys Gly Cys Ser
            660                 665                 670

Ala Trp Arg Ser Ala Ala Arg Arg Arg Ser Gly Ala Trp Lys Met Thr
        675                 680                 685

Ala Phe Gln Lys Leu Glu Phe Ser Ala Glu Asp Val Val Glu Cys Val
    690                 695                 700

Lys Glu Asp Asn Ile Ile Gly Lys Gly Gly Ala Gly Ile Val Tyr His
705                 710                 715                 720
```

-continued

Gly Val Thr Arg Gly Ala Glu Leu Ala Ile Lys Arg Leu Val Gly Arg
725 730 735

Gly Gly Gly Glu His Asp Arg Gly Phe Ser Ala Glu Val Thr Thr Leu
740 745 750

Gly Arg Ile Arg His Arg Asn Ile Val Arg Leu Leu Gly Phe Val Ser
755 760 765

Asn Arg Glu Thr Asn Leu Leu Leu Tyr Glu Tyr Met Pro Asn Gly Ser
770 775 780

Leu Gly Glu Met Leu His Gly Gly Lys Gly Gly His Leu Gly Trp Glu
785 790 795 800

Ala Arg Ala Arg Val Ala Ala Glu Ala Ala Cys Gly Leu Cys Tyr Leu
805 810 815

His His Asp Cys Ala Pro Arg Ile Ile His Arg Asp Val Lys Ser Asn
820 825 830

Asn Ile Leu Leu Asp Ser Ala Phe Glu Ala His Val Ala Asp Phe Gly
835 840 845

Leu Ala Lys Phe Leu Gly Gly Ala Thr Ser Glu Cys Met Ser Ala Ile
850 855 860

Ala Gly Ser Tyr Gly Tyr Ile Ala Pro Glu Tyr Ala Tyr Thr Leu Arg
865 870 875 880

Val Asp Glu Lys Ser Asp Val Tyr Ser Phe Gly Val Val Leu Leu Glu
885 890 895

Leu Ile Thr Gly Arg Arg Pro Val Gly Gly Phe Gly Asp Gly Val Asp
900 905 910

Ile Val His Trp Val Arg Lys Val Thr Ala Glu Leu Pro Asp Asn Ser
915 920 925

Asp Thr Ala Ala Val Leu Ala Val Ala Asp Arg Arg Leu Thr Pro Glu
930 935 940

Pro Val Ala Leu Met Val Asn Leu Tyr Lys Val Ala Met Ala Cys Val
945 950 955 960

Glu Glu Ala Ser Thr Ala Arg Pro Thr Met Arg Glu Val Val His Met
965 970 975

Leu Ser Asn Pro Asn Ser Ala Gln Pro Asn Ser Gly Asp Leu Leu Val
980 985 990

Thr Phe

<210> SEQ ID NO 90
<211> LENGTH: 56
<212> TYPE: PRT
<213> ORGANISM: Oryza sativa

<400> SEQUENCE: 90

Leu Lys Ile Leu Cys Thr Leu Asn Val Ser Arg Asn Arg Leu Thr Gly
1 5 10 15

Glu Leu Pro Pro Glu Met Ser Asn Met Thr Ser Leu Thr Thr Leu Asp
20 25 30

Val Ser Tyr Asn Ser Leu Ser Gly Pro Val Pro Met Gln Gly Gln Phe
35 40 45

Leu Val Phe Asn Glu Ser Ser Phe
50 55

<210> SEQ ID NO 91
<211> LENGTH: 1023
<212> TYPE: PRT
<213> ORGANISM: Oryza sativa

<400> SEQUENCE: 91

Met Arg Leu His Tyr His His Leu Ala Val Val Leu Leu Ala Ala Val
1               5                   10                  15

Ala Ala Ala Ala Thr Ala Ala Ala Gly Gly Glu Ala Asp Ala Leu Leu
            20                  25                  30

Ala Val Lys Ala Ala Leu Asp Asp Pro Thr Gly Ala Leu Ala Ser Trp
        35                  40                  45

Thr Thr Asn Thr Thr Ser Ser Pro Cys Ala Trp Ser Gly Val Ala Cys
    50                  55                  60

Asn Ala Arg Gly Ala Val Val Gly Leu Asp Val Ser Gly Arg Asn Leu
65                  70                  75                  80

Thr Gly Gly Leu Pro Gly Ala Ala Leu Ser Gly Leu Gln His Leu Ala
                85                  90                  95

Arg Leu Asp Leu Ala Ala Asn Ala Leu Ser Gly Pro Ile Pro Ala Ala
            100                 105                 110

Leu Ser Arg Leu Ala Pro Phe Leu Thr His Leu Asn Leu Ser Asn Asn
        115                 120                 125

Gly Leu Asn Gly Thr Phe Pro Pro Gln Leu Ser Arg Leu Arg Ala Leu
    130                 135                 140

Arg Val Leu Asp Leu Tyr Asn Asn Asn Leu Thr Gly Ala Leu Pro Leu
145                 150                 155                 160

Glu Val Val Ser Met Ala Gln Leu Arg His Leu His Leu Gly Gly Asn
                165                 170                 175

Phe Phe Ser Gly Gly Ile Pro Pro Glu Tyr Gly Arg Trp Gly Arg Leu
            180                 185                 190

Gln Tyr Leu Ala Val Ser Gly Asn Glu Leu Ser Gly Lys Ile Pro Pro
        195                 200                 205

Glu Leu Gly Asn Leu Thr Ser Leu Arg Glu Leu Tyr Ile Gly Tyr Phe
    210                 215                 220

Asn Ser Tyr Ser Gly Gly Ile Pro Pro Glu Leu Gly Asn Met Thr Asp
225                 230                 235                 240

Leu Val Arg Leu Asp Ala Ala Asn Cys Gly Leu Ser Gly Glu Ile Pro
                245                 250                 255

Pro Glu Leu Gly Asn Leu Ala Asn Leu Asp Thr Leu Phe Leu Gln Val
            260                 265                 270

Asn Gly Leu Ala Gly Gly Ile Pro Arg Glu Leu Gly Lys Leu Ala Ser
        275                 280                 285

Leu Ser Ser Leu Asp Leu Ser Asn Asn Ala Leu Ala Gly Glu Ile Pro
    290                 295                 300

Ala Thr Phe Ala Asp Leu Lys Asn Leu Thr Leu Leu Asn Leu Phe Arg
305                 310                 315                 320

Asn Lys Leu Arg Gly Asp Ile Pro Glu Phe Val Gly Asp Leu Pro Ser
                325                 330                 335

Leu Glu Val Leu Gln Leu Trp Glu Asn Asn Phe Thr Gly Gly Ile Pro
            340                 345                 350

Arg Arg Leu Gly Arg Asn Gly Arg Phe Gln Leu Leu Asp Leu Ser Ser
        355                 360                 365

Asn Arg Leu Thr Gly Thr Leu Pro Pro Asp Leu Cys Ala Gly Gly Lys
    370                 375                 380

Leu Glu Thr Leu Ile Ala Leu Gly Asn Ser Leu Phe Gly Ala Ile Pro
385                 390                 395                 400

Ala Ser Leu Gly Lys Cys Thr Ser Leu Thr Arg Val Arg Leu Gly Asp
                405                 410                 415

-continued

```
Asn Tyr Leu Asn Gly Ser Ile Pro Glu Gly Leu Phe Glu Leu Pro Asn
            420                 425                 430

Leu Thr Gln Val Glu Leu Gln Asp Asn Leu Ile Ser Gly Gly Phe Pro
        435                 440                 445

Ala Val Ser Gly Thr Gly Ala Pro Asn Leu Gly Gln Ile Ser Leu Ser
    450                 455                 460

Asn Asn Gln Leu Thr Gly Ala Leu Pro Ala Phe Ile Gly Ser Phe Ser
465                 470                 475                 480

Gly Val Gln Lys Leu Leu Leu Asp Gln Asn Ala Phe Thr Gly Glu Ile
                485                 490                 495

Pro Pro Glu Ile Gly Arg Leu Gln Gln Leu Ser Lys Ala Asp Leu Ser
            500                 505                 510

Gly Asn Ser Phe Asp Gly Gly Val Pro Pro Glu Ile Gly Lys Cys Arg
        515                 520                 525

Leu Leu Thr Tyr Leu Asp Leu Ser Arg Asn Asn Leu Ser Gly Glu Ile
    530                 535                 540

Pro Pro Ala Ile Ser Gly Met Arg Ile Leu Asn Tyr Leu Asn Leu Ser
545                 550                 555                 560

Arg Asn Gln Leu Asp Gly Glu Ile Pro Ala Thr Ile Ala Ala Met Gln
                565                 570                 575

Ser Leu Thr Ala Val Asp Phe Ser Tyr Asn Asn Leu Ser Gly Leu Val
            580                 585                 590

Pro Ala Thr Gly Gln Phe Ser Tyr Phe Asn Ala Thr Ser Phe Val Gly
        595                 600                 605

Asn Pro Gly Leu Cys Gly Pro Tyr Leu Gly Pro Cys His Pro Gly Ala
    610                 615                 620

Pro Gly Thr Asp His Gly Gly Arg Ser His Gly Gly Leu Ser Asn Ser
625                 630                 635                 640

Phe Lys Leu Leu Ile Val Leu Gly Leu Leu Ala Leu Ser Ile Ala Phe
                645                 650                 655

Ala Ala Met Ala Ile Leu Lys Ala Arg Ser Leu Lys Lys Ala Ser Glu
            660                 665                 670

Ala Arg Ala Trp Lys Leu Thr Ala Phe Gln Arg Leu Glu Phe Thr Cys
        675                 680                 685

Asp Asp Val Leu Asp Ser Leu Lys Glu Glu Asn Ile Ile Gly Lys Gly
    690                 695                 700

Gly Ala Gly Thr Val Tyr Lys Gly Thr Met Pro Asp Gly Glu His Val
705                 710                 715                 720

Ala Val Lys Arg Leu Pro Ala Met Ser Arg Gly Ser Ser His Asp His
                725                 730                 735

Gly Phe Ser Ala Glu Ile Gln Thr Leu Gly Arg Ile Arg His Arg Tyr
            740                 745                 750

Ile Val Arg Leu Leu Gly Phe Cys Ser Asn Asn Glu Thr Asn Leu Leu
        755                 760                 765

Val Tyr Glu Tyr Met Pro Asn Gly Ser Leu Gly Glu Leu Leu His Gly
    770                 775                 780

Lys Lys Gly Gly His Leu His Trp Asp Thr Arg Tyr Lys Val Ala Val
785                 790                 795                 800

Glu Ala Ala Lys Gly Leu Cys Tyr Leu His His Asp Cys Ser Pro Pro
                805                 810                 815

Ile Leu His Arg Asp Val Lys Ser Asn Asn Ile Leu Leu Asp Ser Asp
            820                 825                 830
```

```
Phe Glu Ala His Val Ala Asp Phe Gly Leu Ala Lys Phe Leu Gln Asp
        835                 840                 845

Ser Gly Thr Ser Glu Cys Met Ser Ala Ile Ala Gly Ser Tyr Gly Tyr
    850                 855                 860

Ile Ala Pro Glu Tyr Ala Tyr Thr Leu Lys Val Asp Glu Lys Ser Asp
865                 870                 875                 880

Val Tyr Ser Phe Gly Val Val Leu Leu Glu Leu Ile Thr Gly Lys Lys
                885                 890                 895

Pro Val Gly Glu Phe Gly Asp Gly Val Asp Ile Val Gln Trp Val Lys
            900                 905                 910

Thr Met Thr Asp Ser Asn Lys Glu His Val Ile Lys Ile Leu Asp Pro
        915                 920                 925

Arg Leu Ser Thr Val Pro Val His Glu Val Met His Val Phe Tyr Val
    930                 935                 940

Ala Leu Leu Cys Val Glu Glu Gln Ser Val Gln Arg Pro Thr Met Arg
945                 950                 955                 960

Glu Val Val Gln Ile Leu Ser Glu Leu Pro Lys Pro Thr Ser Lys Gln
                965                 970                 975

Gly Glu Glu Pro Pro Ser Gly Glu Gly Ala Val Phe Asp Leu Val Val
            980                 985                 990

Pro Ala Glu Ser Ala Glu Ala Asn  Glu Ala Lys Glu Gln  Gln Gln Gln
        995                 1000                1005

Gln Leu  Asn Ser Pro Ser Ser  Pro Pro Pro Asp Leu  Ile Ser Ile
    1010                 1015                 1020
```

<210> SEQ ID NO 92
<211> LENGTH: 56
<212> TYPE: PRT
<213> ORGANISM: Oryza sativa

<400> SEQUENCE: 92

```
Met Arg Ile Leu Asn Tyr Leu Asn Leu Ser Arg Asn Gln Leu Asp Gly
1               5                   10                  15

Glu Ile Pro Ala Thr Ile Ala Ala Met Gln Ser Leu Thr Ala Val Asp
            20                  25                  30

Phe Ser Tyr Asn Asn Leu Ser Gly Leu Val Pro Ala Thr Gly Gln Phe
        35                  40                  45

Ser Tyr Phe Asn Ala Thr Ser Phe
    50                  55
```

<210> SEQ ID NO 93
<211> LENGTH: 1030
<212> TYPE: PRT
<213> ORGANISM: Sorghum bicolor

<400> SEQUENCE: 93

```
Met Arg Leu Leu Pro Leu Leu Leu Leu Leu Ala Leu Ala Ala Gly Ala
1               5                   10                  15

Ala Gly Ala Ala Gly Gly Gly Thr Asp Ser Asp Ala Asp Ala Asp Ala
            20                  25                  30

Leu Leu Ala Ala Lys Ala Ala Leu Ser Asp Pro Thr Gly Ala Leu Ala
        35                  40                  45

Ser Trp Gly Val Ala Ser Ser Asp His Cys Ala Trp Ala Gly Val Thr
    50                  55                  60

Cys Ala Pro Arg Gly Ser Gly Gly Val Val Val Gly Leu Asp Val Ser
65                  70                  75                  80
```

-continued

```
Gly Leu Asn Leu Ser Gly Ala Leu Pro Pro Ala Leu Ser Arg Leu Arg
                85                  90                  95

Gly Leu Gln Arg Leu Ser Val Ala Ala Asn Gly Phe Tyr Gly Pro Ile
            100                 105                 110

Pro Pro Ser Leu Ala Arg Leu Gln Leu Leu Val His Leu Asn Leu Ser
        115                 120                 125

Asn Asn Ala Phe Asn Gly Ser Phe Pro Pro Ala Leu Ala Arg Leu Arg
    130                 135                 140

Ala Leu Arg Val Leu Asp Leu Tyr Asn Asn Asn Leu Thr Ser Ala Thr
145                 150                 155                 160

Leu Pro Leu Glu Val Thr His Met Pro Met Leu Arg His Leu His Leu
                165                 170                 175

Gly Gly Asn Phe Phe Ser Gly Glu Ile Pro Pro Glu Tyr Gly Arg Trp
            180                 185                 190

Pro Arg Leu Gln Tyr Leu Ala Val Ser Gly Asn Glu Leu Ser Gly Lys
        195                 200                 205

Ile Pro Pro Glu Leu Gly Asn Leu Thr Ser Leu Arg Glu Leu Tyr Ile
    210                 215                 220

Gly Tyr Tyr Asn Ser Tyr Thr Gly Gly Leu Pro Pro Glu Leu Gly Asn
225                 230                 235                 240

Leu Thr Glu Leu Val Arg Leu Asp Ala Ala Asn Cys Gly Leu Ser Gly
                245                 250                 255

Glu Ile Pro Pro Glu Leu Gly Arg Leu Gln Asn Leu Asp Thr Leu Phe
            260                 265                 270

Leu Gln Val Asn Gly Leu Thr Gly Ser Ile Pro Ser Glu Leu Gly Tyr
        275                 280                 285

Leu Lys Ser Leu Ser Ser Leu Asp Leu Ser Asn Asn Ala Leu Thr Gly
    290                 295                 300

Glu Ile Pro Ala Ser Phe Ser Glu Leu Lys Asn Leu Thr Leu Leu Asn
305                 310                 315                 320

Leu Phe Arg Asn Lys Leu Arg Gly Asp Ile Pro Asp Phe Val Gly Asp
                325                 330                 335

Leu Pro Ser Leu Glu Val Leu Gln Leu Trp Glu Asn Asn Phe Thr Gly
            340                 345                 350

Gly Val Pro Arg Ser Leu Gly Arg Asn Gly Arg Leu Gln Leu Leu Asp
        355                 360                 365

Leu Ser Ser Asn Lys Leu Thr Gly Thr Leu Pro Pro Glu Leu Cys Ala
    370                 375                 380

Gly Gly Lys Leu Gln Thr Leu Ile Ala Leu Gly Asn Phe Leu Phe Gly
385                 390                 395                 400

Ala Ile Pro Asp Ser Leu Gly Gln Cys Lys Ser Leu Ser Arg Val Arg
                405                 410                 415

Leu Gly Glu Asn Tyr Leu Asn Gly Ser Ile Pro Lys Gly Leu Phe Glu
            420                 425                 430

Leu Pro Lys Leu Thr Gln Val Glu Leu Gln Asp Asn Leu Leu Thr Gly
        435                 440                 445

Asn Phe Pro Ala Val Ile Gly Ala Ala Ala Pro Asn Leu Gly Glu Ile
    450                 455                 460

Ser Leu Ser Asn Asn Gln Leu Thr Gly Ala Leu Pro Ala Ser Leu Gly
465                 470                 475                 480

Asn Phe Ser Gly Val Gln Lys Leu Leu Leu Asp Gln Asn Ala Phe Ser
                485                 490                 495

Gly Ala Ile Pro Pro Glu Ile Gly Arg Leu Gln Gln Leu Ser Lys Ala
```

```
            500                 505                 510

Asp Leu Ser Ser Asn Lys Phe Glu Gly Gly Val Pro Pro Glu Ile Gly
        515                 520                 525

Lys Cys Arg Leu Leu Thr Tyr Leu Asp Met Ser Gln Asn Asn Leu Ser
    530                 535                 540

Gly Lys Ile Pro Pro Ala Ile Ser Gly Met Arg Ile Leu Asn Tyr Leu
545                 550                 555                 560

Asn Leu Ser Arg Asn His Leu Asp Gly Glu Ile Pro Pro Ser Ile Ala
                565                 570                 575

Thr Met Gln Ser Leu Thr Ala Val Asp Phe Ser Tyr Asn Asn Leu Ser
            580                 585                 590

Gly Leu Val Pro Gly Thr Gly Gln Phe Ser Tyr Phe Asn Ala Thr Ser
        595                 600                 605

Phe Val Gly Asn Pro Gly Leu Cys Gly Pro Tyr Leu Gly Pro Cys Gly
    610                 615                 620

Ala Gly Ile Thr Gly Ala Gly Gln Thr Ala His Gly His Gly Gly Leu
625                 630                 635                 640

Thr Asn Thr Val Lys Leu Leu Ile Val Leu Gly Leu Leu Ile Cys Ser
                645                 650                 655

Ile Ala Phe Ala Ala Ala Ala Ile Leu Lys Ala Arg Ser Leu Lys Lys
            660                 665                 670

Ala Ser Glu Ala Arg Val Trp Lys Leu Thr Ala Phe Gln Arg Leu Asp
        675                 680                 685

Phe Thr Ser Asp Asp Val Leu Asp Cys Leu Lys Glu Glu Asn Ile Ile
    690                 695                 700

Gly Lys Gly Gly Ala Gly Ile Val Tyr Lys Gly Ala Met Pro Asn Gly
705                 710                 715                 720

Glu Leu Val Ala Val Lys Arg Leu Pro Ala Met Gly Arg Gly Ser Ser
                725                 730                 735

His Asp His Gly Phe Ser Ala Glu Ile Gln Thr Leu Gly Arg Ile Arg
            740                 745                 750

His Arg His Ile Val Arg Leu Leu Gly Phe Cys Ser Asn Asn Glu Thr
        755                 760                 765

Asn Leu Leu Val Tyr Glu Tyr Met Pro Asn Gly Ser Leu Gly Glu Met
    770                 775                 780

Leu His Gly Lys Lys Gly Gly His Leu His Trp Asp Thr Arg Tyr Ser
785                 790                 795                 800

Ile Ala Ile Glu Ala Ala Lys Gly Leu Cys Tyr Leu His His Asp Cys
                805                 810                 815

Ser Pro Leu Ile Leu His Arg Asp Val Lys Ser Asn Asn Ile Leu Leu
            820                 825                 830

Asp Ser Asn Phe Glu Ala His Val Ala Asp Phe Gly Leu Ala Lys Phe
        835                 840                 845

Leu Gln Asp Ser Gly Ala Ser Glu Cys Met Ser Ala Ile Ala Gly Ser
    850                 855                 860

Tyr Gly Tyr Ile Ala Pro Glu Tyr Ala Tyr Thr Leu Lys Val Asp Glu
865                 870                 875                 880

Lys Ser Asp Val Tyr Ser Phe Gly Val Val Leu Leu Glu Leu Val Thr
                885                 890                 895

Gly Arg Lys Pro Val Gly Glu Phe Gly Asp Gly Val Asp Ile Val Gln
            900                 905                 910

Trp Ala Lys Met Met Thr Asn Ser Ser Lys Glu Gln Val Met Lys Ile
        915                 920                 925
```

```
Leu Asp Pro Arg Leu Ser Thr Val Pro Leu Gln Glu Val Met His Val
    930                 935                 940

Phe Tyr Val Ala Leu Leu Cys Thr Glu Glu Gln Ser Val Gln Arg Pro
945                 950                 955                 960

Thr Met Arg Glu Val Val Gln Ile Leu Ser Glu Leu Pro Lys Pro Ala
                965                 970                 975

Asn Lys Gln Gly Glu Asp Val Pro Asn Ser Gly Asp Gly Ser Ala Ser
            980                 985                 990

Ser Pro Leu His Pro Ala Pro Val  Glu Thr Asn Glu Ala  Pro Thr Val
        995                 1000                 1005

Glu Ala  Arg Asp Gln Gln Gln  Gln Thr Ser Ser Pro  Ser Ser Pro
    1010                 1015                 1020

Pro Pro  Asp Leu Ile Ser Ile
    1025                 1030


<210> SEQ ID NO 94
<211> LENGTH: 56
<212> TYPE: PRT
<213> ORGANISM: Sorghum bicolor

<400> SEQUENCE: 94

Met Arg Ile Leu Asn Tyr Leu Asn Leu Ser Arg Asn His Leu Asp Gly
1               5                   10                  15

Glu Ile Pro Pro Ser Ile Ala Thr Met Gln Ser Leu Thr Ala Val Asp
            20                  25                  30

Phe Ser Tyr Asn Asn Leu Ser Gly Leu Val Pro Gly Thr Gly Gln Phe
        35                  40                  45

Ser Tyr Phe Asn Ala Thr Ser Phe
    50                  55


<210> SEQ ID NO 95
<211> LENGTH: 1001
<212> TYPE: PRT
<213> ORGANISM: Sorghum bicolor

<400> SEQUENCE: 95

Met Ala Met Ala Pro Ser Thr Ala Ala Ala Thr Thr Leu Leu Leu Pro
1               5                   10                  15

Val Phe Leu Leu Ile Ala Thr Ala Thr His Cys Thr Ala Ala Asp Ser
            20                  25                  30

Ser Ser Ser Pro Asp Ala Ala Ala Leu Leu Asn Leu Ser Ala Ala Leu
        35                  40                  45

Ala Asp Pro Ser Gly Tyr Leu Ser Thr His Trp Thr Pro Asp Thr Ala
    50                  55                  60

Leu Cys Ser Trp Pro Arg Val Ser Cys Asp Ala Thr Asp Thr Arg Val
65                  70                  75                  80

Ile Ser Leu Asp Leu Ser Gly Leu Asn Leu Ser Gly Pro Ile Pro Ala
                85                  90                  95

Ala Ala Leu Ser Ser Leu Pro His Leu Gln Ser Leu Asn Leu Ser Asn
            100                 105                 110

Asn Ile Leu Asn Ser Thr Ala Phe Pro Asp Glu Ile Ile Ala Ser Leu
        115                 120                 125

Lys Ser Leu Arg Val Leu Asp Leu Tyr Asn Asn Asn Leu Thr Gly Pro
    130                 135                 140

Leu Pro Ala Ala Leu Pro Asn Leu Thr Asp Leu Val His Val His Leu
145                 150                 155                 160
```

-continued

```
Gly Gly Asn Phe Phe Ser Gly Ser Ile Pro Arg Ser Tyr Gly Gln Trp
                165                 170                 175

Ser Arg Ile Arg Tyr Leu Ala Leu Ser Gly Asn Glu Leu Thr Gly Glu
            180                 185                 190

Ile Pro Glu Glu Leu Gly Asn Leu Thr Thr Leu Arg Glu Leu Tyr Leu
        195                 200                 205

Gly Tyr Tyr Asn Asn Phe Thr Gly Gly Ile Pro Pro Glu Leu Gly Arg
    210                 215                 220

Leu Arg Ala Leu Val Arg Leu Asp Met Ala Asn Cys Gly Ile Ser Arg
225                 230                 235                 240

Glu Ile Pro Pro Glu Val Ala Asn Leu Thr Ser Leu Asp Thr Leu Phe
                245                 250                 255

Leu Gln Ile Asn Ala Leu Ser Gly Arg Leu Pro Thr Glu Ile Gly Ala
            260                 265                 270

Met Gly Ala Leu Lys Ser Leu Asp Leu Ser Asn Asn Leu Phe Val Gly
        275                 280                 285

Glu Ile Pro Ala Ser Phe Ala Ser Leu Lys Asn Leu Thr Leu Leu Asn
    290                 295                 300

Leu Phe Arg Asn Arg Leu Ala Gly Glu Ile Pro Glu Phe Ile Gly Asp
305                 310                 315                 320

Leu Pro Asn Leu Glu Val Leu Gln Leu Trp Glu Asn Asn Phe Thr Gly
                325                 330                 335

Gly Ile Pro Thr Asn Leu Gly Val Ala Ala Thr Ser Leu Lys Ile Val
            340                 345                 350

Asp Val Ser Thr Asn Lys Leu Thr Gly Val Leu Pro Ser Lys Leu Cys
        355                 360                 365

Ala Gly Glu Arg Leu Glu Thr Phe Ile Ala Leu Gly Asn Ser Leu Phe
    370                 375                 380

Gly Asp Ile Pro Asp Gly Leu Ala Gly Cys Pro Ser Leu Thr Arg Ile
385                 390                 395                 400

Arg Leu Gly Glu Asn Phe Leu Asn Gly Thr Ile Pro Glu Lys Leu Phe
                405                 410                 415

Thr Leu Pro Asn Leu Thr Gln Val Glu Leu His Asp Asn Leu Leu Ser
            420                 425                 430

Gly Glu Leu Arg Leu Asp Gly Glu Lys Val Ser Pro Ser Ile Gly Glu
        435                 440                 445

Leu Ser Leu Phe Asn Asn Arg Leu Thr Gly Gln Val Pro Thr Gly Ile
    450                 455                 460

Gly Gly Leu Leu Gly Leu Gln Lys Leu Leu Leu Ala Gly Asn Arg Leu
465                 470                 475                 480

Ser Gly Glu Leu Pro Thr Glu Val Arg Lys Leu Gln Gln Leu Ser Lys
                485                 490                 495

Ala Asp Leu Ser Gly Asn Leu Ile Ser Gly Ala Val Pro Ala Ala Ile
            500                 505                 510

Gly Arg Cys Arg Leu Leu Thr Phe Leu Asp Ile Ser Ser Asn Lys Leu
        515                 520                 525

Ser Gly Ser Ile Pro Pro Glu Leu Ala Ser Leu Arg Ile Leu Asn Tyr
    530                 535                 540

Leu Asn Val Ser His Asn Ala Leu Glu Gly Glu Ile Pro Pro Ala Ile
545                 550                 555                 560

Ala Gly Met Gln Ser Leu Thr Ala Val Asp Phe Ser Tyr Asn Asn Leu
                565                 570                 575
```

-continued

```
Ser Gly Glu Val Pro Ser Thr Gly Gln Phe Ala Tyr Phe Asn Gly Thr
            580                 585                 590

Ser Phe Ala Gly Asn Ala Gly Leu Cys Gly Ala Phe Leu Ser Pro Cys
        595                 600                 605

Arg Ser His Gly Val Ala Thr Ser Gly Phe Gly Ser Leu Ser Ser Thr
    610                 615                 620

Ser Lys Leu Leu Leu Val Leu Gly Leu Leu Ala Leu Ser Ile Ile Phe
625                 630                 635                 640

Ala Ala Ala Ala Val Leu Lys Ala Arg Ser Leu Lys Arg Ser Ala Glu
                645                 650                 655

Ala Arg Ala Trp Arg Leu Thr Ala Phe Gln Arg Leu Asp Phe Ala Val
            660                 665                 670

Asp Asp Val Leu Asp Cys Leu Lys Glu Glu Asn Val Ile Gly Lys Gly
        675                 680                 685

Gly Ser Gly Ile Val Tyr Lys Gly Ala Met Pro Gly Gly Ala Val Val
    690                 695                 700

Ala Val Lys Arg Leu Pro Ala Ile Gly Arg Ser Gly Ala Ala His Asp
705                 710                 715                 720

Asp Tyr Gly Phe Ser Ala Glu Ile Gln Thr Leu Gly Arg Ile Arg His
                725                 730                 735

Arg His Ile Val Arg Leu Leu Gly Phe Ala Ala Asn Arg Glu Thr Asn
            740                 745                 750

Leu Leu Val Tyr Glu Tyr Met Pro Asn Gly Ser Leu Gly Glu Val Leu
        755                 760                 765

His Gly Lys Lys Gly Gly His Leu Gln Trp Ala Thr Arg Phe Lys Ile
    770                 775                 780

Ala Val Glu Ala Ala Lys Gly Leu Cys Tyr Leu His His Asp Cys Ser
785                 790                 795                 800

Pro Pro Ile Leu His Arg Asp Val Lys Ser Asn Asn Ile Leu Leu Asp
                805                 810                 815

Ala Asp Phe Glu Ala His Val Ala Asp Phe Gly Leu Ala Lys Phe Leu
            820                 825                 830

Arg Gly Asn Ala Gly Gly Ser Glu Cys Met Ser Ala Ile Ala Gly Ser
        835                 840                 845

Tyr Gly Tyr Ile Ala Pro Glu Tyr Ala Tyr Thr Leu Lys Val Asp Glu
    850                 855                 860

Lys Ser Asp Val Tyr Ser Phe Gly Val Val Leu Leu Glu Leu Ile Ala
865                 870                 875                 880

Gly Arg Lys Pro Val Gly Glu Phe Gly Asp Gly Val Asp Ile Val Gln
                885                 890                 895

Trp Val Arg Met Val Thr Gly Ser Ser Lys Glu Gly Val Met Lys Ile
            900                 905                 910

Ala Asp Pro Arg Leu Ser Thr Val Pro Leu Tyr Glu Leu Thr His Val
        915                 920                 925

Phe Tyr Val Ala Met Leu Cys Val Ala Glu Gln Ser Val Glu Arg Pro
    930                 935                 940

Thr Met Arg Glu Val Val Gln Ile Leu Ala Asp Val Pro Gly Ser Thr
945                 950                 955                 960

Ser Thr Ser Ile Asp Val Pro Leu Val Ile Glu Pro Lys Glu Asn Gly
                965                 970                 975

Ser Pro Gly Glu Lys Lys Gln Glu Gln Gln Glu Gly Ser His Asp Ser
            980                 985                 990

Pro Pro Gln Gln Asp Leu Leu Ser  Ile
```

995 1000

<210> SEQ ID NO 96
<211> LENGTH: 56
<212> TYPE: PRT
<213> ORGANISM: Sorghum bicolor

<400> SEQUENCE: 96

Leu Arg Ile Leu Asn Tyr Leu Asn Val Ser His Asn Ala Leu Glu Gly
1 5 10 15

Glu Ile Pro Pro Ala Ile Ala Gly Met Gln Ser Leu Thr Ala Val Asp
20 25 30

Phe Ser Tyr Asn Asn Leu Ser Gly Glu Val Pro Ser Thr Gly Gln Phe
35 40 45

Ala Tyr Phe Asn Gly Thr Ser Phe
50 55

<210> SEQ ID NO 97
<211> LENGTH: 1031
<212> TYPE: PRT
<213> ORGANISM: Sorghum bicolor

<400> SEQUENCE: 97

Met Pro Met Arg Leu His His Leu Leu Leu Val Leu Leu Ala Thr Ala
1 5 10 15

Ala Ala Val Ala Gly Ala Ala Ala Ala Gly Ala Gly Ala Asp Ala Asp
20 25 30

Ala Leu Leu Ala Ala Lys Ala Ala Leu Ser Asp Pro Ala Gly Ala Leu
35 40 45

Ala Ser Trp Thr Asn Ala Thr Ser Thr Gly Pro Cys Ala Trp Ser Gly
50 55 60

Val Thr Cys Asn Ala Arg Gly Ala Val Ile Gly Leu Asp Leu Ser Gly
65 70 75 80

Arg Asn Leu Ser Gly Ala Val Pro Ala Ala Ala Leu Ser Arg Leu Ala
85 90 95

His Leu Ala Arg Leu Asp Leu Ala Ala Asn Ala Leu Ser Gly Pro Ile
100 105 110

Pro Ala Pro Leu Ser Arg Leu Gln Ser Leu Thr His Leu Asn Leu Ser
115 120 125

Asn Asn Val Leu Asn Gly Thr Phe Pro Pro Pro Phe Ala Arg Leu Arg
130 135 140

Ala Leu Arg Val Leu Asp Leu Tyr Asn Asn Asn Leu Thr Gly Pro Leu
145 150 155 160

Pro Leu Val Val Val Ala Leu Pro Met Leu Arg His Leu His Leu Gly
165 170 175

Gly Asn Phe Phe Ser Gly Glu Ile Pro Pro Glu Tyr Gly Gln Trp Arg
180 185 190

Arg Leu Gln Tyr Leu Ala Val Ser Gly Asn Glu Leu Ser Gly Lys Ile
195 200 205

Pro Pro Glu Leu Gly Gly Leu Thr Ser Leu Arg Glu Leu Tyr Ile Gly
210 215 220

Tyr Tyr Asn Ser Tyr Ser Ser Gly Ile Pro Pro Glu Phe Gly Asn Met
225 230 235 240

Thr Asp Leu Val Arg Leu Asp Ala Ala Asn Cys Gly Leu Ser Gly Glu
245 250 255

Ile Pro Pro Glu Leu Gly Asn Leu Glu Asn Leu Asp Thr Leu Phe Leu

-continued

```
            260                 265                 270

Gln Val Asn Gly Leu Thr Gly Ala Ile Pro Pro Glu Leu Gly Arg Leu
        275                 280                 285

Arg Ser Leu Ser Ser Leu Asp Leu Ser Asn Asn Gly Leu Thr Gly Glu
    290                 295                 300

Ile Pro Ala Ser Phe Ala Ala Leu Lys Asn Leu Thr Leu Leu Asn Leu
305                 310                 315                 320

Phe Arg Asn Lys Leu Arg Gly Ser Ile Pro Glu Leu Val Gly Asp Leu
                325                 330                 335

Pro Asn Leu Glu Val Leu Gln Leu Trp Glu Asn Asn Phe Thr Gly Gly
            340                 345                 350

Ile Pro Arg Arg Leu Gly Arg Asn Gly Arg Leu Gln Leu Val Asp Leu
        355                 360                 365

Ser Ser Asn Arg Leu Thr Gly Thr Leu Pro Pro Glu Leu Cys Ala Gly
    370                 375                 380

Gly Lys Leu Glu Thr Leu Ile Ala Leu Gly Asn Phe Leu Phe Gly Ser
385                 390                 395                 400

Ile Pro Glu Ser Leu Gly Lys Cys Glu Ala Leu Ser Arg Ile Arg Leu
                405                 410                 415

Gly Glu Asn Tyr Leu Asn Gly Ser Ile Pro Glu Gly Leu Phe Glu Leu
            420                 425                 430

Pro Asn Leu Thr Gln Val Glu Leu Gln Asp Asn Leu Leu Ser Gly Gly
        435                 440                 445

Phe Pro Ala Val Ala Gly Thr Gly Ala Pro Asn Leu Gly Ala Ile Thr
    450                 455                 460

Leu Ser Asn Asn Gln Leu Thr Gly Ala Leu Pro Ala Ser Ile Gly Asn
465                 470                 475                 480

Phe Ser Gly Leu Gln Lys Leu Leu Leu Asp Gln Asn Ala Phe Thr Gly
                485                 490                 495

Ala Val Pro Pro Glu Ile Gly Arg Leu Gln Gln Leu Ser Lys Ala Asp
            500                 505                 510

Leu Ser Gly Asn Ala Leu Asp Gly Gly Met Pro Pro Glu Ile Gly Lys
        515                 520                 525

Cys Arg Leu Leu Thr Tyr Leu Asp Leu Ser Arg Asn Asn Leu Ser Gly
    530                 535                 540

Glu Ile Pro Pro Ala Ile Ser Gly Met Arg Ile Leu Asn Tyr Leu Asn
545                 550                 555                 560

Leu Ser Arg Asn His Leu Asp Gly Glu Ile Pro Ala Thr Ile Ala Ala
                565                 570                 575

Met Gln Ser Leu Thr Ala Val Asp Phe Ser Tyr Asn Asn Leu Ser Gly
            580                 585                 590

Leu Val Pro Ala Thr Gly Gln Phe Ser Tyr Phe Asn Ala Thr Ser Phe
        595                 600                 605

Val Gly Asn Pro Gly Leu Cys Gly Pro Tyr Leu Gly Pro Cys His Ser
    610                 615                 620

Gly Gly Ala Gly Thr Gly His Gly Ala His Thr His Gly Gly Met Ser
625                 630                 635                 640

Asn Thr Phe Lys Leu Leu Ile Val Leu Gly Leu Leu Val Cys Ser Ile
                645                 650                 655

Ala Phe Ala Ala Met Ala Ile Trp Lys Ala Arg Ser Leu Lys Lys Ala
            660                 665                 670

Ser Glu Ala Arg Ala Trp Arg Leu Thr Ala Phe Gln Arg Leu Glu Phe
        675                 680                 685
```

Thr Cys Asp Asp Val Leu Asp Ser Leu Lys Glu Glu Asn Ile Ile Gly
690 695 700

Lys Gly Gly Ala Gly Ile Val Tyr Lys Gly Thr Met Pro Asp Gly Glu
705 710 715 720

His Val Ala Val Lys Arg Leu Ser Ser Met Ser Arg Gly Ser Ser His
725 730 735

Asp His Gly Phe Ser Ala Glu Ile Gln Thr Leu Gly Arg Ile Arg His
740 745 750

Arg Tyr Ile Val Arg Leu Leu Gly Phe Cys Ser Asn Asn Glu Thr Asn
755 760 765

Leu Leu Val Tyr Glu Phe Met Pro Asn Gly Ser Leu Gly Glu Leu Leu
770 775 780

His Gly Lys Lys Gly Gly His Leu His Trp Asp Thr Arg Tyr Lys Ile
785 790 795 800

Ala Val Glu Ala Ala Lys Gly Leu Ser Tyr Leu His His Asp Cys Ser
805 810 815

Pro Pro Ile Leu His Arg Asp Val Lys Ser Asn Asn Ile Leu Leu Asp
820 825 830

Ser Asp Phe Glu Ala His Val Ala Asp Phe Gly Leu Ala Lys Phe Leu
835 840 845

Gln Asp Ser Gly Ala Ser Gln Cys Met Ser Ala Ile Ala Gly Ser Tyr
850 855 860

Gly Tyr Ile Ala Pro Glu Tyr Ala Tyr Thr Leu Lys Val Asp Glu Lys
865 870 875 880

Ser Asp Val Tyr Ser Phe Gly Val Val Leu Leu Glu Leu Val Thr Gly
885 890 895

Lys Lys Pro Val Gly Glu Phe Gly Asp Gly Val Asp Ile Val Gln Trp
900 905 910

Val Lys Thr Met Thr Asp Ala Asn Lys Glu Gln Val Ile Lys Ile Met
915 920 925

Asp Pro Arg Leu Ser Thr Val Pro Val His Glu Val Met His Val Phe
930 935 940

Tyr Val Ala Leu Leu Cys Val Glu Glu Gln Ser Val Gln Arg Pro Thr
945 950 955 960

Met Arg Glu Val Val Gln Met Leu Ser Glu Leu Pro Lys Pro Ala Ala
965 970 975

Arg Gln Gly Asp Glu Pro Pro Ser Val Asp Asp Asp Gly Ser Ala Ala
980 985 990

Pro Ser Asp Ala Pro Ala Gly Asp Gly Ser Val Glu Ala Pro His Asp
995 1000 1005

Glu Ala Thr Asn Glu Gln Gln Pro Gln Pro Ile Ser Gln Ser Ser
1010 1015 1020

Pro Thr Thr Asp Leu Ile Ser Met
1025 1030

<210> SEQ ID NO 98
<211> LENGTH: 56
<212> TYPE: PRT
<213> ORGANISM: Sorghum bicolor

<400> SEQUENCE: 98

Met Arg Ile Leu Asn Tyr Leu Asn Leu Ser Arg Asn His Leu Asp Gly
1 5 10 15

Glu Ile Pro Ala Thr Ile Ala Ala Met Gln Ser Leu Thr Ala Val Asp

```
            20                  25                  30

Phe Ser Tyr Asn Asn Leu Ser Gly Leu Val Pro Ala Thr Gly Gln Phe
        35                  40                  45

Ser Tyr Phe Asn Ala Thr Ser Phe
    50                  55


<210> SEQ ID NO 99
<211> LENGTH: 1000
<212> TYPE: PRT
<213> ORGANISM: Sorghum bicolor

<400> SEQUENCE: 99

Met Pro Pro Pro Ile Leu Leu Cys Phe Leu Leu Leu Leu Leu Leu Leu
1               5                   10                  15

Leu Leu Leu Pro Ala Pro Ala Ser Ala Thr Pro Glu Arg Asp Ala Tyr
            20                  25                  30

Ala Leu Ser Lys Leu Lys Ser Ser Leu Val Pro Ser Thr Asn Ser Thr
        35                  40                  45

Ser Asn Ala Leu Ser Asp Trp Asp Pro Thr Ala Thr Pro Pro Ala His
    50                  55                  60

Cys Ala Phe Thr Gly Val Thr Cys Asp Ala Ala Thr Ser Arg Val Val
65                  70                  75                  80

Ala Ile Asn Leu Thr Ala Val Pro Leu His Gly Gly Ala Leu Pro Pro
                85                  90                  95

Glu Val Ala Leu Leu Asp Ala Leu Ala Ser Leu Thr Val Ala Ala Cys
            100                 105                 110

Ser Leu His Gly Arg Val Pro Pro Val Leu Ser Ser Met Pro Ala Leu
        115                 120                 125

Arg His Leu Asn Leu Ser Asn Asn Asn Leu Ser Gly Ser Phe Pro Ser
    130                 135                 140

Pro Pro Pro Ser Pro Ser Thr Pro Tyr Phe Pro Ala Leu Glu Leu Val
145                 150                 155                 160

Asp Val Tyr Asn Asn Asn Leu Ser Gly Pro Leu Pro Pro Leu Gly Ala
                165                 170                 175

Ser Gln Ala Arg Thr Leu Arg Tyr Leu His Leu Gly Gly Asn Tyr Phe
            180                 185                 190

Asn Gly Ser Ile Pro Asp Thr Phe Gly Asp Leu Ala Ala Leu Glu Tyr
        195                 200                 205

Leu Gly Leu Asn Gly Asn Ala Leu Ser Gly Arg Val Pro Pro Ser Leu
    210                 215                 220

Ser Arg Leu Ser Arg Leu Arg Glu Met Tyr Val Gly Tyr Tyr Asn Gln
225                 230                 235                 240

Tyr Ser Gly Gly Val Pro Pro Glu Phe Gly Asp Leu Gln Ser Leu Val
                245                 250                 255

Arg Leu Asp Met Ser Ser Cys Thr Leu Thr Gly Pro Ile Pro Pro Glu
            260                 265                 270

Leu Ala Arg Leu Ser Arg Leu Asp Thr Leu Phe Leu Ser Met Asn Gln
        275                 280                 285

Leu Thr Gly Leu Ile Pro Pro Glu Leu Gly Gly Leu Thr Ser Leu Gln
    290                 295                 300

Ser Leu Asp Leu Ser Ile Asn Asp Leu Ser Gly Glu Ile Pro Asp Ser
305                 310                 315                 320

Phe Ala Gly Leu Thr Asn Leu Thr Leu Leu Asn Leu Phe Arg Asn His
                325                 330                 335
```

```
Leu Arg Gly Glu Ile Pro Glu Phe Val Gly Glu Phe Pro Phe Leu Glu
            340                 345                 350

Val Leu Gln Val Trp Asp Asn Asn Leu Thr Gly Ser Leu Pro Pro Ala
        355                 360                 365

Leu Gly Arg Asn Gly Arg Leu Lys Thr Leu Asp Val Thr Gly Asn His
    370                 375                 380

Leu Thr Gly Thr Ile Pro Pro Asp Leu Cys Ala Gly Arg Lys Leu Gln
385                 390                 395                 400

Met Leu Val Leu Met Asp Asn Ala Phe Phe Gly Ser Ile Pro Asp Ser
                405                 410                 415

Leu Gly Asp Cys Lys Thr Leu Thr Arg Val Arg Leu Gly Lys Asn Met
            420                 425                 430

Leu Thr Gly Pro Val Pro Pro Gly Leu Phe Asp Leu Pro Leu Ala Asn
        435                 440                 445

Met Leu Glu Leu Thr Asp Asn Met Leu Thr Gly Glu Leu Pro Asp Val
    450                 455                 460

Ile Ala Gly Asp Lys Ile Gly Met Leu Met Leu Gly Asn Asn Gly Ile
465                 470                 475                 480

Gly Gly Arg Ile Pro Ala Ala Ile Gly Asn Leu Ala Ala Leu Gln Thr
                485                 490                 495

Leu Ser Leu Glu Ser Asn Asn Phe Ser Gly Pro Leu Pro Pro Glu Ile
            500                 505                 510

Gly Arg Leu Arg Asn Leu Thr Arg Phe Asn Ala Ser Gly Asn Ala Leu
        515                 520                 525

Thr Gly Gly Ile Pro Arg Glu Leu Met Gly Cys Gly Ser Leu Gly Ala
    530                 535                 540

Ile Asp Leu Ser Arg Asn Gly Leu Thr Gly Glu Ile Pro Asp Thr Val
545                 550                 555                 560

Thr Ser Leu Lys Ile Leu Cys Thr Phe Asn Val Ser Arg Asn Met Leu
                565                 570                 575

Ser Gly Glu Leu Pro Pro Ala Ile Ser Asn Met Thr Ser Leu Thr Thr
            580                 585                 590

Leu Asp Val Ser Tyr Asn Gln Leu Trp Gly Pro Val Pro Met Gln Gly
        595                 600                 605

Gln Phe Leu Val Phe Asn Glu Ser Ser Phe Val Gly Asn Pro Gly Leu
    610                 615                 620

Cys Gly Ala Pro Phe Ala Gly Gly Ser Asp Pro Cys Pro Pro Ser Phe
625                 630                 635                 640

Gly Gly Ala Arg Ser Pro Phe Ser Leu Arg Gln Trp Asp Thr Lys Lys
                645                 650                 655

Leu Leu Val Trp Leu Val Val Leu Leu Thr Leu Leu Ile Leu Ala Ile
            660                 665                 670

Leu Gly Ala Arg Lys Ala Arg Glu Ala Trp Arg Glu Ala Ala Arg Arg
        675                 680                 685

Arg Ser Gly Ala Trp Lys Met Thr Ala Phe Gln Lys Leu Asp Phe Ser
    690                 695                 700

Ala Asp Asp Val Val Glu Cys Leu Lys Glu Asp Asn Ile Ile Gly Lys
705                 710                 715                 720

Gly Gly Ala Gly Ile Val Tyr His Gly Val Thr Arg Ser Gly Ala Glu
                725                 730                 735

Leu Ala Ile Lys Arg Leu Val Gly Arg Gly Cys Gly Asp His Asp Arg
            740                 745                 750

Gly Phe Thr Ala Glu Val Thr Thr Leu Gly Arg Ile Arg His Arg Asn
```

```
        755                 760                 765

Ile Val Arg Leu Leu Gly Phe Val Ser Asn Arg Glu Thr Asn Leu Leu
    770                 775                 780

Leu Tyr Glu Tyr Met Pro Asn Gly Ser Leu Gly Glu Met Leu His Gly
785                 790                 795                 800

Gly Lys Gly Gly His Leu Gly Trp Glu Ala Arg Ala Arg Val Ala Val
            805                 810                 815

Glu Ala Ala Arg Gly Leu Cys Tyr Leu His His Asp Cys Ala Pro Arg
            820                 825                 830

Ile Ile His Arg Asp Val Lys Ser Asn Asn Ile Leu Leu Asp Ser Gly
        835                 840                 845

Phe Glu Ala His Val Ala Asp Phe Gly Leu Ala Lys Phe Leu Gly Gly
    850                 855                 860

Ala Thr Ser Glu Cys Met Ser Ala Ile Ala Gly Ser Tyr Gly Tyr Ile
865                 870                 875                 880

Ala Pro Glu Tyr Ala Tyr Thr Leu Arg Val Asp Glu Lys Ser Asp Val
            885                 890                 895

Tyr Ser Phe Gly Val Val Leu Leu Glu Leu Ile Thr Gly Arg Arg Pro
            900                 905                 910

Val Gly Ser Phe Gly Asp Gly Val Asp Ile Val His Trp Val Arg Lys
        915                 920                 925

Val Thr Ala Glu Leu Pro Asp Ala Ala Gly Ala Glu Pro Val Leu Ala
    930                 935                 940

Val Ala Asp Arg Arg Leu Ala Pro Glu Pro Val Pro Leu Leu Ala Asp
945                 950                 955                 960

Leu Tyr Lys Val Ala Met Ala Cys Val Glu Asp Ala Ser Thr Ala Arg
            965                 970                 975

Pro Thr Met Arg Glu Val Val His Met Leu Ser Thr Ser Ala Ala Ala
            980                 985                 990

Gln Pro Asp Val Leu His Ala Phe
        995                 1000


<210> SEQ ID NO 100
<211> LENGTH: 56
<212> TYPE: PRT
<213> ORGANISM: Sorghum bicolor

<400> SEQUENCE: 100

Leu Lys Ile Leu Cys Thr Phe Asn Val Ser Arg Asn Met Leu Ser Gly
1               5                   10                  15

Glu Leu Pro Pro Ala Ile Ser Asn Met Thr Ser Leu Thr Thr Leu Asp
            20                  25                  30

Val Ser Tyr Asn Gln Leu Trp Gly Pro Val Pro Met Gln Gly Gln Phe
        35                  40                  45

Leu Val Phe Asn Glu Ser Ser Phe
    50                  55


<210> SEQ ID NO 101
<211> LENGTH: 56
<212> TYPE: PRT
<213> ORGANISM: Brassica rapa

<400> SEQUENCE: 101

Val Ile Asn Leu Gly Thr Leu Asn Leu Ser Gly Asn Gln Leu Thr Gly
1               5                   10                  15

Ser Ile Pro Ile Gly Ile Gly Lys Met Thr Ser Leu Thr Thr Leu Asp
```

-continued 20 25 30

Leu Ser Phe Asn Asp Leu Ser Gly Arg Val Pro Leu Gly Gly Gln Phe
35 40 45

Leu Val Phe Asn Asp Thr Ser Phe
50 55

<210> SEQ ID NO 102
<211> LENGTH: 11743
<212> TYPE: DNA
<213> ORGANISM: Artificial Sequence
<220> FEATURE:
<223> OTHER INFORMATION: plasmid AtproCLV1:BrCLV1

<400> SEQUENCE: 102
aagcggccgc ggggtttatc tgaattggat ggtgatgaaa tgttattaac agattttcta 60
atttttgtct ctatcgattt tgtttccgta aatacatctt ttgtgtatat attgtcttgt 120
agaaagaaac attgattaag tagagaaata ggataatcaa tctctgtact taatacatca 180
tccattgaaa caagttagga atcgatccaa tatgaggctc tgcaaaaaca attcaggaaa 240
agattctgca aaaacaattt aggagaatga gtgaaatcgc aggggcaatt tcgtcaattt 300
atttcccaaa aactgcctat cttcataaac tcaatcataa tgtgctcttt ctctaattta 360
tggcccaaaa tgtacccaat attataaaag cccccacaat taagcaccaa agagttttgg 420
tacattaact tgggaggaaa cagagacact tgttaactgg taaggcaaca tttcaaattc 480
catatcttgt tctctcaagt ccaatgcatt tatccttgca cgcttgattg tttaaaccat 540
ttagattaat gggttggcat tggtcacgct gatccaatgt ttcaaatggg taagtgaatg 600
ttgattgccg acgtgactga agacccaagg cccaacgacc tactggtcca ggttgactat 660
gaacaaaaga actagatttt tttttcccct acattttaaa gaaaatactt gatgaagatg 720
tggtgccttt tcataagatc taaaaagttt caaatcttta cgatggaaca aaaagtgaaa 780
ggtgaagtaa gggtcatttg ggattgagaa gtttcttcgt ccaaaatcat tgcatgagtt 840
gaatagattt gggattaaag ctgccaatac aagaggattc ggtaatgact gaagcaaaag 900
cccagcaggg ccattaggca aacaccagtt tccaagacgg atttgtgtaa gaccacttat 960
gacacaagtt tgtcttcact atcatcatct tcttcttcta cttctactac tacttttgta 1020
gccttgtcgt ttttatcatt aacatgattg acaagactat gacctatata tcttattatt 1080
atcattgctc tctctatttg tttatattga ttattacttt ttgagatttt tcaatggttt 1140
tatctctaac taaacattat aattagtgaa acaagcttag tagaagtaaa agtattattc 1200
tatgctaaag tacattgatt agtagagtgt gtaattgtgt atacagataa tctataaaca 1260
attggtgcat ctgtatataa aactttatga tttatttatt gtatttaata agtatatgaa 1320
ttgggtacct aactttctaa acagttccaa atttattctt aaatcaaatt gcatatgatt 1380
tttaaatatt ttgagacgat tttattataa cgcaaacaac agagtaaaag aagcatatgt 1440
tgcaaattgt actatggcaa gttcaaatcg aaacattttt gtgaaaatca aacatgtgaa 1500
ccaagcttct acagtttaat tccctttcgt ataatttaat ttcaacaaat ttattgatat 1560
ccatctagaa attggtccaa agttctttca cccttgagtc atttagtgat aaagatgaca 1620
tgatttttgg tgataaattt tccatcgttg ctatatgtcg ttatattatt ctcctatatg 1680
tatattatac tatttacatc agaaaataat ccaaagttta gagattcttt tttacaataa 1740
taaaatttcc cacttactaa aaagagctcc ttttctgctg aagagaacct aaacctttat 1800
tcccaaagtt cattgagtta gagcattttc agcgaatcac ataagagatg ctctcttctt 1860

-continued

```
catcactaat tgacatctca ttgttttaaa ggttgcactt gtacctgttg atctgattct   1920
caatccactt aagttaaacc aaatagacac gagaaaaaag cacatttatt tgttgctaag   1980
tatgcatatt tttcagcgtt tacttcttaa tctaatgtat atcataagat aatatctaaa   2040
agagaatgca caaaagatta ttaatatgag aaattcgctg ccatttagga aggaccttta   2100
taccaatata ccgcaataat aatagaacat tggtccccaa gtgtatgtca accccaagtg   2160
tatagatttc tttaaagatt aaaatccctt tttgttgcta aagcacctga tatatttttc   2220
tatcaaacta aaaaaattgt tagcgggatg aagatatatt cgccaagaac catagtgctt   2280
gtataacggc agaccattaa ttcacaacta ttattatttt attgttagat tgttgataga   2340
atcgattttg attgtggcag aatcgatctt gtaaaaactg ctttaaggtg cttacttata   2400
attaagaaag attcacttat gtaagttaag catattaatc atatcattcg gcctaattca   2460
ttaggaatat tttgctattc gttttgccat cattaacaac aaaattgaca cgttttcagc   2520
caaaagtatt aacaactaaa cctaaaactt caaacattaa atagttttta gtatctttag   2580
tttcaaacta gtgatttgtc ctaatatcaa cactacgaac gaatttatat acattgaact   2640
tttttctgaa tcaccgatta caaaacgaat ataatttggt atcggcagtt gctattaatt   2700
tgatcggttt ggactttgga ctaatcacga tcaaatctta aatggaccga agtgaataaa   2760
tccctaatgt tttcaagaga gtcacacgaa cgaaacaaag gtaaaatatg aacatagagc   2820
gtggggacct tgaagcagaa ggtctgtatg gtgacagacc ggtgagtgga gtgtatgaat   2880
gaacgagaag tgagaagaca aaatacaaga aagagcgttg acttggaagt taaagccaaa   2940
aaaaccacaa ggggcaaatt tgtctcttta ggaaaaggac acagacagac tttctatacg   3000
ggccaattag aaaaataggc cctacttcta attaaagccc atttacttct ctccttgtct   3060
tcttattcct cttttctccc catcacgtga cgacgatgct ataaacgccg tcggattata   3120
taactggtgc cgttgacaag acggcgacag aagaaagaaa gaagaaacca caggctctag   3180
ggaacgtaac gttatgtcct gtctatagca tttataacgg tcagatcaac gccgtttaga   3240
taaagatctg tcaatgttaa agaagagatg catctctaca ccgttaaatt taaaacgccg   3300
tgaacctctt atctattgat ttttgtttga tgaagccaaa acaaatcgtg tcagaagact   3360
tatcagagaa gaagaaaacg acgacgttcc cgtttctcca tgtctaataa gtgtagtagt   3420
ggcggctact aaaaactcta aagtttgact ccagtaaaac tgcctttcta gtgtaattcc   3480
agtgatttta gagtttgaat agtgtgtgac caaatttgaa agtacaatct cagcaatatt   3540
attgatcact cgttataaaa gaatcgaatg taaaaatagc caatgagaga ctgagacgta   3600
tgtgtttgac cataagtcgt atagtttgta tctatctacc tgcaagatca gcagatggtt   3660
ctctgatcaa ttgtacctta attatctttt attttcgtaa aatttctcta ttcacaaatg   3720
ataaatctac ttaagacagt aaccataaca agatttacaa gataatttga aaaatgaaca   3780
cataaaagta ttttggcgca ttatttttaa taataacaat atttatgtaa agtcacataa   3840
aagtatatat tcgctcacaa agtcttacgg tatttagaac agtagtacca catcgattct   3900
cttcatcttc ttcttcataa tatgccattg ttcatgtctc tgtgtcctat cgcataacac   3960
tcacgctatc ttattatttt ctctcgctct ttctcactga gaggacacta aaaaaatgag   4020
acttctgaaa actcaccttc tgtttctcca tcttcattac gttatctcga tttcgcttct   4080
atgtttctca ccatgcctcg cttccactga catggaccat ctcctcaacc tcaaatcctc   4140
catgattggt cccaacggca acggcctcca cgactgggtt cactcccctt cccccacagc   4200
```

-continued

```
tcactgttct ttctccggcg tttcctgcga cggcgacgct cgtgtcatct ccctcaacgt   4260
ctctttcact cctctcttcg gaaccatctc cccggagatt gggatgctga accgtcttgt   4320
gaatctcacg ttagctgcta ataacttctc cggtatgttg ccgttagaga tgaagagtct   4380
cacttctcta aaggttctca acatctccaa caacgtaaac ctcaacggaa cgttccccgg   4440
agagattctc actcccatgg tcgacctcga agtcctcgac gcgtacaaca acaacttcac   4500
aggcccatta ccgccagaga tccccgggct caagaaactg agacacctct ctctcggagg   4560
aaacttctta accggagaga tcccagagag ttacggagat atccaaagct tggagtatct   4620
cggcctcaac ggagccggac tctccggtga atctccggcg ttcttgtcac gcctcaagaa   4680
tcttaaagaa atgtacgtcg gctacttcaa cagctacacc ggcggcgtac cgccggagtt   4740
cggtgaattg acaaacttag aagtcctcga catggcgagc tgtactctca ccggagagat   4800
tccgacaaca ctaagtaatc taaaacattt gcacactttg tttctccaca tcaacaactt   4860
aaccggaaac atcccacccg aactctccgg tttaatcagc ttaaaatctc tagacctctc   4920
aataaaccag ctaaccggag agattcctca gagcttcatc tccctaggga acatcactct   4980
catcaacctc ttccgaaaca atctccacgg gccgataccg gacttcatcg gagacatgcc   5040
gaacctccaa gtcctccagg tgtgggagaa caacttcacg ctagagctac cggcgaatct   5100
cggccggaac gggaatctga aaaagctcga cgtctctgat aaccatctca ccggactcat   5160
ccccatggat ttgtgcagag gcgggaagct ggagacgctg gtgctctcca acaacttctt   5220
cttcggctcg atccctgaga agctaggtca atgcaaatcg ctaaacaaga tcagaatcgt   5280
caagaatctc ctcaacggca cggttccgga gggcttattc aatctaccgc tcgtaacgat   5340
catcgagctc accgataact tcttctccgg ggagcttccg gggagatgt caggcgacgt   5400
tctcgatcat atctacttat ctaacaattg gtttaccggt ttaatccccc cggctatcgg   5460
taattttaaa aatctacagg atttattctt agaccggaac cggtttagcg ggaatattcc   5520
gagagaagtt ttcgagttga agcatctaac gaagatcaac acgagtgcta acaacctaac   5580
cggcgatatc cctgactcaa tctcacgttg cacttcctta atctccgtcg atctcagccg   5640
taaccgaatc ggcggagata tccctaaaga catccacgat gtgatcaatc tcggaactct   5700
aaatctctcc gggaatcaac tcaccggctc gatcccgatc ggaatcggga agatgacgaa   5760
cttaaccact ctggatctct ccttcaacga cctctccggg agagtcccac tcggcggcca   5820
gttcctagtc ttcaacgaca cttccttcgc cggaaaccct tacctctgcc tccctcacca   5880
cgtctcgtgc cttacgcgtc cggaacaaac ctccgatcgt atccacacgg ctctcttctc   5940
tccgtcgagg atcgttatca cgatcgtcgc ggcgataacg gcgttgatcc tcatcagcgt   6000
cgcgattcgt cagatgaaca agaagaaaca cgagaggtct ctctcgtgga agctaaccgc   6060
cttccaaaga ctcgatttca aagcggaaga cgtcctcgag tgtctccagg aagagaacat   6120
aatcggcaaa ggcggagctg ggatcgtcta ccgcggatcc atgccgaaca acgtagacgt   6180
cgcgatcaaa cggttagtag gacgcggaac agggaggagc gatcacggat tcacggcgga   6240
gatacaaact ctagggagaa tccgccaccg tcatatagtg agactcctcg gatacgtggc   6300
gaacaaggac acgaacctgc ttctctacga gtacatgcct aacgggagcc tcggggagct   6360
tttgcacgga tctaaaggag gtcatcttca gtgggagacg aggcacagag tagccgtgga   6420
agcggcgaaa ggactgtgtt atcttcatca tgactgttcg ccgttgatct tgcatagaga   6480
cgttaagtcc aataacatac tactggactc tgattttgag gcccatgttg ctgattttgg   6540
gcttgctaag ttcttagtgg acggtgctgc ttctgagtgt atgtcttcga tagctggctc   6600
```

-continued

```
ctatggatac atcgctccag gttagtttta aacttgtttt aaataacaaa taatatgtat   6660
aaaactaact attgtttgtt ttggttttgg tagagtatgc ttacactctc aaagtggacg   6720
agaagagtga tgtgtatagt ttcggagtgg tgttattgga actgatagct gggaagaaac   6780
cggttggtga gtttggggaa ggagtggata tagtgaggtg ggtgaggaac acggagggtg   6840
agatacctca gccgtcggat gcagctactg ttgtggcgat cgttgaccag aggttgactg   6900
gttacccgtt gactagtgtg attcacgtgt tcaagatagc gatgatgtgt gtggaggatg   6960
aggcagcgac aaggccgacg atgagggaag ttgtgcacat gctcactaac cctcccaagt   7020
ccgtcactaa cttgatcgcc ttctgaccca atcgaagatt aatggaaaaa tagaagatgt   7080
gttttgtgtg taatgatatt ttgttgtggt gtttctctaa gttaaattac ttttgagttg   7140
tatgtatgta tatttgttgt gggatcgatt tgtatattta ttgctcttat gtgtttttat   7200
ctactctctg taatgtgatt tgtatgctta ttgatgatgg cttttaaact tcctagataa   7260
cctttacctt cattccctgt aaattggtac cctgcatctc gtctctgtta tgcttaagaa   7320
gttcaatgtt tcgtttcatg taaaactttg gtggtttgtg ttttggggcc ttgtataatc   7380
cctgatgaat aagtgttcta ctatgtttcc gttcctgtta tctctttctt tctaatgaca   7440
agtcgaactt cttctttatc atcgcttcgt ttttattatc tgtgcttctt ttgtttaata   7500
cgcctgcaaa gtgactcgac tctgtttagt gcagttctgc gaaacttgta aatagtccaa   7560
ttgttggcct ctagtaatag atgtagcgaa agtgttgagc tgttgggttc taaggatggc   7620
ttgaacatgt taatctttta ggttctgagt atgatgaaca ttcgttgttg ctaagaaatg   7680
cctgtaatgt cccacaaatg tagaaaatgg ttcgtacctt tgtccaagca ttgatatgtc   7740
tgatgagagg aaactgcaag atactgagct tggtttaacg aaggagaggc agtttcttcc   7800
ttccaaagca tttcatttga caatgccttg atcatcttaa gtagagtttc tgttgtggaa   7860
agtttgaaac tttgaagaaa cgactctcaa gtaaattgat gatcacaagt gaaagtgtat   7920
gttactagtt tttcaaatca gtgcgcaaga cgtgacgtaa gtatccgagt cagtttttat   7980
ttttctacta atttggtcgt ttatttcggc gtgtaggaca tggcaaccgg gcctgaattt   8040
cgcgggtatt ctgtttctat tccaactttt tcttgatccg cagccattaa cgacttttga   8100
atagatacgc tgacacgcca agcctcgcta gtcaaaagtg taccaaacaa cgctttacag   8160
caagaacgga atgcgcgtga cgctcgcggt gacgccattt cgccttttca gaaatggata   8220
aatagccttg cttcctatta tatcttccca aattaccaat acattacact agcatctgaa   8280
tttcataacc aatctcgata caccaaatcg ggtaccaaca atgagcccag aacgacgccc   8340
ggccgacatc cgccgtgcca ccgaggcgga catgccggcg gtctgcacca tcgtcaacca   8400
ctacatcgag acaagcacgg tcaacttccg taccgagccg caggaaccgc aggagtggac   8460
ggacgacctc gtccgtctgc gggagcgcta tccctggctc gtcgccgagg tggacggcga   8520
ggtcgccggc atcgcctacg cgggtccctg gaaggcacgc aacgcctacg actggacggc   8580
cgagtccacc gtgtacgtct cccccgcca ccagcggacg ggactgggct ccacgctcta   8640
cacccacctg ctgaagtccc tggaggcaca gggcttcaag agcgtggtcg ctgtcatcgg   8700
gctgcccaac gacccgagcg tgcgcatgca cgaggcgctc ggatatgccc cccgcggcat   8760
gctgcgggcg gccggcttca agcacgggaa ctggcatgac gtgggtttct ggcagctgga   8820
cttcagcctg ccggtgccgc cccgtccggt cctgcccgtc accgaaatct gagagctctt   8880
ggactcccat gttggcaaag gcaaccaaac aaacaatgaa tgatccgctc ctgcatatgg   8940
```

```
ggcggtttga gtatttcaac tgccatttgg gctgaattga agacatgctc ctgtcagaaa   9000
ttccgtgatc ttactcaata ttcagtaatc tcggccaata tcctaaatgt gcgtggcttt   9060
atctgtcttt gtattgtttc atcaattcat gtaacgtttg cttttcttat gaattttcaa   9120
ataaattatc gtattctaga ccaagcatgc acagctggcg ttctcagcca gatccaacgt   9180
tacaccacaa tatatcctgc caagatctaa ttccggggat cggaaatcca gaagcccgag   9240
aggttgccgc ctttcgggct ttttcttttt caaaaaaaaa aatttataaa acgatctgtt   9300
gcggccggcc gccgggttgt gggcaaaggc gctcgacggt gggcaaccgc ttgcggttgt   9360
ccacgggcgg agccggtgcg cgtagcgcat tgtccacaag ccaagggcga ccaataattg   9420
atatatatat tcataattga aaagctaatt gaacatacta cttgctgtaa ctacttgccg   9480
gagcgagggg tgtttgcaag ctgttgatct gaaagggcta ttagcgttct cacgtgcctt   9540
tttgattagc gatttcacgt gaccttatta gcgatttcac gtactccgat tagcgatttc   9600
acgtaccctg attagcgatt tcacgtggat agtttttgga gcgggccgga aagccccgtg   9660
aatcaaggct ttgcggggca ttagcggttt cacgtggata actaccctct atccacaggc   9720
ttccggggat aaaaaagccc gctcgacggc gggctgttgg atggggatcg cctgaatcgc   9780
cccatcatcc agccagaaag tgagggagcc acggttgatg agagctttgt tgtaggtgga   9840
ccagttggtg attttgaact tttgctttgc cacggaacgg tctgcgttgt cgggaagatg   9900
cgtgatctga tccttcaact cagcaaaagt tcgatttatt caacaaagcc acgttgtgtc   9960
tcaaaatctc tgatgttaca ttgcacaaga taaaaatata tcatcatgaa caataaaact  10020
gtctgcttac ataaacagta atacaagggg tgttatgagg gaagcggtga tcgccgaagt  10080
atcgactcaa ctatcagagg tagttggcgt catcgagcgc catctcgaac cgacgttgct  10140
ggccgtacat ttgtacggct ccgcagtgga tggcggcctg aagccacaca gtgatattga  10200
tttgctggtt acggtgaccg taaggcttga tgaaacaacg cggcgagctt tgatcaacga  10260
ccttttggaa acttcggctt cccctggaga gagcgagatt ctccgcgctg tagaagtcac  10320
cattgttgtg cacgacgaca tcattccgtg gcgttatcca gctaagcgcg aactgcaatt  10380
tggagaatgg cagcgcaatg acattcttgc aggtatcttc gagccagcca cgatcgacat  10440
tgatctggct atcttgctga caaaagcaag agaacatagc gttgccttgg taggtccagc  10500
ggcggaggaa ctctttgatc cggttcctga acaggatcta tttgaggcgc taaatgaaac  10560
cttaacgcta tggaactcgc cgcccgactg ggctggcgat gagcgaaatg tagtgcttac  10620
gttgtcccgc atttggtaca gcgcagtaac cggcaaaatc gcgccgaagg atgtcgctgc  10680
cgactgggca atggagcgcc tgccggccca gtatcagccc gtcatacttg aagctaggca  10740
ggcttatctt ggacaagaag atcgcttggc ctcgcgcgca gatcagttgg aagaatttgt  10800
tcactacgtg aaaggcgaga tcaccaaggt agtcggcaaa taatcactag accaatgtta  10860
cacatatata ctttagattg atttaaaact tcatttttaa tttaaaagga tctaggtgaa  10920
gatccttttt gataatctca tgaccaaaat cccttaacgt gagttttcgt tccactgagc  10980
gtcagacccc gtagaaaaga tcaaaggatc ttcttgagat cctttttttc tgcgcgtaat  11040
ctgctgcttg caaacaaaaa aaccaccgct accagcggtg gtttgtttgc cggatcaaga  11100
gctaccaact cttcttccga aggtaactgg cttcagcaga gcgcagatac caaatactgt  11160
tcttctagtg tagccgtagt taggccacca cttcaagaac tctgtagcac cgcctacata  11220
cctcgctctg ctaatcctgt taccagtggc tgctgccagt ggcgataagt cgtgtcttac  11280
cgggttggac tcaagacgat agttaccgga taaggcgcag cggtcgggct gaacgggggg  11340
```

ttcgtgcaca cagcccagct tggagcgaac gacctacacc gaactgagat acctacagcg 11400
tgagctatga gaaagcgcca cgcttcccga agggagaaag gcggacaggt atccggtaag 11460
cggcagggtc ggaacaggag agcgcacgag ggagcttcca gggggaaacg cctggtatct 11520
ttatagtcct gtcgggtttc gccacctctg acttgagcgt cgatttttgt gatgctcgtc 11580
aggggggcgg agcctatgga aaaacgccag caacgcggcc tttttacggt tcctggcctt 11640
ttgctggcct tttgctcaca tgagatctca aacaaacaca tacagcgact tagtttaccc 11700
gccaatatat cctgtcaagg ctcgaactag gctcggacga agt 11743

<210> SEQ ID NO 103
<211> LENGTH: 11743
<212> TYPE: DNA
<213> ORGANISM: Artificial Sequence
<220> FEATURE:
<223> OTHER INFORMATION: plasmid AtproCLV1:BrCLV1_S582N

<400> SEQUENCE: 103
aagcggccgc ggggtttatc tgaattggat ggtgatgaaa tgttattaac agattttcta 60
atttttgtct ctatcgattt tgtttccgta aatacatctt ttgtgtatat attgtcttgt 120
agaaagaaac attgattaag tagagaaata ggataatcaa tctctgtact taatacatca 180
tccattgaaa caagttagga atcgatccaa tatgaggctc tgcaaaaaca attcaggaaa 240
agattctgca aaaacaattt aggagaatga gtgaaatcgc aggggcaatt tcgtcaattt 300
atttcccaaa aactgcctat cttcataaac tcaatcataa tgtgctcttt ctctaattta 360
tggcccaaaa tgtacccaat attataaaag cccccacaat taagcaccaa agagttttgg 420
tacattaact tgggaggaaa cagagacact tgttaactgg taaggcaaca tttcaaattc 480
catatcttgt tctctcaagt ccaatgcatt tatccttgca cgcttgattg tttaaaccat 540
ttagattaat gggttggcat tggtcacgct gatccaatgt ttcaaatggg taagtgaatg 600
ttgattgccg acgtgactga agacccaagg cccaacgacc tactggtcca ggttgactat 660
gaacaaaaga actagatttt tttttccct acattttaaa gaaaatactt gatgaagatg 720
tggtgccttt tcataagatc taaaaagttt caaatcttta cgatggaaca aaaagtgaaa 780
ggtgaagtaa gggtcatttg ggattgagaa gtttcttcgt ccaaaatcat tgcatgagtt 840
gaatagattt gggattaaag ctgccaatac aagaggattc ggtaatgact gaagcaaaag 900
cccagcaggg ccattaggca aacaccagtt tccaagacgg atttgtgtaa gaccacttat 960
gacacaagtt tgtcttcact atcatcatct tcttcttcta cttctactac tacttttgta 1020
gccttgtcgt ttttatcatt aacatgattg acaagactat gacctatata tcttattatt 1080
atcattgctc tctctatttg tttatattga ttattacttt ttgagatttt tcaatggttt 1140
tatctctaac taaacattat aattagtgaa acaagcttag tagaagtaaa agtattattc 1200
tatgctaaag tacattgatt agtagagtgt gtaattgtgt atacagataa tctataaaca 1260
attggtgcat ctgtatataa aactttatga tttatttatt gtatttaata agtatatgaa 1320
ttgggtacct aactttctaa acagttccaa atttattctt aaatcaaatt gcatatgatt 1380
tttaaatatt ttgagacgat tttattataa cgcaaacaac agagtaaaag aagcatatgt 1440
tgcaaattgt actatggcaa gttcaaatcg aaacattttt gtgaaaatca aacatgtgaa 1500
ccaagcttct acagtttaat tccctttcgt ataatttaat ttcaacaaat ttattgatat 1560
ccatctagaa attggtccaa agttctttca cccttgagtc atttagtgat aaagatgaca 1620

-continued

```
tgatttttgg tgataaattt tccatcgttg ctatatgtcg ttatattatt ctcctatatg   1680

tatattatac tatttacatc agaaaataat ccaaagttta gagattcttt tttacaataa   1740

taaaatttcc cacttactaa aaagagctcc ttttctgctg aagagaacct aaacctttat   1800

tcccaaagtt cattgagtta gagcattttc agcgaatcac ataagagatg ctctcttctt   1860

catcactaat tgacatctca ttgttttaaa ggttgcactt gtacctgttg atctgattct   1920

caatccactt aagttaaacc aaatagacac gagaaaaaag cacatttatt tgttgctaag   1980

tatgcatatt tttcagcgtt tacttcttaa tctaatgtat atcataagat aatatctaaa   2040

agagaatgca caaaagatta ttaatatgag aaattcgctg ccatttagga aggaccttta   2100

taccaatata ccgcaataat aatagaacat tggtccccaa gtgtatgtca accccaagtg   2160

tatagatttc tttaaagatt aaaatccctt tttgttgcta aagcacctga tatatttttc   2220

tatcaaacta aaaaaattgt tagcgggatg aagatatatt cgccaagaac catagtgctt   2280

gtataacggc agaccattaa ttcacaacta ttattatttt attgttagat tgttgataga   2340

atcgattttg attgtggcag aatcgatctt gtaaaaactg ctttaaggtg cttacttata   2400

attaagaaag attcacttat gtaagttaag catattaatc atatcattcg gcctaattca   2460

ttaggaatat tttgctattc gttttgccat cattaacaac aaaattgaca cgttttcagc   2520

caaaagtatt aacaactaaa cctaaaactt caaacattaa atagttttta gtatctttag   2580

tttcaaacta gtgatttgtc ctaatatcaa cactacgaac gaatttatat acattgaact   2640

tttttctgaa tcaccgatta caaaacgaat ataatttggt atcggcagtt gctattaatt   2700

tgatcggttt ggactttgga ctaatcacga tcaaatctta aatggaccga agtgaataaa   2760

tccctaatgt tttcaagaga gtcacacgaa cgaaacaaag gtaaaatatg aacatagagc   2820

gtggggacct tgaagcagaa ggtctgtatg gtgacagacc ggtgagtgga gtgtatgaat   2880

gaacgagaag tgagaagaca aaatacaaga aagagcgttg acttggaagt taaagccaaa   2940

aaaaccacaa ggggcaaatt tgtctcttta ggaaaaggac acagacagac tttctatacg   3000

ggccaattag aaaaataggc cctacttcta attaaagccc atttacttct ctccttgtct   3060

tcttattcct cttttctccc catcacgtga cgacgatgct ataaacgccg tcggattata   3120

taactggtgc cgttgacaag acggcgacag aagaaagaaa gaagaaacca caggctctag   3180

ggaacgtaac gttatgtcct gtctatagca tttataacgg tcagatcaac gccgtttaga   3240

taaagatctg tcaatgttaa agaagagatg catctctaca ccgttaaatt taaaacgccg   3300

tgaacctctt atctattgat ttttgtttga tgaagccaaa acaaatcgtg tcagaagact   3360

tatcagagaa gaagaaaacg acgacgttcc cgtttctcca tgtctaataa gtgtagtagt   3420

ggcggctact aaaaactcta aagtttgact ccagtaaaac tgcctttcta gtgtaattcc   3480

agtgatttta gagtttgaat agtgtgtgac caaatttgaa agtacaatct cagcaatatt   3540

attgatcact cgttataaaa gaatcgaatg taaaaatagc caatgagaga ctgagacgta   3600

tgtgtttgac cataagtcgt atagtttgta tctatctacc tgcaagatca gcagatggtt   3660

ctctgatcaa ttgtacctta attatctttt attttcgtaa aatttctcta ttcacaaatg   3720

ataaatctac ttaagacagt aaccataaca agatttacaa gataatttga aaaatgaaca   3780

cataaaagta ttttggcgca ttatttttaa taataacaat atttatgtaa agtcacataa   3840

aagtatatat tcgctcacaa agtcttacgg tatttagaac agtagtacca catcgattct   3900

cttcatcttc ttcttcataa tatgccattg ttcatgtctc tgtgtcctat cgcataacac   3960

tcacgctatc ttattatttt ctctcgctct ttctcactga gaggacacta aaaaaatgag   4020
```

acttctgaaa actcaccttc tgtttctcca tcttcattac gttatctcga tttcgcttct 4080
atgtttctca ccatgcctcg cttccactga catggaccat ctcctcaacc tcaaatcctc 4140
catgattggt cccaacggca acggcctcca cgactgggtt cactcccctt cccccacagc 4200
tcactgttct ttctccggcg tttcctgcga cggcgacgct cgtgtcatct ccctcaacgt 4260
ctctttcact cctctcttcg gaaccatctc cccggagatt gggatgctga accgtcttgt 4320
gaatctcacg ttagctgcta ataacttctc cggtatgttg ccgttagaga tgaagagtct 4380
cacttctcta aaggttctca acatctccaa caacgtaaac ctcaacggaa cgttccccgg 4440
agagattctc actcccatgg tcgacctcga agtcctcgac gcgtacaaca acaacttcac 4500
aggcccatta ccgccagaga tccccgggct caagaaactg agacacctct ctctcggagg 4560
aaacttctta accggagaga tcccagagag ttacggagat atccaaagct tggagtatct 4620
cggcctcaac ggagccggac tctccggtga atctccggcg ttcttgtcac gcctcaagaa 4680
tcttaaagaa atgtacgtcg gctacttcaa cagctacacc ggcggcgtac cgccggagtt 4740
cggtgaattg acaaacttag aagtcctcga catggcgagc tgtactctca ccggagagat 4800
tccgacaaca ctaagtaatc taaaacattt gcacactttg tttctccaca tcaacaactt 4860
aaccggaaac atcccacccg aactctccgg tttaatcagc ttaaaatctc tagacctctc 4920
aataaaccag ctaaccggag agattcctca gagcttcatc tccctaggga acatcactct 4980
catcaacctc ttccgaaaca atctccacgg gccgataccg gacttcatcg gagacatgcc 5040
gaacctccaa gtcctccagg tgtgggagaa caacttcacg ctagagctac cggcgaatct 5100
cggccggaac gggaatctga aaaagctcga cgtctctgat aaccatctca ccggactcat 5160
ccccatggat ttgtgcagag gcgggaagct ggagacgctg gtgctctcca acaacttctt 5220
cttcggctcg atccctgaga agctaggtca atgcaaatcg ctaaacaaga tcagaatcgt 5280
caagaatctc ctcaacggca cggttccgga gggcttattc aatctaccgc tcgtaacgat 5340
catcgagctc accgataact tcttctccgg ggagcttccg ggggagatgt caggcgacgt 5400
tctcgatcat atctacttat ctaacaattg gtttaccggt ttaatccccc cggctatcgg 5460
taattttaaa aatctacagg atttattctt agaccggaac cggtttagcg ggaatattcc 5520
gagagaagtt ttcgagttga agcatctaac gaagatcaac acgagtgcta acaacctaac 5580
cggcgatatc cctgactcaa tctcacgttg cacttcctta atctccgtcg atctcagccg 5640
taaccgaatc ggcggagata tccctaaaga catccacgat gtgatcaatc tcggaactct 5700
aaatctctcc gggaatcaac tcaccggctc gatcccgatc ggaatcggga agatgacgag 5760
cttaaccact ctggatctct ccttcaacga cctctccggg agagtcccac tcggcggcca 5820
gttcctagtc ttcaacgaca cttccttcgc cggaaaccct tacctctgcc tccctcacca 5880
cgtctcgtgc cttacgcgtc cggaacaaac ctccgatcgt atccacacgg ctctcttctc 5940
tccgtcgagg atcgttatca cgatcgtcgc ggcgataacg gcgttgatcc tcatcagcgt 6000
cgcgattcgt cagatgaaca agaagaaaca cgagaggtct ctctcgtgga agctaaccgc 6060
cttccaaaga ctcgatttca aagcggaaga cgtcctcgag tgtctccagg aagagaacat 6120
aatcggcaaa ggcggagctg ggatcgtcta ccgcggatcc atgccgaaca acgtagacgt 6180
cgcgatcaaa cggttagtag gacgcggaac agggaggagc gatcacggat tcacggcgga 6240
gatacaaact ctagggagaa tccgccaccg tcatatagtg agactcctcg gatacgtggc 6300
gaacaaggac acgaacctgc ttctctacga gtacatgcct aacgggagcc tcggggagct 6360

-continued

```
tttgcacgga tctaaaggag gtcatcttca gtgggagacg aggcacagag tagccgtgga   6420
agcggcgaaa ggactgtgtt atcttcatca tgactgttcg ccgttgatct tgcatagaga   6480
cgttaagtcc aataacatac tactggactc tgattttgag gcccatgttg ctgattttgg   6540
gcttgctaag ttcttagtgg acggtgctgc ttctgagtgt atgtcttcga tagctggctc   6600
ctatggatac atcgctccag gttagtttta aacttgtttt aaataacaaa taatatgtat   6660
aaaactaact attgtttgtt ttggttttgg tagagtatgc ttacactctc aaagtggacg   6720
agaagagtga tgtgtatagt ttcggagtgg tgttattgga actgatagct gggaagaaac   6780
cggttggtga gtttggggaa ggagtggata tagtgaggtg ggtgaggaac acggagggtg   6840
agatacctca gccgtcggat gcagctactg ttgtggcgat cgttgaccag aggttgactg   6900
gttacccgtt gactagtgtg attcacgtgt tcaagatagc gatgatgtgt gtggaggatg   6960
aggcagcgac aaggccgacg atgagggaag ttgtgcacat gctcactaac cctcccaagt   7020
ccgtcactaa cttgatcgcc ttctgaccca atcgaagatt aatggaaaaa tagaagatgt   7080
gttttgtgtg taatgatatt ttgttgtggt gtttctctaa gttaaattac ttttgagttg   7140
tatgtatgta tatttgttgt gggatcgatt tgtatattta ttgctcttat gtgtttttat   7200
ctactctctg taatgtgatt tgtatgctta ttgatgatgg cttttaaact tcctagataa   7260
cctttacctt cattccctgt aaattggtac cctgcatctc gtctctgtta tgcttaagaa   7320
gttcaatgtt tcgtttcatg taaaactttg gtggtttgtg ttttggggcc ttgtataatc   7380
cctgatgaat aagtgttcta ctatgtttcc gttcctgtta tctctttctt tctaatgaca   7440
agtcgaactt cttctttatc atcgcttcgt ttttattatc tgtgcttctt ttgtttaata   7500
cgcctgcaaa gtgactcgac tctgtttagt gcagttctgc gaaacttgta aatagtccaa   7560
ttgttggcct ctagtaatag atgtagcgaa agtgttgagc tgttgggttc taaggatggc   7620
ttgaacatgt taatctttta ggttctgagt atgatgaaca ttcgttgttg ctaagaaatg   7680
cctgtaatgt cccacaaatg tagaaaatgg ttcgtacctt tgtccaagca ttgatatgtc   7740
tgatgagagg aaactgcaag atactgagct tggtttaacg aaggagaggc agtttcttcc   7800
ttccaaagca tttcatttga caatgccttg atcatcttaa gtagagtttc tgttgtggaa   7860
agtttgaaac tttgaagaaa cgactctcaa gtaaattgat gatcacaagt gaaagtgtat   7920
gttactagtt tttcaaatca gtgcgcaaga cgtgacgtaa gtatccgagt cagtttttat   7980
ttttctacta atttggtcgt ttatttcggc gtgtaggaca tggcaaccgg gcctgaattt   8040
cgcgggtatt ctgtttctat tccaactttt tcttgatccg cagccattaa cgacttttga   8100
atagatacgc tgacacgcca agcctcgcta gtcaaaagtg taccaaacaa cgctttacag   8160
caagaacgga atgcgcgtga cgctcgcggt gacgccattt cgccttttca gaaatggata   8220
aatagccttg cttcctatta tatcttccca aattaccaat acattacact agcatctgaa   8280
tttcataacc aatctcgata caccaaatcg ggtaccaaca atgagcccag aacgacgccc   8340
ggccgacatc cgccgtgcca ccgaggcgga catgccggcg gtctgcacca tcgtcaacca   8400
ctacatcgag acaagcacgg tcaacttccg taccgagccg caggaaccgc aggagtggac   8460
ggacgacctc gtccgtctgc gggagcgcta tccctggctc gtcgccgagg tggacggcga   8520
ggtcgccggc atcgcctacg cgggtccctg gaaggcacgc aacgcctacg actggacggc   8580
cgagtccacc gtgtacgtct ccccccgcca ccagcggacg ggactgggct ccacgctcta   8640
cacccacctg ctgaagtccc tggaggcaca gggcttcaag agcgtggtcg ctgtcatcgg   8700
gctgcccaac gacccgagcg tgcgcatgca cgaggcgctc ggatatgccc cccgcggcat   8760
```

```
gctgcgggcg gccggcttca agcacgggaa ctggcatgac gtgggtttct ggcagctgga   8820
cttcagcctg ccggtgccgc cccgtccggt cctgcccgtc accgaaatct gagagctctt   8880
ggactcccat gttggcaaag gcaaccaaac aaacaatgaa tgatccgctc ctgcatatgg   8940
ggcggtttga gtatttcaac tgccatttgg gctgaattga agacatgctc ctgtcagaaa   9000
ttccgtgatc ttactcaata ttcagtaatc tcggccaata tcctaaatgt gcgtggcttt   9060
atctgtcttt gtattgtttc atcaattcat gtaacgtttg cttttcttat gaattttcaa   9120
ataaattatc gtattctaga ccaagcatgc acagctggcg ttctcagcca gatccaacgt   9180
tacaccacaa tatatcctgc caagatctaa ttccggggat cggaaatcca gaagcccgag   9240
aggttgccgc ctttcgggct ttttcttttt caaaaaaaaa aatttataaa acgatctgtt   9300
gcggccggcc gccgggttgt gggcaaaggc gctcgacggt gggcaaccgc ttgcggttgt   9360
ccacgggcgg agccggtgcg cgtagcgcat tgtccacaag ccaagggcga ccaataattg   9420
atatatatat tcataattga aaagctaatt gaacatacta cttgctgtaa ctacttgccg   9480
gagcgagggg tgtttgcaag ctgttgatct gaaagggcta ttagcgttct cacgtgcctt   9540
tttgattagc gatttcacgt gaccttatta gcgatttcac gtactccgat tagcgatttc   9600
acgtaccctg attagcgatt tcacgtggat agtttttgga gcgggccgga aagccccgtg   9660
aatcaaggct ttgcggggca ttagcggttt cacgtggata actaccctct atccacaggc   9720
ttccggggat aaaaaagccc gctcgacggc gggctgttgg atggggatcg cctgaatcgc   9780
cccatcatcc agccagaaag tgagggagcc acggttgatg agagctttgt tgtaggtgga   9840
ccagttggtg attttgaact tttgctttgc cacggaacgg tctgcgttgt cgggaagatg   9900
cgtgatctga tccttcaact cagcaaaagt tcgatttatt caacaaagcc acgttgtgtc   9960
tcaaaatctc tgatgttaca ttgcacaaga taaaaatata tcatcatgaa caataaaact  10020
gtctgcttac ataaacagta atacaagggg tgttatgagg gaagcggtga tcgccgaagt  10080
atcgactcaa ctatcagagg tagttggcgt catcgagcgc catctcgaac cgacgttgct  10140
ggccgtacat ttgtacggct ccgcagtgga tggcggcctg aagccacaca gtgatattga  10200
tttgctggtt acggtgaccg taaggcttga tgaaacaacg cggcgagctt tgatcaacga  10260
ccttttggaa acttcggctt cccctggaga gagcgagatt ctccgcgctg tagaagtcac  10320
cattgttgtg cacgacgaca tcattccgtg gcgttatcca gctaagcgcg aactgcaatt  10380
tggagaatgg cagcgcaatg acattcttgc aggtatcttc gagccagcca cgatcgacat  10440
tgatctggct atcttgctga caaaagcaag agaacatagc gttgccttgg taggtccagc  10500
ggcggaggaa ctctttgatc cggttcctga acaggatcta tttgaggcgc taaatgaaac  10560
cttaacgcta tggaactcgc cgcccgactg ggctggcgat gagcgaaatg tagtgcttac  10620
gttgtcccgc atttggtaca gcgcagtaac cggcaaaatc gcgccgaagg atgtcgctgc  10680
cgactgggca atggagcgcc tgccggccca gtatcagccc gtcatacttg aagctaggca  10740
ggcttatctt ggacaagaag atcgcttggc ctcgcgcgca gatcagttgg aagaatttgt  10800
tcactacgtg aaaggcgaga tcaccaaggt agtcggcaaa taatcactag accaatgtta  10860
cacatatata ctttagattg atttaaaact tcatttttaa tttaaaagga tctaggtgaa  10920
gatccttttt gataatctca tgaccaaaat cccttaacgt gagttttcgt tccactgagc  10980
gtcagacccc gtagaaaaga tcaaaggatc ttcttgagat cctttttttc tgcgcgtaat  11040
ctgctgcttg caaacaaaaa aaccaccgct accagcggtg gtttgtttgc cggatcaaga  11100
```

-continued

```
gctaccaact cttcttccga aggtaactgg cttcagcaga gcgcagatac caaatactgt  11160
tcttctagtg tagccgtagt taggccacca cttcaagaac tctgtagcac cgcctacata  11220
cctcgctctg ctaatcctgt taccagtggc tgctgccagt ggcgataagt cgtgtcttac  11280
cgggttggac tcaagacgat agttaccgga taaggcgcag cggtcgggct gaacgggggg  11340
ttcgtgcaca cagcccagct tggagcgaac gacctacacc gaactgagat acctacagcg  11400
tgagctatga gaaagcgcca cgcttcccga agggagaaag gcggacaggt atccggtaag  11460
cggcagggtc ggaacaggag agcgcacgag ggagcttcca gggggaaacg cctggtatct  11520
ttatagtcct gtcgggtttc gccacctctg acttgagcgt cgatttttgt gatgctcgtc  11580
aggggggcgg agcctatgga aaaacgccag caacgcggcc tttttacggt tcctggcctt  11640
ttgctggcct tttgctcaca tgagatctca aacaaacaca tacagcgact tagtttaccc  11700
gccaatatat cctgtcaagg ctcgaactag gctcggacga agt                    11743
```